US008110334B2

(12) United States Patent
Echigo et al.

(10) Patent No.: US 8,110,334 B2
(45) Date of Patent: Feb. 7, 2012

(54) RADIATION-SENSITIVE COMPOSITION

(75) Inventors: Masatoshi Echigo, Kanagawa (JP); Dai Oguro, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 95 days.

(21) Appl. No.: 12/312,258

(22) PCT Filed: Nov. 1, 2007

(86) PCT No.: PCT/JP2007/071346
§ 371 (c)(1),
(2), (4) Date: May 1, 2009

(87) PCT Pub. No.: WO2008/053974
PCT Pub. Date: May 8, 2008

(65) Prior Publication Data
US 2010/0047709 A1 Feb. 25, 2010

(30) Foreign Application Priority Data

| Nov. 2, 2006 | (JP) | 2006-299522 |
|---|---|---|
| Apr. 23, 2007 | (JP) | 2007-113185 |
| Apr. 23, 2007 | (JP) | 2007-113186 |
| May 9, 2007 | (JP) | 2007-124918 |
| May 25, 2007 | (JP) | 2007-139763 |
| May 25, 2007 | (JP) | 2007-139764 |

(51) Int. Cl.
*G03F 7/039* (2006.01)
*G03F 7/09* (2006.01)
*C07C 39/04* (2006.01)
*C07C 39/08* (2006.01)
*C07C 39/10* (2006.01)

(52) U.S. Cl. .................. 430/270.1; 430/271.1; 430/905; 430/907; 430/908; 568/720; 568/717; 568/722; 568/723; 568/726; 568/727; 568/744; 560/57; 560/81; 560/83

(58) Field of Classification Search .................. None
See application file for complete search history.

(56) References Cited

U.S. PATENT DOCUMENTS

| 5,968,985 | A | 10/1999 | Kuno et al. |
|---|---|---|---|
| 6,093,517 | A | 7/2000 | Ito et al. |
| 6,197,473 | B1 | 3/2001 | Kihara et al. |
| 2008/0113294 | A1 | 5/2008 | Echigo et al. |
| 2008/0153031 | A1 | 6/2008 | Echigo et al. |
| 2009/0042123 | A1* | 2/2009 | Kinoshita et al. .......... 430/270.1 |

FOREIGN PATENT DOCUMENTS

| JP | 11-153863 A | 6/1999 |
|---|---|---|
| JP | 11-322656 A | 11/1999 |
| JP | 2002-328473 A | 11/2002 |
| JP | 2003-321423 A | 11/2003 |
| JP | 2005-170902 A | 6/2005 |
| JP | 2005-326838 A | 11/2005 |
| JP | 2006-276459 A | 10/2006 |
| JP | 2006-276742 A | 10/2006 |
| JP | 2007-008875 A | 1/2007 |
| JP | 2007-041501 A | 2/2007 |
| WO | 96/04241 A2 | 2/1996 |
| WO | 2006/110173 A2 | 10/2006 |
| WO | WO2006/129574 A1 * | 12/2006 |

OTHER PUBLICATIONS

English language Abstract of JP 2007-041501 A, Feb. 15, 2007.
English language Abstract of JP 2005-326838 A, Nov. 24, 2005.
English language Abstract of JP 11-153863 A, Jun. 8, 1999.
English language Abstract of JP 11-322656 A, Nov. 24, 1999.
English language Abstract of JP 2002-328473 A, Nov. 15, 2002.
English language Abstract of JP 2003-321423 A, Nov. 11, 2003.
English language Abstract of JP 2005-170902 A, Jun. 30, 2005.
English language Abstract of JP 2006-276459 A, Oct. 12, 2006.
English language Abstract of JP 2006-276742 A, Oct. 12, 2006.
English language Abstract of JP 2007-008875 A, Jan. 18, 2007.
S. W. Chang et al., "Materials for Future Lithography", Proc. SPIE, vol. 5753, (9 pages total), 2005.
D. Bratton et al., "Molecular Glass Resists for Next Generation Lithography", Proc. SPIE, vol. 6153, 61531D-1, (9 pages total), 2006.
T. Nakayama et al., "A New Three-Component Photoresist Based on Calix[4]resorcinarene Derivative, a Cross-linker, and a Photo-acid Generator", Bull. Chem. Soc. Jpn., 71, pp. 2979-2984, 1998.
T. Gerkensmeier et al., "Synthesis and Structural Studies of 5, 11, 17, 23-Tetrahydroxyresorc[4]arenes", Zeitschrift fuer Naturforschung, B: Chemical Sciences, 56(10), pp. 1063-1073, 2001.

(Continued)

*Primary Examiner* — Sin J. Lee
(74) *Attorney, Agent, or Firm* — Greenblum & Bernstein, P.L.C.

(57) ABSTRACT

A radiation-sensitive composition containing a resist compound having a high sensitivity, a high resolution, a high etching resistance, and a low outgas which forms a resist pattern with a good shape is described. Further described is a method of forming a resist pattern using the radiation-sensitive composition. Still further described are a novel composition for forming a photoresist under coat film which is excellent in optical properties and etching resistance and contains substantially no sublimable substance and an under coat film formed by the composition. Still further described are a radiation-sensitive composition containing a solvent and a cyclic compound having a specific structure, for example, a cyclic compound (A) having a molecular weight of 700 to 5000 which is synthesized by the condensation reaction of a compound having 2 to 59 carbon atoms and 1 to 4 formyl groups (aldehyde compound (A1)) with a compound having 6 to 15 carbon atoms and 1 to 3 phenolic hydroxyl groups (phenol compound (A2)), and a cyclic compound for use in the radiation-sensitive composition.

4 Claims, No Drawings

OTHER PUBLICATIONS

L. Tunstad et al., "Host-Guest Complexation. 48. Octol Building Blocks for Cavitands and Carcerands", Journal of Organic Chemistry, 54(6), pp. 1305-1312, 1989.
S. Cho et al., "PTP-1B Inhibitors: Cyclopenta[d][1,2]-oxazine derivatives", Bioorganic & Medicinal Chemistry Letters, 16(3), pp. 499-502, 2006.
International Search Report for PCT/JP2007/071346, mailed Jan. 22, 2008.
International Preliminary Report on Patentability for PCT/JP2007/071346, issued May 26, 2009.
Bratton et al., "Recent Progress in High Resolution Lithography" *Polymers for Advanced Technologies*, vol. 17, pp. 94-103, 2006.
Ueda et al., "Three-Component Negative-Type Photoresist Based on Calix[4]resorcinarene, a Cross-linker, and a Photoacid Generator" *Chem. Mater.*, vol. 10, pp. 2230-2234, 1998.
Ryzhkina et al., "Aggregation of Amphiphilic Aminomethylated Calix[4]resorcinarenes and the Nonion Surfactant Triton-X-100 in Organic Solvents" *Russian Chemical Bulletin, International Edition*, vol. 53, No. 7, pp. 1528-1535, 2004.
Supplementary European Search Report for European Patent App. No. 07831080.2, dated Mar. 11, 2011.

* cited by examiner

RADIATION-SENSITIVE COMPOSITION

TECHNICAL FIELD

The present invention relates to a cyclic compound having a specific chemical structure which is useful as an acid-amplified, non-polymeric resist material, a radiation-sensitive composition containing the cyclic compound and a composition for under coat film, and further relates to a method of forming a resist pattern and a method of forming an under coat film, each using the respective composition.

BACKGROUND ART

Conventionally known resist materials are generally polymeric materials capable of forming amorphous thin film. For example, a solution of a polymeric resist material such as polymethyl methacrylate, polyhydroxystyrene having an acid-dissociating reactive group and polyalkyl methacrylate is applied on a substrate to form a thin resist film, which is then irradiated with ultraviolet rays, far ultraviolet rays, electron beams, extreme ultraviolet rays (EUV), X-rays, etc., to form line patterns having a width of about 45 to 100 nm.

The polymeric resist compounds generally have a molecular weight as large as about 10,000 to 100,000 and a broad molecular weight distribution. Therefore, in a lithographic fine process using the polymeric resist compounds, the surface of the fine patterns is roughened, thereby making it difficult to control the dimension of patterns and reducing the product yield. Thus, the conventional lithographic techniques using the known polymeric resist materials have limitations in fine processing. To produce finer patterns, there have been proposed various low-molecular resist materials.

For example, there have been proposed a positive-type resist composition mainly composed of a low molecular weight, polynuclear polyphenol compound having at least one phenolic hydroxyl group into which an acid-dissociating functional group is introduced (Patent Document 1) and an alkali-developable, negative-type resist composition mainly composed of a low molecular weight, polynuclear polyphenol compound (Patent Document 2). However, these compositions are insufficient in heat resistance to form resist patterns with deformed shapes.

As a low molecular weight resist material, there have been proposed a positive-type resist composition mainly composed of a low molecular weight, cyclic polyphenol compound having at least one phenolic hydroxyl group into which an acid-dissociating functional group is introduced (Patent Documents 3 to 10 and Non-Patent Documents 1 and 2) and an alkali-developable, negative-type resist composition mainly composed of a low molecular weight, cyclic polyphenol compound (Non-Patent Document 3).

It is expected that these low molecular weight, cyclic polyphenol compounds form resist patterns with a high resolution and a small roughness because of their small molecular sizes. In addition, although the molecular weight is low, the low molecular weight, cyclic polyphenol compound has a high heat resistance because of a rigid cyclic structure in its skeletal structure.

However, known low molecular weight, cyclic polyphenol compounds have several drawbacks such as a low etching resistance, a large outgas, a low solubility in safety solvents used in semiconductor production process, and a poor shape of resist patterns. Therefore, the improvement is still required.

It has been recognized that the homogeneity of the solid component of the positive-type resist composition influences the resolution of resist patterns and the roughness. Therefore, a positive-type resist composition is required to contain the low molecular weight, cyclic polyphenol compound having an acid-dissociating functional group which is structurally highly homogeneous, preferably structurally single. However, a low molecular weight, cyclic polyphenol of a single structure is generally obtained by 100% introduction of the acid-dissociating functional group. Such a low molecular weight, cyclic polyphenol of a single structure reduces the sensitivity of a positive-type resist composition. Thus, a low molecular weight, cyclic polyphenol providing a positive-type resist composition with a high sensitivity has not yet been reported.

Patent Document 1: JP 2005-369761A
Patent Document 2: JP 2005-326838A
Patent Document 3: JP 11-153863A
Patent Document 4: JP 11-322656A
Patent Document 5: JP 2002-328473A
Patent Document 6: JP 2003-321423A
Patent Document 7: JP 2005-170902A
Patent Document 8: JP 2006-276459A
Patent Document 9: JP 2006-276742A
Patent Document 10: JP 2007-8875A
Non-Patent Document 1: Seung Wook Chang et al. "Materials for Future Lithography", Proc. SPIE, Vol. 5753, p. 1
Non-Patent Document 2: Daniel Bratton et al. "Molecular Glass Resists for Next Generation Lithography", Proc. SPIE, Vol. 6153, 61531D-1
Non-Patent Document 3: T. Nakayama, M. Nomura, K. Haga, M. Ueda, Bull. Chem. Soc. Jpn., 71, 2979 (1998)

DISCLOSURE OF THE INVENTION

Problems to be Solved by the Invention

The object of the present invention is to provide:

(1) a radiation-sensitive composition comprising a resist compound having a high sensitivity, a high resolution, a high etching resistance, and a low outgas which forms a resist pattern with a good shape, and a method of forming a resist pattern using the radiation-sensitive composition;

(2) a radiation-sensitive composition comprising a resist compound which forms a resist pattern with a good shape, and a method of forming a resist pattern using the radiation-sensitive composition; and (3) a composition for a new-type photoresist under coat film which is excellent in optical properties and etching resistance and contains substantially no sublimable substance, an under coat film formed from the composition, and a method of forming a pattern using the composition.

Means for Solving the Problems

The present invention relates to:
(1) a cyclic compound represented by the following formula (1):

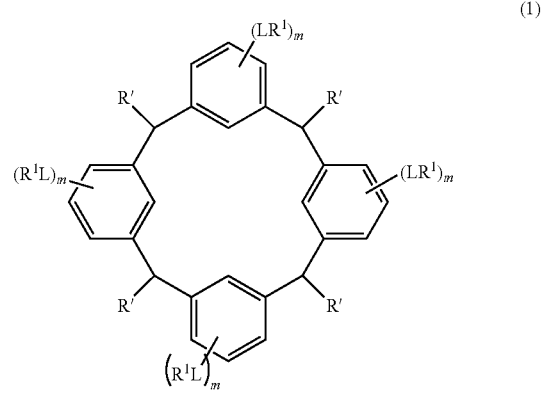

wherein L is independently a single bond or a divalent organic group selected from the group consisting of a linear or branched alkylene group having 1 to 20 carbon atoms, a cycloalkylene group having 3 to 20 carbon atoms, an arylene group having 6 to 24 carbon atoms, —O—, —OC(=O)—, —OC(=O)O—, —N($R^5$)—C(=O)—, —N($R^5$)—C(=O)O—, —S—, —SO—, —$SO_2$—, and any combination of the preceding groups; $R^1$ is independently hydrogen atom; a functional group selected from the group consisting of an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, heterocyclic group, halogen atom, carboxyl group, an alkylsilyl group having 1 to 20 carbon atoms, and a group derived from the preceding groups; or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; R' is independently an alkyl group having 2 to 20 carbon atoms, an aryl group having 6 to 24 carbon atoms represented by the following formula:

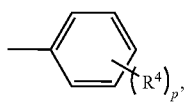

or a group derived from the preceding groups; $R^4$ is a functional group selected from the group consisting of an alkyl group having 1 to 20 carbon atoms exclusive of t-butyl group, a cycloalkyl group having 3 to 20 carbon atoms, an aryl group having 6 to 20 carbon atoms, an alkoxyl group having 1 to 20 carbon atoms, cyano group, nitro group, heterocyclic group, halogen atom, carboxyl group, an alkylsilyl group having 1 to 20 carbon atoms, and a group derived from the preceding groups; $R^5$ is hydrogen atom or an alkyl group having 1 to 10 carbon atoms; m is an integer of 1 to 4; and p is an integer of 0 to 5;
(2) a radiation-sensitive composition comprising the cyclic compound described in the section 1 and a solvent;
(3) a composition for under coat film comprising the radiation-sensitive composition described in the section 2;
(4) a method of producing a cyclic compound (B0), comprising a first stage reaction in which an aldehyde compound (A1b) having 2 to 59 carbon atoms, a reactive functional group and 1 to 4 formyl groups is allowed to react with a reagent for introducing an acid-dissociating functional group, thereby synthesizing an aldehyde compound (A1c) having the acid-dissociating functional group introduced, and a second stage reaction in which the aldehyde compound (A1c) and a phenol compound (A2) are subjected to a condensation reaction;
(5) a method of producing a cyclic compound (B0), comprising a first stage reaction in which an aldehyde compound (A1d) having 2 to 59 carbon atoms, 1 to 4 formyl groups, and 1 to 2 carboxyl groups or ester groups and a phenol compound (A2) are subjected to a condensation reaction, thereby synthesizing a cyclic compound (A0) having 1 to 8 carboxyl groups and a molecular weight of 800 to 5000, and a second stage reaction in which the cyclic compound (A0) is allowed to react with a compound (A3) having a halomethyl ether group;
(6) an under coat film formed from the composition for under coat film described in the section 3; and
(7) a method of forming a resist pattern comprising a step of forming a resist film on a substrate using the radiation-sensitive composition described in the section 2, a step of exposing the resist film to radiation, and a step of developing the resist film to form the resist pattern.

Effects of the Invention

The present invention provides:
(1) a radiation-sensitive composition comprising a resist compound having a high sensitivity, a high resolution, a high etching resistance, and a low outgas which forms a resist pattern with a good shape, and a method of forming a resist pattern using the radiation-sensitive composition;
(2) a radiation-sensitive composition comprising a resist compound which forms a resist pattern with a good shape, and a method of forming a resist pattern using the radiation-sensitive composition; and
(3) a composition for a new photoresist under coat film which is excellent in optical properties and etching resistance and contains substantially no sublimable substance, an under coat film formed from the composition, and a method of forming a pattern using the composition.

BEST MODE FOR CARRYING OUT THE INVENTION

The present invention will be described below in more detail.
Cyclic Compound
The present invention relates to a cyclic compound useful as a resist material.
The cyclic compound of the invention is represented by the following formula (1):

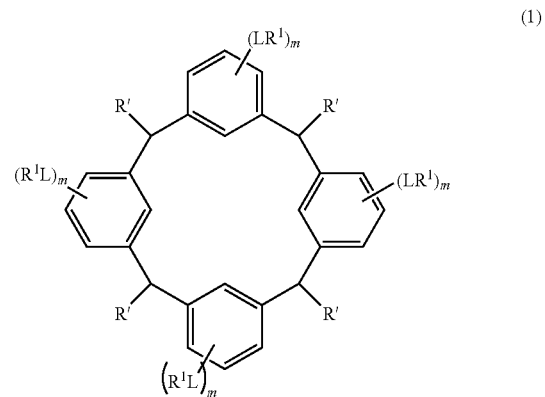

wherein L is independently a single bond or a divalent organic group selected from the group consisting of a linear or branched alkylene group having 1 to 20 carbon atoms, a cycloalkylene group having 3 to 20 carbon atoms, an arylene group having 6 to 24 carbon atoms, —O—, —OC(=O)—, —OC(=O)O—, —N($R^5$)—C(=O)—, —N($R^5$)—C(=O)O—, —S—, —SO—, —$SO_2$—, and any combination of the preceding groups; $R^1$ is independently hydrogen atom, a functional group selected from the group consisting of an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, heterocyclic group, halogen atom, carboxyl group, an alkylsilyl group having 1 to 20 carbon atoms, and a group derived from the preceding groups, or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; R' is independently an alkyl group having 2 to 20 carbon atoms, an aryl group having 6 to 24 carbon atoms represented by the following formula:

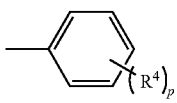

or a group derived from the preceding groups; $R^4$ is a functional group selected from the group consisting of an alkyl group having 1 to 20 carbon atoms exclusive of t-butyl group, a cycloalkyl group having 3 to 20 carbon atoms, an aryl group having 6 to 20 carbon atoms, an alkoxyl group having 1 to 20 carbon atoms, cyano group, nitro group, heterocyclic group, halogen atom, carboxyl group, an alkylsilyl group having 1 to 20 carbon atoms, and a group derived from the preceding groups, or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; $R^5$ is hydrogen atom or an alkyl group having 1 to 10 carbon atoms; m is an integer of 1 to 4; and p is an integer of 0 to 5.

Examples of the cyclic compounds of the formula (1) preferably include the following compounds.

(1-1)

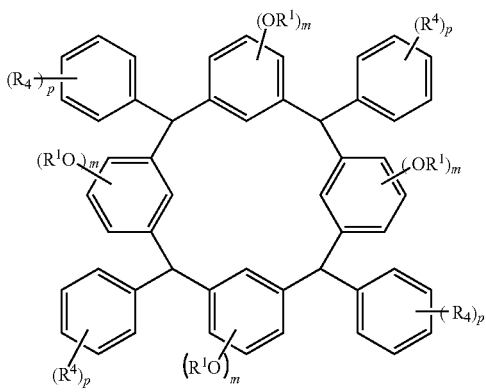

(1-1-1)

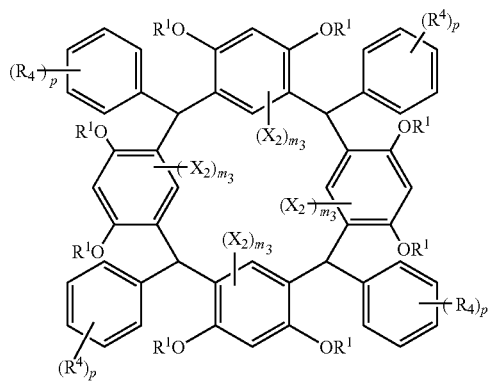

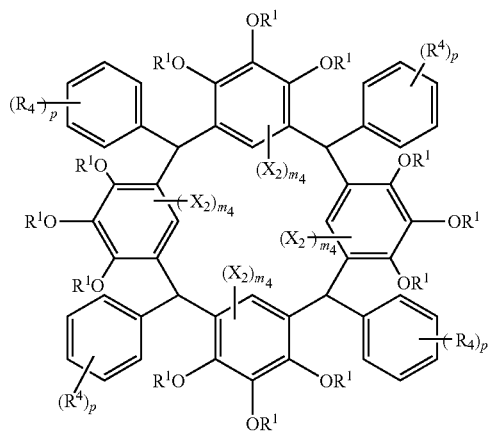

(1-2)

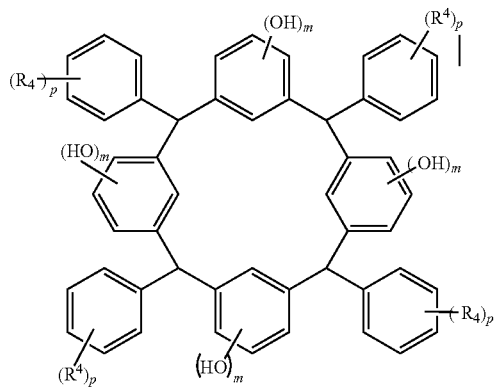

(1-2-1)

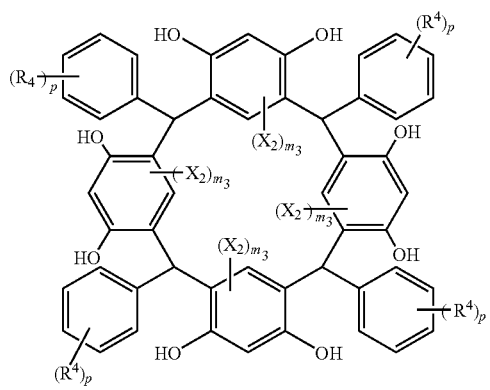

-continued

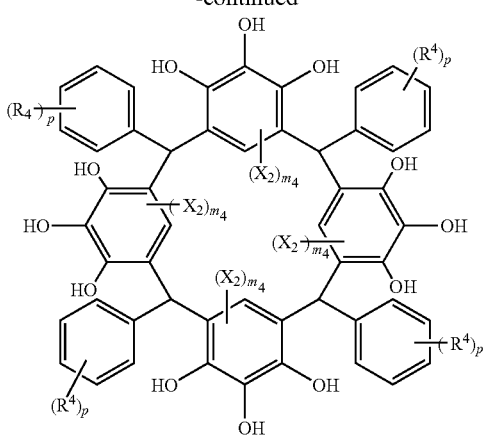

In each of the formulae (1-1), (1-1-1), (1-2) and (1-2-1), $X_2$ is hydrogen atom or a halogen atom, $m_3$ is an integer of 1 to 2, $m_4$ is 1, and $R^4$ and p are the same as defined above.

The above cyclic compounds are highly heat-resistant, excellent in the film-forming properties because of their good amorphous nature, not sublimable, and excellent in the alkali developability, and therefore, suitably used as a resist material, particularly, as a main component (base material) of a resist material. Although having benzene structures, the above cyclic compound surprisingly has a relatively low extinction coefficient for light at a wavelength of 193 nm and a high refractive index, and therefore, is suitably used as a material for under coat film.

In addition, the above cyclic compounds are practically very advantageous because the compounds can be produced in high yields by a condensation reaction with elimination of water in the presence of a non-metallic catalyst such as hydrochloric acid while using various kinds of aldehydes such as aromatic aldehydes and phenols such as resorcinol and pyrogallol, each being industrially produced and available, as the starting materials.

Further, the above cyclic compounds are sparingly soluble in propylene glycol monomethyl ether acetate (PGMEA) which is generally used as a resist solvent but soluble in propylene glycol monomethyl ether (PGME) and cyclohexanone, and therefore, the intermixing is prevented during the production of a multi-layered resist.

The cyclic compound of the invention may be a cis-isomer, a trans-isomer or a mixture thereof. In view of forming a highly uniform resist film, an isomerically pure compound consisting of one of the cis-isomer and the trans-isomer is preferred for the resist component of a radiation-sensitive composition. The cyclic compound of only one of the cis-isomer and the trans-isomer may be obtained by a known method, for example, the separation by column chromatography and preparative liquid chromatography and the optimization of the reaction solvent, reaction temperature, etc.

Of the above cyclic compounds, more preferred are those described below.

(a) Cyclic compound represented by the following formula (2):

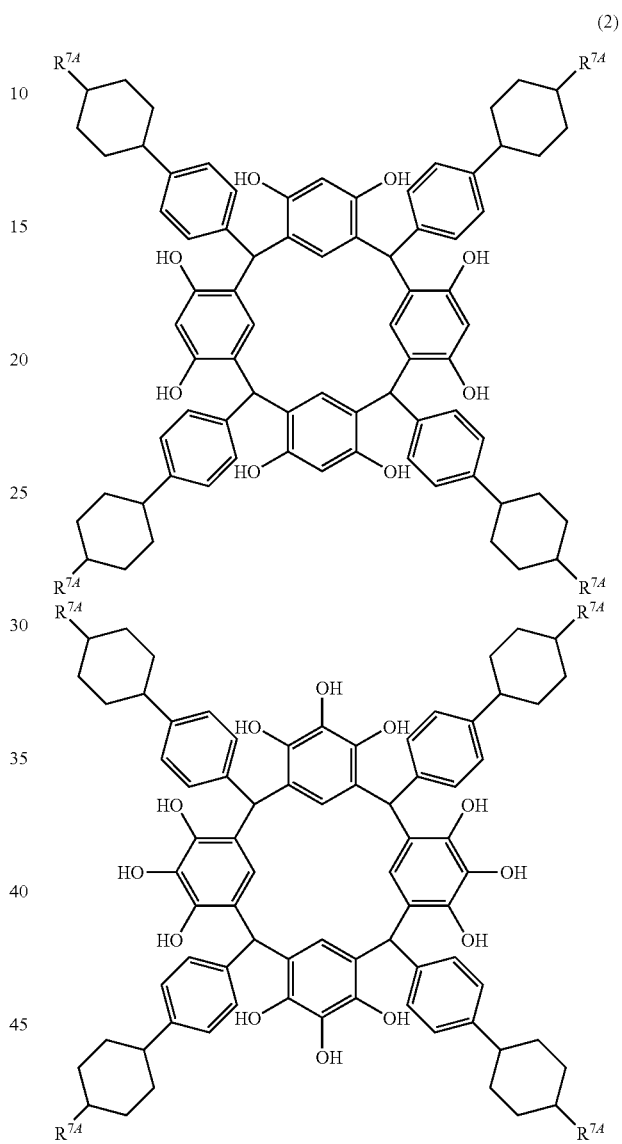

wherein $R^{7A}$ is independently hydrogen atom, a linear alkyl group having 1 to 12 carbon atoms, a halogen atom, cyano group, hydroxyl group, an alkoxyl group, or an ester group.

With the above structure, a high refractive index and a moderate extinction coefficient are obtained for light of 193 nm wavelength.

Examples of $R^{7A}$ include hydrogen atom, a linear alkyl group having 1 to 10 carbon atoms such as methyl group, ethyl group, propyl group, isopropyl group, butyl group, isobutyl group, t-butyl group, pentyl group, isopentyl group, neopentyl group, hexyl group, heptyl group, octyl group, nonyl group, and decyl group, a halogen atom, cyano group, hydroxyl group, an alkoxyl group, and an ester group.

Of the above, hydrogen atom, propyl group and pentyl group are preferred particularly for the composition for under coat film, because a high refractive index and a moderate extinction coefficient are obtained for light of 193 nm wavelength.

(b) Cyclic compound represented by the following formula (3):

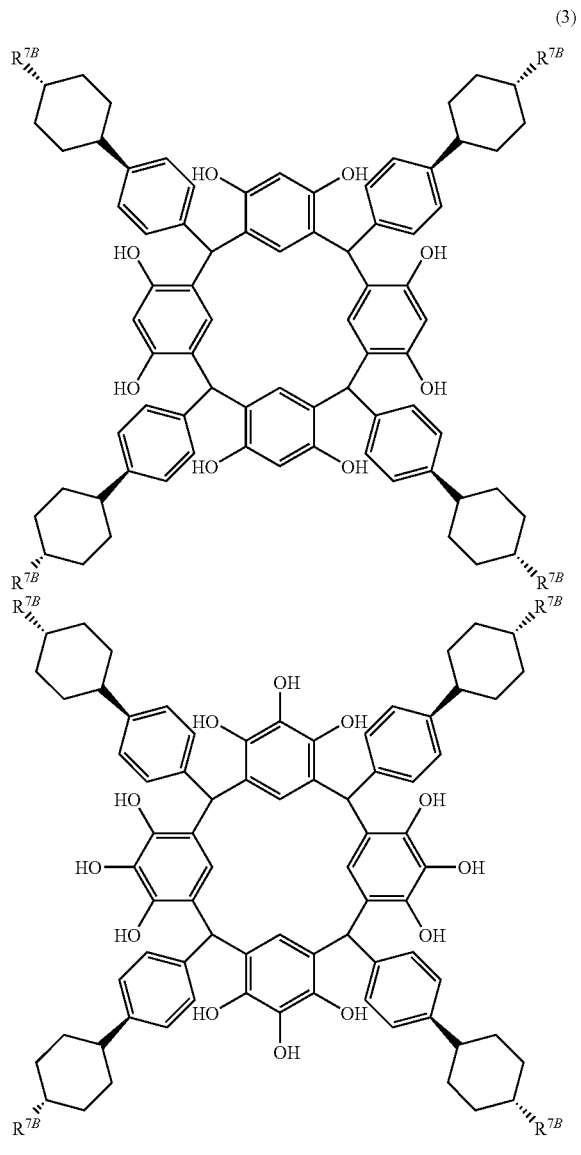

wherein $R^{7B}$ is independently a linear alkyl group having 1 to 6 carbon atoms.

$R^{7B}$ is a linear alkyl group having 1 to 6 carbon atoms such as methyl group, ethyl group, propyl group, isopropyl group, butyl group, isobutyl group, t-butyl group, pentyl group, isopentyl group, neopentyl group, and hexyl group, and preferably in the trans-configuration.

Particularly preferred is propyl group, because a high refractive index and a moderate extinction coefficient are obtained for light of 193 nm wavelength.

The cyclic compounds (a) and (b) are produced by the condensation reaction between an aromatic aldehyde having 6 to 24 carbon atoms and a compound having a resorcinol or pyrogallol structure.

The above cyclic compounds may be produced by a known method. For example, 1 mol of a carbonyl compound such as aromatic aldehyde is allowed to react with 1 mol to excess of a phenolic compound such as resorcinol and pyrogallol in an organic solvent such as toluene, methanol and ethanol in the presence of thioacetic acid or β-mercaptopropionic acid and an acid catalyst (hydrochloric acid, sulfuric acid or p-toluenesulfonic acid) at 60 to 150° C. for about 0.5 to 20 h. After the reaction, the reaction product solution is added with toluene, heated to 60 to 80° C., stirred for 0.5 to 2 h, and cooled to room temperature. Then, the precipitate is separated by filtration and dried, to obtain the cyclic compound.

The molecular weight of the cyclic compound is preferably 400 to 2000, more preferably 600 to 2000, and still more preferably 800 to 1500. Within the above ranges, a resist material, particularly, a material for under coat film which is excellent in the film-forming properties and etching resistance and contains a minimized quantity of sublimable component is obtained.

(c) Cyclic compound selected from the compounds represented by the following formulae (4-0) and (4):

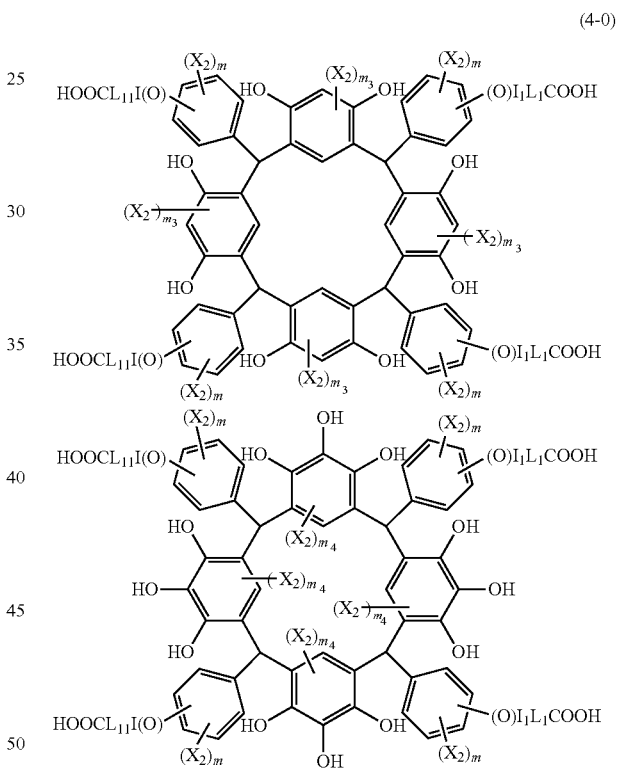

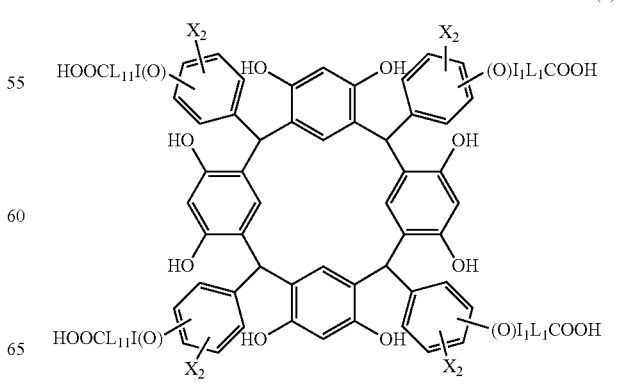

-continued

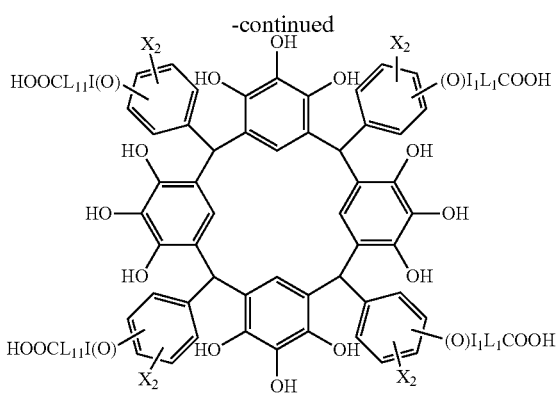

In each of the formulae (4-0) and (4), $X_2$ is hydrogen atom or a halogen atom; $L_1$ is a single bond or a divalent organic group selected from a linear or branched alkylene group having 1 to 4 carbon atoms; 1 is 0 or 1; m is an integer of 1 to 4, $m_3$ is an integer of 1 to 2; and $m_4$ is 1.

(d) Cyclic compound selected from the group consisting of the compounds represented by the following formula (5), or cyclic compound selected from the group consisting of the compounds represented by the following formula (6):

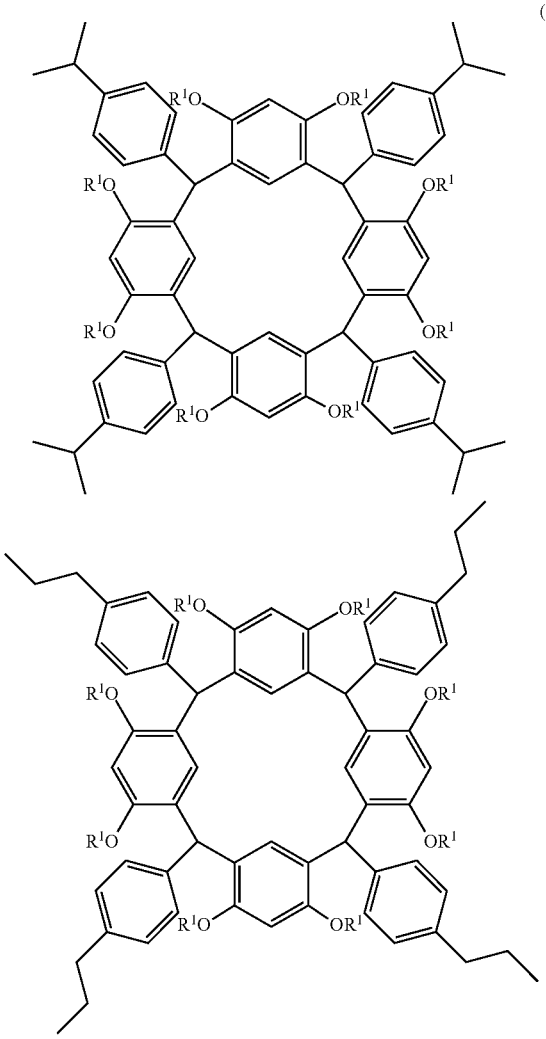

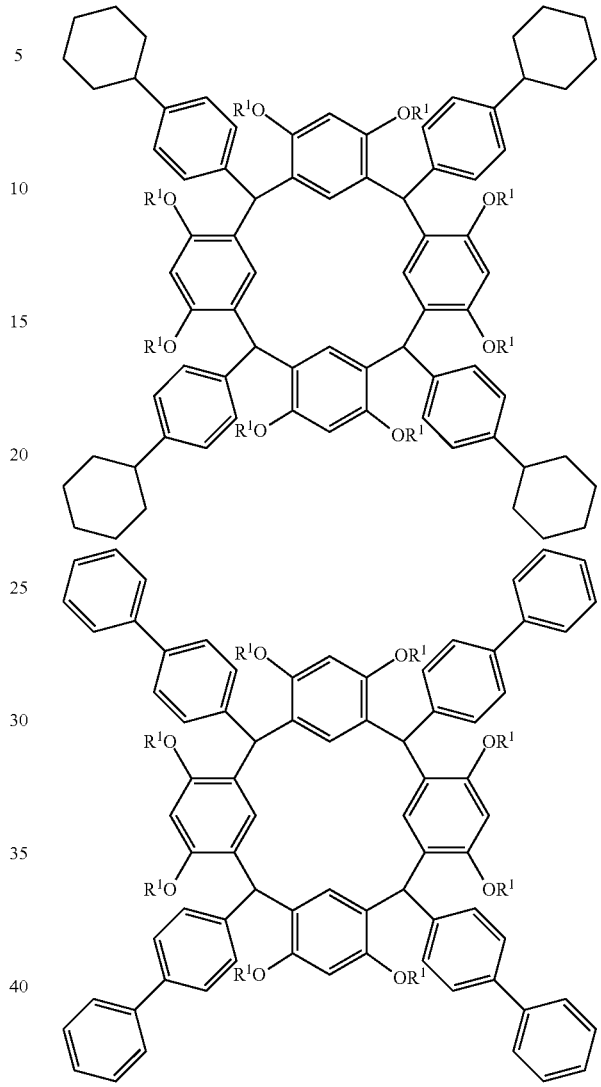

In the formulae (5) and (6), $R^1$ is the same as defined above, with the proviso that at least one $R^1$ is an acid-dissociating functional group.

The acid-dissociating functional group is suitably selected from those proposed as the groups for hydroxystyrene resins and (meth)acrylic acid resins which are used in the chemical-amplified resist composition for KrF and ArF. Preferred examples thereof include a substituted methyl group, a 1-substituted ethyl group, a 1-substituted n-propyl group, a 1-branched alkyl group, silyl group, an acyl group, a 1-substituted alkoxymethyl group, a cyclic ether group, and an alkoxycarbonyl group. The acid-dissociating functional group is preferably free from a crosslinkable functional group.

The molecular weight of the cyclic compound (d) is preferably 800 to 5000, more preferably 800 to 2000, and still more preferably 1000 to 2000. Within the above ranges, the resolution is improved while maintaining the film-forming properties necessary for the resists.

The substituted methyl group has generally 2 to 20 carbon atoms, preferably 4 to 18 carbon atoms, and more preferably 6 to 16 carbon atoms. Examples thereof include methoxymethyl group, methylthiomethyl group, ethoxymethyl group, n-propoxymethyl group, isopropoxymethyl group, n-butoxymethyl group, t-butoxymethyl group, 2-methylpropoxymethyl group, ethylthiomethyl group, methoxyethoxymethyl group, phenyloxymethyl group, 1-cyclopentyloxymethyl group, 1-cyclohexyloxymethyl group, benzylthiomethyl group, phenacyl, 4-bromophenacyl, 4-methoxyphenacyl, piperonyl group, and the groups represented by the following formula (7):

(7)

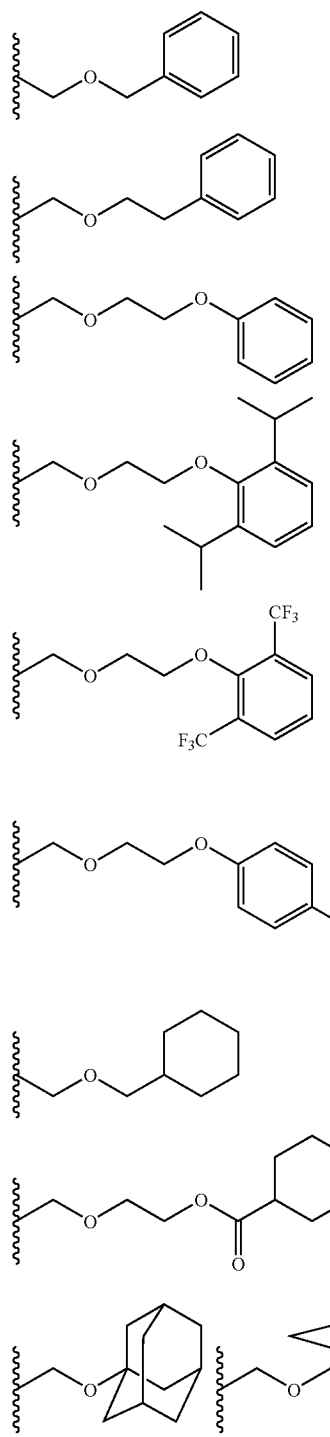

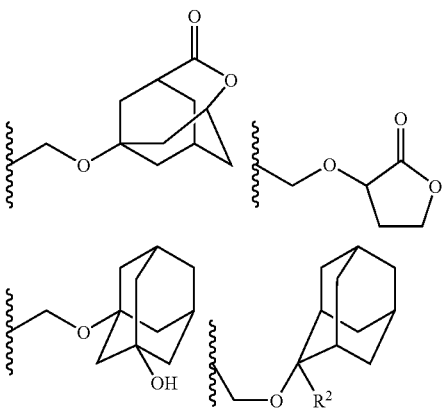

wherein $R^2$ is an alkyl group having 1 to 4 carbon atoms such as methyl group, ethyl group, isopropyl group, n-propyl group, t-butyl group, and n-butyl group.

The 1-substituted ethyl group has generally 3 to 20 carbon atoms, preferably 5 to 18 carbon atoms, and more preferably 7 to 16 carbon atoms. Examples thereof include 1-methoxyethyl group, 1-methylthioethyl group, 1,1-dimethoxyethyl group, 1-ethoxyethyl group, 1-ethylthioethyl group, 1,1-diethoxyethyl group, n-propoxyethyl group, isopropoxyethyl group, n-butoxyethyl group, t-butoxyethyl group, 2-methylpropoxyethyl group, 1-phenoxyethyl group, 1-phenylthioethyl group, 1,1-diphenoxyethyl group, 1-cyclopentyloxyethyl group, 1-cyclohexyloxyethyl group, 1-phenylethyl group, 1,1-diphenylethyl group, and the groups represented by the following formula (8):

(8)

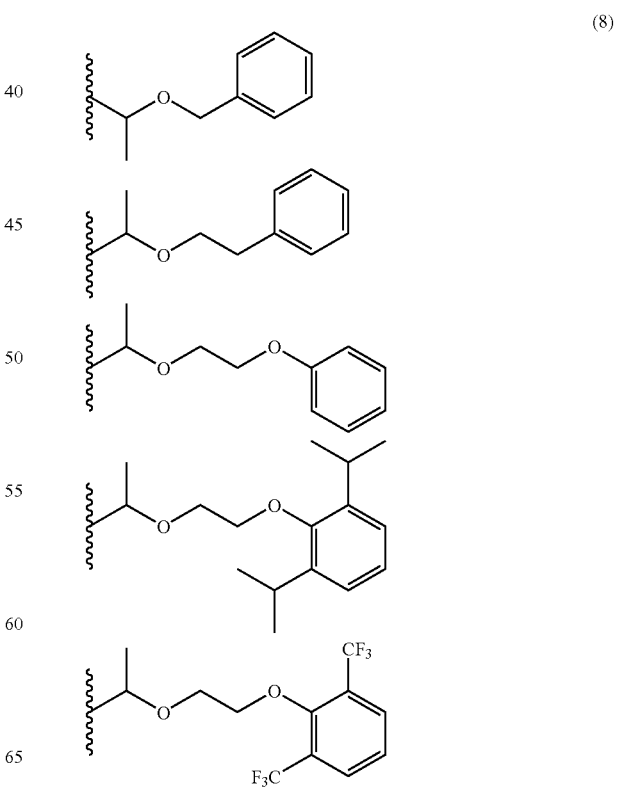

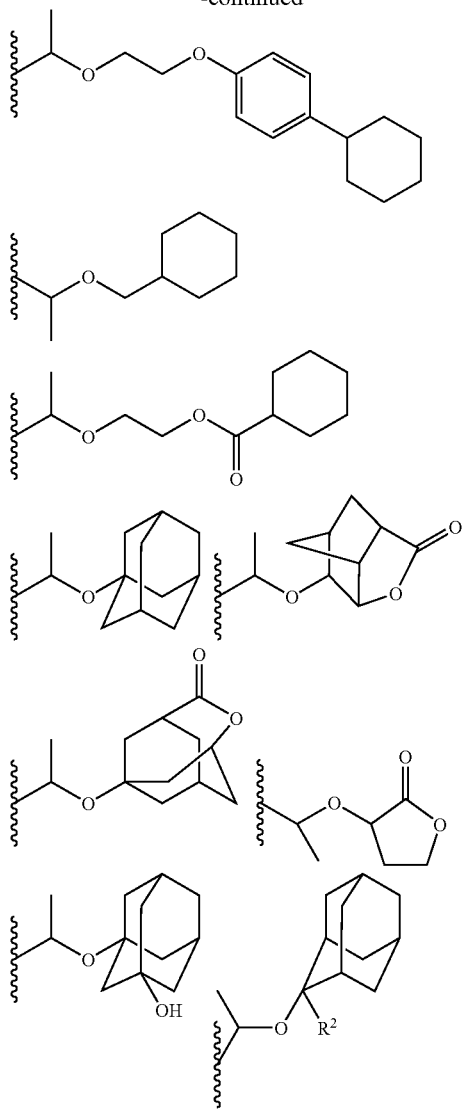

wherein R² is the same as defined above.

The 1-substituted n-propyl group has generally 4 to 20 carbon atoms, preferably 6 to 18 carbon atoms, and more preferably 8 to 16 carbon atoms. Examples thereof include 1-methoxy-n-propyl group and 1-ethoxy-n-propyl group.

The 1-branched alkyl group has generally 3 to 20 carbon atoms, preferably 5 to 18 carbon atoms, and more preferably 7 to 16 carbon atoms. Examples thereof include isopropyl group, sec-butyl group, tert-butyl group, 1,1-dimethylpropyl group, 1-methylbutyl group, 1,1-dimethylbutyl group, 2-methyladamantyl group, and 2-ethyladamantyl group.

The silyl group has generally 1 to 20 carbon atoms, preferably 3 to 18 carbon atoms, and more preferably 5 to 16 carbon atoms. Examples thereof include trimethylsilyl group, ethyldimethylsilyl group, methyldiethylsilyl group, triethylsilyl group, tert-butyldimethylsilyl group, tert-butyldimethylsilyl group, tert-butyldiphenylsilyl group, tri-tert-butylsilyl group, and triphenylsilyl group.

The acyl group has generally 2 to 20 carbon atoms, preferably 4 to 18 carbon atoms, and more preferably 6 to 16 carbon atoms. Examples thereof include acetyl group, phenoxyacetyl group, propionyl group, butyryl group, heptanoyl group, hexanoyl group, valeryl group, pivaloyl group, isovaleryl group, lauroyl group, adamantylcarbonyl group, benzoyl group, and naphthoyl group.

The 1-substituted alkoxymethyl group has generally 2 to 20 carbon atoms, preferably 4 to 18 carbon atoms, and more preferably 6 to 16 carbon atoms. Examples thereof include 1-cyclopentylmethoxymethyl group, 1-cyclopentylethoxymethyl group, 1-cyclohexylmethoxymethyl group, 1-cyclohexylethoxymethyl group, 1-cyclooctylmethoxymethyl group, and 1-adamantylmethoxymethyl group.

The cyclic ether group has generally 2 to 20 carbon atoms, preferably 4 to 18 carbon atoms, and more preferably 6 to 16 carbon atoms. Examples thereof include tetrahydropyranyl group, tetrahydrofuranyl group, tetrahydrothiopyranyl group, tetrahydrothiofuranyl group, 4-methoxytetrahydropyranyl group, and 4-methoxytetrahydrothiopyranyl group.

The alkoxycarbonyl group has generally 2 to 20 carbon atoms, preferably 4 to 18 carbon atoms, and more preferably 6 to 16 carbon atoms. Examples thereof include methoxycarbonyl group, ethoxycarbonyl group, n-propoxycarbonyl group, isopropoxycarbonyl group, n-butoxycarbonyl group, tert-butoxycarbonyl group, and an acid-dissociating functional group represented by the following formula (9) wherein n=0.

The alkoxycarbonylalkyl group has generally 2 to 20 carbon atoms, preferably 4 to 18 carbon atoms, and more preferably 6 to 16 carbon atoms. Examples thereof include methoxycarbonylmethyl group, ethoxycarbonylmethyl group, n-propoxycarbonylmethyl group, isopropoxycarbonylmethyl group, n-butoxycarbonylmethyl group, and an acid-dissociating functional group represented by the following formula (9) wherein n=1 to 4.

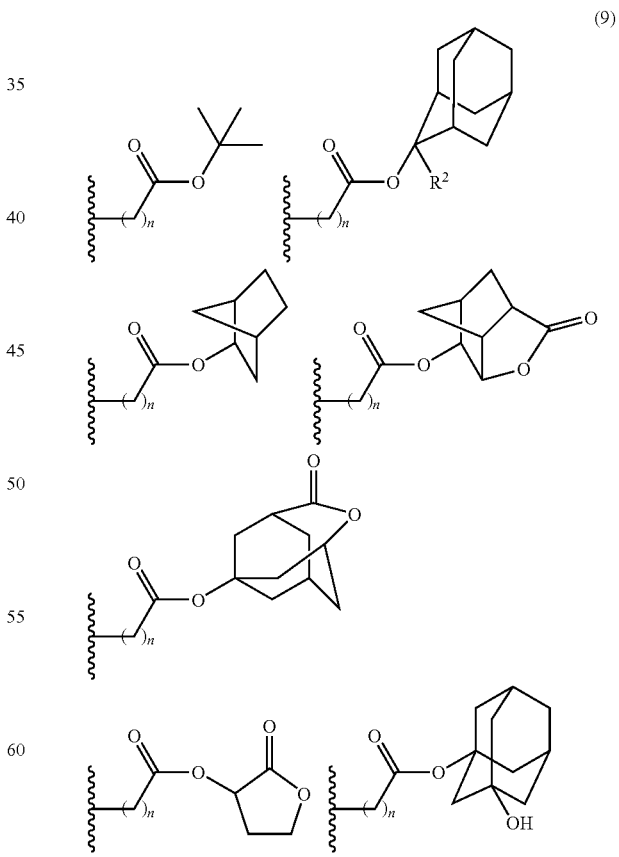

(9)

wherein R² is hydrogen atom or a linear or branched alkyl group having 1 to 4 carbon atoms and n is an integer of 0 to 4.

Of the above acid-dissociating functional groups, preferred are the substituted methyl group, 1-substituted ethyl group, 1-substituted alkoxymethyl group, cyclic ether group, alkoxycarbonyl group, and alkoxycarbonylalkyl group, more preferred are the substituted methyl group, 1-substituted ethyl group, alkoxycarbonyl group, and alkoxycarbonylalkyl group because of their high sensitivity, and still more preferred are the acid-dissociating functional groups having a structure selected from a cycloalkane having 3 to 12 carbon atoms, a lactone, and an aromatic ring having 6 to 12 carbon atoms. The cycloalkane having 3 to 12 carbon atoms may be monocyclic or polycyclic, and preferably polycyclic. Examples thereof include a monocycloalkane, a bicycloalkane, a tricycloalkane, and a tetracycloalkane, and more specifically include a monocycloalkane such as cyclopropane, cyclobutane, cyclopentane, and cyclohexane and a polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred. The cycloalkane having 3 to 12 carbon atoms may be substituted. Examples of the lactone include butyrolactone and a cycloalkane having 3 to 12 carbon atoms and a lactone ring. Examples of the aromatic ring having 6 to 12 carbon atoms include benzene ring, naphthalene ring, anthracene ring, phenanthrene ring, and pyrene ring, with benzene ring and naphthalene ring being preferred and naphthalene ring being particularly preferred.

An acid-dissociating functional group selected from the group consisting of the groups represented by the following formula (10) is preferred because of their high resolution.

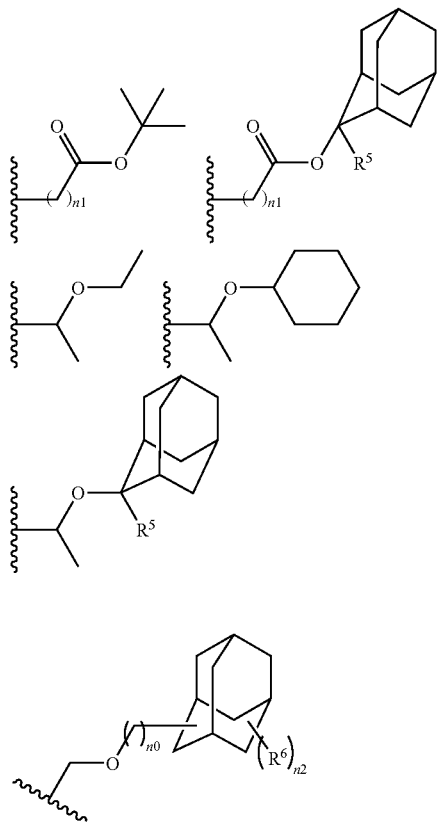

(10)

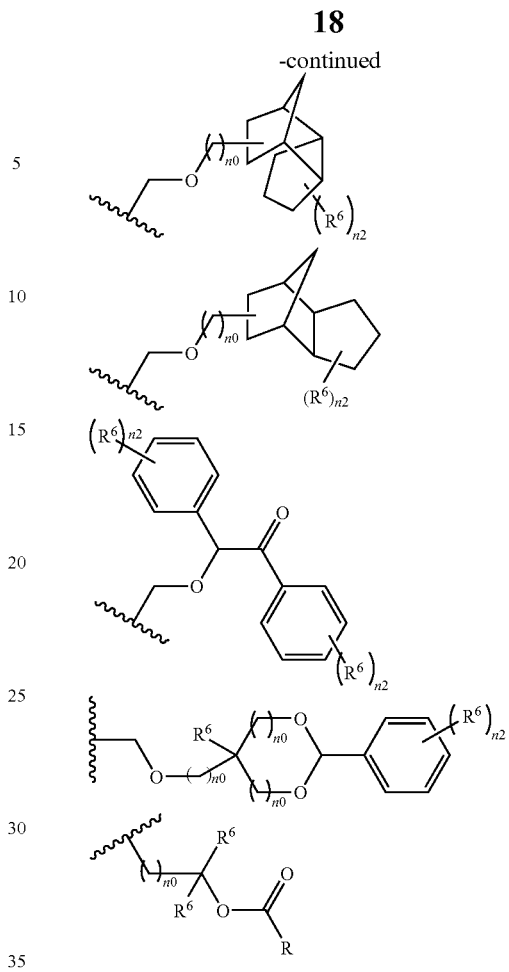

-continued

In the formula (10), $R^5$ is hydrogen atom or a linear or branched alkyl group having 1 to 4 carbon atoms, $R^6$ is hydrogen atom, a linear or branched alkyl group having 1 to 4 carbon atoms, cyano group, nitro group, a heterocyclic group, a halogen atom, or carboxyl group, n1 is an integer of 0 to 4, n2 is an integer of 1 to 5, and n0 is an integer of 0 to 4.

The acid-dissociating functional group $R^1$ may be a group composed of a repeating unit represented by the following formula (11) and a terminal group represented by the following formula (12) or $R^1$ ($R^1$ is the same as defined above) as long as the effect of the present invention is not adversely affected.

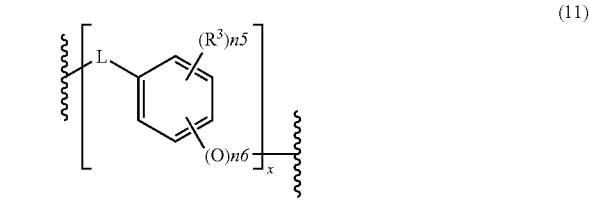

(11)

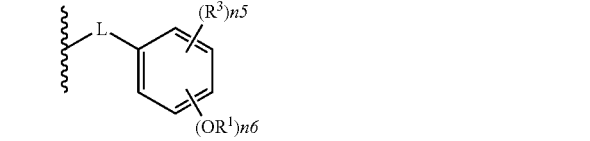

(12)

In the formula (11) and/or formula (12), $R^1$ is the same as defined above. L is a single bond, methylene group, ethylene group or carbonyl group, n5 is an integer of 0 to 4, n6 is an integer of 1 to 3, x is an integer of 0 to 3, and n5 and n6 satisfy $1 \leq n5+n6 \leq 5$. Plural n5's, n6's and x's are the same or different, respectively. $R^3$ is selected from the group consisting of a halogen atom, an alkyl group, a cycloalkyl group, an aryl group, an aralkyl group, an alkoxyl group, an aryloxy group, an alkenyl group, an acyl group, an alkoxycarbonyl group, an alkyloyloxy group, an aryloyloxy group, cyano group, and nitro group. The halogen atom includes chlorine atom, bromine atom and iodine atom; the alkyl group has 1 to 4 carbon atoms and includes methyl group, ethyl group, propyl group, n-propyl group, n-butyl group, isobutyl group, sec-butyl group, and tert-butyl group; the cycloalkyl group includes cyclohexyl group, norbornyl group and adamantyl group; the aryl group includes phenyl group, tolyl group, xylyl group, and naphthyl group; the aralkyl group includes benzyl group, hydroxybenzyl group and dihydroxybenzyl group; the alkoxyl group has 1 to 4 carbon atoms and includes methoxy group, ethoxy group, hydroxyethoxy group, propoxy group, hydroxypropoxy group, isopropoxy group, n-butoxy group, isobutoxy group, sec-butoxy group, and tert-butoxy group; the aryloxy group includes phenoxy group; the alkenyl group has 2 to 4 carbon atoms and includes vinyl group, propenyl group, allyl group, and butenyl group; the acyl group includes an aliphatic acyl group having 1 to 6 carbon atoms such as formyl group, acetyl group, propionyl group, butyryl group, valeryl group, isovaleryl group, and pivaloyl group, and an aromatic acyl group such as benzoyl group and toluoyl group; the alkoxycarbonyl group has 2 to 5 carbon atoms and includes methoxycarbonyl group, ethoxycarbonyl group, propoxycarbonyl group, isopropoxycarbonyl group, n-butoxycarbonyl group, isobutoxycarbonyl group, sec-butoxycarbonyl group, and tert-butoxycarbonyl group; the alkyloyloxy group includes acetoxy group, propionyloxy group, butyryloxy group, isobutyryloxy group valeryloxy group, isovaleryloxy group, and pivaloyloxy group; and the aryloyloxy group includes benzoyloxy group. Plural $R^3$'s are the same or different.

The acid-dissociating functional group is introduced into at least one phenolic hydroxyl group of the cyclic compound (A) by a known method as described below. The compound for introducing the acid-dissociating functional group is synthesized by a known method or commercially easily available and is selected from, but not limited to, active carboxylic acid derivatives such as an acid chloride, an acid anhydride and a dicarbonate, an alkyl halide, a vinyl alkyl ether, dihydropyran, and an alkyl halocarboxylate.

For example, the cyclic compound (A) is dissolved or suspended in an aprotic solvent such as acetone, tetrahydrofuran (THF) and propylene glycol monomethyl ether acetate. After adding vinyl alkyl ether such as ethyl vinyl ether or dihydropyran, the reaction is allowed to proceed in the presence of an acid catalyst such as pyridinium p-toluenesulfonate under atmospheric pressure at 20 to 60° C. for 6 to 72 h. The reaction product liquid is neutralized by an alkali compound and then poured into distilled water to precipitate a white solid matter. The white solid matter is separated, washed with distilled water and dried to obtain the cyclic compound (d).

Alternatively, the cyclic compound (A) is dissolved or suspended in an aprotic solvent such as acetone, THF and propylene glycol monomethyl ether acetate. After adding an alkyl halide such as ethyl chloromethyl ether or an alkyl halocarboxylate such as methyladamantyl bromoacetate, the reaction is allowed to proceed in the presence of an alkali catalyst such as potassium carbonate under atmospheric pressure at 20 to 110° C. for 6 to 72 h. The reaction product liquid is neutralized by an acid such as hydrochloric acid and poured into distilled water to precipitate a white solid matter. The white solid matter is separated, washed with distilled water and dried to obtain the cyclic compound (d).

The acid-dissociating functional group referred to in the present invention is a characteristic group which generates an alkali-soluble group by dissociation in the presence of an acid. Examples of the alkali-soluble group include phenolic hydroxyl group, carboxyl group, sulfonic acid group, and hexafluoroisopropyl group, with phenolic hydroxyl group and carboxyl group being preferred and phenolic hydroxyl group being particularly preferred. To form a pattern with a high sensitivity and resolution, it is preferred that the acid-dissociating functional group is dissociated succeedingly by a chain reaction in the presence of acid.

The cyclic compound (A) is produced by the condensation reaction between at least one kind of the aromatic carbonyl compound (A1) and at least one kind of the phenol compound (A2).

The aromatic carbonyl compound (A1) is a benzaldehyde compound having 10 to 24 carbon atoms which has at least one alicyclic or aromatic ring in addition to the aromatic ring of the benzaldehyde moiety. Examples thereof include cyclopropylbenzaldehyde, cyclobutanebenzaldehyde, cyclopentanebenzaldehyde, cyclohexanebenzaldehyde, phenylbenzaldehyde, naphthylbenzaldehyde, adamantylbenzaldehyde, norbornylbenzaldehyde, and lactylbenzaldehyde, with cyclohexylbenzaldehyde and phenylbenzaldehyde being preferred, and cyclohexylbenzaldehyde being more preferred. The aromatic carbonyl compound (A1) may have a linear or branched alkyl group having 1 to 4 carbon atoms, cyano group, hydroxyl group, or a halogen atom as long as the effect of the present invention is not adversely affected. The aromatic carbonyl compound (A1) may be used alone or in combination of two or more.

Examples of the phenol compound (A2) include phenol, catechol, resorcinol, hydroquinone, and pyrogallol, with resorcinol and pyrogallol being preferred, and resorcinol being more preferred. The phenol compound (A2) may have a linear or branched alkyl group having 1 to 4 carbon atoms, cyano group, hydroxyl group, or a halogen atom as long as the effect of the present invention is not adversely affected. The phenol compound (A2) may be used alone or in combination of two or more.

The cyclic compound (A) is produced by a known method. For example, 1 mol of the aromatic carbonyl compound (A1) and 0.1 to 10 mol of the phenol compound (A2) are allowed to react in an organic solvent such as methanol and ethanol in the presence of an acid catalyst (hydrochloric acid, sulfuric acid, p-toluenesulfonic acid, etc.) at 60 to 150° C. for about 0.5 to 20 h. After filtration, the collected precipitates are washed with an alcohol such as methanol, washed with water, and dried to obtain the cyclic compound (A). Alternatively, the cyclic compound (A) may be obtained by the same reaction except for using a basic catalyst (sodium hydroxide, barium hydroxide, 1,8-diazabicyclo[5.4.0]undecane 7, etc.) in place of the acid catalyst. In addition, the cyclic compound (A) may be produced by converting the aromatic carbonyl compound (A1) to a dihalide using a hydrogen halide or halogen gas and allowing the isolated dihalide to react with the phenol compound (A2).

The cyclic compound (A) may be purified to reduce the amount of residual metal, if necessary. If the acid catalyst and co-catalyst remain, the storage stability of the radiation-sensitive composition is generally lowered. If the basic catalyst remains, the sensitivity of the radiation-sensitive composition is generally lowered. Therefore, the cyclic compound (A)

may be purified to reduce the remaining amount of such catalytic compounds. The purification may be carried out by any of known methods without limitation as long as the cyclic compound (A) is not unfavorably changed, for example, by washing with water, washing with an acidic aqueous solution, washing with a basic aqueous solution, treating with an ion exchange resin, and treating with a silica gel column chromatography. The purification is preferably conducted in a combination of two or more of the above methods. The acidic aqueous solution, basic aqueous solution, ion exchange resin and silica gel column may be suitably selected taking the amounts and kinds of the metal, acidic compound and basic compound to be removed and the kind of the cyclic compound (A) to be purified into consideration. For example, hydrochloric acid, an aqueous solution of nitric acid and an aqueous solution of acetic acid, each having a concentration of 0.01 to 10 mol/L, are used as the acidic aqueous solution, an aqueous ammonia solution having a concentration of 0.01 to 10 mol/L is used as the basic aqueous solution, and a cation exchange resin such as Amberlyst 15J-HG Dry manufactured by Organo Corporation is used as the ion exchange resin. The purified product may be dried by a known method such as, but not limited to, a vacuum drying and a hot-air drying under the conditions not changing the cyclic compound (A).

It is preferred that the cyclic compound (d) shows a low sublimation ability under atmospheric pressure at 100° C. or lower, preferably at 120° C. or lower, more preferably at 130° C. or lower, still more preferably at 140° C. or lower, particularly preferably at 150° C. or lower. The low sublimation ability referred to herein means that the weight loss after a thermogravimetric analysis wherein a sample is kept at predetermined temperature for 10 min is 10% or less, preferably 5% or less, more preferably 3% or less, still more preferably 1% or less, and particularly preferably 0.1% or less. If the sublimation ability is low, the contamination of the exposure apparatus by the outgas generated in the exposing process is prevented. In addition, a fine pattern with small LER is obtained.

The cyclic compound (d) preferably satisfies the requirement of F<3.0 wherein F is (total number of atoms)/(total number of carbon atoms−total number of oxygen atoms), and more preferably F<2.5. By satisfying the above requirements, the dry-etching resistance is improved.

The cyclic compound (d) dissolves in a solvent at 23° C. preferably in 1% by weight or more, more preferably in 3% by weight or more, still more preferably in 5% by weight or more, and particularly preferably in 10% by weight or more when measured using the solvent having the highest dissolving power to the cyclic compound (d) among propylene glycol monomethyl ether acetate, propylene glycol monomethyl ether, 2-heptanone, anisole, butyl acetate, ethyl propionate, and ethyl lactate. With such solubility, the safety solvent acceptable in the semiconductor factory can be used.

The cyclic compound (d) is made into an amorphous film by a spin-coating and applicable to a general semiconductor production process.

The dissolving speed of the amorphous film of the cyclic compound (d) in a 2.38 mass % aqueous solution of TMAH at 23° C. is preferably 5 Å/sec or less, more preferably 0.05 to 5 Å/sec, and still more preferably 0.0005 to 5 Å/sec. If being 5 Å/sec or less, the cyclic compound (d) is insoluble in an alkali developing solution to form a resist. If being 0.0005 Å/sec or more, the resolution may be improved in some cases. This may be because that the micro surface of the cyclic compound (d) is dissolved to reduce LER. In addition, the number of defects is reduced.

The cyclic compound (A0) which is generated by the dissociation of the acid-dissociating functional group of the cyclic compound (d) preferably has an ability of forming an amorphous film by a spin coating. The dissolving speed of the amorphous film of the cyclic compound (A0) in a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the cyclic compound (A0) dissolves in an alkali developing solution to leave a resist pattern. If being 1000 Å/sec or less, the resolution may be improved in some cases. This may be because that the contrast at the interface between the exposed portion soluble in an alkali developing solution and the non-exposed portion insoluble in an alkali developing solution is enhanced by the change of solubility due to the dissociation of the acid-dissociating group of the cyclic compound (d). In addition, LER is reduced and the number of defects is reduced.

The solid component of the radiation-sensitive composition is formed into an amorphous film by a spin coating. The dissolving speed of the amorphous film in a 2.38 mass % aqueous solution of TMAH at 23° C. is preferably 5 Å/sec or less. After exposing the amorphous film to a radiation such as KrF excimer lasers, extreme ultraviolet rays, electron beams and X-rays and optionally heating at 20 to 250° C., the dissolving speed of the treated amorphous film in a 2.38 mass % aqueous solution of TMAH at 23° C. is preferably 10 Å/sec or more. By satisfying the above requirements, a pattern with a good shape can be obtained in good yields.

The glass transition temperature of the cyclic compound (d) is preferably 100° C. or higher, more preferably 120° C. or higher, still more preferably 140° C. or higher, and particularly preferably 150° C. or higher. Within the above ranges, a heat resistance enough to maintain the shape of pattern in the semiconductor lithography process is obtained, thereby increasing the resolution.

The crystallization heat of the cyclic compound (d) is preferably less than 20 J/g when measured by a differential scanning calorimetry of the glass transition temperature. The difference, (crystallization temperature)−(glass transition temperature), is preferably 70° C. or higher, more preferably 80° C. or higher, still more preferably 100° C. or higher, and particularly preferably 130° C. or higher. If the crystallization heat is less than 20 J/g or the difference, (crystallization temperature)−(glass transition temperature), is within the above ranges, the radiation-sensitive composition is easily made into an amorphous film by a spin coating and the film-forming properties required for the resist can be maintained for a long period of time, thereby improving the resolution.

In the present invention, the crystallization heat, crystallization temperature and glass transition temperature are measured by a differential scanning calorimetry using DSC/TA-50WS manufactured by Shimadzu Corporation as described below. A sample (about 10 mg) placed in a non-sealed aluminum container is heated to a temperature higher than the melting point at a temperature rising rate of 20° C./min in a nitrogen gas flow (50 ml/min). After rapid cooling, the sample is again heated to a temperature higher than the melting point at a temperature rising rate of 20° C./min in a nitrogen gas flow (30 ml/min). After rapid cooling, the sample is again heated to 400° C. at a temperature rising rate of 20° C./min in a nitrogen gas flow (30 ml/min). The middle point of the region at which the base line turns discontinuous (the point at which the specific heat reduces to half) is taken as the glass transition temperature (Tg) and the temperature of the exothermic peak appearing after the discontinuous region is taken as the crystallization temperature. The crystallization heat is determined by the area of the region which is surrounded by the exothermic peak and the base line.

(e) Cyclic compound represented by the following formula (13-0) or (13):

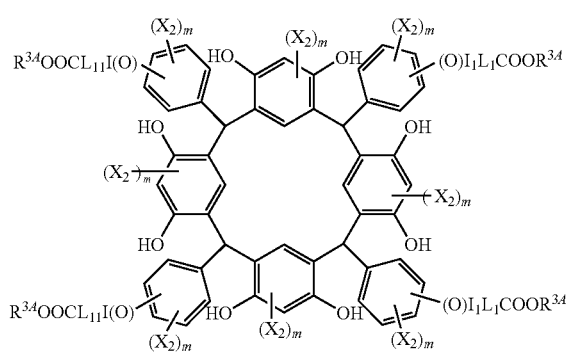

(13-0)

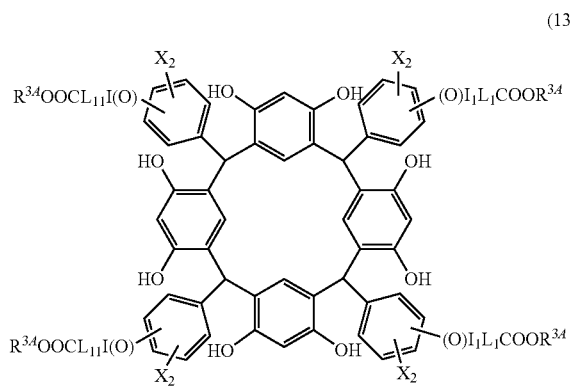

(13)

wherein $R^{34}$ is a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms, and an alkoxycarbonylalkyl group having 2 to 20 carbon atoms; and $X_2$, $L_1$, $l_1$, and m are the same as defined in the formula (4-0).

Examples of the substituted methyl group having 2 to 20 carbon atoms, the 1-substituted ethyl group having 3 to 20 carbon atoms, the 1-substituted n-propyl group having 4 to 20 carbon atoms, the 1-branched alkyl group having 3 to 20 carbon atoms, the silyl group having 1 to 20 carbon atoms, the acyl group having 2 to 20 carbon atoms, the 1-substituted alkoxyalkyl group having 2 to 20 carbon atoms, the cyclic ether group having 2 to 20 carbon atoms, the alkoxycarbonyl group having 2 to 20 carbon atoms and the alkoxycarbonylalkyl group having 2 to 20 carbon atoms may be selected from the acid-dissociating functional groups mentioned above with respect to $R^1$.

More preferably, the cyclic compound (e) is selected from the compounds represented by the following formula (14):

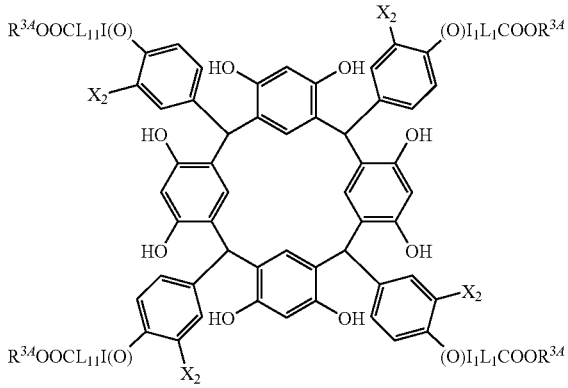

(14)

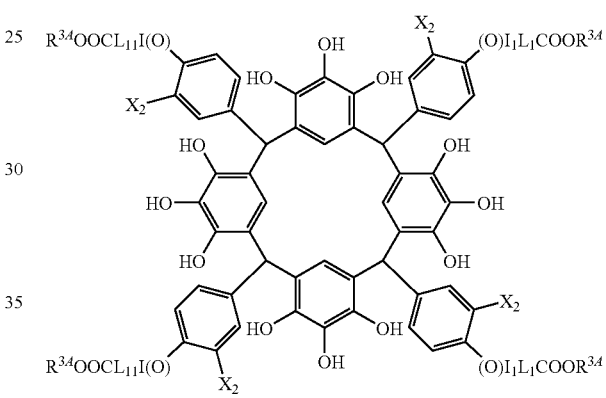

wherein $R^{34}$, $X_2$, $L_1$, and $l_1$ are the same as defined above.

Particularly preferably, the cyclic compound (e) is selected from the compounds represented by the following formula (15):

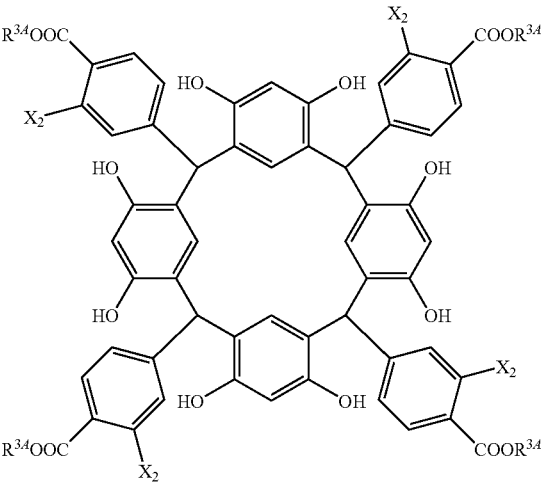

(15)

-continued

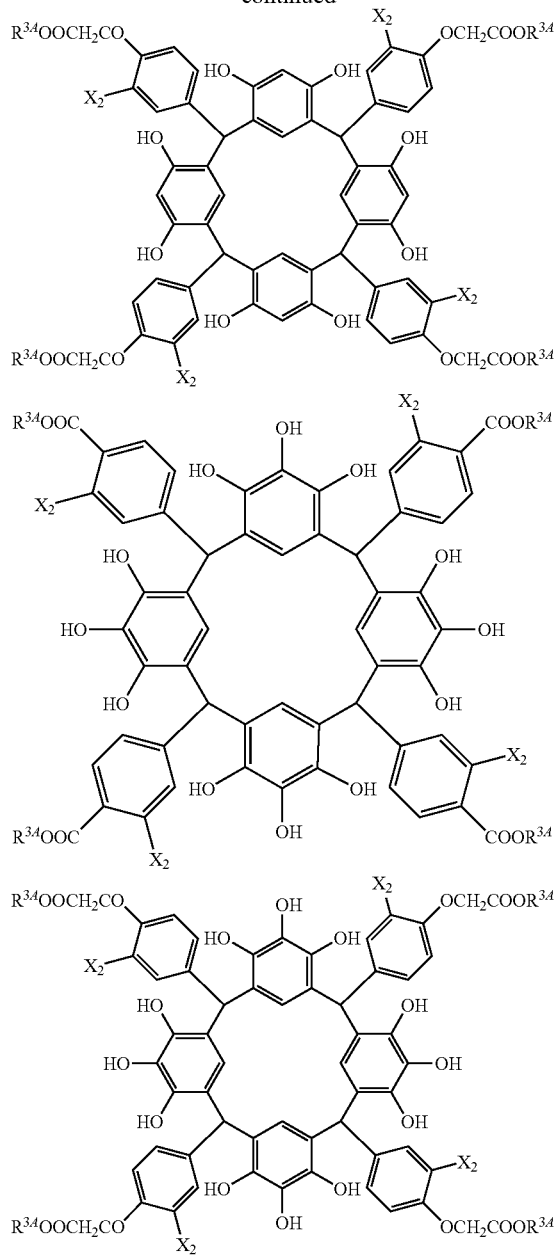

wherein $X_2$, and $R^{3A}$ are the same as defined above.

$R^{3A}$ is more preferably an acid-dissociating functional group having a structure selected from a cycloalkane having 3 to 20 carbon atoms, lactone and an aromatic ring having 6 to 12 carbon atoms. The cycloalkane having 3 to 20 carbon atoms may be a monocyclic or polycyclic alkane and preferably a polycylic alkane, such as a monocycloalkane, a bicycloalkane, a tricycloalkane, and a tetracycloalkane. Examples thereof include a monocycloalkane such as cyclopropane, cyclobutane, cyclopentane, and cyclohexane, and a polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred. The cycloalkane having 3 to 20 carbon atoms is optionally substituted. Examples of the lactone include butyrolactone and a cycloalkane (3 to 20 carbon atoms) having a lactone group. Example of the aromatic ring having 6 to 12 carbon atoms include benzene ring, naphthalene ring, anthracene ring, phenanthrene ring, and pyrene ring, with benzene ring and naphthalene ring being preferred, naphthalene ring being more preferred, and an acid-dissociating functional group represented by the following formula (16) being still more preferred. The acid-dissociating functional group improves the resolution of the resist pattern to be obtained and reduces LER.

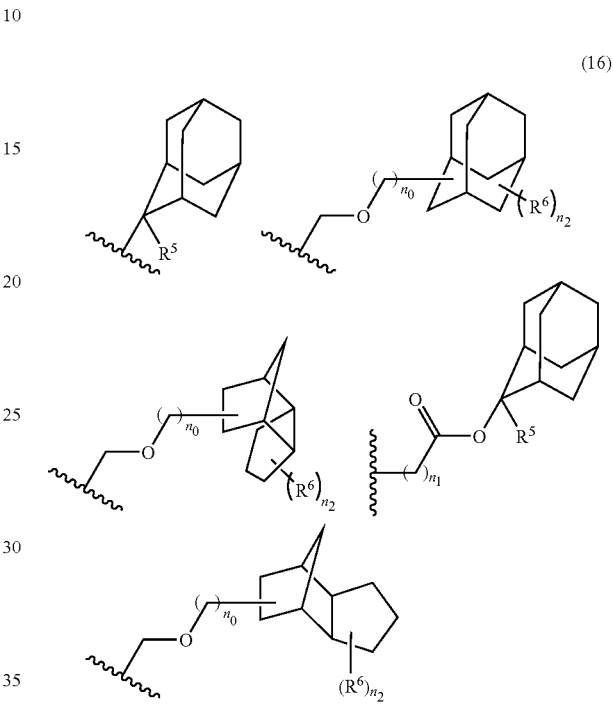

(16)

In the formula (16), $R^5$, $R^6$, $n_0$, $n_1$, and $n_2$ are the same as defined above.

The cyclic compound (e) may be also produced by a water-eliminating condensation reaction of the cyclic compound (A0) having a carboxyl group with a compound having an alcoholic hydroxyl group.

The cyclic compound (e) may be also produced by an ester exchange reaction between a compound having an alcoholic hydroxyl group and a cyclic compound (A0a) which corresponds to a compound obtained by changing the carboxyl group of the cyclic compound (A0) to an ester group of the following formula (17). The ester exchange reaction is conducted by a known manner. The compound having an alcoholic hydroxyl group may be a primary, secondary or tertiary alcohol, with a secondary or tertiary alcohol being preferred and a tertiary alcohol being particularly preferred.

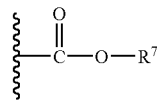

(17)

In the formula (17), $R^{3B}$ is a linear alkyl group having 1 to 20 carbon atoms, a branched alkyl group having 3 to 20 carbon atoms, a cycloalkyl group having 3 to 20 carbon atoms or an aryl group having 6 to 20 carbon atoms.

Examples of the linear alkyl group having 1 to 20 carbon atoms, preferably 1 to 12 carbon atoms include methyl group, ethyl group, n-propyl group, n-butyl group, n-pentyl group, n-octyl group, and n-dodecyl group.

Examples of the branched alkyl group having 3 to 20 carbon atoms, preferably 3 to 10 carbon atoms include isopropyl group, t-butyl group, isopentyl group, and neopentyl group, with t-butyl group being preferred.

The aliphatic ring of the cycloalkyl group having 3 to 20 carbon atoms, preferably 6 to 14 carbon atoms may be monocyclic or polycyclic and preferably polycyclic. Examples thereof include a monocycloalkane, a bicycloalkane, a tricycloalkane, and a tetracycloalkane, specifically, the monocycloalkane such as cyclopropane, cyclobutane, cyclopentane, and cyclohexane, and the polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred.

Examples of the aryl group having 6 to 20 carbon atoms include phenyl group, tolyl group, xylyl group, and naphthyl group.

The cyclic compound (e) may be produced by the reaction between the cyclic compound (A0) having a carboxyl group and a compound (A3) having a halomethyl ether group. For example, the cyclic compound (A0) having a carboxyl group is dissolved or suspended in an aprotic solvent such as acetone, THF and propylene glycol monomethyl ether acetate. After adding the compound (A3) having a halomethyl ether group, the reaction is allowed to proceed under atmospheric pressure at 0 to 110° C. for 1 to 72 h in the presence of an alkali catalyst such as pyridine, triethylamine, diazabicycloundecene and potassium carbonate in an amount of 0.5 to 4 equivalent, preferably 0.9 to 1.1 equivalent, more preferably 1.0 equivalent based on the carboxyl group of the cyclic compound (A0). After washing with an alcohol such as methanol, washing with water and filtering, the separated matter is dried to obtain the cyclic compound (B0), which may be purified by a column chromatography, etc., if necessary.

The molecular weight of the cyclic compound (e) is 800 to 5000, preferably 1000 to 2500, and more preferably 1500 to 2000. Within the above ranges, the resolution is improved while maintaining the film-forming properties required for the resist.

Radiation-Sensitive Composition and Cyclic Compound for Use Therein

The present invention relates to a radiation-sensitive composition containing any of the cyclic compounds of the formulae (1) and (a) to (e) and a solvent.

The present invention also relates to a radiation-sensitive composition wherein the cyclic compound has a molecular weight of 700 to 5000 and is synthesized by the condensation reaction between a compound having 2 to 59 carbon atoms and 1 to 4 formyl groups (aldehyde compound (A1)) and a compound having 6 to 15 carbon atoms and 1 to 3 phenolic hydroxyl group (phenol compound (A2)).

Radiation-Sensitive Composition A

The radiation-sensitive composition preferably contains the cyclic compound (B) having at least one phenolic hydroxyl group into which the acid-dissociating functional group is introduced and having a molecular weight of 800 to 5000.

Namely, a preferred radiation-sensitive composition of the invention contains 1 to 80% by weight of a solid component and 20 to 99% by weight of a solvent, wherein the solid component contains the cyclic compound (B) in an amount of 50 to 99.999% by weight of a total weight of the solid component, and wherein the cyclic compound (B) has (a) a structure which is derived by introducing the acid-dissociating functional group into at least one phenolic hydroxyl group of the cyclic compound (A) which is synthesized by a condensation reaction of a benzaldehyde compound having 7 to 24 carbon atoms and having neither hydroxyl group nor t-butyl group with a compound having 6 to 15 carbon atoms and 1 to 3 phenolic hydroxyl groups and (b) a molecular weight of 800 to 5000.

Another preferred radiation-sensitive composition of the invention contains 1 to 80% by weight of a solid component and 20 to 99% by weight of a solvent, wherein the solid component contains the cyclic compound (B) in an amount of 50% by weight or more of a total weight of the solid component, and wherein the cyclic compound (B) has (a) a structure which is derived by introducing an acid-dissociating functional group into at least one phenolic hydroxyl group of the cyclic compound (A) which is synthesized by a condensation reaction of a benzaldehyde compound having 10 to 24 carbon atoms and a substituent having an aliphatic or aromatic ring with a compound having 6 to 15 carbon atoms and 1 to 3 phenolic hydroxyl groups and (b) a molecular weight of 800 to 5000.

The cyclic compound (B) has a structure derived by introducing an acid-dissociating functional group into at least one phenolic hydroxyl group of the cyclic compound (A) which is synthesized by a condensation reaction of a benzaldehyde compound having 10 to 24 carbon atoms and a substituent having an aliphatic or aromatic ring or a benzaldehyde compound having 7 to 24 carbon atoms and having neither hydroxyl group nor t-butyl group (each being referred to as "aromatic carbonyl compound (A1)") with a compound having 6 to 15 carbon atoms and 1 to 3 phenolic hydroxyl groups (referred to as "phenol compound (A2)"). The molecular weight of the cyclic compound (B) is 800 to 5000.

The cyclic compound (A) is synthesized by a condensation reaction of at least one aromatic carbonyl compound (A1) with at least one phenol compound (A2).

The aromatic carbonyl compound (A1) is a benzaldehyde compound having 7 to 24 carbon atoms and having neither hydroxyl group nor t-butyl group or a benzaldehyde compound having 10 to 24 carbon atoms and a substituent having an aliphatic or aromatic ring. Examples thereof include benzaldehyde, methylbenzaldehyde, dimethylbenzaldehyde, ethylbenzaldehyde, propylbenzaldehyde, butylbenzaldehyde (exclusive of t-butylbenzaldehyde), ethylmethylbenzaldehyde, isopropylmethylbenzaldehyde, diethylbenzaldehyde, anisaldehyde, naphthaldehyde, anthraldehyde, cyclopropylbenzaldehyde, cyclobutanebenzaldehyde, cyclopentanebenzaldehyde, cyclohexanebenzaldehyde, phenylbenzaldehyde, naphthylbenzaldehyde, adamantylbenzaldehyde, norbornylbenzaldehyde, lactylbenzaldehyde, isopropylbenzaldehyde, n-propylbenzaldehyde, bromobenzaldehyde, and dimethylaminobenzaldehyde, with isopropylbenzaldehyde, n-propylbenzaldehyde, bromobenzaldehyde, dimethylaminobenzaldehyde, cyclohexylbenzaldehyde, and phenylbenzaldehyde being preferred, and cyclohexylbenzaldehyde, 4-isopropylbenzaldehyde and 4-n-propylbenzaldehyde being more preferred.

The aromatic carbonyl compound (A1) may include a linear or branched alkyl group having 1 to 4 carbon atoms, cyano group and a halogen atom as long as the effect of the present invention is not adversely affected. The aromatic carbonyl compound (A1) may be used alone or in combination of two or more.

Examples of the phenol compound (A2) include phenol, catechol, resorcinol, hydroquinone, and pyrogallol, with resorcinol and pyrogallol being preferred, and resorcinol being more preferred. The phenol compound (A2) may include a linear or branched alkyl group having 1 to 4 carbon atoms, cyano group, hydroxyl group, and a halogen atom as long as the effect of the present invention is not adversely affected. The phenol compound (A2) may be used alone or in combination of two or more.

The details of the cyclic compound (A) are as described above with respect to the formulae (4), (5) and (6).

The use of two or more kinds of the aromatic carbonyl compounds (A1) and/or two or more kinds of the phenol compounds (A2) is preferred, because the solubility of the cyclic compound (A) to be obtained in semiconductor safety solvents is increased.

The cyclic compound (A) is made into an amorphous film by a spin coating and can be applied to a general semiconductor production process.

The dissolving speed of the amorphous film of the cyclic compound (A) at 23° C. in a 2.38 mass % aqueous solution of tetramethylammonium hydroxide (TMAH) is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. In addition, LER and the number of defects are reduced.

The acid-dissociating functional group is suitably selected from those proposed as the groups for hydroxystyrene resins and (meth)acrylic acid resins which are used in the chemical-amplified resist composition for KrF and ArF. Examples thereof include a substituted methyl group, a 1-substituted ethyl group, a 1-substituted n-propyl group, a 1-branched alkyl group, silyl group, an acyl group, a 1-substituted alkoxymethyl group, a cyclic ether group, and an alkoxycarbonyl group. An acid-dissociating functional group having no crosslinkable functional group is preferred.

The molecular weight of the cyclic compound (B) is 800 to 5000, preferably 800 to 2000, and more preferably 1000 to 2000. Within the above ranges, the resolution is improved while maintaining the film-forming properties necessary for the resists.

The cyclic compound of the invention may be a cis-isomer, a trans-isomer or a mixture thereof. In view of forming a highly uniform resist film, an isomerically pure compound consisting of one of the cis-isomer and the trans-isomer is preferred for the resist component of a radiation-sensitive composition. The cyclic compound of only one of the cis-isomer and the trans-isomer may be obtained by a known method, for example, the separation by column chromatography and preparative liquid chromatography and the optimization of the reaction solvent, reaction temperature, etc.

In an embodiment of the present invention, the cyclic compound (B) is preferably represented by the following formula (18):

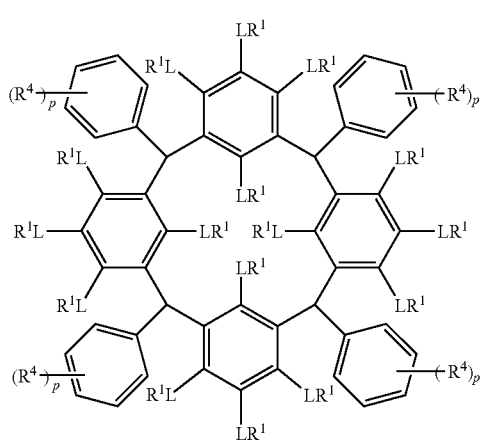

(18)

wherein $R^4$ is hydrogen atom, an alkyl group having 1 to 20 carbon atoms (exclusive of t-butyl group), a cycloalkyl group having 3 to 20 carbon atoms, an aryl group having 6 to 20 carbon atoms, an alkoxyl group having 1 to 20 carbon atoms, cyano group, nitro group, a heterocyclic group, a halogen atom, carboxyl group, an alkylsilyl group having 1 to 20 carbon atoms, and a functional group selected from derivatives of the preceding groups, L, $R^1$, $R^5$ and p are the same as defined in the formula (1), and at least one $R^1$ is an acid-dissociating functional group.

The cyclic compound (B) is preferably represented by the following formula (19) or (19-0), and more preferably represented by the following formula (19-1) or (10-0-1):

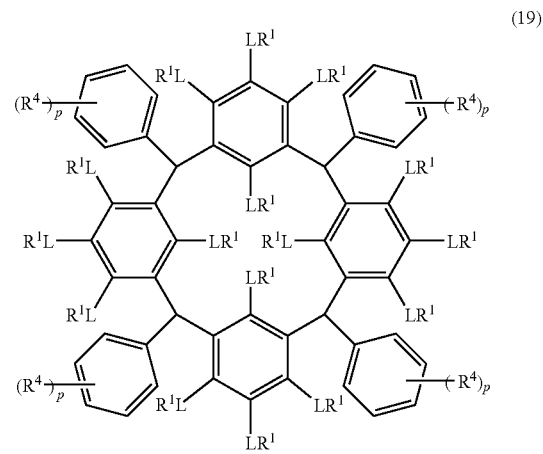

(19)

wherein L, $R^1$, $R^4$ and p are the same as defined above;

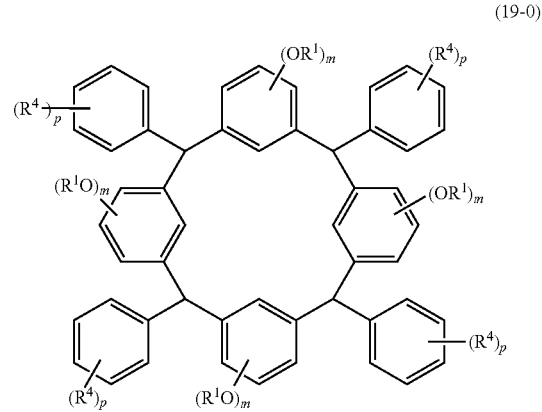

(19-0)

wherein $R^1$, $R^4$, p and m are the same as defined above;

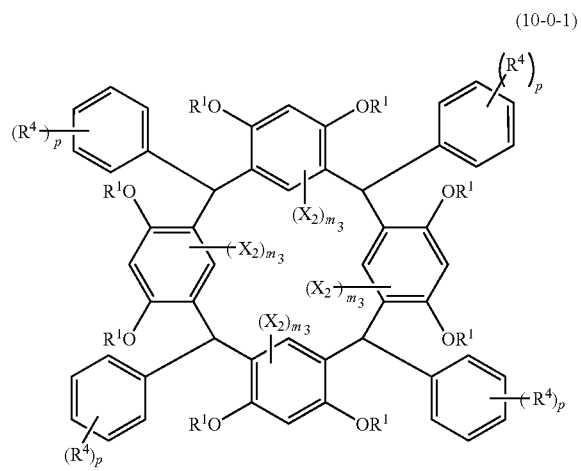
(10-0-1)
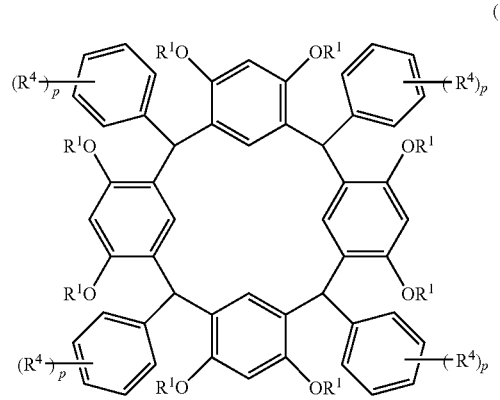
(19-1)
wherein $R^1$, $R^4$, p, $m_3$ and $m_4$ are the same as defined above; and
wherein $R^1$, $R^4$ and p are the same as defined above.
More preferably, the cyclic compound (B) is selected from the compounds represented by the following formula (20) or (21):
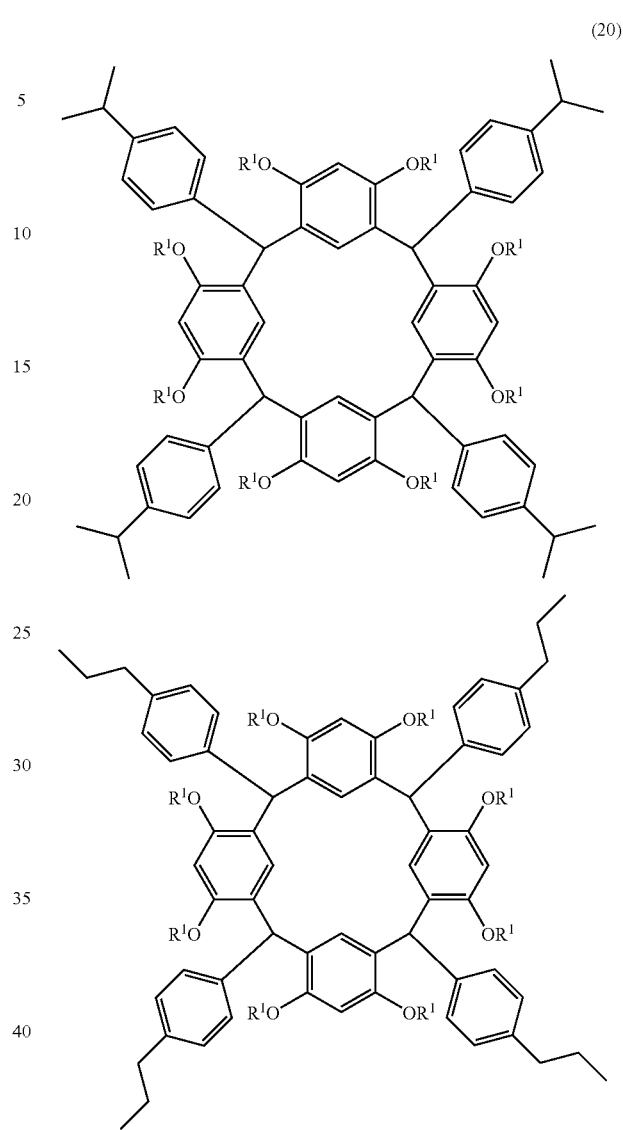
(20)
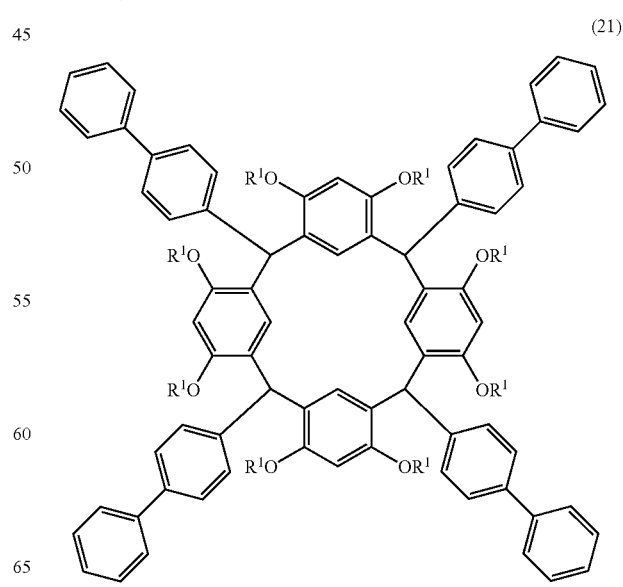
(21)

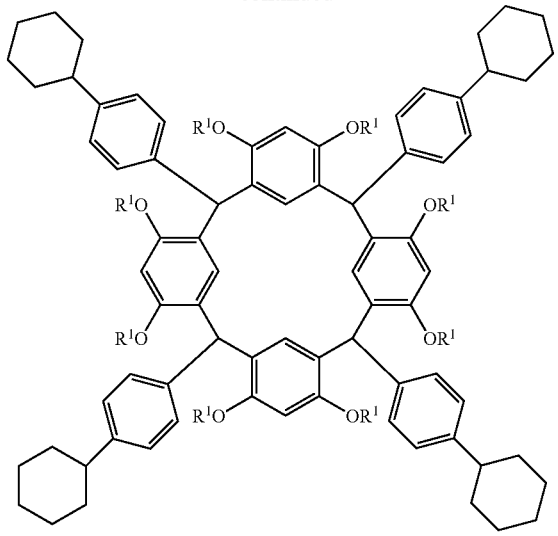

wherein R¹ is the same as defined in the formula (18).

In the formulae (20) and (21), R¹ is independently hydrogen atom or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, and an alkoxycarbonyl group and alkoxycarbonylalkyl group each having 2 to 20 carbon atoms. At least one R¹ is preferably the acid-dissociating functional group.

The details of the acid-dissociating functional group selected from the group consisting of the substituted methyl group, the 1-substituted ethyl group having 3 to 20 carbon atoms, the 1-substituted n-propyl group having 4 to 20 carbon atoms, the 1-branched alkyl group having 3 to 20 carbon atoms, the silyl group having 1 to 20 carbon atoms, the acyl group having 2 to 20 carbon atoms, the 1-substituted alkoxyalkyl group having 2 to 20 carbon atoms, the cyclic ether group having 2 to 20 carbon atoms, and the alkoxycarbonyl group and alkoxycarbonylalkyl group each having 2 to 20 carbon atoms are the same as described above.

Of the above acid-dissociating functional groups, preferred are the substituted methyl group, the 1-substituted ethyl group, the 1-substituted alkoxymethyl group, the cyclic ether group, the alkoxycarbonyl group, and the alkoxycarbonylalkyl group; more preferred are the substituted methyl group, the 1-substituted ethyl group, the alkoxycarbonyl group and the alkoxycarbonylalkyl group because a high sensitivity is obtained; and still more preferred are acid-dissociating functional groups having a structure selected from a cycloalkane having 3 to 12 carbon atoms, lactone and an aromatic ring having 6 to 12 carbon atoms. The cycloalkane having 3 to 12 carbon atoms may be a monocyclic or polycyclic compound such as a monocycloalkane, a bicycloalkane, a tricycloalkane, and a tetracycloalkane, and preferably a polycyclic compound. Examples thereof include the monocycloalkane such as cyclopropane, cyclobutane, cyclopentane, and cyclohexane, and the polycycloalkane such as adamantane, norbornane, isobornane, tricyclodecane, and tetracyclodecane, with adamantane, tricyclodecane, and tetracyclodecane being preferred and adamantane and tricyclodecane being particularly preferred. The cycloalkane having 3 to 12 carbon atoms may have a substituent. Examples of the lactone include butyrolactone and a cycloalkane having 3 to 12 carbon atoms and a lactone group. Examples of the aromatic ring having 6 to 12 carbon atoms include benzene ring, naphthalene ring, anthracene ring, phenanthrene ring, and pyrene ring, with benzene ring and naphthalene ring being preferred, and naphthalene ring being particularly preferred.

The acid-dissociating functional group represented by the following formula (22) is particularly preferred because a high resolution is obtained.

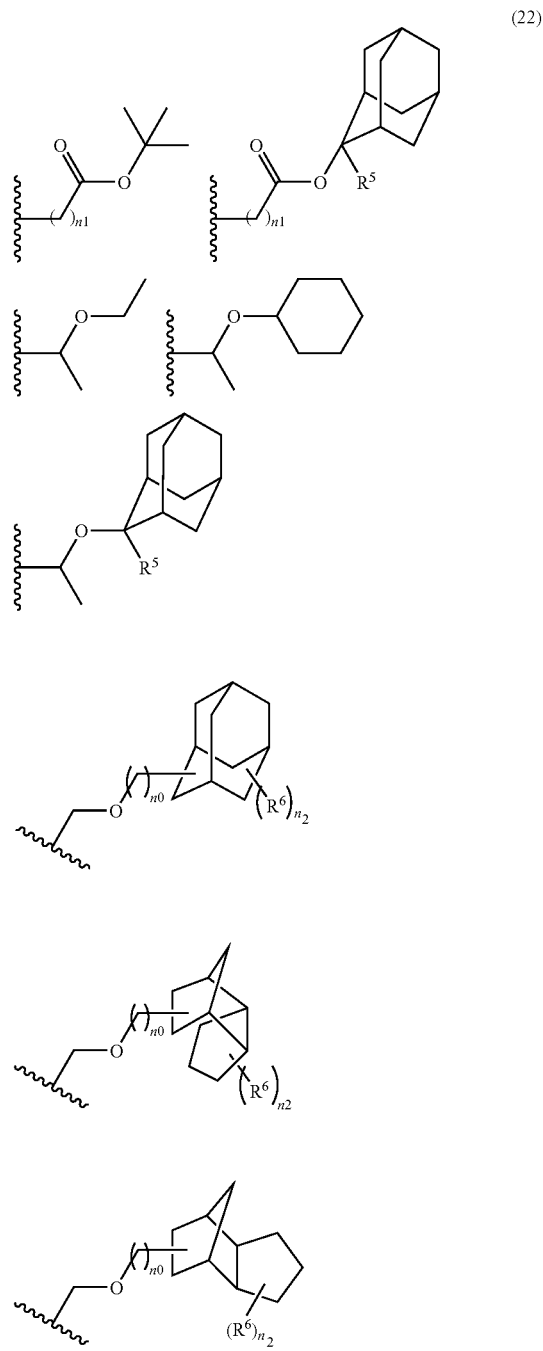

(22)

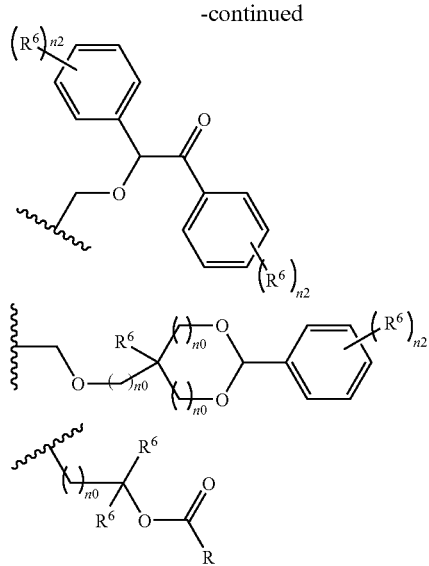

In the formula (22), $R^5$ is hydrogen atom or a linear or branched alkyl group having 1 to 4 carbon atoms; $R^6$ is hydrogen atom, a linear or branched alkyl group having 1 to 4 carbon atoms, cyano group, nitro group, a heterocyclic group, a halogen atom, or carboxyl group; $n_1$ is an integer of 0 to 4; $n_2$ is an integer of 1 to 5; and $n_0$ is an integer of 0 to 4.

In the cyclic compound (B), the ratio of the number of halogen atoms to the total number of constituent atoms is preferably 0.1 to 60%, more preferably 0.1 to 40%, still more preferably 0.1 to 20%, particularly preferably 0.1 to 10%, and most preferably 1 to 5%. Within the above ranges, the film-forming properties can be maintained while increasing the sensitivity to radiation. In addition, the solubility in safety solvents is increased.

The ratio of the number of nitrogen atoms to the total number of constituent atoms is preferably 0.1 to 40%, more preferably 0.1 to 20%, still more preferably 0.1 to 10%, and particularly preferably 0.1 to 5%. Within the above ranges, the film-forming properties can be maintained while reducing the line edge roughness of the resist pattern to be obtained. The nitrogen atom constituting a secondary or tertiary amine is preferred and the nitrogen atom constituting a tertiary amine is more preferred.

The acid-dissociating group referred to in the present invention is a characteristic group which generates an alkali-soluble group by dissociation in the presence of an acid. Examples of the alkali-soluble group include phenolic hydroxyl group, carboxyl group, sulfonic acid group, and hexafluoroisopropyl group, with the phenolic hydroxyl group and carboxyl group being preferred and the phenolic hydroxyl group being particularly preferred. To form a pattern with a high sensitivity and resolution, it is preferred that the acid-dissociating group is successively dissociated in the presence of acid.

Irrespective of its low molecular weight, the cyclic compound (B) of the formula (20) or (21) is excellent in the film-forming properties, heat resistance, and dry-etching resistance and is of low outgas, therefore, preferably used as a resist component of a radiation-sensitive composition. With a radiation-sensitive composition containing the cyclic compound (B) of the formula (20) or (21), a high resolution, a high sensitivity, and a small line edge roughness are obtained.

The cyclic compound (B) may be used as the main component of a positive-type radiation-sensitive composition or may be added to a radiation-sensitive composition as an additive for increasing the sensitivity and etching resistance in place of using as the main component. When used as an additive, the cyclic compound (B) is used in an amount of 1 to 49.999% by weight of the total weight of the solid component.

The cyclic compound (B) is made into an amorphous film by a spin coating and applicable to a general semiconductor production process.

An acid-non-dissociating functional group may be introduced into at least one phenolic hydroxyl group of the cyclic compound (B), as long as the effect of the present invention is not adversely affected. The acid-non-dissociating functional group is a characteristic group which is not dissociated in the presence of acid, thereby failing to generate an alkali-soluble group. Examples thereof include a group which is not dissociated by the action of acid such as a $C_{1-20}$ alkyl group, a $C_{3-20}$ cycloalkyl group, a $C_{6-20}$ aryl group, a $C_{1-20}$ alkoxyl group, cyano group, nitro group, hydroxyl group, a heterocyclic group, a halogen atom, carboxyl group, a $C_{1-20}$ alkylsilyl group, and functional groups derived from derivatives of the preceding groups.

A naphthoquinonediazido ester group may be introduced into at least one phenolic hydroxyl group of the cyclic compound (B). The cyclic compound (B) having at least one phenolic hydroxyl group into which the naphthoquinonediazido ester group is introduce may be used as the main component of a positive-type radiation-sensitive composition, or may be added to a radiation-sensitive composition as an acid generator or additive.

An acid-generating functional group which generates an acid upon the irradiation with radiation may be introduced into at least one phenolic hydroxyl group of the cyclic compound (B). The cyclic polyphenol compound obtained by introducing the acid-generating functional group into at least one phenolic hydroxyl group of the cyclic compound (B) may be used as the main component of a positive-type radiation-sensitive composition, or may be added to a radiation-sensitive composition as an acid generator or additive.

The dissolving speed of the amorphous film of the cyclic compound (B) in a 2.38 mass % aqueous solution of TMAH at 23° C. is preferably 5 Å/sec or less, more preferably 0.05 to 5 Å/sec, and still more preferably 0.0005 to 5 Å/sec. If being 5 Å/sec or less, the amorphous film is insoluble in an alkali developing solution to form a resist. If being 0.0005 Å/sec or more, the resolution may be improved in some cases. This may be because that the micro surface of the cyclic compound (B) is dissolved to reduce LER. In addition, the number of defects is reduced.

It is preferred that the cyclic compound (A) generated by the dissociation of the acid-dissociating functional group of the cyclic compound (B) is also capable of forming an amorphous film by a spin coating. The dissolving speed of the amorphous film of the cyclic polyphenol compound (A) in a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. This may be because that the contrast at the interface between the exposed portion soluble in an alkali developing solution and the non-exposed portion insoluble in an alkali developing solution is enhanced by the change of solubility due to the dissociation of the acid-dissociating functional group of the cyclic compound (B). In addition, LER and the number of defects are reduced.

The solid component of the radiation-sensitive composition is made into an amorphous film by a spin coating. The dissolving speed of the amorphous film of the solid component of the radiation-sensitive composition in a 2.38 mass % aqueous solution of TMAH at 23° C. is preferably 5 Å/sec or less. After exposing the amorphous film to a radiation such as KrF excimer lasers, extreme ultraviolet rays, electron beams and X-rays in a desired pattern and optionally heating at 20 to 250° C., the dissolving speed of the treated amorphous film in a 2.38 mass % aqueous solution of TMAH at 23° C. is preferably 10 Å/sec or more. By satisfying the above requirements, a pattern with a good shape can be obtained in good yields.

The radiation-sensitive composition of the invention comprises preferably 1 to 80% by weight of the solid component and 20 to 99% by weight of the solvent, more preferably 1 to 50% by weight of the solid component and the 50 to 99% by weight of the solvent, still more preferably 2 to 40% by weight of the solid component and 60 to 98% by weight of the solvent, and particularly preferably 2 to 10% by weight of the solid component and 90 to 98% by weight of the solvent. The content of the cyclic compound (B) is 50% by weight or more, preferably 65% by weight or more, and more preferably 81% by weight or more, each based on the total weight of the solid component. Within the above ranges, a high resolution is obtained and the line edge roughness is reduced.

The composition of the invention preferably contains at least one kind of acid generator (C) which generates an acid directly or indirectly by the irradiation with radiation which is selected from visible lights, ultraviolet rays, excimer lasers, electron beams, extreme ultraviolet rays (EUV), X-rays, and ion beams. The amount of the acid generator (C) to be used is preferably 0.001 to 50% by weight, more preferably 1 to 40% by weight, and still more preferably 3 to 30% by weight based on the total weight of the solid component (total of the cyclic polyphenol compound (B) and the optional solid component such as the acid generator (C), low molecular weight solubilizer (D), acid-diffusion controller (E) and other components (F), the same being applied below). Within the above ranges, a high sensitivity and a pattern profile with a small line edge roughness is obtained. In the present invention, the acid can be generated by any method as long as the acid is suitably generated within the system. The use of excimer lasers in place of ultraviolet rays such as g-rays and i-rays enables a finer processing. If high-energy rays such as electron beams, extreme ultraviolet rays, X-rays and ion beams are used, the resist composition can be still more finely processed.

The acid generator (C) is preferably at least one compound selected from the group consisting of the compounds represented by the following formulae (23-1) to (23-8).

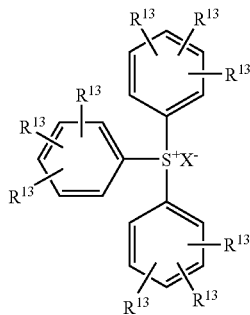

(23-1)

In the formula (23-1), plural $R^{13}$ are the same or different, and each independently hydrogen atom, a linear, branched or cyclic alkyl group, a linear, branched or cyclic alkoxy group, hydroxyl group or a halogen atom; and $X^-$ is a sulfonic acid ion having an alkyl group, an aryl group, a haloalkyl group or a haloaryl group or a halide ion.

The compound of the formula (23-1) is preferably at least one compound selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium 2-trifluoromethylbenzenesulfonate, diphenyl-2,4,6-trimethylphenylsulfonium 4-trifluoromethylbenzenesulfonate, diphenyl-2,4,6-trimethylphenylsulfonium 2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium p-toluenesulfonate, triphenylsulfonium 10-camphorsulfonate, diphenyl-4-hydroxyphenylsulfonium 10-camphorsulfonate, and cyclo(1,3-perfluoropropanedisulfon)imidate.

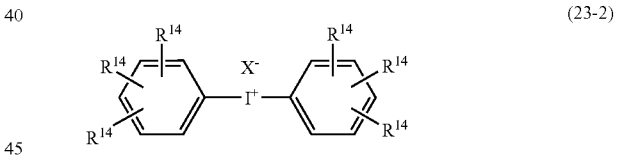

(23-2)

In the formula (23-2), plural $R^{14}$ are the same or different, and each independently hydrogen atom, a linear, branched or cyclic alkyl group, a linear, branched or cyclic alkoxy group, hydroxyl group or a halogen atom, and $X^-$ is the same as defined above.

The compound of the formula (23-2) is preferably at least one compound selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphorsulfonate.

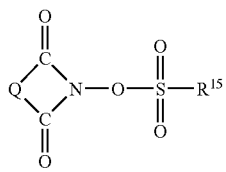

(23-3)

In the formula (23-3), Q is an alkylene group, an arylene group or an alkoxylene group, and $R^{15}$ is an alkyl group, an aryl group, a haloalkyl group or a haloaryl group.

The compound of the formula (23-3) is preferably at least one compound selected from the group consisting of N-(trifluoromethylsulfonyloxy)succinimide, N-(trifluoromethylsulfonyloxy)phthalimide, N-(trifluoromethylsulfonyloxy) diphenylmaleimide, N-(trifluoromethylsulfonyloxy)bicyclo[2.2.1]hept-5-ene-2,3-dicarboximide, N-(trifluoromethylsulfonyloxy)naphthylimide, N-(10-camphorsulfonyloxy)succinimide, N-(10-camphorsulfonyloxy) phthalimide, N-(10-camphorsulfonyloxy)diphenylmaleimide, N-(10-camphorsulfonyloxy)bicyclo[2.2.1]hept-5-ene-2,3-dicarboximide, N-(10-camphorsulfonyloxy) naphthylimide, N-(n-octanesulfonyloxy)bicyclo[2.2.1]hept-5-ene-2,3-dicarboximide, N-(n-octanesulfonyloxy) naphthylimide, N-(p-toluenesulfonyloxy)bicyclo[2.2.1] hept-5-ene-2,3-dicarboximide, N-(p-toluenesulfonyloxy) naphthylimide, N-(2-trifluoromethylbenzenesulfonyloxy) bicyclo[2.2.1]hept-5-ene-2,3-dicarboximide, N-(2-trifluoromethylbenzenesulfonyloxy)naphthylimide, N-(4-trifluoromethylbenzenesulfonyloxy)bicyclo[2.2.1]hept-5-ene-2,3-dicarboximide, N-(4-trifluoromethylbenzenesulfonyloxy)naphthylimide, N-(perfluorobenzenesulfonyloxy)bicyclo[2.2.1]hept-5-ene-2,3-dicarboximide, N-(perfluorobenzenesulfonyloxy)naphthylimide, N-(1-naphthalenesulfonyloxy)bicyclo[2.2.1] hept-5-ene-2,3-dicarboximide, N-(1-naphthalenesulfonyloxy)naphthylimide, N-(nonafluoro-n-butanesulfonyloxy)bicyclo[2.2.1]hept-5-ene-2,3-dicarboximide, N-(nonafluoro-n-butanesulfonyloxy) naphthylimide, N-(perfluoro-n-octanesulfonyloxy)bicyclo [2.2.1]hept-5-ene-2,3-dicarboximide, and N-(perfluoro-n-octanesulfonyloxy)naphthylimide.

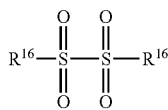

(23-4)

In the formula (23-4), plural $R^{16}$ are the same or different, and each independently an optionally substituted linear, branched or cyclic alkyl group, an optionally substituted aryl group, an optionally substituted heteroaryl group or an optionally substituted aralkyl group.

The compound of the formula (23-4) is preferably at least one compound selected from the group consisting of diphenyl disulfone, di(4-methylphenyl)disulfone, dinaphthyl disulfone, di(4-tert-butylphenyl)disulfone, di(4-hydroxyphenyl) disulfone, di(3-hydroxynaphthyl)disulfone, di(4-fluorophenyl)disulfone, di(2-fluorophenyl)disulfone, and di(4-trifluoromethylphenyl) disulfone.

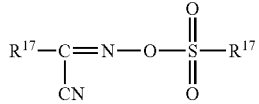

(23-5)

In the formula (23-5), plural $R^{17}$ are the same or different, and each independently an optionally substituted linear, branched or cyclic alkyl group, an optionally substituted aryl group, an optionally substituted heteroaryl group or an optionally substituted aralkyl group.

The compound of the formula (23-5) is at least one compound selected from the group consisting of α-(methylsulfonyloxyimino)phenylacetonitrile, α-(methylsulfonyloxyimino)-4-methoxyphenylacetonitrile, α-(trifluoromethylsulfonyloxyimino)phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

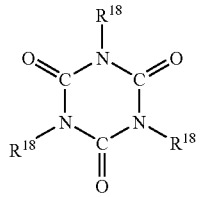

(23-6)

In the formula (23-6), plural $R^{18}$ are the same or different, and each independently a haloalkyl group having one or more chlorine atoms and one or more bromine atoms. The haloalkyl group preferably has 1 to 5 carbon atoms.

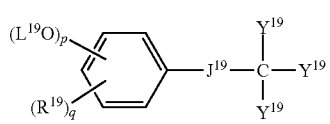

(23-7)

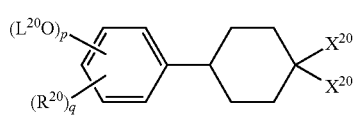

(23-8)

In the formulae (23-7) and (23-8), $R^{19}$ and $R^{20}$ are each independently an alkyl group having 1 to 3 carbon atoms such as methyl group, ethyl group, n-propyl group, and isopropyl group; a cycloalkyl group such as cyclopentyl group and cyclohexyl group; an alkoxy group having 1 to 3 carbon atoms such as methoxy group, ethoxy group, and propoxy group; or an aryl group such as phenyl group, tolyl group, and naphthyl group, preferably an aryl group having 6 to 10 carbon atoms. $L^{19}$ and $L^{20}$ are each independently an organic group having a 1,2-naphthoquinonediazido group, preferred examples thereof including 1,2-quinonediazidesulfonyl groups such as 1,2-naphthoquinonediazido-4-sulfonyl group, 1,2-naphthoquinonediazido-5-sulfonyl group, and 1,2-naphthoquinonediazido-6-sulfonyl group, with 1,2-naphthoquinonediazido-4-sulfonyl group and 1,2-naphthoquinonediazido-5-sulfonyl group being particularly preferred. Subscript p is an integer of 1 to 3, and q is an integer of 0 to 4, satisfying $1 \leq p+q \leq 5$. $J^{19}$ is a single bond, a polymethylene group having 1 to 4 carbon atoms, a cycloalkylene group, phenylene group, or a group represented by the following formula (23-7-1); $Y^{19}$ is hydrogen atom, an alkyl group or an aryl group; and each $X^{20}$ is independently a group represented by the following formula (23-8-1).

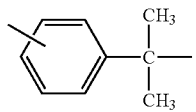

(23-7-1)

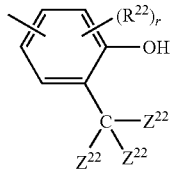

(23-8-1)

In the formula (23-8-1), each $Z^{22}$ is independently an alkyl group, a cycloalkyl group or an aryl group, $R^{22}$ is an alkyl group, a cycloalkyl group or an alkoxy group, and r is an integer of 0 to 3.

Examples of other acid generators include bissulfonyldiazomethanes such as bis(p-toluenesulfonyl)diazomethane, bis (2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl) diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl) propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halotriazine derivatives such as 2-(4-methoxyphenyl)-4,6-(bis-trichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Of the above acid generators, preferred is an acid generator having an aromatic ring, and more preferred is an acid generator represented by the formula (23-1) or (23-2). Still more preferred is an acid generator of the formula (23-1) or (23-2) wherein $X^-$ is a sulfonic acid ion having an aryl group or a haloaryl group, still further more preferred is an acid generator having a sulfonic acid ion having an aryl group, and particularly preferred is diphenyltrimethylphenylsulfonium p-toluenesulfonate, triphenylsulfonium p-toluenesulfonate, triphenylsulfonium trifluoromethanesulfonate, triphenylsulfonium nonafluoromethanesulfonate. The use of such acid generators reduces LER.

The acid generator (C) may be used alone or in combination of two or more.

The low molecular weight solubilizer (D) adequately increases the dissolving speed of the cyclic compound (B) in an alkali or other developing solutions by increasing the solubility, if the solubility is excessively low, and may be used as long as the effect of the invention is not adversely affected. Examples of the solubilizer include low molecular weight phenol compounds such as bisphenols and tris(hydroxyphenyl)methane. The solubilizer may be used alone or in combination of two or more. The blending amount of the solubilizer varies depending upon the kind of the cyclic compound (B), and the solubilizer is blended so that the total weight of the cyclic compound (B) and the low molecular weight solubilizer (D) is 50 to 99.999% by weight, preferably 60 to 99% by weight, more preferably 70 to 99% by weight, and still more preferably 80 to 99% by weight, each based on the total weight of the solid component.

The low molecular weight solubilizer (D) is preferably selected from the cyclic compounds (A) mentioned above. Considering its low molecular weight, the cyclic compound (A) is highly heat-resistant, highly amorphous, and highly compatible with the cyclic compound (B), and provides a uniform resist film with a high resolution and small LER. The cyclic compound (A) for use as the low molecular weight solubilizer (D) is preferably the same as the cyclic compound (A) which is used to produce the cyclic compound (B), because the compatibility between the cyclic compound (B) and the low molecular weight solubilizer (D) is more enhanced to enable the formation of a more uniform resist film with a high resolution and small LER.

The radiation-sensitive composition may contain an acid-diffusion controller (E) which prevents the undesirable chemical reactions in the unexposed areas by controlling the diffusion of the acid, which is generated from the acid generator upon the irradiation of radiation, throughout the resist film. Using the acid-diffusion controller (E), the resolution is improved and the change of line width of resist patterns due to the change in the process time-delay before the irradiation of electron beams and the change in the process time-delay after the irradiation of electron beams is prevented, to ensure the stable production. In addition, the storage stability of the radiation-sensitive composition is improved. Examples of the acid-diffusion controller (E) include basic compounds decomposable by the irradiation of electron beams such as nitrogen-containing basic compounds, basic sulfonium compounds, and basic iodonium compounds. The acid-diffusion controller may be used alone or in combination of two or more.

The acid-diffusion controller may be a nitrogen-containing compound or a basic compound which is decomposable upon the exposure to lights. Examples of the nitrogen-containing compound include a compound of the formula (24) (nitrogen-containing compound (I)):

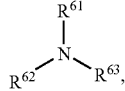

(24)

a diamino compound having two nitrogen atoms in its molecule (nitrogen-containing compound (II)), a polyamino compound having three or more nitrogen atoms or its polymer (nitrogen-containing compound (III)), an amido group-containing compound, an urea compound, and a nitrogen-containing heterocyclic compound. The acid-diffusion controller may be used alone or in combination of two or more.

In the formula (24), $R^{61}$, $R^{62}$ and $R^{63}$ are each independently hydrogen atom, a linear, branched or cyclic alkyl group, an aryl group, or an aralkyl group. The alkyl group, aryl group, and aralkyl group may be non-substituted or substituted by another functional group such as hydroxyl group. The linear, branched or cyclic alkyl group has 1 to 15 carbon atoms and preferably 1 to 10 carbon atoms. Examples thereof include methyl group, ethyl group, n-propyl group, isopropyl group, n-butyl group, isobutyl group, sec-butyl group, t-butyl group, n-pentyl group, neopentyl group, n-hexyl group, thexyl group, n-heptyl group, n-octyl group, n-ethylhexyl group, n-nonyl group, and n-decyl group. The aryl group may include a $C_{6-12}$ group such as phenyl group, tolyl group, xylyl group, cumenyl group, and 1-naphthyl group. The aralkyl group may include a $C_{7-19}$ group, preferably a $C_{7-13}$ group such as benzyl group, α-methylbenzyl group, phenethyl group, and naphthylmethyl group.

Examples of the nitrogen-containing compound (I) include mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo) alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Examples of the nitrogen-containing compound (II) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis (4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Examples of the nitrogen-containing compound (III) include polyethyleneimine, polyarylamine, and polymer of N-(2-dimethylaminoethyl)acrylamide.

Examples of the amido group-containing compound include formamide, N-methylformamide, N,N-dimethylformamide, acetamide, N-methylacetamide, N,N-dimethylacetamide, propionamide, benzamide, pyrrolidone, and N-methylpyrrolidone.

Examples of the urea compound include urea, methylurea, 1,1-dimethylurea, 1,3-dimethylurea, 1,1,3,3-tetramethylurea, 1,3-diphenylurea, and tri-n-butylthiourea.

Examples of the nitrogen-containing heterocyclic compound include imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic amide, quinoline, 8-oxyquinoline, and acridine; and pyrazine, pyrazole, pyridazine, quinoxaline, purine, pyrrolidine, piperidine, morpholine, 4-methylmorpholine, piperazine, 1,4-dimethylpiperazine, and 1,4-diazabicyclo[2.2.2]octane.

Examples of the basic compound which is decomposable upon the exposure to lights include the sulfonium compounds represented by the following formula (25-1):

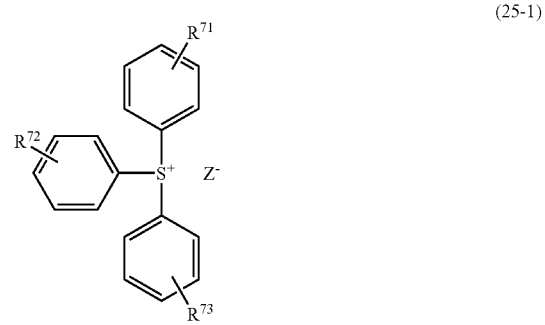

(25-1)

and the iodonium compounds represented by the following formula (25-2):

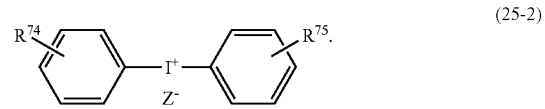

(25-2)

In the formulae (25-1) and (25-2), $R^{71}$, $R^{72}$, $R^{73}$, $R^{74}$, and $R^{75}$ are each independently hydrogen atom, a $C_{1-6}$ alkyl group, a $C_{1-6}$ alkoxyl group, hydroxyl group or a halogen atom. $Z^-$ is $HO^-$, $R\text{—}COO^-$ wherein R is a $C_{1-6}$ alkyl group, a $C_{1-6}$ aryl group or a $C_{1-6}$ alkaryl group, or an anion represented by the following formula (25-3):

(25-3)

Examples of the basic compound which is decomposable upon the exposure to lights include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis (4-t-butylphenyl)iodonium hydroxide, bis(4-t-butylphenyl) iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The blending amount of the acid-diffusion controller (E) is preferably 0 to 10% by weight, more preferably 0.001 to 5% by weight, and still more preferably 0.001 to 3% by weight, each based on the total weight of the solid component. Within the above ranges, the lowering of resolution and the deterioration of pattern profiles and dimension accuracy are prevented. In addition, the unfavorable change of the upper profile of pattern is prevented even if the process time delay between the irradiation of radiation and the post-irradiation heating is prolonged. If being 10% by weight or less, the sensitivity and developability of the unexposed area can be prevented from being reduced. Further, the use of the acid-diffusion controller improves the storage stability of the radiation-sensitive composition, improves the sensitivity, and prevents the change of line width of resist patterns due to the change in the process time delay before the irradiation of electron beams and the change in the process time delay after the irradiation of electron beams, to ensure the stable production.

The radiation-sensitive composition of the invention may contain, if necessary, one or more kinds of other component (F), for example, additives such as a solubility controller, a sensitizer, a surfactant, an organic carboxylic acid and its derivatives, and a phosphorus-containing oxoacid and its derivatives, as long as the effect of the invention is not adversely affected.

(1) Solubility Controller

The solubility controller is a component for adequately reducing the dissolving speed of the cyclic compound (B) in an alkali or other type of developing solution in the developing operation by lowering the solubility in the developing solution, if the solubility is excessively high. It is preferred that the solubility controller is not chemically changed in the step of baking the resist film, irradiating radiation and developing.

Examples of the solubility controller include aromatic hydrocarbons such as naphthalene, phenanthrene, anthracene, and acenaphthene; ketones such as acetophenone, benzophenone, and phenyl naphthyl ketone; and sulfones such as methyl phenyl sulfone, diphenyl sulfone, and dinaphthyl sulfone. These solubility controllers may be used alone or in combination of two or more.

The blending amount of the solubility controller varies depending upon the kind of the cyclic compound (B) to be used, and preferably 30 parts by weight or less and more preferably 10 parts by weight or less, each based on 100 parts by weight of the cyclic compound (B).

(2) Sensitizer

The sensitizer is a component for increasing the generation of acid by absorbing the energy of irradiated radiation and transferring the absorbed energy to the acid generator (C), thereby increasing the apparent sensitivity of the resist. Examples of the sensitizer include, but not limited to, benzophenones, biacetyls, pyrenes, phenothiazines, and fluorenes.

The sensitizer may be used alone or in combination of two or more. The blending amount of the sensitizer is preferably 30 parts by weight or less and more preferably 10 parts by weight or less, each based on 100 parts by weight of the cyclic compound (B).

(3) Surfactant

The surfactant is a component for improving the coating properties and striation of the radiation-sensitive composition and the developability of the resist, etc. The surfactant may be anionic, cationic, nonionic or ampholytic, with nonionic surfactants being preferred because they are more effective due to a good affinity to the solvents to be used for the production of the radiation-sensitive composition. Examples of the nonionic surfactant include, but not limited to, polyoxyethylene higher alkyl ethers, polyoxyethylene higher alkyl phenyl ethers, and higher fatty acid diesters of polyethylene glycol, which are commercially available under the tradename of: "EFTOP" of Jemco Inc.; "MEGAFACE" of Dai-Nippon Ink & Chemicals, Inc.; "FLUORAD" of Sumitomo 3M Ltd.; "ASAHIGUARD" and "SURFLON" of Asahi Glass Co., Ltd.; "PEPOL" of Toho Chemical Industry Co., Ltd.; "KP" of Shin-Etsu Chemical Co., Ltd.; and "POLYFLOW" of Kyoeisha Chemical Co., Ltd.

The blending amount of the surfactant, based on the effective component, is preferably 2 parts by weight or less per 100 parts by weight of the cyclic compound (B).

(4) Organic Carboxylic Acid, Phosphorus-Containing Oxoacid and their Derivative

To prevent the deterioration of sensitivity and improve the profile of resist pattern and the process lag stability, an organic carboxylic acid, a phosphorus-containing oxoacid or a derivative thereof may be optionally added to the radiation-sensitive composition. These additives may be combinedly used with the acid-diffusion controller or may be used alone. Preferred examples of the organic carboxylic acid include malonic acid, citric acid, malic acid, succinic acid, benzoic acid, and salicylic acid. Examples of the phosphorus-containing oxoacid and its derivatives include phosphoric acid and its ester derivatives such as phosphoric acid, di-n-butyl phosphate and diphenyl diphenyl; phosphonic acid and its ester derivatives such as phosphonic acid, dimethyl phosphonate, di-n-butyl phosphonate, phenyl phosphonate, diphenyl phosphonate, and dibenzyl phosphonate; and phosphinic acid and its ester derivatives such as phosphinic acid and phenyl phosphite, with phosphoric acid being particularly preferred.

The organic carboxylic acid, phosphorus-containing oxoacid and their derivatives may be used alone or in combination of two or more. The blending amount is preferably 0 to 50% by weight, more preferably 0 to 20% by weight, still more preferably 0 to 5% by weight, and particularly preferably 0 to 1% by weight, each based on the total weight of the solid component.

(5) Additives Other than Solubility Controller, Sensitizer, Surfactant, Organic Carboxylic Acid Phosphorus-Containing Oxoacid and their Derivatives The radiation-sensitive composition may contain, if necessary, one or more kinds of additives other than the solubility controller, sensitizer, and surfactant. Examples thereof include a dye, a pigment and an adhesive. The dye and pigment visualize the latent image of the exposed area to reduce the influence of the halation during exposure. The adhesive improves the adhesion of a resist film to a substrate. Other additives may include a halation inhibitor, a storage stabilizer, a defoaming agent and a shape improver, for example, 4-hydroxy-4'-methylchalcone.

The radiation-sensitive composition is prepared just before use by dissolving the components in a solvent into a uniform solution and, if necessary, filtering the solution through a filter with about 0.2 μm pore size.

Examples of the solvent for preparing the radiation-sensitive composition include, but not limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; lactic esters such as methyl lactated, ethyl lactate, n-propyl lactate, n-butyl lactate, and n-amyl lactate; aliphatic carboxylic esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutyl acetate, 3-methyl-3-methoxybutyl acetate, butyl 3-methoxy-3-methylpropionate, butyl 3-methoxy-3-methyl butyrate, methyl acetoacetate, methyl pyruvate, and ethyl pyruvate; aromatic hydrocarbons such as toluene and xylene; ketones such as 2-heptanone, 3-heptanone, 4-heptanone, and cyclohexanone; amides such as N,N-dimethylformamide, N-methylacetamide, N,N-dimethylacetamide, and N-methylpyrrolidone; and lactones such as γ-lactone. These solvents may be use alone or in combination of two or more.

The radiation-sensitive composition may contain a resin soluble in an aqueous alkali solution, as long as the effect of the invention is not adversely affected. Examples of the resin soluble in an aqueous alkali solution include novolak resins, polyvinylphenols, polyacrylic acid, polyvinyl alcohol, styrene-maleic anhydride resins, polymers containing the monomer units derived from acrylic acid, vinyl alcohol or vinylphenol, and their derivatives. The blending amount of the resin soluble in an aqueous alkali solution varies depending upon the kind of the resist compound to be used, and preferably 30 parts by weight or less, more preferably 10 parts by weight or less, still more preferably 5 parts by weight or less, and particularly preferably 0 part by weight, each based on 100 parts by weight the cyclic compound (B).

Radiation-Sensitive Composition B

The present invention further relates to a radiation-sensitive composition containing the cyclic compound (B0) having a molecular weight of 700 to 5000 and a solvent, wherein the aldehyde compound (A1) having 2 to 59 carbon atoms and 1 to 4 formyl groups is an aldehyde compound (A1c) having an acid-dissociating functional group and the cyclic compound (B0) is synthesized by the condensation reaction of the aldehyde compound (A1c) with a phenol compound (A2) having 6 to 15 carbon atoms and 1 to 3 phenolic hydroxyl groups. The details of the method of synthesizing the cyclic compound (B0) will be described in the production method (1) of the cyclic compound (B0).

The cyclic compound (B0) is also produced by the reaction of a cyclic compound (A0) having a carboxyl group with a compound (A3) having a halomethyl ether group. Since the carboxyl group of the cyclic compound (A0) is highly reactive with the halogen of the compound (A3), the reaction proceeds predominantly over the side reactions such as the reaction between the phenolic hydroxyl group of the cyclic compound (A0) and the halogen of the compound (A3), and the cyclic compound (B0) having a carboxyl group into which an acid-dissociating functional group is introduced is selectively produced in high yields and high production efficiency.

The cyclic compound (A0) is a cyclic compound having a molecular weight of 800 to 5000 and 1 to 8 carboxyl groups, which is synthesized by the condensation reaction of a compound having 2 to 59 carbon atoms, 1 to 2 carboxyl groups or ester groups, and 1 to 4 formyl groups (aldehyde compound (A1d)) with a compound having 6 to 15 carbon atoms and 1 to 3 phenolic hydroxyl groups (phenol compound (A2)).

Examples of the aldehyde compound (A1d) include, but not limited to, an aliphatic aldehyde compound having 1 to 2 carboxyl groups or ester groups, an alicyclic aldehyde compound having 1 to 2 carboxyl groups or ester groups, and an aromatic aldehyde compound having 1 to 2 carboxyl groups or ester groups.

Examples of the aliphatic aldehyde compound having 1 to 2 carboxyl groups or ester groups include Ra—CHO wherein Ra is an alkyl group having 1 to 2 carboxyl groups or ester groups and the alkyl group optionally has a substituent having 1 to 20 carbon atoms, OHC—Rb—CHO wherein Rb is an alkylene group having 1 to 2 carboxyl groups or ester groups and the alkylene group optionally has a substituent having 1 to 20 carbon atoms, $Rc(CHO)_3$ wherein Rc is a trivalent organic group having 1 to 2 carboxyl groups or ester groups and the trivalent organic group optionally has a substituent having 2 to 20 carbon atoms, and $Rd-(CHO)_4$ wherein Rd is a tetravalent organic group having 1 to 2 carboxyl groups and the tetravalent organic group optionally has a substituent having 2 to 20 carbon atoms. In the above, the substituent is an alkyl group, a cycloalkyl group, an aryl group, an alkoxyl group, cyano group, nitro group, hydroxyl group, a heterocyclic group, a halogen atom, carboxyl group, an alkylsilyl group, or a functional group selected from derivatives of the preceding groups.

Examples of the alicyclic aldehyde compound include carboxycyclohexane carbaldehyde, and carboxycyclohexane carbaldehyde, carboxycyclooctane carbaldehyde, carboxynorbornane carbaldehyde, carboxyadamantane carbaldehyde, carboxyfurfural, carboxydiformylcyclohexane, carboxydiformylcyclooctane, carboxydiformylnorbornane, carboxydiformyladamantane, carboxytriformylcyclohexane, carboxytriformylcyclooctane, carboxytriformylnorbornane, carboxytriformyladamantane, carboxytriformylcyclohexane, carboxytetraformylcyclooctane, carboxytetraformylnorbornane, and carboxytetraformyladamantane, each optionally having a substituent having 2 to 20 carbon atoms. In the above, the substituent is an alkyl group, a cycloalkyl group, an aryl group, an alkoxyl group, cyano group, nitro group, hydroxyl group, a heterocyclic group, a halogen atom, an alkylsilyl group, or a functional group selected from derivatives of the preceding groups.

Examples of the aromatic aldehyde compound include carboxybenzaldehyde, carboxytolylaldehyde, and carboxybenzaldehyde, carboxyanisaldehyde, carboxynaphthaldehyde, carboxyanthraldehyde, carboxybiphenylaldehyde, carboxyformylfluorene, carboxyformylbiphenyl, carboxyformylanthracene, carboxyformylphenanthrene, carboxyformylphenothiazine, carboxyformylpyrene, carboxyformylbenzopyrene, carboxyformylindacene, carboxyformylphenacene, carboxyformylacenaphthylene, carboxyformylnaphthacene, carboxyformylpentacene, carboxyformyltriphenylene, carboxyformylpyridine, carboxyformylovalene, carboxydiformylbenzene, carboxydiformyltoluene, carboxydiformylxylene, carboxydiformylnaphtharene, carboxydiformylbiphenyl, carboxydiformylterphenyl, carboxydiformylanthracene, carboxydiformylphenanthrene, carboxydiformylpyrene, carboxydiformylindacene, carboxydiformylphenalene, carboxydiformylacenaphthylene, carboxydiformylphenalene, carboxydiformylnaphthacene, carboxydiformylpentacene, carboxydiformyltriphenylene, carboxydiformylpyridine, carboxydiformylimidazole, carboxydiformylfuran, carboxydiformylthiazole, carboxydiformylflavone, carboxydiformylisoflavone, carboxytriformylbenzene, carboxytriformyltoluene, carboxytriformylxylene, carboxytriformylnaphtharene, carboxytriformylbiphenyl, carboxytriformylterphenyl, carboxytriformylanthracene, carboxytriformylphenanthrene, carboxytriformylpyrene, carboxytriformylindacene, carboxytriformylphenalene, carboxytriformylacenaphthylene, carboxytriformylphenalene, carboxytriformylnaphthacene, carboxytriformylpentacene, carboxytriformyltriphenylene, carboxytriformylterpyridine, carboxytriformylimidazole, carboxytriformylfuran, carboxytriformylthiazole, carboxytriformylflavone, carboxytriformylisoflavone, carboxytetraformylbenzene, carboxytetraformytnaphtharene, carboxytetraformylbiphenyl, carboxytetraformylterphenyl, carboxytetraformylanthracene, carboxytetraformylphenanthrene, carboxytetraformylpyrene, carboxytetraformylindacene, carboxytetraformylphenalene, carboxytetraformylacenaphthylene, carboxytetraformylphenalene, carboxytetraformylnaphthacene, carboxytetraformylpentacene, carboxytetraformyltetraphenylene, carboxytetraformylquaterpyridine, carboxytetraformylimidazole, carboxytetraformylfuran, carboxytetraformylthiazole, carboxytetraformylflavone, and carboxytetraformylisoflavone, each optionally having a substituent having 2 to 20 carbon atoms. In the above, the substituent is alkyl group, cycloalkyl group, aryl group, alkoxyl group, cyano group, nitro group, hydroxyl group, boronic acid group, heterocyclic group, halogen atom, carboxyl group, alkylsilyl group, or a functional group selected from derivatives of the preceding groups.

Examples of heterocyclic aldehyde compound include carboxyfurfural, carboxynicotinealdehyde, carboxy-2-tetrahydrofuran carbaldehyde, and 2-thiophene carbaldehyde.

Examples of the aldehyde compound having 1 to 2 ester groups include compounds which are derived from the aldehyde compound having 1 to 2 carboxyl groups by a water-eliminating condensation with an alcohol to convert the 1 to 2 carboxyl groups to the ester group as shown by the formula (17).

In the formula (17), examples of the linear alkyl group having 1 to 20 carbon atoms, preferably 1 to 12 carbon atoms include methyl group, ethyl group, n-propyl group, n-butyl group, n-pentyl group, n-octyl group, and n-dodecyl group.

Examples of the branched alkyl group having 3 to 20 carbon atoms, preferably 3 to 10 carbon atoms include isopropyl group, t-butyl group, isopentyl group, and neopentyl group, with t-butyl group being preferred.

The cycloalkyl group has 3 to 20 carbon atoms, preferably 6 to 14 carbon atoms. The aliphatic ring in the cycloalkyl group may be a monocyclic or polycyclic ring, preferably a polycyclic ring, for example, a monocycloalkane, a bicycloalkane, a tricycloalkane, and a tetracycloalkane, particularly, a monocycloalkane such as cyclopropane, cyclobutane, cyclopentane, and cyclohexane or a polycycloalkane such as adamantane, norbornane, isobornane, tricyclodecane, and tetracyclodecane. Preferred are adamantane, tricyclodecane, and tetracyclodecane, and particularly preferred are adamantane and tricyclodecane.

The aldehyde compound having 1 to 2 ester groups may be commercially available as a reagent or may be synthesized by a known method. For example, an aldehyde compound having 1 to 2 carboxyl groups is dissolved or suspended in an organic solvent such as acetone and then a base such as potassium carbonate is added. Thereafter, the aldehyde compound is allowed to react with 0.5 to 4 equivalent of a compound represented by the following formula (27) at 0 to 100° C. for 1 to 72 h. After removing the base such as potassium carbonate by filtration, the aimed compound is obtained by removing the solvent, optionally followed by purification such as column chromatography.

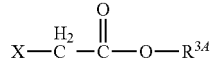

(27)

In the formula (27), X is a halogen atom and $R^{34}$ is the same as defined above.

The halogen atom include fluorine, chlorine, bromine, and iodine, with chlorine, bromine, and iodine being preferred, bromine and iodine being more preferred, and bromine being still more preferred.

Of the above compounds, an aromatic aldehyde having 1 to 2 carboxyl groups or ester groups and 1 to 4 formyl groups is preferred in view of the etching resistance; an aromatic aldehyde having 1 to 2 carboxyl groups or ester groups and 1 to 2 formyl groups is preferred in view of forming fine patterns; and an aromatic aldehyde having 1 to 2 carboxyl groups or ester groups and one formyl group is more preferred because the aromatic aldehyde and the cyclic compound (A) are produced in high yields and high purity.

The aromatic aldehyde compound having 1 to 2 carboxyl groups or ester groups is preferably the compound represented by the following formula (28-0) or (28):

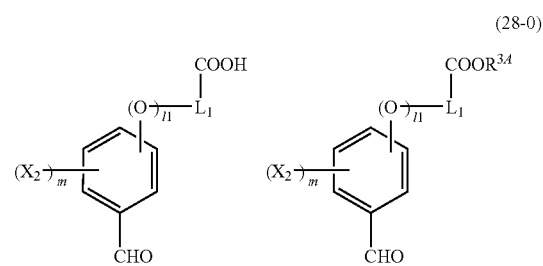

(28-0)

wherein $X_2$ is hydrogen atom or a halogen atom, preferably hydrogen atom, fluorine, chlorine, bromine, or iodine, more preferably hydrogen atom, chlorine, bromine, or iodine, still more preferably hydrogen atom, bromine, or iodine, and particularly preferably bromine, m is an integer of 1 to 4, and $L_1$, $l_1$, and $R^{34}$ are the same as defined above; and

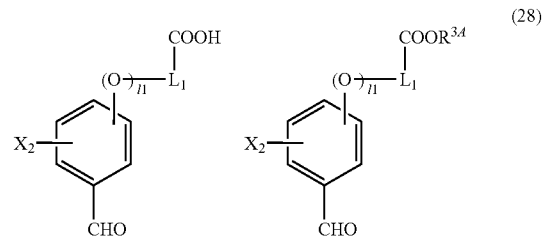

(28)

wherein $X_2$, $L_1$, $l_1$, and $R^{34}$ are the same as defined above.

Other preferred compounds are those represented by the following formulae (28-1) to (28-4):

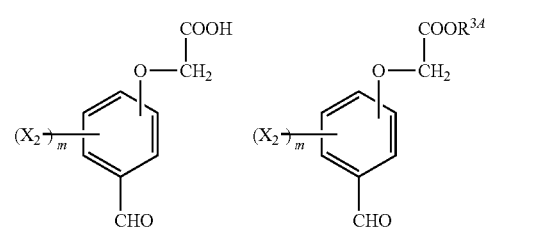

(28-1)

-continued

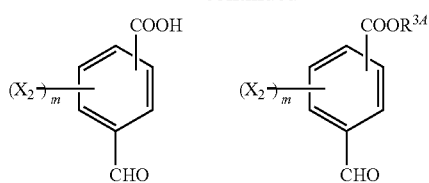

wherein m, $X_2$ and $R^{3A}$ are the same as defined above;

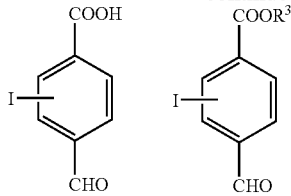

wherein $R^{3A}$ is the same as defined above; and

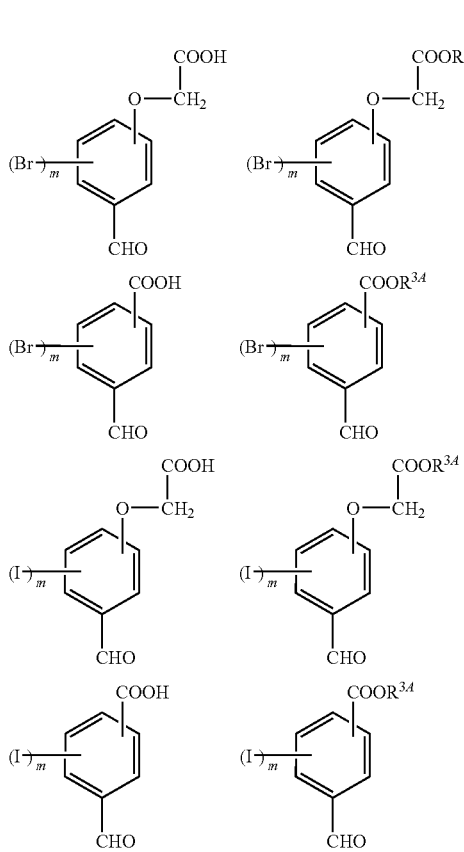

(28-2)

(28-3)

wherein m and $R^{3A}$ are the same as defined above;

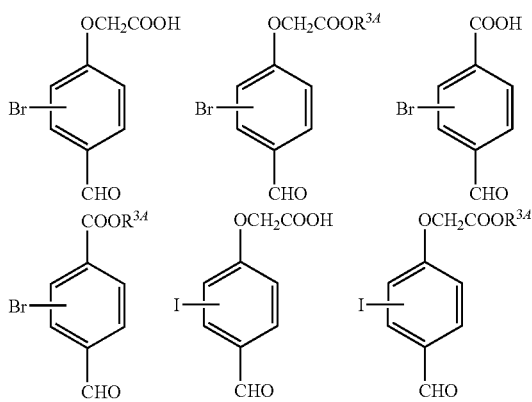

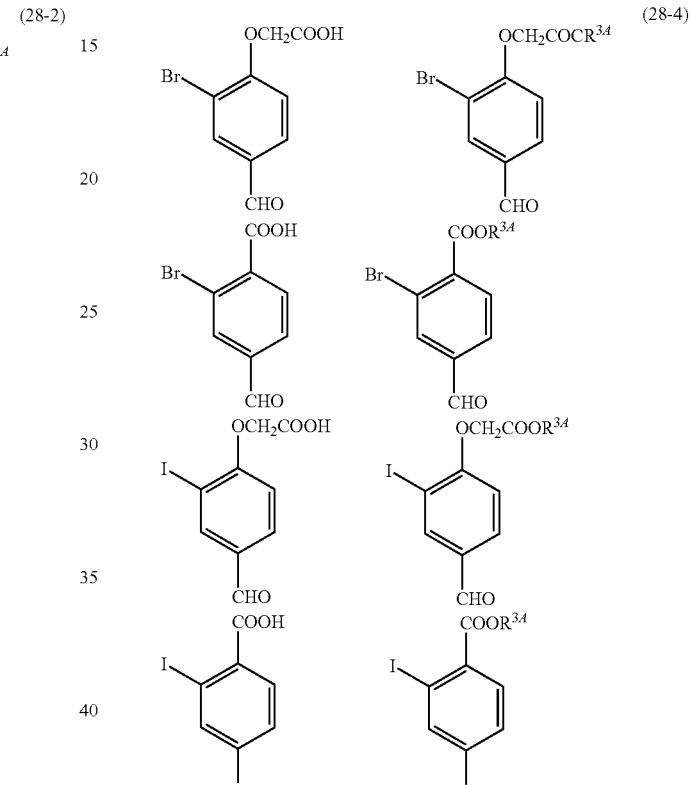

(28-4)

wherein $R^{3A}$ is the same as defined above.

The aldehyde compound (A1d) may be used alone or in combination of two or more, preferably used alone in view of the uniformity of the solid component in resist films.

Examples of the phenol compound (A2) include phenol, catechol, resorcinol, hydroquinone, and pyrogallol, with resorcinol and pyrogallol being preferred and resorcinol being more preferred. The phenol compound (A2) may have a substituent selected from the group consisting of a halogen atom, an alkyl group, a cycloalkyl group, an aryl group, an aralkyl group, an alkoxyl group, an alkenyl group, carboxyl group, an acyl group, an alkoxycarbonyl group, an alkyloyloxy group, an aryloyloxy group, cyano group, nitro group, a heterocyclic group, an alkylsilyl group, a substituted methyl group, a 1-substituted ethyl group, a 1-substituted n-propyl group, a 1-branched alkyl group, silyl group, a 1-substituted alkoxyalkyl group, a cyclic ether group, and an alkoxycarbonylalkyl group, as long as the effect of the present invention is not adversely affected. The purity of the phenol compound (A2) is, but not particularly limited, generally 95% by weight or more and preferably 99% by weight or more. The phenol compound (A2) may be used alone or in combination of two or more and preferably used alone in view of the uniformity of the solid component in resist films.

The cyclic compound (A0) having a carboxyl group is produced, for example, by the following method. In an organic solvent such as methanol, ethanol, and acetonitrile, 1 mol of the aldehyde compound (A1d) is allowed to react with 0.1 to 10 mol of the phenol compound (A2) in the presence of an acid catalyst (hydrochloric acid, sulfuric acid, p-toluene-sulfonic acid, etc.) at 60 to 150° C. for about 0.5 to 20 h. After filtering, washing with alcohol such as methanol and washing with water, the solid matter is separated by filtration and dried to obtain the cyclic compound (A0), which may be purified by column chromatography, if necessary.

If an alcohol such as methanol and ethanol is used as the reaction solvent or if an aliphatic aldehyde compound having an ester group is used as the aldehyde compound (A1d), a cyclic compound (Aa) in which the carboxyl groups are partly or completely esterified is obtained by the reaction in some cases. In this case, the reaction product solution is stirred at 10 to 100° C. for about 0.5 to 20 h in the presence of a base such as sodium hydroxide to hydrolyze the ester group. Then, the obtained solution is shaken with an organic solvent such as diethyl ether in a separatory funnel. After drawing off the aqueous layer, the organic layer is neutralized by an acid such as hydrochloric acid, and then, the precipitated solid matter is recovered by filtration to obtain the cyclic compound (A0) having the carboxyl groups not esterified.

The molecular weight of the cyclic compound (A0) is 700 to 5000, preferably 1000 to 2500, and more preferably 1500 to 2000. Within the above ranges, the resolution is improved while maintaining the film-forming properties required for the resists.

The cyclic compound of the invention may be a cis-isomer, a trans-isomer or a mixture thereof. In view of forming a highly uniform resist film, an isomerically pure compound consisting of one of the cis-isomer and the trans-isomer is preferred for the resist component of a radiation-sensitive composition. The cyclic compound of only one of the cis-isomer and the trans-isomer may be obtained by a known method, for example, the separation by column chromatography and preparative liquid chromatography and the optimization of the reaction solvent, reaction temperature, etc.

The cyclic compound (A0) having a carboxyl group is preferably selected from the compounds represented by the following formula (29-0) or (29):

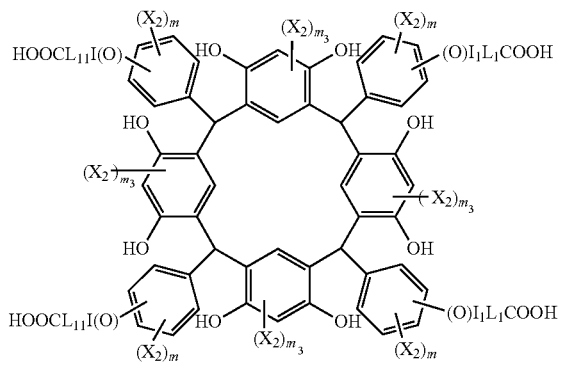

(29-0)

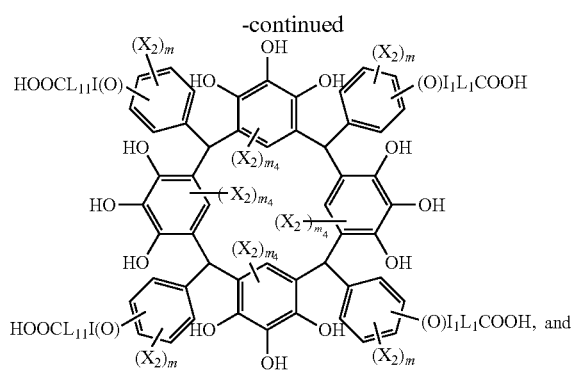

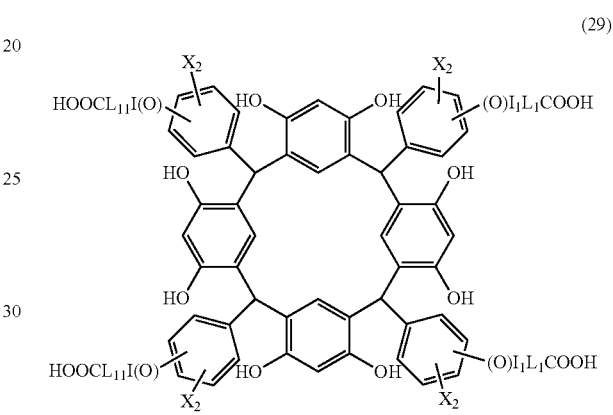

(29)

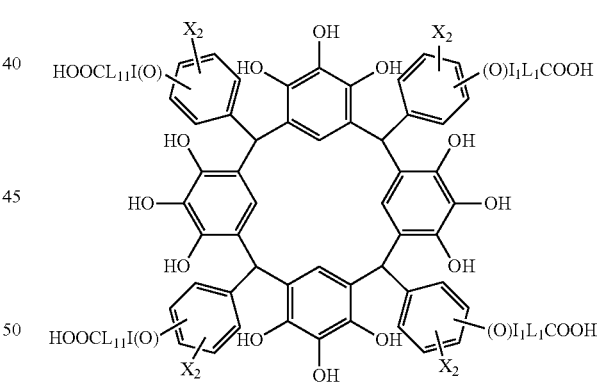

wherein $X_2$ is hydrogen atom or a halogen atom, $L_1$ is a single bond or a divalent organic group selected from linear or branched alkylene groups having 1 to 4 carbon atoms, $l_1$ is 0 or 1, m is an integer of 1 to 4, $m_3$ is an integer of 1 to 2, and $m_4$ is 1.

The cyclic compound (A0) having a carboxyl group is more preferably selected form the compounds represented by the following formula (30) or (31):

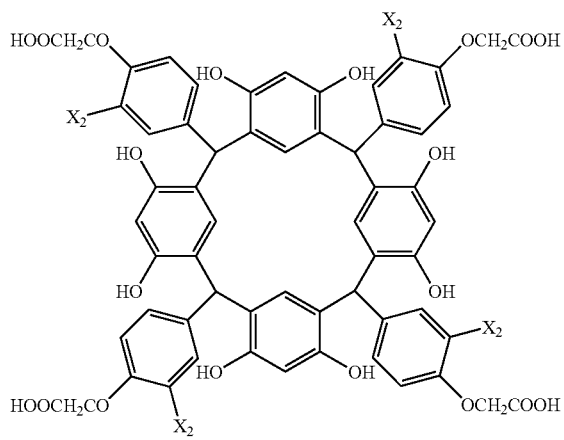

(30)

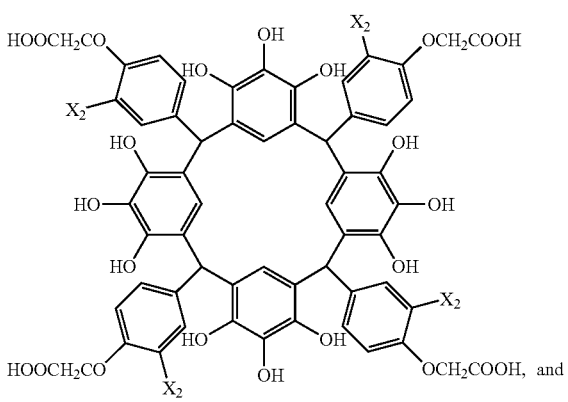

(31)

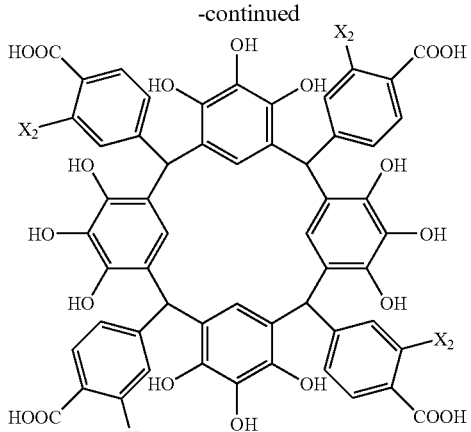

wherein $X_2$ is the same as defined above.

Examples of the compound (A3) having a halomethyl ether group include, but not particularly limited, an aliphatic compound having 1 to 2 halomethyl groups, an alicyclic compound having 1 to 2 halomethyl groups, and an aromatic compound having 1 to 2 halomethyl groups. Preferred is a compound represented by the following formula (32):

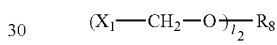

(32)

wherein $R_8$ is a linear alkyl group having 1 to 20 carbon atoms, a branched alkyl group having 3 to 20 carbon atoms, a cycloalkyl group having 3 to 20 carbon atoms, or an aryl group having 6 to 20 carbon atoms, $X_1$ is a halogen atom, and $l_2$ is 1 or 2.

The linear alkyl group having 1 to 20 carbon atoms is preferably one having 1 to 12 carbon atoms, and examples thereof include methyl group, ethyl group, n-propyl group, n-butyl group, n-pentyl group, n-octyl group, and n-dodecyl group.

The branched alkyl group having 3 to 20 carbon atoms is preferably one having 3 to 10 carbon atoms, and examples thereof include isopropyl group, t-butyl group, isopentyl group, and neopentyl group.

The cycloalkyl group having 3 to 20 carbon atoms is preferably one having 6 to 14 carbon atoms. The aliphatic ring of the cycloalkyl group may be monocyclic or polycyclic and preferably polycyclic. Examples thereof include a monocycloalkane, a bicycloalkane, a tricycloalkane, and a tetracycloalkane, specifically, the monocycloalkane such as cyclopropane, cyclobutane, cyclopentane, and cyclohexane, and the polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred.

The halogen atom may be fluorine, chlorine, bromine, or iodine, with chlorine, bromine, and iodine being preferred, bromine and iodine being more preferred, and bromine being still more preferred.

$l_2$ is 1 or 2, and preferably 1.

The compound (A3) having a halomethyl ether group is produced, for example, by the following method. An alcohol such as cyclohexanol is dissolve in an organic solvent such as n-hexane, and then, paraformaldehyde is added to the solution. Then a hydrogen halide such as hydrogen chloride gas is blown into the solution in an amount of 2.0 to 3.0 equivalent to the alcohol to allow the reaction to proceed at 0 to 100° C. After the reaction, the product is isolated by a vacuum distillation to obtain the aimed compound (A3) having a halomethyl ether group.

The compound (A3) having a halomethyl ether group is preferably represented by the following formula (32-1):

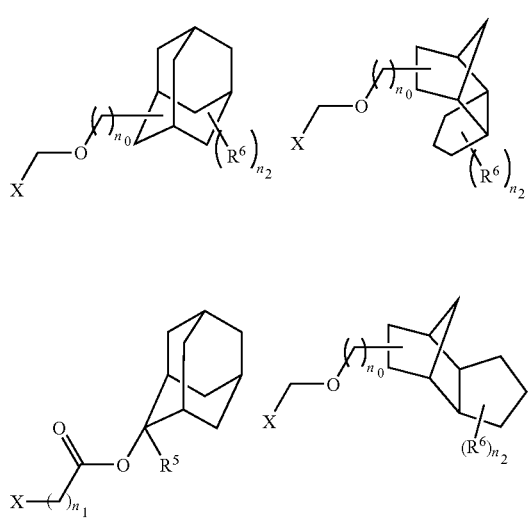

(32-1)

Wherein X, $R^5$, $R^6$, $n_0$, $n_1$, and $n_2$ are the same as defined in the formulae (22) and (27).

The cyclic compound (B0) is produced by the reaction of the cyclic compound (A0) having a carboxyl group and the compound (A3) having a halomethyl ether group. For example, the cyclic compound (A0) having a carboxyl group is dissolved or suspended in an aprotic solvent such as acetone, THF, and propylene glycol monomethyl ether acetate and then the compound (A3) having a halomethyl ether group is added. The reaction is allowed to proceed under atmospheric pressure at 0 to 110° C. for 1 to 72 h in the presence of an alkali catalyst such as pyridine, triethylamine, diazabicycloundecene, and potassium carbonate in an amount of 0.5 to 4 equivalent, preferably 0.9 to 1.1 equivalent, and more preferably 1.0 equivalent to the carboxyl group in the cyclic compound (A0) having a carboxyl group. After washing with an alcohol such as methanol and washing with water, the solid product is separated by filtration and dried to obtain the cyclic compound (B0), which may be purified by column chromatography.

The molecular weight of the cyclic compound (B0) is 800 to 5000, preferably 1000 to 2500, and more preferably 1500 to 2000. Within the above ranges, the resolution is improved while maintaining the film-forming properties required for resists.

The cyclic compound (B0) is preferably selected from the compounds represented by the following formula (33-0) or (33):

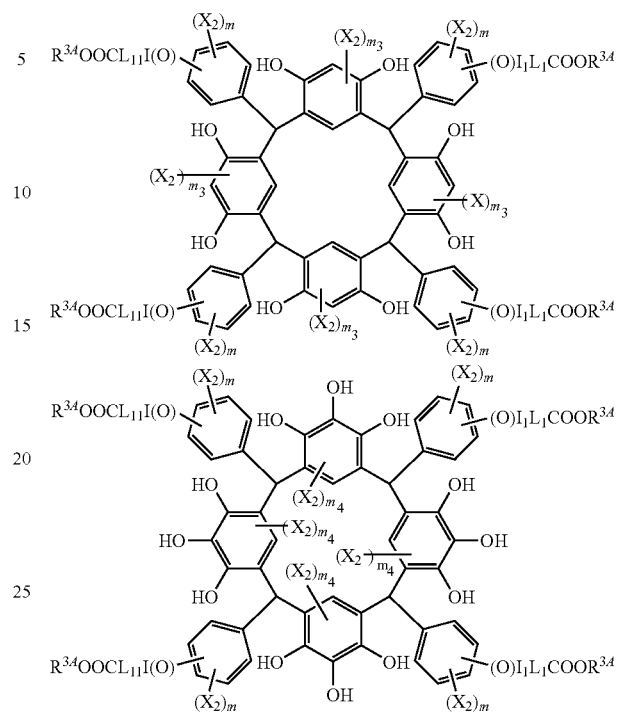

(33-0)

wherein $R^{34}$, $X_2$, $L_1$, $l_1$, m, $m_3$, and $m_4$ are the same as defined in the formula (13-0), and

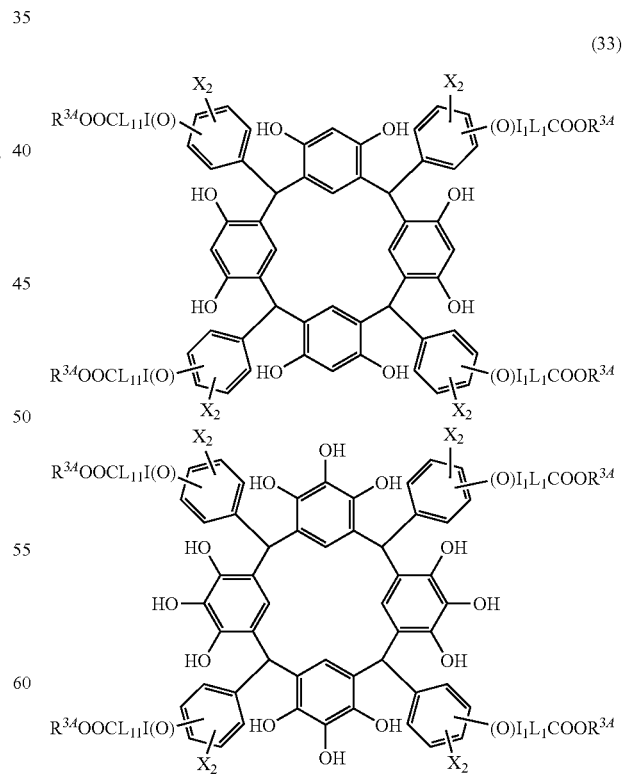

(33)

wherein $R^{34}$, $X_2$, $L_1$, and $l_1$ are the same as defined in the formula (13).

The cyclic compound (B0) is more preferably represented by the following formula (34):

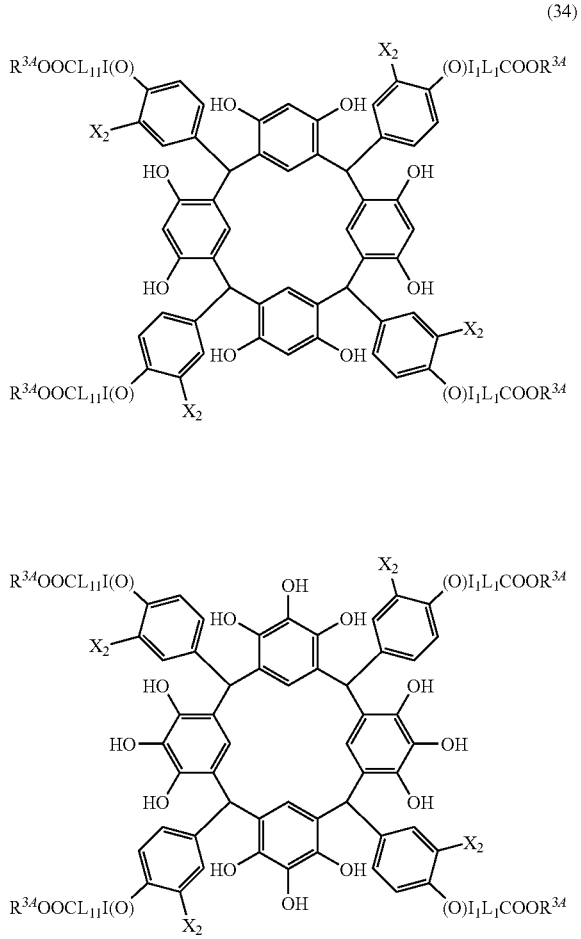

(34)

wherein $R^{34}$, $X_2$, $L_1$, and $l_1$ are the same as defined above.

The cyclic compound (B0) is particularly preferably represented by the following formula (35):

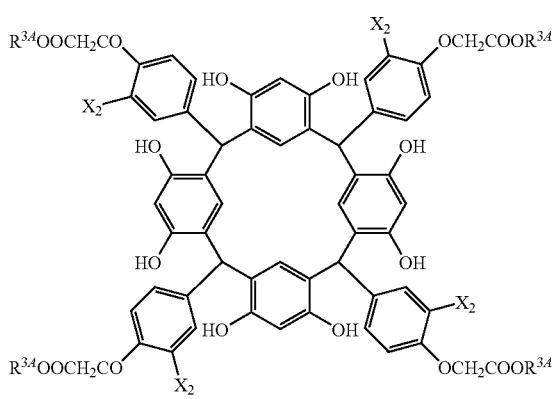

(35)

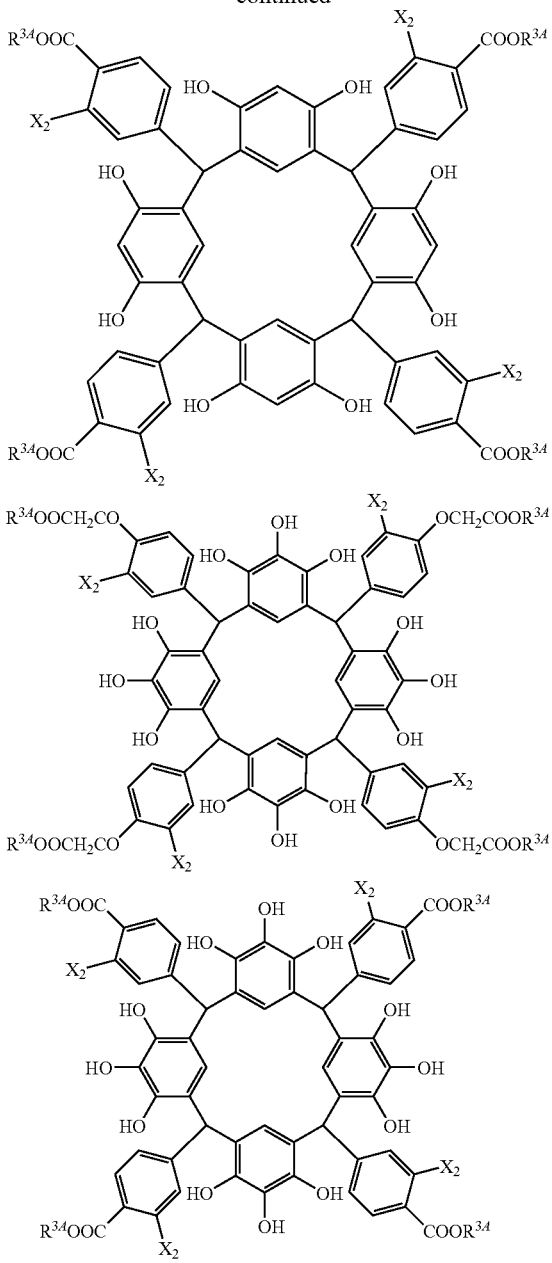

wherein $R^{34}$ and $X_2$ are the same as defined above.

$R^{34}$ is more preferably an acid-dissociating functional group having a structure selected from a cycloalkane having 3 to 20 carbon atoms, lactone and an aromatic ring having 6 to 12 carbon atoms. The cycloalkane having 3 to 12 carbon atoms may be a monocyclic or polycyclic alkane and preferably a polycyclic alkane, such as a monocycloalkane, a bicycloalkane, a tricycloalkane, and a tetracycloalkane. Examples thereof include a monocycloalkane such as cyclopropane, cyclobutane, cyclopentane, and cyclohexane, and a polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred. The cycloalkane having 3 to 12 carbon atoms is optionally substituted. Examples of the lactone include butyrolactone and a cycloalkane (3 to 12 carbon atoms) having a lactone group. Example of the aromatic ring having 6 to 12 carbon atoms include benzene ring, naphthalene ring, anthracene ring, phenanthrene ring, and pyrene ring, with benzene ring and naphthalene ring being preferred, and naphthalene ring being more preferred.

Particularly, an acid-dissociating functional group represented by the following formula (36) is preferred. The acid-dissociating functional group improves the resolution of the resist pattern to be obtained and reduces LER.

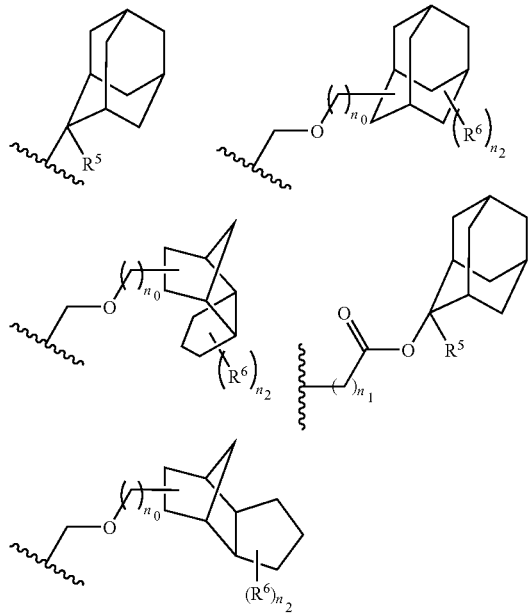

(36)

In the formula (36), $R^5$, $R^6$, $n_0$, $n_1$, and $n_2$ are the same as defined above.

The cyclic compound (B0) is also produced by the water-eliminating condensation reaction of the cyclic compound (A0) having a carboxyl group and a compound having an alcoholic hydroxyl group.

The cyclic compound (B0) is also produced by the ester exchange reaction between the cyclic compound (A0a) which is derived by converting the carboxyl group of the cyclic compound (A0) to the ester group as represented by the formula (17) and the compound having an alcoholic hydroxyl group. The ester exchange reaction is conducted by a known manner. The compound having an alcoholic hydroxyl group may be a primary, secondary or tertiary alcohol, preferably a secondary or tertiary alcohol, and particularly preferably a tertiary alcohol.

The compound (A3) having a halomethyl ether group is produced, for example, by the following method. An alcohol such as cyclohexanol is dissolved in an organic solvent such as n-hexane, and then, paraformaldehyde is added to the solution. Then a hydrogen halide such as hydrogen chloride gas is blown into the solution in an amount of 2.0 to 3.0 equivalent to the alcohol to allow the reaction to proceed at 0 to 100° C. After the reaction, the product is isolated by a vacuum distillation to obtain the aimed compound (A3) having a halomethyl ether group.

The cyclic compound (B0) is produced by the reaction of the cyclic compound (A0) having a carboxyl group and the compound (A3) having a halomethyl ether group. For example, the cyclic compound (A0) having a carboxyl group is dissolved or suspended in an aprotic solvent such as acetone, THF, and propylene glycol monomethyl ether acetate and then the compound (A3) having a halomethyl ether group is added. The reaction is allowed to proceed under atmospheric pressure at 0 to 110° C. for 1 to 72 h in the presence of an alkali catalyst such as pyridine, triethylamine, diazabicycloundecene, and potassium carbonate in an amount of 0.5 to 4 equivalent, preferably 0.9 to 1.1 equivalent, and more preferably 1.0 equivalent to the carboxyl group in the cyclic compound (A0) having a carboxyl group. After washing with an alcohol such as methanol and washing with water, the solid product is separated by filtration and dried to obtain the cyclic compound (B0), which may be purified by column chromatography.

The cyclic compound (B0) may be purified to reduce the amount of residual metal, if necessary. If the acid catalyst and co-catalyst remain, the storage stability of the radiation-sensitive composition is generally lowered. If the basic catalyst remains, the sensitivity of the radiation-sensitive composition is generally lowered. Therefore, the cyclic compound (B0) may be purified to reduce the remaining amount of such catalytic compounds. The purification may be carried out by any of known methods without limitation as long as the cyclic compound (B0) is not unfavorably changed, for example, by washing with water, washing with an acidic aqueous solution, washing with a basic aqueous solution, treating with an ion exchange resin, and treating with a silica gel column chromatography. The purification is preferably conducted in a combination of two or more of the above methods.

The acidic aqueous solution, basic aqueous solution, ion exchange resin and silica gel column may be suitably selected by taking the amounts and kinds of the metal, acidic compound and basic compound to be removed and the kind of the cyclic compound (B0) to be purified into consideration. For example, hydrochloric acid, an aqueous solution of nitric acid and an aqueous solution of acetic acid, each having a concentration of 0.01 to 10 mol/L, are used as the acidic aqueous solution; an aqueous ammonia solution having a concentration of 0.01 to 10 mol/L is used as the basic aqueous solution; and a cation exchange resin such as Amberlyst 15J-HG Dry manufactured by Organo Corporation is used as the ion exchange resin. The purified product may be dried by a known method such as, but not limited to, a vacuum drying and a hot-air drying under the conditions not changing the cyclic compound (B0).

In the cyclic compound (B0), the ratio of the number of halogen atoms to the total number of constituent atoms is preferably 0.1 to 60%, more preferably 0.1 to 40%, still more preferably 0.1 to 20%, particularly preferably 0.1 to 10%, and most preferably 1 to 5%. Within the above ranges, the film-forming properties can be maintained while increasing the sensitivity to radiation. In addition, the solubility in safety solvents is increased.

The ratio of the number of nitrogen atoms to the total number of constituent atoms is preferably 0.1 to 40%, more preferably 0.1 to 20%, still more preferably 0.1 to 10%, and particularly preferably 0.1 to 5%. Within the above ranges, the film-forming properties can be maintained while reducing the line edge roughness of the resist pattern to be obtained. The nitrogen atom constituting a secondary or tertiary amine is preferred and the nitrogen atom constituting a tertiary amine is more preferred.

The solid component of the radiation-sensitive composition and the cyclic compound (B0) are made into an amorphous film by spin coating and applicable to a general semiconductor production process.

The dissolving speed of the amorphous film of the cyclic compound (B0) in a 2.38 mass % aqueous solution of tetramethylammonium hydroxide (TMAH) at 23° C. is preferably 5 Å/sec or less, more preferably 0.05 to 5 Å/sec, and still more preferably 0.0005 to 5 Å/sec. If being 5 Å/sec or less, the amorphous film is insoluble in an alkali developing solution to form a resist. If being 0.0005 Å/sec or more, the resolution may be improved in some cases. This may be because that the micro surface of the cyclic compound (B0) is dissolved to reduce LER. In addition, the number of defects is reduced.

It is preferred that the cyclic compound generated by the dissociation of the acid-dissociating functional group of the cyclic compound (B0) is also capable of forming an amorphous film by spin coating. The dissolving speed of the amorphous film of the cyclic compound (A3) in a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. This may be because that the contrast at the interface between the exposed portion soluble in an alkali developing solution and the non-exposed portion insoluble in an alkali developing solution is enhanced by the change of solubility due to the dissociation of the acid-dissociating functional group of the cyclic compound (B0). In addition, LER is reduced and the number of defects is reduced.

The dissolving speed of the amorphous film of the solid component of the radiation-sensitive composition in a 2.38 mass % aqueous solution of TMAH at 23° C. is preferably 5 Å/sec or less. After exposing the amorphous film to a radiation such as KrF excimer lasers, extreme ultraviolet rays, electron beams and X-rays in a desired pattern and optionally heating at 20 to 250° C., the dissolving speed of the treated amorphous film in a 2.38 mass % aqueous solution of TMAH at 23° C. is preferably 10 Å/sec or more. By satisfying the above requirements, a pattern with a good shape can be obtained in good yields.

The glass transition temperature of the cyclic compound (B0) is preferably 100° C. or higher, more preferably 120° C. or higher, still more preferably 140° C. or higher, and particularly preferably 150° C. or higher. Within the above ranges, a heat resistance enough to maintain the shape of pattern in the semiconductor lithography process is obtained, thereby increasing the resolution.

The crystallization heat of the cyclic compound (d) is preferably less than 20 J/g when measured by a differential scanning calorimetry of the glass transition temperature. The difference, (crystallization temperature)–(glass transition temperature), is preferably 70° C. or higher, more preferably 80° C. or higher, still more preferably 100° C. or higher, and particularly preferably 130° C. or higher. If the crystallization heat is less than 20 J/g or the difference, (crystallization temperature)–(glass transition temperature), is within the above ranges, the radiation-sensitive composition is easily made into an amorphous film by spin coating and the film-forming properties required for the resist can be maintained for a long period of time, thereby improving the resolution.

The cyclic compound (B0) may be used as the main component of a positive-type radiation-sensitive composition or may be added to a radiation-sensitive composition as an additive for increasing the sensitivity and etching resistance in place of using as the main component. When used as an additive, the cyclic compound (B0) is used in an amount of 1 to 50% by weight of the total weight of the solid component.

The radiation-sensitive composition of the invention comprises preferably 1 to 80% by weight of the solid component and 20 to 99% by weight of the solvent, more preferably 1 to 50% by weight of the solid component and the 50 to 99% by weight of the solvent, still more preferably 2 to 40% by weight of the solid component and 60 to 98% by weight of the solvent, and particularly preferably 2 to 10% by weight of the solid component and 90 to 98% by weight of the solvent. The content of the cyclic compound (B0) is preferably 50% by weight or more, more preferably 60 to 95% by weight, still more preferably 65 to 90% by weight, and particularly preferably 70 to 85% by weight, each based on the total weight of the solid component. Within the above ranges, a high resolution is obtained and the line edge roughness is reduced. The solvent is selected from those described above with respect to the radiation-sensitive composition A.

An acid-non-dissociating functional group may be introduced into at least one phenolic hydroxyl group of the cyclic compound (B0), as long as the effect of the present invention is not adversely affected. The acid-non-dissociating functional group is a characteristic group which is not dissociated in the presence of acid, thereby failing to generate an alkali-soluble group. Examples thereof include a group which is not dissociated by the action of acid such as a $C_{1-20}$ alkyl group, a $C_{3-20}$ cycloalkyl group, a $C_{6-20}$ aryl group, a $C_{1-20}$ alkoxyl group, cyano group, nitro group, hydroxyl group, a heterocyclic group, a halogen atom, carboxyl group, a $C_{1-20}$ alkylsilyl group, and a functional group derived from derivatives of the preceding groups.

A naphthoquinonediazido ester group may be introduced into at least one phenolic hydroxyl group of the cyclic compound (B0). The cyclic compound (B0) having at least one phenolic hydroxyl group into which the naphthoquinonediazido ester group is introduced may be used as the main component of a positive-type radiation-sensitive composition, or may be added to a radiation-sensitive composition as an acid generator or additive.

An acid-generating functional group which generates an acid upon the irradiation with radiation may be introduced into at least one phenolic hydroxyl group of the cyclic compound (B0). The cyclic polyphenol compound obtained by introducing the acid-generating functional group into at least one phenolic hydroxyl group of the cyclic compound (B0) may be used as the main component of a positive-type radiation-sensitive composition, or may be added to a radiation-sensitive composition as an acid generator or additive.

The composition of the invention preferably contains at least one kind of acid generator (C) which generates an acid directly or indirectly by the irradiation with radiation selected from visible lights, ultraviolet rays, excimer lasers, electron beams, extreme ultraviolet rays (EUV), X-rays, and ion beams. The amount of the acid generator (C) to be added is preferably 0.001 to 50% by weight, more preferably 1 to 40% by weight, and still more preferably 3 to 30% by weight based on the total weight of the solid components (total of the cyclic compound (B0), the acid generator (C), the low molecular weight solubilizer (D), the acid-diffusion controller (E) and other components (F), the same being applied below). Within the above ranges, a high sensitivity and a pattern profile with a small edge roughness is obtained. In the present invention, the acid can be generated by any method as long as the acid is suitably generated within the system. The use of excimer lasers in place of ultraviolet rays such as g-rays and i-rays enables a finer processing. If high-energy rays such as electron beams, extreme ultraviolet rays, X-rays and ion beams are used, the resist composition can be still more finely processed.

The acid generator (C) is used particularly preferably in an amount of 15 to 25% by weight of the total weight of the solid component. Within the above range, a high sensitivity is obtained.

The radiation-sensitive composition is prepared just before use by dissolving the components in a solvent into a uniform solution and, if necessary, filtering the solution through a filter with about 0.2 μm pore size.

The radiation-sensitive composition may contain a resin soluble in an aqueous alkali solution, as long as the effect of the invention is not adversely affected. Examples of the resin soluble in an aqueous alkali solution include novolak resins, polyvinylphenols, polyacrylic acid, polyvinyl alcohol, styrene-maleic anhydride resins, polymers containing the monomer units derived from acrylic acid, vinyl alcohol or vinylphenol, and their derivatives. The blending amount of the resin soluble in an aqueous alkali solution varies depending upon the kind of the resist compound to be used, and preferably 30 parts by weight or less, more preferably 10 parts by weight or less, still more preferably 5 parts by weight or less, and particularly preferably 0 part by weight, each based on 100 parts by weight the cyclic compound (B0).

Radiation-Sensitive Composition C

The present invention further relates to a radiation-sensitive composition comprising any one of the cyclic compounds of formulae (1) and (a) to (e), and a solvent.

The present invention further relates to a radiation-sensitive composition wherein the cyclic compound is a cyclic compound (A) having a molecular weight of 700 to 5000 which is synthesized by the condensation reaction of a compound having 2 to 59 carbon atoms and 1 to 4 formyl groups (aldehyde compound (A1)) with a compound having 6 to 15 carbon atoms and 1 to 3 phenolic hydroxyl groups (phenol compound (A2)).

Namely, another preferred radiation-sensitive composition of the present invention comprises 1 to 80% by weight of a solid component and 20 to 99% by weight of a solvent, wherein the solid component contains a cyclic compound (A) having a molecular weight of 700 to 5000 in an amount of 50% by weight or more of the total weight of the solid component, and wherein the cyclic compound (A) is synthesized by the condensation reaction of a benzaldehyde compound having 7 to 24 carbon atoms and having neither hydroxyl group nor t-butyl group with a compound having 6 to 15 carbon atoms and 1 to 3 phenolic hydroxyl groups.

Still another preferred radiation-sensitive composition of the present invention comprises 1 to 80% by weight of a solid component and 20 to 99% by weight of a solvent, wherein the solid component comprises a cyclic compound (A) having a molecular weight of 700 to 5000 in an amount of 50% by weight or more of the total weight of the solid component, an acid generator (C) which generates an acid directly or indirectly upon the irradiation with radiation selected from the group consisting of visible lights, ultraviolet rays, excimer lasers, electron beams, extreme ultraviolet rays (EUV), X-rays, and ion beams, an acid crosslinking agent (G), and an acid-diffusion controller (E), and wherein the cyclic compound (A) is synthesized by the condensation reaction of a benzaldehyde compound having 10 to 24 carbon atoms and having a substituent containing an alicyclic or aromatic ring with a compound having 6 to 15 carbon atoms and 1 to 3 phenolic hydroxyl groups.

The radiation-sensitive composition contains the cyclic polyphenol compound (A) in an amount of 50% by weight or more of the total weight of the solid components.

The cyclic compound (A) has a molecular weight of 700 to 5000 which is synthesized by the condensation reaction of a benzaldehyde compound having 10 to 24 carbon atoms and having a substituent containing an alicyclic or aromatic ring or a benzaldehyde compound having 7 to 24 carbon atoms and having neither hydroxyl group nor t-butyl group (aromatic carbonyl compound (A1)) with a compound having 6 to 15 carbon atoms and 1 to 3 phenolic hydroxyl groups (phenol compound (A2)).

The cyclic compound (A) enhances the film-forming properties, heat resistance, alkali developability, and etching resistance.

The cyclic compound (A) is produced by the condensation reaction of at least one compound selected from the aromatic carbonyl compound (A1) with at least one compound selected from the phenol compound (A2).

The aromatic carbonyl compound (A1) is a benzaldehyde compound having 10 to 24 carbon atoms and a substituent containing an aliphatic or aromatic ring, or a benzaldehyde compound having 7 to 24 carbon atoms and having neither hydroxyl group nor t-butyl group. Examples thereof include benzaldehyde, methylbenzaldehyde, dimethylbenzaldehyde, trimethylbenzaldehyde, ethylbenzaldehyde, propylbenzaldehyde, butylbenzaldehyde (exclusive of t-butylbenzaldehyde), ethylmethylbenzaldehyde, isopropylmethylbenzaldehyde, diethylbenzaldehyde, anisaldehyde, cyclopropylbenzaldehyde, cyclobutanebenzaldehyde, cyclopentanebenzaldehyde, cyclohexanebenzaldehyde, phenylbenzaldehyde, naphthylbenzaldehyde, adamantylbenzaldehyde, norbornylbenzaldehyde, lactylbenzaldehyde, isopropylbenzaldehyde, n-propylbenzaldehyde, bromobenzaldehyde, and dimethylaminobenzaldehyde, with isopropylbenzaldehyde, n-propylbenzaldehyde, bromobenzaldehyde, dimethylaminobenzaldehyde, cyclohexylbenzaldehyde, and phenylbenzaldehyde being preferred, and 4-isopropylbenzaldehyde, cyclohexylbenzaldehyde and 4-n-propylbenzaldehyde being more preferred.

The aromatic carbonyl compound (A1) may have a linear or branched alkyl group having 1 to 4 carbon atoms, cyano group, hydroxyl group, or a halogen atom, as long as the effect of the present invention is not adversely affected. The aromatic carbonyl compound (A1) may be used alone or in combination of two or more.

Examples of the phenol compound (A2) include phenol, catechol, resorcinol, hydroquinone, and pyrogallol, with resorcinol and pyrogallol being preferred and resorcinol being more preferred. The phenol compound (A2) may have a linear or branched alkyl group having 1 to 4 carbon atoms, cyano group, hydroxyl group, or a halogen atom, as long as the effect of the present invention is not adversely affected. The phenol compound (A2) may be used alone or in combination of two or more.

The cyclic compound (A) may have a crosslinking group which causes a crosslinking reaction induced by the irradiation with visible lights, ultraviolet rays, excimer lasers, electron beams, extreme ultraviolet rays (EUV), X-rays, or ion beams. The crosslinking group is introduced into the cyclic compound (A), for example, by a reaction with a crosslinking group-introducing agent in the presence of a base catalyst. Examples of the crosslinking group include a carbon-carbon multiple bond, an epoxy group, an azide group, a halogenate phenyl group, and chloromethyl group. Examples of the crosslinking group-introducing agent include an acid, an acid halide, an acid anhydride, a derivative of carboxylic acid such as dicarbonate, and an alkyl halide. A resist composition containing the cyclic compound (A) having a crosslinking group is also effective as a solvent-soluble, non-polymeric radiation-sensitive composition with a high resolution and heat resistance.

The cyclic compound (A) may be used as the main component of a negative-type radiation-sensitive composition or may be added to a radiation-sensitive composition as an additive for increasing the sensitivity and etching resistance in place of using as the main component. When used as an additive, the cyclic compound (B0) is used in an amount of 1 to 49.999% by weight of the total weight of the solid component.

The cyclic compound (A) is useful as a negative-type resist material which is made sparingly soluble in an alkali developing solution upon the irradiation of KrF excimer lasers, extreme ultraviolet rays, electron beams or X-rays. It is recognized that the irradiation of KrF excimer lasers, extreme ultraviolet rays, electron beams or X-rays induces a condensation reaction between the cyclic compounds (A) to form a compound sparingly soluble in an alkali developing solution. The resist pattern thus obtained has a very small LER.

An acid-non-dissociating functional group may be introduced into at least one phenolic hydroxyl group of the cyclic compound (A), as long as the effect of the present invention is not adversely affected. The acid-non-dissociating functional group is a characteristic group which is not dissociated in the presence of acid, thereby failing to generate an alkali-soluble group. Examples thereof include a group which is not dissociated by the action of acid such as a $C_{1-20}$ alkyl group, a $C_{3-20}$ cycloalkyl group, a $C_{6-20}$ aryl group, a $C_{1-20}$ alkoxyl group, cyano group, nitro group, hydroxyl group, a heterocyclic group, a halogen atom, carboxyl group, a $C_{1-20}$ alkylsilyl group, and a functional group derived from derivatives of the preceding groups.

A naphthoquinonediazido ester group may be introduced into at least one phenolic hydroxyl group of the cyclic compound (A). The cyclic compound (A) having at least one phenolic hydroxyl group into which the naphthoquinonediazido ester group is introduced may be used as the main component of a negative/positive-type radiation-sensitive composition or a positive-type radiation-sensitive composition, or may be added to a radiation-sensitive composition as an acid generator or additive.

An acid-generating functional group which generates an acid upon the irradiation with radiation may be introduced into at least one phenolic hydroxyl group of the cyclic compound (A). The cyclic polyphenol compound obtained by introducing the acid-generating functional group into at least one phenolic hydroxyl group of the cyclic compound (A) may be used as the main component of a negative/positive-type radiation-sensitive composition or a positive-type radiation-sensitive composition, or may be added to a radiation-sensitive composition as an acid generator or additive.

The cyclic compound (A) is produced by a known method. For example, 1 mol of the aromatic carbonyl compound (A1) and 0.1 to 10 mol of the phenol compound (A2) are allowed to react in an organic solvent such as methanol and ethanol in the presence of an acid catalyst (hydrochloric acid, sulfuric acid, p-toluenesulfonic acid, etc.) at 60 to 150° C. for about 0.5 to 20 h. After filtration, the collected precipitates are washed with an alcohol such as methanol, washed with water, and dried to obtain the cyclic compound (A). Alternatively, the cyclic compound (A) may be obtained by the same reaction except for using a basic catalyst (sodium hydroxide, barium hydroxide, 1,8-diazabicyclo[5.4.0]undecane 7, etc.) in place of the acid catalyst. In addition, the cyclic polyphenol compound (A) may be produced by converting the aromatic carbonyl compound (A1) to a dihalide using a hydrogen halide or halogen gas and allowing the isolated dihalide to react with the phenol compound (A2).

In the production of the cyclic compound (A), the use of two or more kinds of the aromatic carbonyl compounds (A1) and/or two or more kinds of the phenol compounds (A2) is preferred, because the solubility of the cyclic compound (A) to be obtained in semiconductor safety solvents is increased.

The cyclic compound (A) may be purified to reduce the amount of residual metal, if necessary. If the acid catalyst and co-catalyst remain, the storage stability of the radiation-sensitive composition is generally lowered. If the basic catalyst remains, the sensitivity of the radiation-sensitive composition is generally lowered. Therefore, the cyclic compound (A) may be purified to reduce the remaining amount of such catalytic compounds. The purification may be carried out by any of known methods without limitation as long as the cyclic compound (A) is not unfavorably changed, for example, by washing with water, washing with an acidic aqueous solution, washing with a basic aqueous solution, treating with an ion exchange resin, and treating with a silica gel column chromatography. The purification is preferably conducted in a combination of two or more of the above methods. The acidic aqueous solution, basic aqueous solution, ion exchange resin and silica gel column may be suitably selected by taking the amounts and kinds of the metal, acidic compound and basic compound to be removed and the kind of the cyclic compound (A) to be purified into consideration. For example, hydrochloric acid, an aqueous solution of nitric acid and an aqueous solution of acetic acid, each having a concentration of 0.01 to 10 mol/L, are used as the acidic aqueous solution; an aqueous ammonia solution having a concentration of 0.01 to 10 mol/L is used as the basic aqueous solution; and a cation exchange resin such as Amberlyst 15J-HG Dry manufactured by Organo Corporation is used as the ion exchange resin. The purified product may be dried by a known method such as, but not limited to, a vacuum drying and a hot-air drying under the conditions not changing the cyclic compound (A).

It is preferred that the cyclic compound (d) has a low sublimation ability under atmospheric pressure at 100° C. or lower, preferably at 120° C. or lower, more preferably at 130° C. or lower, still more preferably at 140° C. or lower, and particularly preferably at 150° C. or lower. The low sublimation ability referred to herein means that the weight loss after a thermogravimetric analysis wherein a sample is kept at predetermined temperature for 10 min is 10% or less, preferably 5% or less, more preferably 3% or less, still more preferably 1% or less, and particularly preferably 0.1% or less. If the sublimation ability is low, the contamination of the exposure apparatus by the outgas generated in the exposing process is prevented. In addition, a fine pattern with small LER is obtained.

The cyclic compound (A) preferably satisfies the requirement of F<3.0 wherein F is (total number of atoms)/(total number of carbon atoms−total number of oxygen atoms), and more preferably F<2.5. By satisfying the above requirements, the dry-etching resistance is improved.

The cyclic compound (A) dissolves in a solvent at 23° C. preferably in 1% by weight or more, more preferably in 3% by weight or more, still more preferably in 5% by weight or more, and particularly preferably in 10% by weight or more when measured using the solvent having the highest dissolving power to the cyclic polyphenol compound (A) among propylene glycol monomethyl ether acetate, propylene glycol monomethyl ether, 2-heptanone, anisole, butyl acetate, ethyl propionate, and ethyl lactate. With such solubility, the safety solvent acceptable in the semiconductor factory can be used.

The crystallization heat of the cyclic compound (d) is preferably less than 20 J/g when measured by a differential scanning calorimetry of the glass transition temperature. The difference, (crystallization temperature)−(glass transition temperature), is preferably 70° C. or higher, more preferably 80° C. or higher, still more preferably 100° C. or higher, and particularly preferably 130° C. or higher. If the crystallization heat is less than 20 J/g or the difference, (crystallization temperature)−(glass transition temperature), is within the above ranges, the radiation-sensitive composition is easily made into an amorphous film by spin coating and the film-forming properties required for the resist can be maintained for a long period of time, thereby improving the resolution.

In the present invention, the crystallization heat, crystallization temperature and glass transition temperature are measured by a differential scanning calorimetry using DSC/TA-50WS manufactured by Shimadzu Corporation as described below. A sample (about 10 mg) placed in a non-sealed aluminum container is heated to a temperature higher than the melting point at a temperature rising rate of 20° C./min in a nitrogen gas flow (50 ml/min). After rapid cooling, the sample is again heated to a temperature higher than the melting point at a temperature rising rate of 20° C./min in a nitrogen gas flow (30 ml/min). After rapid cooling, the sample is again heated to 400° C. at a temperature rising rate of 20° C./min a nitrogen gas flow (30 ml/min). The middle point of the region at which the base line turns discontinuous (the point at which the specific heat reduces to half) is taken as the glass transition temperature (Tg) and the temperature of the exothermic peak appearing after the discontinuous region is taken as the crystallization temperature. The crystallization heat is determined by the area of the region which is surrounded by the exothermic peak and the base line.

The molecular weight of the cyclic compound (A) is 700 to 5000, preferably 800 to 2000, and more preferably 900 to 1500. Within the above ranges, the resolution is improved while maintaining the film-forming properties necessary for the resists.

The cyclic compound of the invention may be a cis-isomer, a trans-isomer or a mixture thereof. In view of forming a highly uniform resist film, an isomerically pure compound consisting of one of the cis-isomer and the trans-isomer is preferred for the resist component of a radiation-sensitive composition. The cyclic compound of only one of the cis-isomer and the trans-isomer may be obtained by a known method, for example, the separation by column chromatography and preparative liquid chromatography and the optimization of the reaction solvent, reaction temperature, etc.

In an embodiment of the present invention, the cyclic compound (A) is preferably represented by the following formula (37), (37-1) or (37-2):

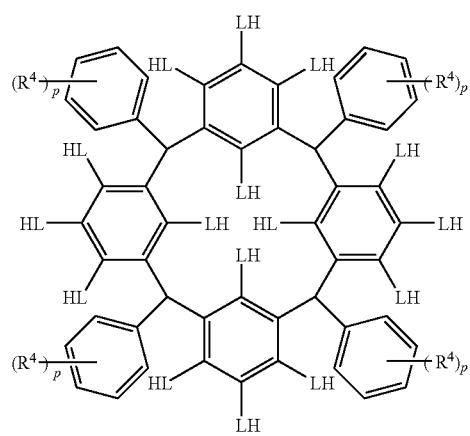

(37)

wherein $R^4$ is hydrogen atom, an alkyl group having 1 to 20 carbon atoms (exclusive of t-butyl group), a cycloalkyl group having 3 to 20 carbon atoms, an aryl group having 6 to 20 carbon atoms, an alkoxyl group having 1 to 20 carbon atoms, cyano group, nitro group, an heterocyclic group, a halogen atom, carboxyl group, an alkylsilyl group having 1 to 20 carbon atoms, and a functional group selected from derivatives of the preceding groups, L is the same as defined above, and p is an integer of 0 to 5;

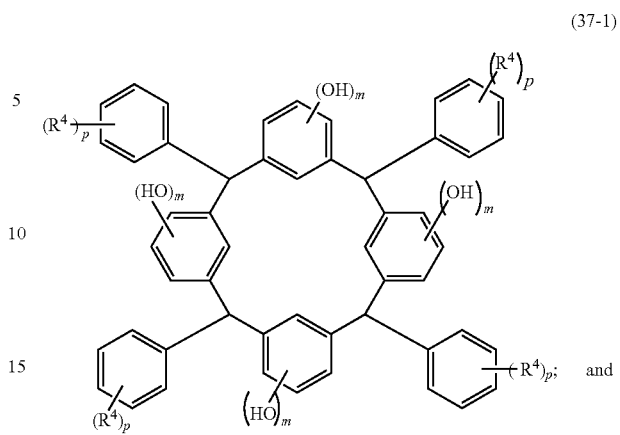

(37-1)

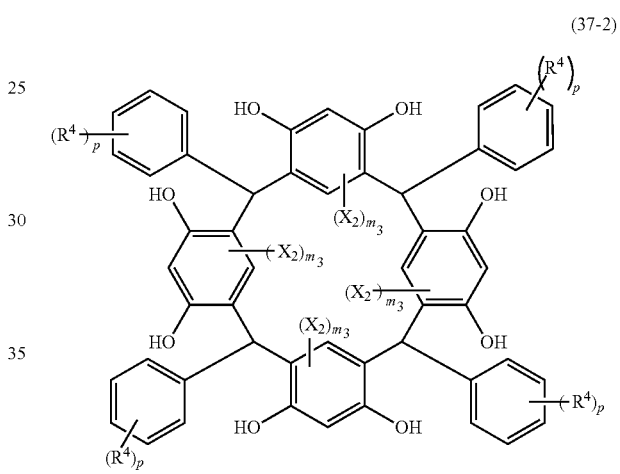

(37-2)

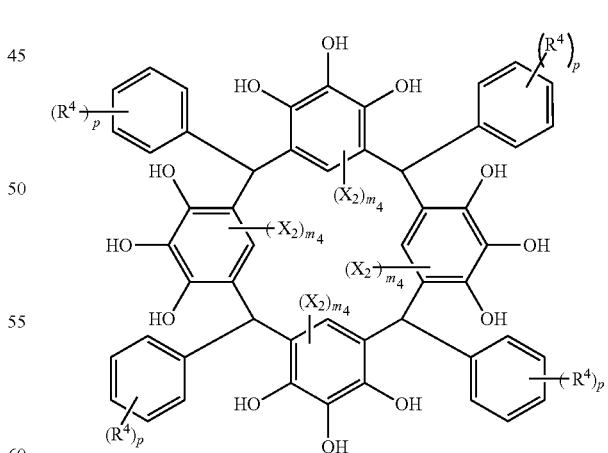

in the formulae (37-1) and (37-2), $X_2$ is hydrogen atom or a halogen atom, m is an integer of 1 to 4, $m_3$ is an integer of 1 to 2, $m_4$ is 1, and $R^4$ and p are the same as defined above.

The cyclic compound (A) is more preferably represented by the following formula (38):

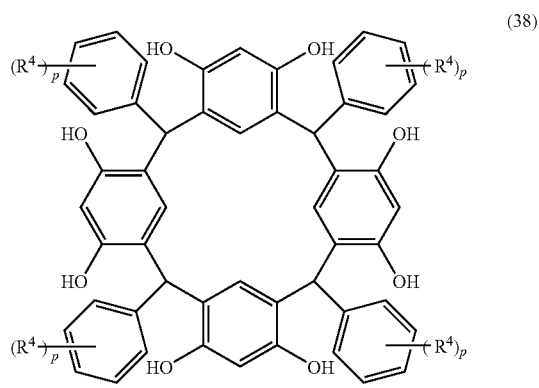
(38)

wherein R⁴ and p are the same as defined above.

The cyclic compound (A) is still more preferably represented by the following formula (39):

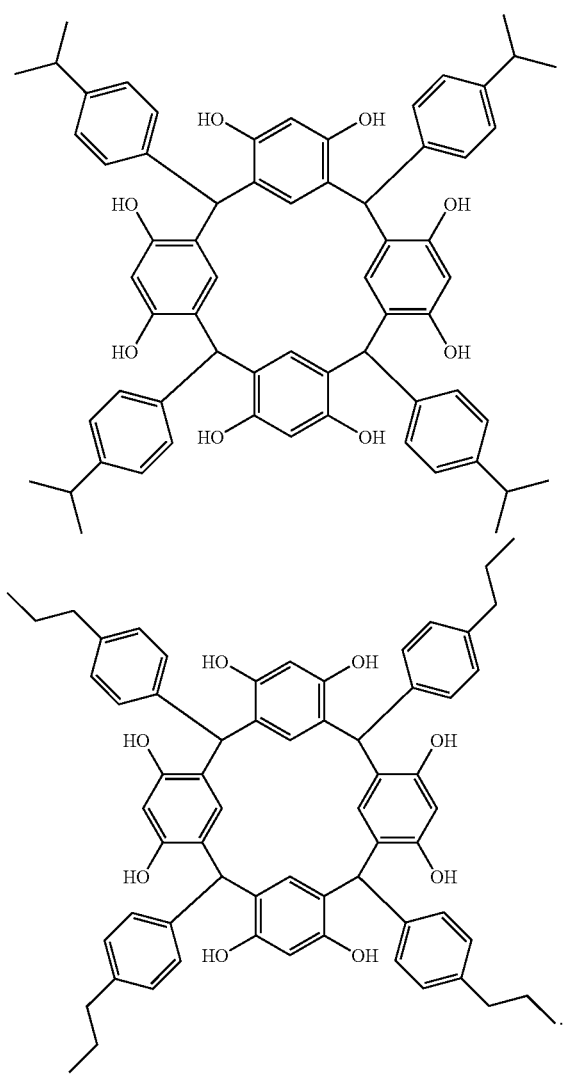
(39)

Also, the cyclic compound (A) is preferably represented by the following formula (40), and more preferably by the following formula (41):

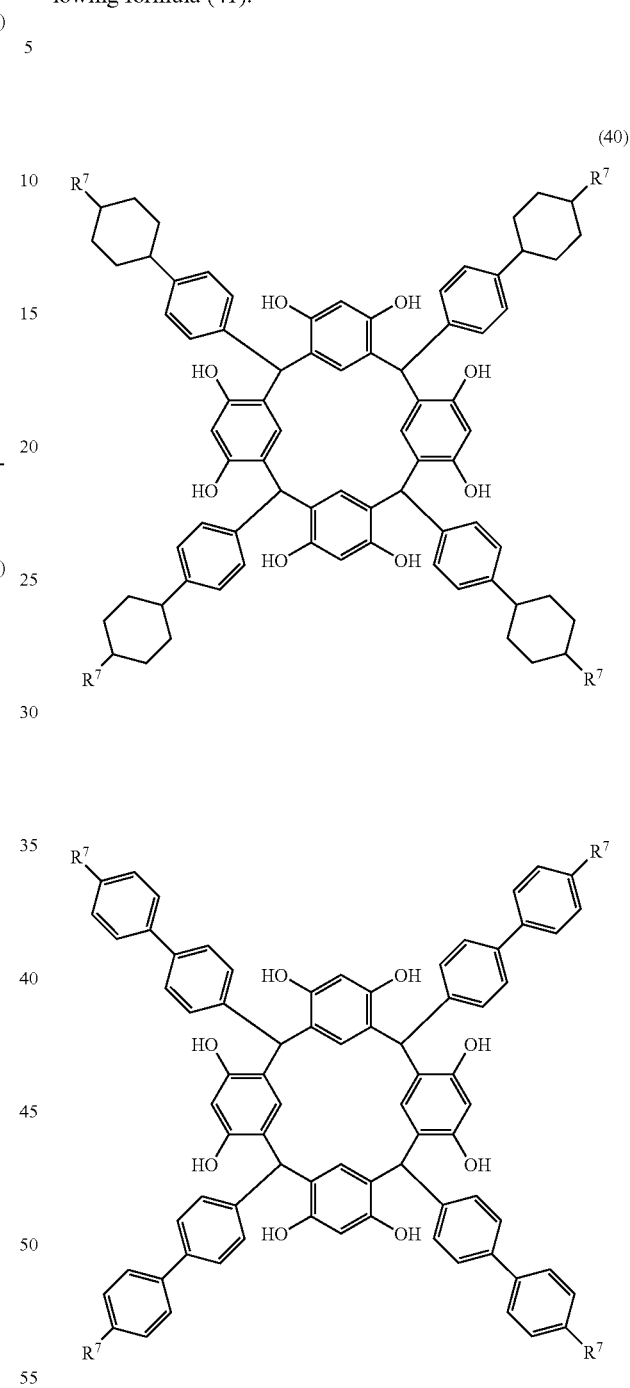
(40)

wherein $R^7$ is independently hydrogen atom, a linear alkyl group having 1 to 12 carbon atoms, a halogen atom, cyano group, hydroxyl group, an alkoxyl group or an ester group, and (41)

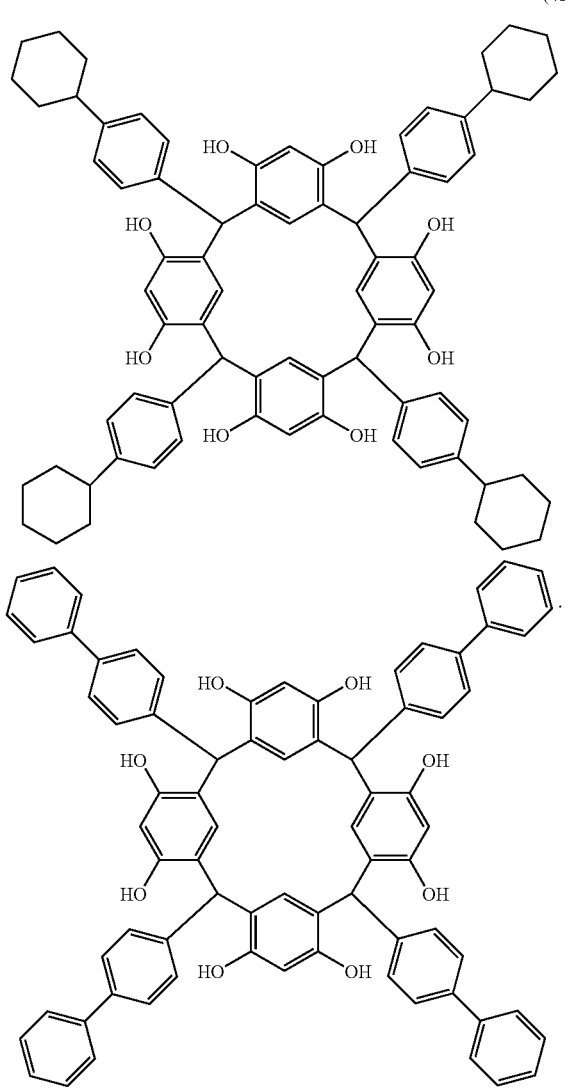

In the above formulae, the repeating unit represented by the following formula (42-1) may intervene between the hydrogen atom and the oxygen atom of the hydroxyl group or the hydrogen atom of the hydroxyl group may be replaced by the terminal group represented by the following formula (42-2):

(42-1)

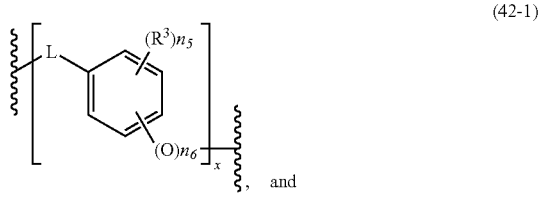, and (42-2)

In the formulae (42-1) and (42-2), L is a single bond, methylene group, ethylene group or carbonyl group. Plural L are the same or different. $n_5$ is an integer of 0 to 4 and $n_6$ is an integer of 1 to 3, satisfying $1 \leq n_5+n_6 \leq 5$. x is an integer of 0 to 3. Plural $n_5$, $n_6$ and x are the same or different, respectively. $R^3$ is a substituent selected from the group consisting of halogen atom, an alkyl group, a cycloalkyl group, an aryl group, an aralkyl group, an alkoxyl group, an aryloxy group, an alkenyl group, an acyl group, an alkoxycarbonyl group, an alkyloyloxy group, an aryloyloxy group, cyano group, and nitro group. The halogen atom may include fluorine atom, chlorine atom, bromine atom and iodine atom. The alkyl group has 1 to 4 carbon atoms and may include methyl group, ethyl group, propyl group, n-propyl group, n-butyl group, isobutyl group, sec-butyl group, and tert-butyl group. The cycloalkyl group may include cyclohexyl group, norbornyl group, and adamantyl group. The aryl group may include phenyl group, tolyl group, xylyl group, and naphthyl group. The aralkyl group may include benzyl group, hydroxybenzyl group, and dihydroxybenzyl group. The alkoxyl group has 1 to 4 carbon atoms and may include methoxy group, ethoxy group, hydroxyethoxy group, propoxy group, hydroxypropoxy group, isopropoxy group, n-butoxy group, isobutoxy group, sec-butoxy group, and tert-butoxy group. The aryloxy group may include phenoxy group. The alkenyl group has 2 to 4 carbon atoms and may include vinyl group, propenyl group, allyl group, and butenyl group. The acyl group may include an aliphatic acyl group having 1 to 6 carbon atoms such as formyl group, acetyl group, propionyl group, butyryl group, valeryl group, isovaleryl group, and pivaloyl group and an aromatic acyl group such as benzoyl group and toluoyl group. The alkoxycarbonyl group has 2 to 5 carbon atoms and may include methoxycarbonyl group, ethoxycarbonyl group, propoxycarbonyl group, isopropoxycarbonyl group, n-butoxycarbonyl group, isobutoxycarbonyl group, sec-butoxycarbonyl group, and tert-butoxycarbonyl group. The alkyloyloxy group may include acetoxy group, propionyloxy group, butyryloxy group, isobutyryloxy group, valeryloxy group, isovaleryloxy group, and pivaloyloxy group. The aryloyloxy group may include benzoyloxy group. Plural $R^3$ are the same or different.

In the cyclic compound (A), the ratio of the number of halogen atoms to the total number of constituent atoms is preferably 0.1 to 60%, more preferably 0.1 to 40%, still more preferably 0.1 to 20%, particularly preferably 0.1 to 10%, and most preferably 1 to 5%. Within the above ranges, the film-forming properties can be maintained while increasing the sensitivity to radiation. In addition, the solubility in safety solvents is increased.

The ratio of the number of nitrogen atoms to the total number of constituent atoms is preferably 0.1 to 40%, more preferably 0.1 to 20%, still more preferably 0.1 to 10%, and particularly preferably 0.1 to 5%. Within the above ranges, the line edge roughness of the resist pattern to be obtained is reduced. The nitrogen atom constituting a secondary or tertiary amine is preferred and the nitrogen atom constituting a tertiary amine is more preferred.

The cyclic compound (A) is made into an amorphous film by spin coating and can be applied to a general semiconductor production process.

The dissolving speed of the amorphous film of the cyclic compound (A) at 23° C. in a 2.38 mass % aqueous solution of tetramethylammonium hydroxide (TMAH) is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. This may be because that the contrast at the interface between the non-exposed portion soluble in an alkali developing solution and the exposed portion insoluble in an alkali developing solution is enhanced by the change of solubility before and after exposing the cyclic compound (A) to radiation. In addition, LER and the number of defects are reduced.

The solid component of the radiation-sensitive composition is formed into an amorphous film by spin coating. The dissolving speed of the amorphous film in a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. This may be because that the contrast at the interface between the non-exposed portion soluble in an alkali developing solution and the exposed portion insoluble in an alkali developing solution is enhanced by the change of solubility before and after exposing the cyclic compound (A) to radiation. In addition, LER and the number of defects are reduced.

After exposing an amorphous film formed by spin-coating the solid component of the radiation-sensitive composition to radiation such as KrF excimer lasers, extreme ultraviolet rays, electron beams and X-rays, the dissolving speed of the exposed area in a 2.38 mass % aqueous solution of TMAH at 23° C. is preferably 5 Å/sec or less, more preferably 0.05 to 5 Å/sec, and still more preferably 0.0005 to 5 Å/sec. If being 5 Å/sec or less, the exposed area is insoluble in an alkali developing solution to form a resist. If being 0.0005 Å/sec or more, the resolution may be improved in some cases. This may be because that the micro surface of the cyclic compound (A) is dissolved to reduce LER. In addition, the number of defects is reduced.

The radiation-sensitive composition of the invention comprises preferably 1 to 80% by weight of the solid component and 20 to 99% by weight of the solvent, more preferably 1 to 50% by weight of the solid component and the 50 to 99% by weight of the solvent, still more preferably 2 to 40% by weight of the solid component and 60 to 98% by weight of the solvent, and particularly preferably 2 to 10% by weight of the solid component and 90 to 98% by weight of the solvent. The content of the cyclic polyphenol compound (A) is 50% by weight or more, preferably 65% by weight or more, and more preferably 81% by weight or more, each based on the total weight of the solid component. Within the above ranges, a high resolution is obtained and the line edge roughness is reduced.

The composition of the invention preferably contains at least one kind of acid generator (C) which generates an acid directly or indirectly by the irradiation with radiation which is selected from visible lights, ultraviolet rays, excimer lasers, electron beams, extreme ultraviolet rays (EUV), X-rays, and ion beams. The amount of the acid generator (C) to be used is preferably 0.001 to 50% by weight, more preferably 1 to 40% by weight, and still more preferably 3 to 30% by weight based on the total weight of the solid component (total of the cyclic polyphenol compound (A) and the optional solid component such as the acid generator (C), acid crosslinking agent (G), acid-diffusion controller (E) and other components (F), the same being applied below). Within the above ranges, a high sensitivity and a pattern profile with a small line edge roughness is obtained. In the present invention, the acid can be generated by any method as long as the acid is suitably generated within the system. The use of excimer lasers in place of ultraviolet rays such as g-rays and i-rays enables a finer processing. If high-energy rays such as electron beams, extreme ultraviolet rays, X-rays and ion beams are used, the resist composition can be still more finely processed.

The acid generator (C) is selected from those described above with respect to the radiation-sensitive composition A.

The radiation-sensitive composition of the present invention preferably contains at least one kind of the acid crosslinking agent (G). The acid crosslinking agent (G) referred to herein is a compound capable of crosslinking the cyclic compound (A) intramolecularly or intermolecularly in the presence of the acid generated from the acid generator (C). The acid crosslinking agent (G) may include, for example, a compound having at least one group crosslinkable to the cyclic compound (A) (crosslinkable group).

Examples of the crosslinkable groups include (i) a hydroxyalkyl group or a group derived therefrom such as a hydroxy(C1-C6 alkyl) group, a C1-C6 alkoxy(C1-C6 alkyl) group, and an acetoxy(C1-C6 alkyl) group; (ii) a carbonyl group or a group derived therefrom such as formyl group and a carboxy(C1-C6 alkyl) group; (iii) a group having a nitrogen-containing group such as dimethylaminomethyl group, diethylaminomethyl group, dimethylolaminomethyl group, diethylolaminomethyl group, and morpholinomethyl group; (iv) a group having a glycidyl group such as glycidyl ether group, glycidyl ester group, and glycidylamino group; (v) a group derived from an aromatic group, for example, a C1-C6 aryloxy(C1-C6 alkyl) group and a C1-C6 aralkyloxy(C1-C6 alkyl) group such as benzyloxymethyl group and benzoyloxymethyl group; and (vi) a group having a polymerizable multiple bond such as vinyl group and isopropenyl group. The crosslinkable group of the acid crosslinking agent (G) is preferably the hydroxyalkyl group and the alkoxyalkyl group and particularly preferably the alkoxymethyl group.

Examples of the acid crosslinking agent (G) having the crosslinkable group include (i) a methylol group-containing compound such as a methylol group-containing melamine compound, a methylol group-containing benzoguanamine compound, a methylol group-containing urea compound, a methylol group-containing glycoluril compound, and a methylol group-containing phenol compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluril compound, and an alkoxyalkyl group-containing phenol compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluril compound, and a carboxymethyl group-containing phenol compound; and (iv) an epoxy compound such as a bisphenol A-based epoxy compound, a bisphenol F-based epoxy compound, a bisphenol S-based epoxy compound, a novolak resin-based epoxy compound, a resol resin-based epoxy compound, and a poly(hydroxystyrene)-based epoxy compound.

Other examples of the acid crosslinking agent (G) include a crosslinkable compound or resin which is obtained by introducing the crosslinkable group into the acidic functional group of a compound having a phenolic hydroxyl group or an alkali-soluble resin. The crosslinkable group is introduced in an amount of generally 5 to 100 mol %, preferably 10 to 60 mol %, and still more preferably 15 to 40 mol %, each based on the total acidic functional groups of the compound having a phenolic hydroxyl group and the alkali-soluble resin. Within the above range, the crosslinking reaction proceeds sufficiently, the percentage film remaining is reduced, and the swelling and serpentine of patterns are prevented.

The acid crosslinking agent (G) preferred for the radiation-sensitive composition is an alkoxyalkylated urea compound or its resin or an alkoxyalkylated glycoluril compound or its resin. Particularly preferred as the acid crosslinking agents (G) are the compound represented by the following formula (43) and an alkoxymethylated melamine compound (acid crosslinking agent (G1)).

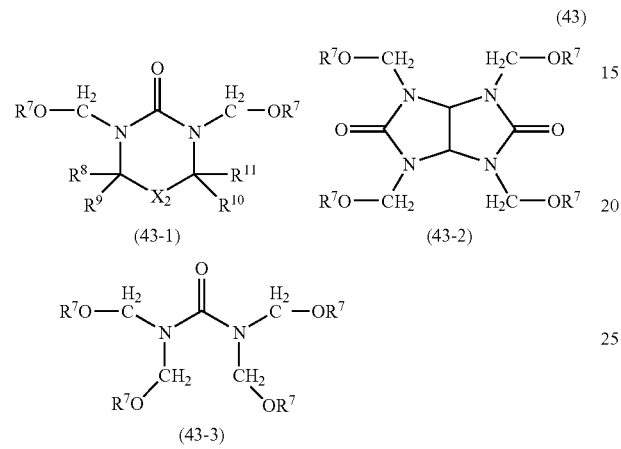

In the formula (43), $R^7$ is independently hydrogen atom, an alkyl group or an acyl group; $R^8$ to $R^{11}$ are each independently hydrogen atom, hydroxyl group, an alkyl group, or an alkoxyl group; and $X^2$ is a single bond, methylene group, or oxygen atom.

In the formula (43), $R^7$ is preferably hydrogen atom, an alkyl group having 1 to 6 carbon atoms or an acyl group having 2 to 6 carbon atoms. An alkyl group having 1 to 3 carbon atoms such as methyl group, ethyl group, and propyl group is more preferred. An acyl group having 2 to 4 carbon atoms such as acetyl group and propionyl group is more preferred. $R^8$ to $R^{11}$ are each preferably hydrogen atom, hydroxyl group, an alkyl group having 1 to 6 carbon atoms, and an alkoxyl group having 1 to 6 carbon atoms. An alkyl group having 1 to 3 carbon atoms such as methyl group, ethyl group, and propyl group is more preferred. An alkoxyl group having 1 to 3 carbon atoms such as methoxy group, ethoxy group, and propoxy group is more preferred. $X^2$ is a single bond, methylene group or oxygen, and preferably a single bond or methylene group. The groups representing $R^7$ to $R^{11}$ and $X^2$ may be substituted by an alkyl group such as methyl group and ethyl group, an alkoxyl group such as methoxy group and ethoxy group, hydroxyl group, or a halogen atom. Plural $R^7$, $R^8$ to $R^{11}$ are the same or different, respectively.

Examples of the compound of the formula (43-1) include the following compounds.

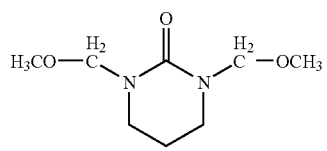

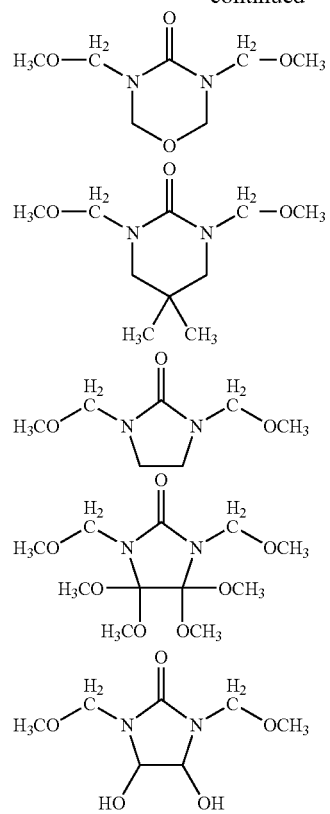

Examples of the compound of the formula (43-2) include N,N,N,N-tetra(methoxymethyl)glycoluril, N,N,N,N-tetra(ethoxymethyl)glycoluril, N,N,N,N-tetra(n-propoxymethyl)glycoluril, N,N,N,N-tetra(isopropoxymethyl)glycoluril, N,N,N,N-tetra(n-butoxymethyl)glycoluril, and N,N,N,N-tetra(t-butoxymethyl)glycoluril, with N,N,N,N-tetra(methoxymethyl)glycoluril being particularly preferred.

Examples of the compound of the formula (43-3) include the following compounds.

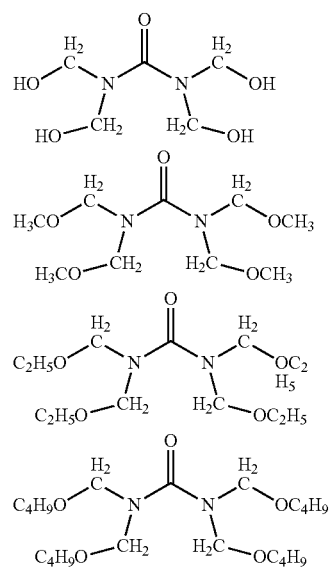

-continued

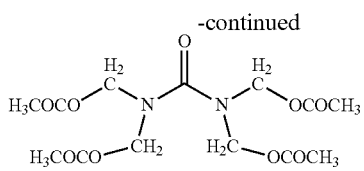

Examples of the alkoxymethylated melamine compound include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine, with N,N,N,N,N,N-hexa(methoxymethyl)melamine being particularly preferred.

The acid crosslinking agent (G1) is produced as follows. First, a methylol group is introduced into a urea compound or a glycoluril compound by the condensation reaction with formalin. The obtained product is then etherified by a lower alcohol such as methyl alcohol, ethyl alcohol, propyl alcohol, and butyl alcohol. After cooling the reaction product liquid, the precipitated compound or resin is recovered. Also, the acid crosslinking agent (G1) is commercially available under tradename of Cymel (manufactured by Mitsui Cyanamid, Inc.) and Nikalac (manufactured by Sanwa Chemical Co., Ltd.).

Another preferred acid crosslinking agent (G) is a phenol derivative (acid crosslinking agent (G2)) having in its molecule 1 to 6 benzene rings and two or more hydroxyalkyl group and/or alkoxyalkyl group in total which are bonded to any of the benzene rings. Preferred is a phenol derivative having a molecular weight of 1500 or less and having in its molecule 1 to 6 benzene rings and two or more hydroxyalkyl group and/or alkoxyalkyl group in total which are bonded to any one or more of the benzene rings.

Preferred examples of the hydroxyalkyl group to be bonded to the benzene ring include those having 1 to 6 carbon atoms such as hydroxymethyl group, 2-hydroxyethyl group, and 2-hydroxyl-propyl group. Preferred examples of the alkoxyalkyl group to be bonded to the benzene ring include those having 2 to 6 carbon atoms such as methoxymethyl group, ethoxymethyl group, n-propoxymethyl group, isopropoxymethyl group, n-butoxymethyl group, isobutoxymethyl group, sec-butoxymethyl group, t-butoxymethyl group, 2-methoxyethyl group, and 2-methoxy-1-propyl group.

Particularly preferred phenol derivatives are listed below.

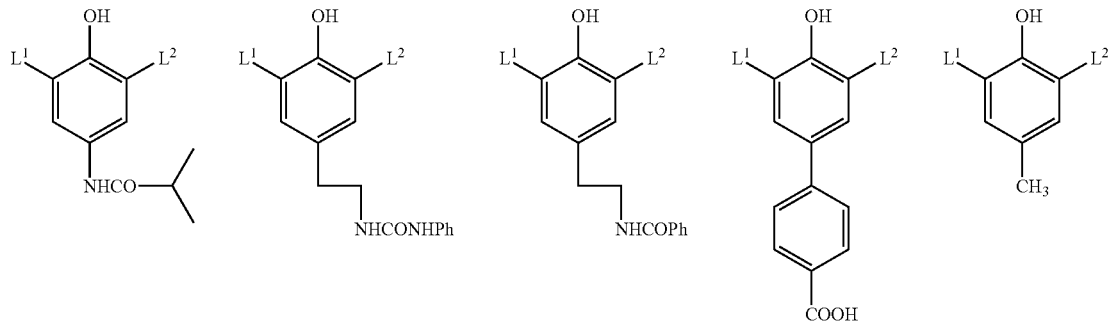

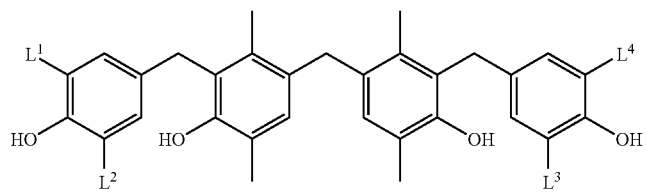

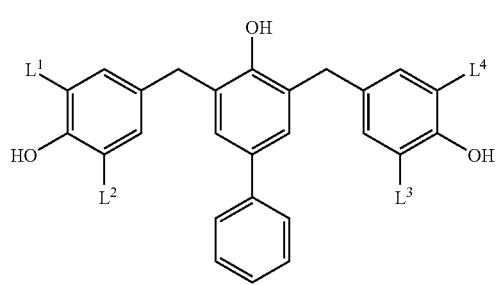

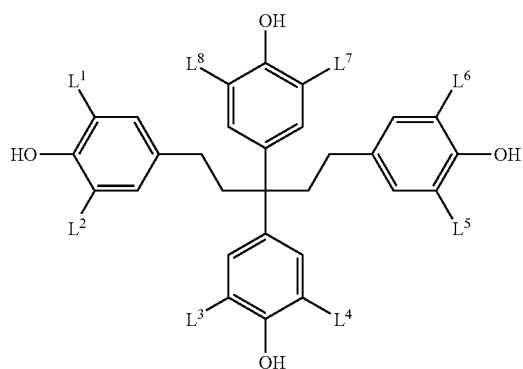

-continued
81
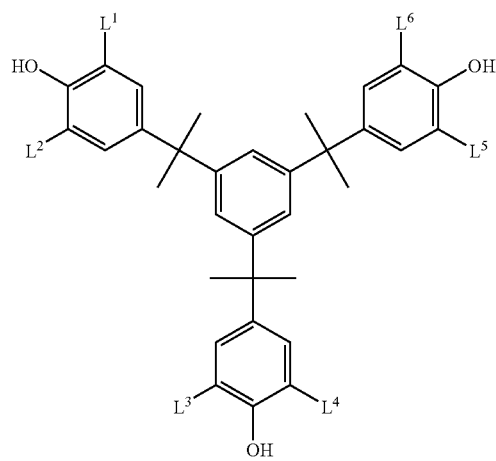
82
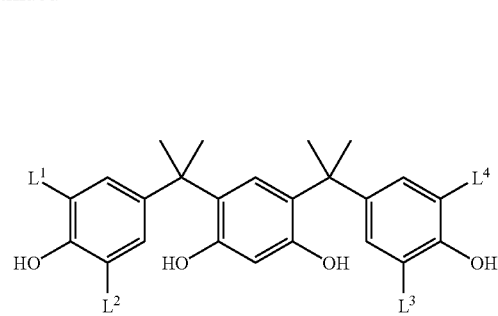
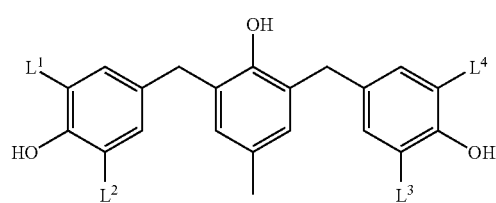
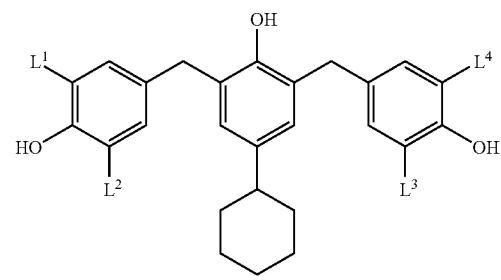
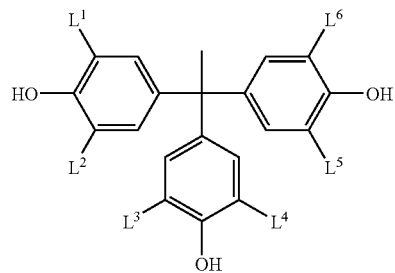
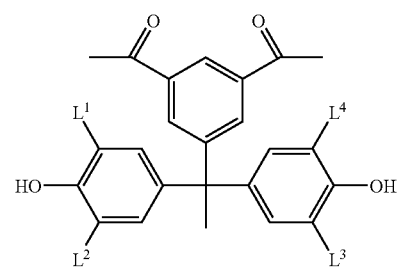
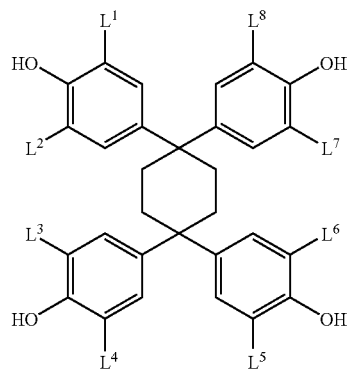
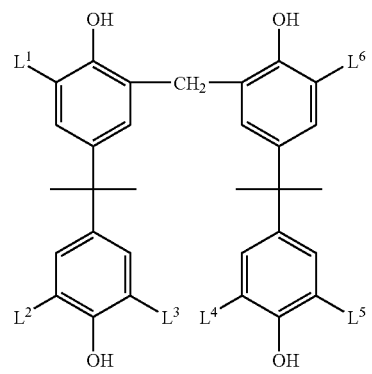
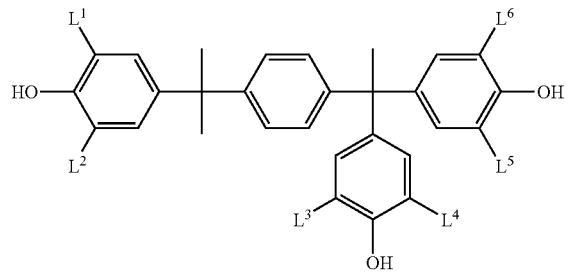
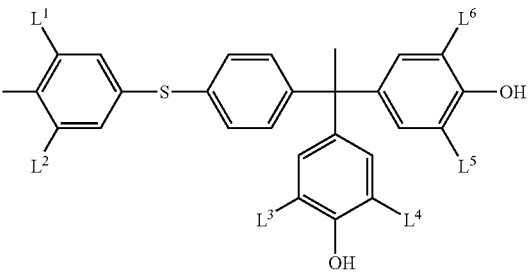

-continued
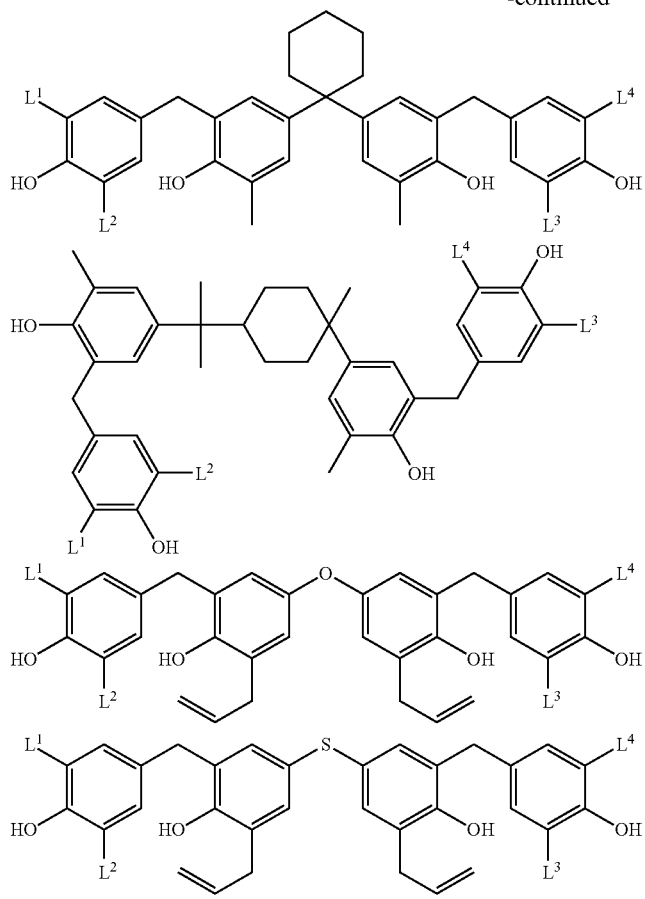
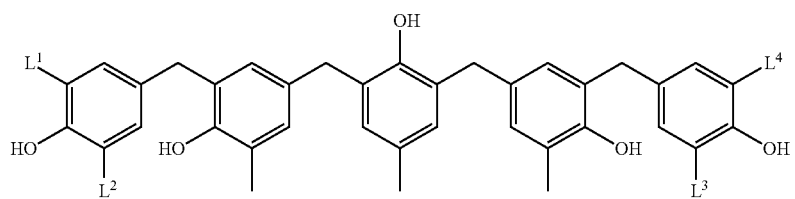
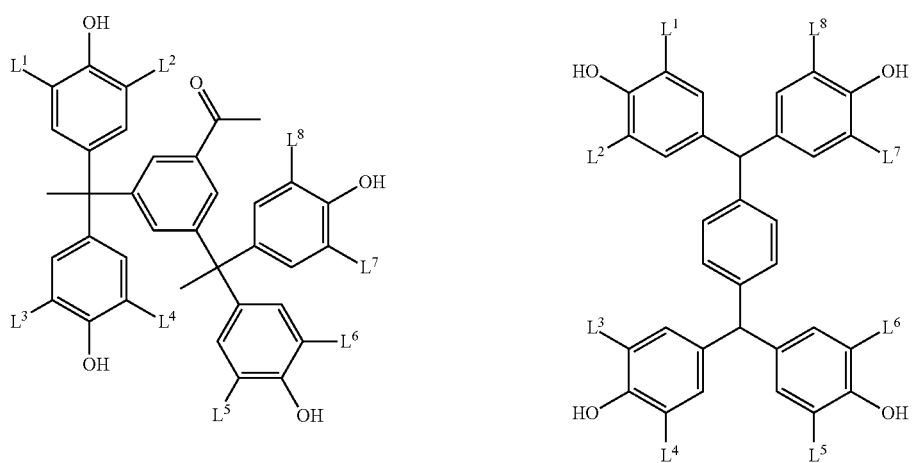

In the above formulae, $L^1$ to $L^8$ are the same or different and each independently hydroxymethyl group, methoxymethyl group or ethoxymethyl group. The phenol derivative having a hydroxymethyl group is produced by the reaction of a corresponding phenol compound having no hydroxymethyl group (compound of the above formulae in which $L^1$ to $L^8$ are each hydrogen atom) with formaldehyde in the presence of a basic catalyst. The reaction is preferably performed at 60° C. or lower to prevent the product from being made resinous or gelated. For example, the phenol derivative is produced by a method described in JP 6-282067A or JP 7-64285A.

The phenol derivative having an alkoxymethyl group is produced by the reaction of a corresponding phenol derivative having hydroxymethyl group and an alcohol in the presence of an acid catalyst. The reaction is preferably performed at 100° C. or lower to prevent the product from being made resinous or gelated. For example, the phenol derivative is produced by a method described in EP 632003A1.

The phenol derivative having hydroxymethyl group and/or an alkoxymethyl group produced in the above manner is excellent in the storage stability, and the phenol derivative having an alkoxymethyl groups is particularly preferred in view of the storage stability. The acid crosslinking agent (G2) may be used alone or in combination of two or more.

Still another preferred acid crosslinking agent (G) (acid crosslinking agent (G3)) is a compound having at least one α-hydroxyisopropyl group. The structure of such compounds is not specifically limited as far as the compounds have α-hydroxyisopropyl group. The hydrogen atom in the hydroxyl group of α-hydroxyisopropyl group may be replaced by at least one acid-dissociating group such as R—COO— and R—SO$_2$— wherein R is a group selected from the group consisting of a linear hydrocarbon group having 1 to 12 carbon atoms, a cyclic hydrocarbon group having 3 to 12 carbon atoms, an alkoxy group having 1 to 12 carbon atoms, a 1-branched alkyl group having 3 to 12 carbon atoms, and an aromatic hydrocarbon group having 6 to 12 carbon atoms. Examples of the compound having α-hydroxyisopropyl group may be one or more kinds of compounds selected from aromatic compounds, diphenyl compounds, naphthalene compounds, and furan compounds, each being substituted or non-substituted and having at least one α-hydroxyisopropyl group. Specific examples thereof are the compound of the following formula (44-1) (benzene compound (1)), the compound of the formula (44-2) (diphenyl compound (2)), the compound of the formula (44-3) (naphthalene compound (3)), and the compound of the formula (44-4) (furan compound (4)).

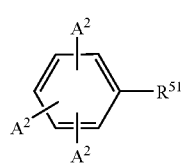

(44-1)

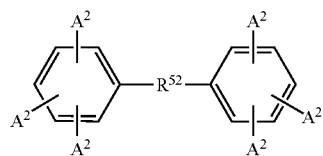

(44-2)

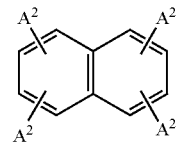

(44-3)

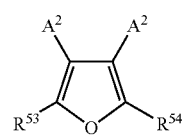

(44-4)

In the formulae (44-1) to (44-4), each $A^2$ is independently α-hydroxyisopropyl group or hydrogen atom, and at least one $A^2$ is α-hydroxyisopropyl group. In the formula (44-1), $R^{51}$ is hydrogen atom, hydroxyl group, a linear or branched alkylcarbonyl group having 2 to 6 carbon atoms, or a linear or branched alkoxycarbonyl group having 2 to 6 carbon atoms. In the formula (44-2), $R^{52}$ is a single bond, a linear or branched alkylene group having 1 to 5 carbon atoms, —O—, —CO—, or —COO—. In the formula (44-4), $R^{53}$ and $R^{54}$ are each independently hydrogen atom or a linear or branched alkyl group having 1 to 6 carbon atoms.

Examples of the benzene compound (1) include α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl n-propyl ketone, 4-α-hydroxyisopropylphenyl isopropyl ketone, 4-α-hydroxyisopropylphenyl n-butyl ketone, 4-α-hydroxyisopropylphenyl t-butyl ketone, 4-α-hydroxyisopropylphenyl n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; and alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Examples of the diphenyl compound (2) include α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6-tetrakis(α-hydroxyisopropyl)biphenyl, 2,4,4',6-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyl)diphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; and phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Examples of the naphthalene compound (3) include 1-(α-hydroxyisopropyl)naphthalene, 2-α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Examples of the furan compound (4) include 3-(α-hydroxyisopropyl)furan, 2-methyl-3-α-hydroxyisopropyl)furan, 2-methyl-4-α-hydroxyisopropyl)furan, 2-ethyl-4-α-hydroxyisopropyl)furan, 2-n-propyl-4-(α-hydroxyisopropyl)furan, 2-isopropyl-4-α-hydroxyisopropyl)furan, 2-n-butyl-4-α-hydroxyisopropyl)furan, 2-t-butyl-4-α-hydroxyisopropyl)furan, 2-n-pentyl-4-α-hydroxyisopropyl)furan, 2,5-dimethyl-3-α-hydroxyisopropyl)furan, 2,5-diethyl-3-α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

The acid crosslinking agent (G3) is preferably the compound having two or more free α-hydroxyisopropyl groups, more preferably the benzene compound (1) having two or more α-hydroxyisopropyl groups, the diphenyl compound (2) having two or more α-hydroxyisopropyl groups or the naphthalene compound (3) having two or more α-hydroxyisopropyl groups, and particularly preferably the α-hydroxyisopropylbiphenyl compound having two or more α-hydroxyisopropyl groups or the naphthalene compound (3) having two or more α-hydroxyisopropyl groups.

The acid crosslinking agent (G2) is generally produced by a method in which an acetyl group-containing compound such as 1,3-diacetylbenzene is methylated by a Grignard reagent such as $CH_3MgBr$ and then hydrolyzed, or a method in which an isopropyl group-containing compound such as 1,3-diisopropylbenzene is converted into a peroxide by the oxidation by oxygen, etc. and then the peroxide is reduced.

The blending ratio of the acid crosslinking agent (G) is 0.5 to 70 parts by weight, preferably 0.5 to 40 parts by weight, and still more preferably 1 to 30 parts by weight, each based on 100 parts by weight of the cyclic compound (A). A blending ratio of 0.5 parts by weight or more is preferred because the effect of controlling the solubility of the resist film in an alkali developing solution is enhanced, to prevent the reduction of film residue and prevent the patterns from being swelled and made serpentine. If the blending ratio is 70 parts by weight or less, the reduction of the resist in the heat resistance is preferably prevented.

The blending ratio of at least one compound selected from the acid crosslinking agent (G1), acid crosslinking agent (G2), and acid crosslinking agent (G3) in the acid crosslinking agent (G) is not limited, and suitably determined according to the kind of substrate to be used in the formation of resist patterns.

The content of the alkoxymethylated melamine compound and/or the compounds of the formulae (43-1) to (43-3) in the total acid crosslinking agent component is 50 to 99% by weight, preferably 60 to 99% by weight, more preferably 70 to 98% by weight, and still more preferably 80 to 97% by weight. If being 50% by weight or more, the resolution is preferably improved. If being 99% by weight or less, the cross section of the patterns is easily made into a rectangular shape.

The radiation-sensitive composition may contain the acid-diffusion controller (E) which prevents the undesirable chemical reactions in the unexposed areas by controlling the diffusion of the acid, which is generated from the acid generator upon the irradiation of radiation, throughout the resist film. Using the acid-diffusion controller (E), the storage stability of the radiation-sensitive composition is improved. In addition, the resolution is improved and the change of line width of resist patterns due to the change in the process time-delay before the irradiation of electron beams and the change in the process time-delay after the irradiation of electron beams is prevented, to ensure the stable production. Examples of the acid-diffusion controller (E) include basic compounds decomposable by the irradiation of electron beams such as nitrogen-containing basic compounds, basic sulfonium compounds, and basic iodonium compounds. The acid-diffusion controller may be used alone or in combination of two or more. Specific examples thereof are mentioned above with respect to the radiation-sensitive composition A.

The blending amount of the acid-diffusion controller (E) is preferably 0.001 to 10% by weight, more preferably 0.001 to 5% by weight, and still more preferably 0.001 to 3% by weight, each based on the total weight of the solid component. Within the above ranges, the lowering of resolution and the deterioration of pattern profiles and dimension accuracy are prevented. In addition, the unfavorable change of the upper profile of pattern is prevented even if the process-time delay between the irradiation of radiation and the post-irradiation heating is prolonged. If being 10% by weight or less, the sensitivity and developability of the unexposed area can be prevented from being reduced. Further, the use of the acid-diffusion controller improves the storage stability of the radiation-sensitive composition, improves the sensitivity, and prevents the change of line width of resist patterns due to the change in the process-time delay before the irradiation of electron beams and the change in the process-time delay after the irradiation of electron beams, to ensure the stable production.

The radiation-sensitive composition of the invention may contain, if necessary, one or more kinds of other component (F), for example, additives such as a dissolution promoter, a solubility controller, a sensitizer, a surfactant, an organic carboxylic acid and its derivatives, and a phosphorus-containing oxoacid and its derivatives, as long as the effect of the invention is not adversely affected.

Low Molecular Weight Dissolution Promoter

The low molecular weight dissolution promoter is a compound for adequately increasing the dissolving speed of the cyclic compound (A) in an alkali or other developing solutions by increasing its solubility in the developing solutions, if the solubility is excessively low. The low molecular weight dissolution promoter may be used in an amount which does not adversely affect the effects of the present invention. Examples of the dissolution promoter include a low-molecular weight phenol compound such as bisphenol and tris(hydroxyphenyl)methane. The dissolution promoter may be used singly or in combination of two or more.

The blending amount of the dissolution promoter varies depending upon the kind of the cyclic compound (A) to be used. The total of the cyclic compound (A) and the low molecular weight dissolution promoter is 50 to 99.999% by weight, preferably 60 to 99% by weight, more preferably 70 to 99% by weight, and still more preferably 80 to 99% by weight, each base on the total weight of the solid component.

The additives such as the solubility controller, sensitizer, surfactant, organic carboxylic acid, phosphorus-containing oxoacid and derivatives thereof are as mentioned above with respect to the radiation-sensitive composition A.

In the radiation-sensitive composition, the blending ratio (cyclic compound (A)/acid generator (C)/acid crosslinking agent (G)/acid-diffusion controller (E)/optional component (F)) is, when expressed by weight percentages based on solid, preferably 3-96.9/0.1-30/3-65/0.01-30/0-93.9, more preferably 65-96.9/0.1-30/0.3-34.9/0.01-30/0-30, still more preferably 65-96.9/0.1-30/0.3-34.9/0.01-30/0-10, particularly preferably 65-96.9/0.1-30/0.6-34.9/0.01-30/0-5, and most preferably 65-96.9/0.1-30/0.6-30/0.01-30/0. With the above ratio, the sensitivity, resolution and alkali developability are good.

If the optional component (F) is not contained, the proportion of the solid components in the radiation-sensitive composition is preferably (A): 3 to 96.9% by weight, (C): 0.1 to 30% by weight, (G): 0.3 to 96.9% by weight, and (E): 0.01 to 30% by weight ((A)+(C)+(G)+(E)=100% by weight), more preferably (A): 65 to 96.9% by weight, (C): 0.1 to 32% by weight, (G): 0.3 to 34.9% by weight, and (E): 0.01 to 30% by weight ((A)+(C)+(G)+(E)=100% by weight), still more preferably (A): 70 to 96.9% by weight, (C): 0.1 to 27% by weight, (G): 3.0 to 29.9% by weight, and (E): 0.01 to 30% by weight ((A)+(C)+(G)+(E)=100% by weight), particularly preferably (A): 80 to 96.9% by weight, (C): 0.1 to 17% by weight, (G): 3.0 to 19.9% by weight, and (E): 0.01 to 30% by weight ((A)+(C)+(G)+(E)=100% by weight), and most preferably (A): 90 to 96.9% by weight, (C): 0.1 to 7% by weight, (G): 3.0 to 9.9% by weight, and (E): 0.01 to 30% by weight ((A)+(C)+(G)+(E)=100% by weight). Within the above ranges, the sensitivity, resolution and alkali developability are good.

The radiation-sensitive composition is prepared just before use by dissolving the components in a solvent into a uniform solution and, if necessary, filtering the solution through a filter with about 0.2 µm pore size.

The solvent for use in the preparation of the radiation-sensitive composition is selected from those mentioned above with respect to the radiation-sensitive composition A.

The radiation-sensitive composition may contain a resin soluble in an aqueous alkali solution, as long as the effect of the invention is not adversely affected. Examples of the resin soluble in an aqueous alkali solution include novolak resins, polyvinylphenols, polyacrylic acid, polyvinyl alcohol, styrene-maleic anhydride resins, polymers containing the monomer units derived from acrylic acid, vinyl alcohol or vinylphenol, and their derivatives. The blending amount of the resin soluble in an aqueous alkali solution varies depending upon the kind of the resist compound to be used, and preferably 30 parts by weight or less, more preferably 10 parts by weight or less, still more preferably 5 parts by weight or less, and particularly preferably 0 part by weight, each based on 100 parts by weight the cyclic polyphenol compound (A).

Composition for Under Coat Film D and Under Coat Film

The present invention further relates to a composition for under coat film containing any of the radiation-sensitive compositions C described above.

The present invention still further relates to a composition for under coat film containing the cyclic compound represented by the following formula (45):

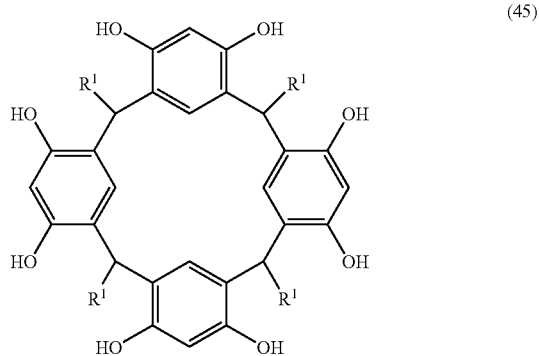

wherein $R^1$ is independently a linear, branched or cyclic alkyl group having 1 to 20 carbon atoms, an aryl group having 6 to 24 carbon atoms, allyl group, a hydroxyalkyl group, a cyanoalkyl group, a haloalkyl group, a hydroxyaryl group, a cyanoaryl group, or a haloaryl group.

The above cyclic compound is highly heat-resistant because of its glass transition point as high as 200° C. or higher, excellent in the film-forming properties because of its amorphous nature, and less sublimable. Although having benzene structures, the above cyclic compound surprisingly has a relatively low extinction coefficient for light at a wavelength of 193 nm and a high refractive index.

In addition, the above cyclic compounds are practically very advantageous because the compounds can be produced in high yields by a condensation reaction with elimination of water in the presence of a non-metallic catalyst such as hydrochloric acid while using various kinds of aldehydes such as aromatic aldehydes and phenols such as resorcinol and pyrogallol as the starting materials, each being industrially produced and easily available.

Further, the above cyclic compounds are sparingly soluble in propylene glycol monomethyl ether acetate (PGMEA) which is generally used as a resist solvent but soluble in propylene glycol monomethyl ether (PGME) and cyclohexanone, and therefore, the intermixing is prevented during the production of a multi-layered resist.

Examples of $R^1$ in the formula (45) include a linear, branched or cyclic alkyl group having 1 to 20 carbon atoms such as methyl group, ethyl group, propyl group, butyl group, pentyl group, hexyl group, heptyl group, octyl group, nonyl group, decanyl group, cyclohexylethyl, and cyclohexylpropyl; a linear, branched or cyclic hydroxyalkyl group having 1 to 20 carbon atoms such as hydroxymethyl group, hydroxyethyl group, hydroxypropyl group, hydroxybutyl group, hydroxypentyl group, hydroxyhexyl group, hydroxyheptyl group, hydroxyoctyl group, hydroxynonyl group, hydroxydecanyl group, hydroxycyclohexylethyl, and hydroxycyclohexylpropyl; a linear, branched or cyclic cyanoalkyl group having 1 to 20 carbon atoms such as cyanomethyl group, cyanoethyl group, cyanopropyl group, cyanobutyl group, cyanopentyl group, cyanohexyl group, cyanoheptyl group, cyanooctyl group, cyanononyl group, cyanodecanyl group, cyanocyclohexylethyl, and cyanocyclohexylpropyl; a linear, branched or cyclic haloalkyl group having 1 to 20 carbon atoms such as halomethyl group, haloethyl group, halopropyl group, halobutyl group, halopentyl group, halohexyl group, haloheptyl group, halooctyl group, halononyl group, halodecanyl group, halocyclohexylethyl, and halocyclohexylpropyl; an aryl group having 6 to 20 carbon atoms such as phenyl group, naphthyl group, indanyl group, indenyl group, fluorenyl group, anthracenyl group, phenanthrenyl group, pyrenyl group, biphenyl group, terphenyl group, tolyl group, ethylphenyl group, isopropylphenyl group, n-propylphenyl group, isobutylphenyl group, t-butylphenyl group, biphenyl group, 4-cyclohexylphenyl group, 4-propyl-4-cyclohexylphenyl group, 4-butyl-4-cyclohexylphenyl group, 4-pentyl-4-cyclohexylphenyl group, 4-salicylphenyl group, 4-norbornylphenyl group, 4-adamantylphenyl group, 4-dicyclopentadienylphenyl group, and 4-tricyclopentylphenyl group; a cyanoaryl group such as 4-cyanophenyl group and 4-cyanobiphenyl group; a haloaryl group such as 4-halophenyl group and 4-halobiphenyl group; and a hydroxyaryl group such as 4-hydroxyphenyl group.

Particularly preferred are the aryl group having 6 to 24 carbon atoms, the hydroxyaryl group, the cyanoaryl group, and the haloaryl group.

The cyclic compound of the invention may be a cis-isomer, a trans-isomer or a mixture thereof. The cyclic compound of only one of the cis-isomer and the trans-isomer may be obtained by a known method, for example, the separation by column chromatography and preparative liquid chromatography and the optimization of the reaction solvent, reaction temperature, etc.

The cyclic compound contained in the composition for under coat film is preferably represented by the following formula (46):

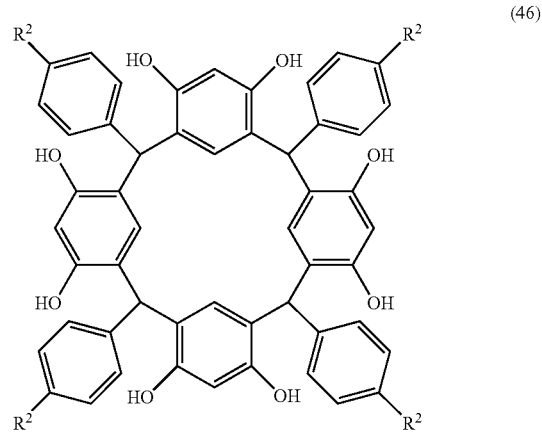

wherein $R^2$ is independently hydrogen atom, a linear, branched or cyclic alkyl group having 1 to 12 carbon atoms, a halogen atom, cyano group, hydroxyl group, an alkoxyl group, or an ester group.

The cyclic compound having the structure represented by the formula (46) can be made into a novolak resin by the reaction with an aldehyde compound such as formalin and acetaldehyde, thereby further enhancing the etching resistance. In addition, the intermixing is prevented without using a relatively expensive crosslinking agent or photo acid generator.

$R^2$ in the formula (46) is a linear, branched or cyclic alkyl group having 1 to 12 carbon atoms such as methyl group, ethyl group, propyl group, isopropyl group, butyl group, isobutyl group, t-butyl group, pentyl group, hexyl group, heptyl group, octyl group, nonyl group, decanyl group, cyclohexyl group, 4-methylcyclohexyl group, 4-ethylcyclohexyl group, 4-n-propylcyclohexyl group, 4-n-butylcyclohexyl group, 4-n-pentylcyclohexyl group, 4-n-hexylcyclohexyl group, bicyclohexyl group, norbornyl group, norbornenyl group, cyclopentanyl group, tricyclopentanyl group, and adamantyl group; a halogen group such as fluoro group, chloro group, bromo group and iodo group; cyano group; hydroxyl group; an alkoxyl group such as methoxy group, ethoxy group, propoxy group, and isopropoxy group; and an ester group such as methyl ester group, ethyl ester group, propyl ester group, isopropyl ester group, butyl ester group, and isobutyl ester group.

Particularly preferred is a linear, branched or cyclic alkyl group having 1 to 12 carbon atoms such as cyclohexyl group, 4-methylcyclohexyl group, 4-ethylcyclohexyl group, 4-n-propylcyclohexyl group, 4-n-butylcyclohexyl group, 4-n-pentylcyclohexyl group, 4-n-hexylcyclohexyl group, and norbornyl group, because a high refractive index and a moderate extinction coefficient to 193 nm light are obtained.

The cyclic compound contained in the composition for under coat film is more preferably represented by the formula (2) or (3) mentioned above.

The cyclic compound of the formula (45) is produced by the condensation reaction of at least one compound selected from the group consisting of an aliphatic aldehyde having 1 to 20 carbon atoms and an aromatic aldehyde having 6 to 24 carbon atoms with a compound having a resorcinol structure.

Examples of the aliphatic aldehyde having 1 to 20 carbon atoms and the aromatic aldehyde having 6 to 24 carbon atoms include a linear or branched aliphatic aldehyde such as formaldehyde, actaldehyde, propanal, isopropanal, 1-butanal, isobutanal, 1-pentanal, isopentanal, neopentanal, 1-hexanal, isohexanal, 1-decanal, and 1-dodecanal; and an aromatic aldehyde such as benzaldehyde, tolylaldehyde, ethylbenzaldehyde, cuminaldehyde, n-propylbenzaldehyde, isobutylaldehyde, t-butylaldehyde, phenylbenzaldehyde, 4-cyclohexylbenzaldehyde, 4-propyl-4-cyclohexylbenzaldehyde, 4-butyl-4-cyclohexylbenzaldehyde, 4-pentyl-4-cyclohexylbenzaldehyde, 4-cyanobenzaldehyde, 4-halobenzaldehyde, 4-hydroxybenzaldehyde, 4-salicylbenzaldehyde, 4-norbornylbenzaldehyde, 4-adamantylbenzaldehyde, 4-dicyclopentadienylbenzaldehyde, 4-tricyclopentylbenzaldehyde, naphthaldehyde, phenanthrenealdehyde, anthraldehyde, and pyrenealdehyde.

Of the above, preferred are 4-propyl-4-cyclohexylbenzaldehyde and 4-pentyl-4-cyclohexylbenzaldehyde, and particularly preferred are 4-(trans-4-n-propylcyclohexyl)benzaldehyde and 4-(trans-4-n-pentylcyclohexyl)benzaldehyde.

The cyclic compound of the formula (45) may be produced by a known method. For example, 1 mol of a carbonyl compound such as aromatic aldehyde is allowed to react with 1 mol to excess of a phenolic compound such as phenol, o-cresol and resorcinol in an organic solvent such as toluene, methanol and ethanol in the presence of thioacetic acid or β-mercaptopropionic acid and an acid catalyst (hydrochloric acid, sulfuric acid or p-toluenesulfonic acid) at 60 to 150° C. for about 0.5 to 20 h. After the reaction, the reaction product solution is added with toluene, heated to 60 to 80° C., stirred for 0.5 to 2 h, and cooled to room temperature. Then, the precipitate is separated by filtration and dried, to obtain the cyclic compound.

The molecular weight of the cyclic compound is preferably 400 to 2000, more preferably 600 to 2000, and still more preferably 800 to 1500. Within the above ranges, a material for under coat film which is excellent in the film-forming properties and etching resistance and contains a minimized quantity of sublimable component is obtained.

The cyclic compound may be a cis-isomer, a trans-isomer or a mixture thereof.

The composition for under coat film may contain a resin having the repeating units shown below, which is obtained by the water-eliminating condensation reaction of the above cyclic compound with an aldehyde compound.

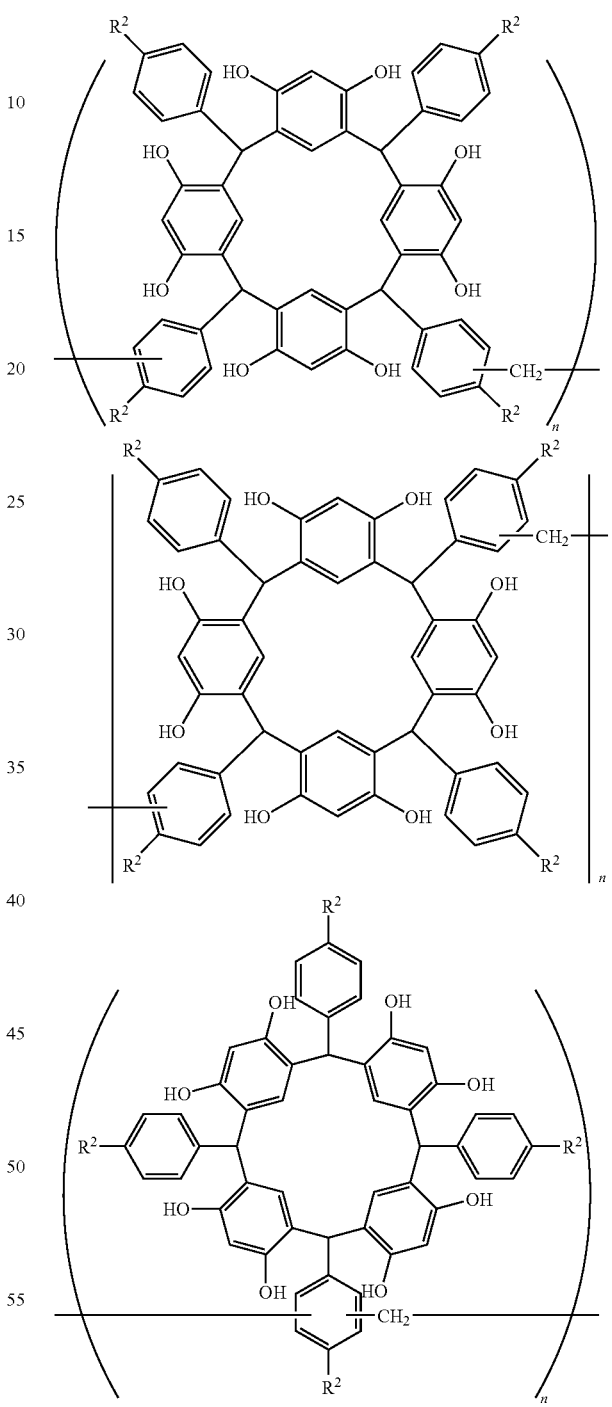

The aldehyde compound to be used may include formaldehyde, trioxane, paraformaldehyde, and acetaldehyde, with formaldehyde being particularly preferred.

The repeating units are not limited to those shown in the above formulae. Since the polyphenol compound is not sublimable, the polyphenol compound is allowed to remain unreacted. However, if Mw exceeds 50000, the spin coating becomes difficult in some cases because of an excessively large viscosity.

To prevent the intermixing, the composition for under coat film may contain a crosslinking agent (G) and an acid generator (C). Examples of the crosslinking agent include a melamine compound, a guanamine compound, a glycoluril compound and a urea compound, each being substituted by at least one group selected from the group consisting of methylol group, an alkoxymethyl group and an acyloxymethyl group. Other examples include an epoxy compound, a thioepoxy compound, an isocyanate compound, an azide compound, and a compound having a group containing a double bond such as an alkenyl ether group. These compounds may be used as additives or may be reacted with a polymer to introduce a crosslinkable pendant group. A compound having hydroxy group is also usable as the crosslinking agent.

Examples of the epoxy compound include tris(2,3-epoxypropyl) isocyanurate, trimethylolmethane triglycidyl ether, trimethylolpropane triglycidyl ether, and trimethylolethane triglycidyl ether. Examples of the melamine compound include hexamethylolmelamine, hexamethoxymethylmelamine, a compound obtained by methoxymethylating 1 to 6 methylol groups of hexamethylolmelamine or a mixture thereof, hexamethoxyethylmelamine, hexaacyloxymethylnelamine, and a compound obtained by acyloxymethylating 1 to 6 methylol groups of hexamethylolmelamine or a mixture thereof. Examples of the guanamine compound include tetramethylolguanamine, tetramethoxymethylguanamine, a compound obtained by methoxymethylating 1 to 4 methylol groups of tetramethylolguanamine or a mixture thereof, tetramethoxyethylguanamine, tetraacyloxyguanamine, and a compound obtained by acyloxymethylating 1 to 4 methylol groups of tetramethylolguanamine or a mixture thereof. Example of the glycoluril compound include tetramethylolglycoluril, tetramethoxyglycoluril, tetramethoxymethylglycoluril, a compound obtained by methoxymethylating 1 to 4 methylol groups of tetramethylolglycoluril or a mixture thereof, and a compound obtained by acyloxymethylating 1 to 4 methylol groups of tetramethylolglycoluril or a mixture thereof. Examples of the urea compound include tetramethylolurea, tetramethoxymethylurea, a compound obtained by methoxymethylating 1 to 4 methylol groups of tetramethylolurea or a mixture thereof, and tetramethoxyethylurea.

Examples of the compound having an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

The blending amount of the crosslinking agent (G) is preferably 5 to 50 parts (parts by mass, hereinafter the same being applied) and particularly preferably 10 to 40 parts. If being less than 5 parts, the mixing with the resist is likely to occur. If exceeding 50 parts, the anti-reflective effect is reduced and a film after crosslinking may crack.

To further promote the crosslinking reaction under heating, an acid generator (C) may be added. Any type of compounds which generate an acid by thermal decomposition or by irradiation with lights is usable as the acid generator (C).

Examples of the acid generator (C) usable in the present invention include
(1) an onium salt represented by the following formula (P1a-1), (P1a-2), (P1a-3) or (P1b);
(2) a diazomethane derivative represented by the following formula (P2);
(3) a glyoxime derivative represented by the following formula (P3);
(4) a bissulfone derivative represented by the following formula (P4);
(5) a sulfonic ester of a N-hydroxyimide compound represented by the following formula (P5);
(6) a β-ketosulfonic acid derivative,
(7) a disulfone derivative,
(8) a nitrobenzyl sulfonate derivative, and
(9) a sulfonic ester derivative.

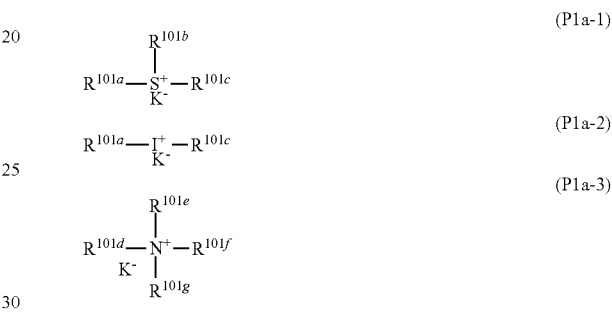

In the above formulae $R^{101a}$, $R^{101b}$ and $R^{101c}$ are each a linear, branched or cyclic alkyl group, alkenyl group, oxoalkyl group or oxoalkenyl group, each having 1 to 12 carbon atoms, an aryl group having 6 to 20 carbon atoms, or an aralkyl group or aryloxoalkyl group each having 7 to 12 carbon atoms. The hydrogen atom of these groups may be partially or completely substituted by an alkoxyl group, etc. $R^{101b}$ and $R^{101c}$ may complete a ring. When completing a ring, each of $R^{101b}$ and $R^{101c}$ is an alkylene group having 1 to 6 carbon atoms. $K^-$ is a non-nucleophilic counter ion. $R^{101d}$, $R^{101e}$, $R^{101f}$, and $R^{101g}$ are each hydrogen atom or a group selected from those as described with respect to $R^{101a}$, $R^{101b}$ and $R^{101c}$. $R^{101d}$ and $R^{101e}$, or $R^{101d}$, $R^{101e}$ and $R^{101f}$ may complete a ring. When completing a ring, each of $R^{101d}$ and $R^{101e}$, or each of $R^{101d}$, $R^{101e}$ and $R^{101f}$ is an alkylene group having 3 to 10 carbon atoms. The ring thus formed may be a nitrogen-containing aromatic ring.

$R^{101a}$, $R^{101b}$, $R^{101c}$, $R^{101d}$, $R^{101e}$, $R^{101f}$, and $R^{101g}$ are the same or different. Examples of the alkyl group include methyl group, ethyl group, propyl group, isopropyl group, n-butyl group, sec-butyl group, tert-butyl group, pentyl group, hexyl group, heptyl group, octyl group, cyclopentyl group, cyclohexyl group, cycloheptyl group, cyclopropylmethyl group, 4-methylcyclohexyl group, cyclohexylmethyl group, norbornyl group, and adamantyl group. Examples of the alkenyl group include vinyl group, allyl group, propenyl group, butenyl group, hexenyl group, and cyclohexenyl group. Examples of the oxoalkyl group include 2-oxocyclopentyl group, 2-oxocyclohexyl group, 2-oxopropyl group, 2-cyclopentyl-2-oxoethyl group, 2-cyclohexyl-2-oxoethyl group, and 2-(4-methylcyclohexyl)-2-oxoethyl group. Examples of the aryl group include phenyl group; naphthyl group; an alkoxyphenyl group such as p-methoxyphenyl group, m-methoxyphenyl group, o-methoxyphenyl group, ethoxyphenyl group, p-tert-butoxyphenyl group, and m-tert-butoxyphenyl group; an alkylphenyl group such as 2-methylphenyl group, 3-methylphenyl group, 4-methylphenyl group, ethylphenyl group, 4-tert-butylphenyl group, 4-butylphenyl group, and dimethylphenyl group; an alkylnaphthyl group such as methylnaphthyl group and ethylnaphthyl group; an alkoxynaphthyl group such as methoxynaphthyl group and ethoxynaphthyl group; a dialkylnaphthyl group such as dimethylnaphthyl group and diethylnaphthyl group; and a dialkoxynaphthyl group such as dimethoxynaphthyl group and diethoxynaphthyl group. Examples of the aralkyl group include benzyl group, phenylethyl group, and phenethyl group. Examples of the aryloxoalkyl group include a 2-aryl-2-oxoethyl group such as 2-phenyl-2-oxoethyl group, 2-(1-naphthyl)-2-oxoethyl group and 2-(2-naphthyl)-2-oxoethyl group. Examples of the non-nucleophilic counter ion $K^-$ include a halide ion such as chloride ion and iodide ion; a fluoroalkylsulfonate such as triflate, 1,1,1-trifluoroethanesulfonate, and nonafluorobutanesulfonate; an arylsulfonate such as tosylate, benzenesulfonate, 4-fluorobenzenesulfonate, and 1,2,3,4,5-pentafluorobenzenesulfonate; and alkylsulfonate such as mesylate and butanesulfonate.

Examples of the nitrogen-containing aromatic ring completed by $R^{101d}$ and $R^{101e}$, or $R^{101d}$, $R^{101e}$ and $R^{101f}$ include imidazole derivative (for example, imidazole, 4-methylimidazole, and 4-methyl-2-phenylimidazole), pyrazole derivative, furazan derivative, pyrroline derivative (for example, pyrroline and 2-methyl-1-pyrroline), pyrrolizine derivative (for example, pyrrolizine, N-methylpyrrolizine, pyrrolizinone, and N-methylpyrrolidone), imidazoline derivative, imidazolidine derivative, pyridine derivative (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolizinopyridine, 1-methyl-4-phenylpyridine, 2-(1-ethylpropyl)pyridine, aminopyridine, and dimethylaminopyridine), pyridazine derivative, pyrimidine derivative, pyrazine derivative, pyrazoline derivative, pyrazolidine derivative, piperidine derivative, piperazine derivative, morpholine derivative, indole derivative, isoindole derivative, 1H-indazole derivative, indoline derivative, quinoline derivative (for example, quinoline and 3-quinolinecarbonitrile), isoquinoline derivative, cinnoline derivative, quinazoline derivative, quinoxaline derivative, phthalazine derivative, purine derivative, pteridine derivative, carbazole derivative, phenanthridine derivative, acridine derivative, phenazine derivative, 1,10-phenanthroline derivative, adenine derivative, adenosine derivative, guanine derivative, guanosine derivative, uracil derivative, and uridine derivative.

The compounds of the formulae (P1a-1) and (P1a-2) act as a photo acid generator and a thermal acid generator, while the compound of the formula (P1a-3) act as a thermal acid generator.

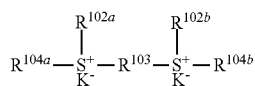

(P1b)

In the above formula, $R^{102a}$ and $R^{102b}$ are each a linear, branched or cyclic alkyl group having 1 to 8 carbon atoms, $R^{103}$ is a linear, branched or cyclic alkylene group having 1 to 10 carbon atoms, $R^{104a}$ and $R^{104b}$ are each a 2-oxoalkyl group having 3 to 7 carbon atoms, and $K^-$ is a non-nucleophilic counter ion.

Examples of $R^{102a}$ and $R^{102b}$ include methyl group, ethyl group, propyl group, isopropyl group, n-butyl group, sec-butyl group, tert-butyl group, pentyl group, hexyl group, heptyl group, octyl group, cyclopentyl group, cyclohexyl group, cyclopropylmethyl group, 4-methylcyclohexyl group, and cyclohexylmethyl group. Examples of $R^{103}$ include methylene group, ethylene group, propylene group, butylene group, pentylene group, hexylene group, heptylene group, octylene group, nonylene group, 1,4-cyclohexylene group, 1,2-cyclohexylene group, 1,3-cyclopentylene group, 1,4-cyclooctylene group, and 1,4-cyclohexanedimethylene group. Examples of $R^{104a}$ and $R^{104b}$ include 2-oxopropyl group, 2-oxocyclopentyl group, 2-oxocyclohexyl group, and 2-oxocycloheptyl group. $K^-$ is selected from the ions which are described above with respect to the formulae (P1a-1), (P1a-2) and (P1a-3).

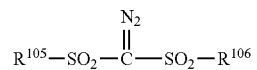

(P2)

In the above formula, $R^{105}$ and $R^{106}$ are each a linear, branched or cyclic alkyl group or haloalkyl group each having 1 to 12 carbon atoms, an aryl group or haloaryl group each having 6 to 20 carbon atoms, or an aralkyl group having 7 to 12 carbon atoms.

Examples of the alkyl group of $R^{105}$ and $R^{106}$ include methyl group, ethyl group, propyl group, isopropyl group, n-butyl group, sec-butyl group, tert-butyl group, pentyl group, hexyl group, heptyl group, octyl group, amyl group, cyclopentyl group, cyclohexyl group, cycloheptyl group, norbornyl group, and adamantyl group. Examples of the haloalkyl group include trifluoromethyl group, 1,1,1-trifluoroethyl group, 1,1,1-trichloroethyl group, and nonafluorobutyl group. Examples of the aryl group include an alkoxyphenyl group such as phenyl group, p-methoxyphenyl group, m-methoxyphenyl group, o-methoxyphenyl group, ethoxyphenyl group, p-tert-butoxyphenyl group, and m-tert-butoxyphenyl group, and an alkylphenyl group such as 2-methylphenyl group, 3-methylphenyl group, 4-methylphenyl group, ethylphenyl group, 4-tert-butylphenyl group, 4-butylphenyl group, and dimethylphenyl group. Examples of the haloaryl group include fluorophenyl group, chlorophenyl group, and 1,2,3,4,5-pentafluorophenyl group. Examples of the aralkyl group include benzyl group and phenethyl group.

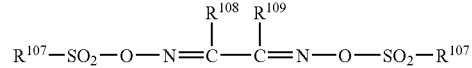

(P3)

In the above formula, $R^{107}$, $R^{108}$ and $R^{109}$ are each a linear, branched or cyclic alkyl group or haloalkyl group each having 1 to 12 carbon atoms, an aryl group or haloaryl group each having 6 to 20 carbon atoms, or an aralkyl group having 7 to 12 carbon atoms. $R^{108}$ and $R^{109}$ may be bonded to complete a cyclic structure. When completing a cyclic structure, $R^{108}$ and $R^{109}$ are each a linear or branched alkylene group having 1 to 6 carbon atoms.

Examples of the alkyl group, haloalkyl group, aryl group, haloaryl group, and aralkyl group of $R^{107}$, $R^{108}$ and $R^{109}$ are selected from the groups which are described above with respect to $R^{105}$ and $R^{106}$. Examples of the alkylene group when $R^{108}$ and $R^{109}$ complete a cyclic structure include methylene group, ethylene group, propylene group, butylene group, and hexylene group.

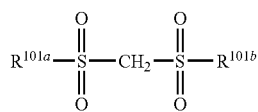
(P4)

In the above formula, $R^{101a}$ and $R^{101b}$ are the same as defined above.

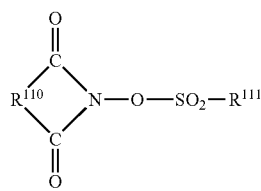
(P5)

In the above formula, $R^{110}$ is an arylene group having 6 to 10 carbon atoms, an alkylene group having 1 to 6 carbon atoms or an alkenylene group having 2 to 6 carbon atoms. The hydrogen atoms of these groups may be partially or completely replaced by a linear or branched alkyl group or an alkoxyl group each having 1 to 4 carbon atoms, nitro group, acetyl group, or phenyl group. $R^{111}$ is a linear, branched or substituted alkyl group, alkenyl group or alkoxyalkyl group each having 1 to 8 carbon atoms, phenyl group, or naphthyl group. The hydrogen atom of these groups may be partially or completely replaced by an alkyl group or alkoxyl group each having 1 to 4 carbon atoms; nitro group; phenyl group optionally substituted by acetyl group; a heteroaromatic group having 3 to 5 carbon atoms; chlorine atom; or fluorine atom.

The arylene group of $R^{110}$ may include 1,2-phenylene group or 1,8-naphthylene group, the alkylene group may include methylene group, ethylene group, trimethylene group, tetramethylene group, phenylethylene group, and norbornane-2,3-diyl group, and the alkenylene group may include 1,2-vinylene group, 1-phenyl-1,2-vinylene group, and 5-norbornene-2,3-diyl group. The alkyl group of $R^{111}$ is selected from those described above with respect to $R^{101a}$ to $R^{101c}$. The alkenyl group may include vinyl group, 1-propenyl group, allyl group, 1-butenyl group, 3-butenyl group, isoprenyl group, 1-pentenyl group, 3-pentenyl group, 4-pentenyl group, dimethylallyl group, 1-hexenyl group, 3-hexenyl group, 5-hexenyl group, 1-heptenyl group, 3-heptenyl group, 6-heptenyl group, and 7-octenyl group. The alkoxyalkyl group may include methoxymethyl group, ethoxymethyl group, propoxymethyl group, butoxymethyl group, pentyloxymethyl group, hexyloxymethyl group, heptyloxymethyl group, methoxyethyl group, ethoxyethyl group, propoxyethyl group, butoxyethyl group, pentyloxyethyl group, hexyloxyethyl group, methoxypropyl group, ethoxypropyl group, propoxypropyl group, butoxypropyl group, methoxybutyl group, ethoxybutyl group, propoxybutyl group, methoxypentyl group, ethoxypentyl group, methoxyhexyl group, and methoxyheptyl group.

The alkyl group having 1 to 4 carbon atoms which is optionally substituted may include methyl group, ethyl group, propyl group, isopropyl group, n-butyl group, isobutyl group, and tert-butyl group. The alkoxyl group having 1 to 4 carbon atoms may include methoxy group, ethoxy group, propoxy group, isopropoxy group, n-butoxy group, isobutoxy group, and tert-butoxy group. The phenyl group which is optionally substituted by an alkyl group or alkoxyl group each having 1 to 4 carbon atoms, nitro group or acetyl group may include phenyl group, tolyl group, p-tert-butoxyphenyl group, p-acetylphenyl group, and p-nitrophenyl group. The heteroaromatic group having 3 to 5 carbon atoms may include pyridyl group and furyl group.

Examples of the onium salt include tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra-n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl 2-oxocyclopentyl)sulfonium trifluoromethanesulfonate], and 1,2'-naphthylcarbonylmethyltetrahydrothiophenium triflate.

Examples of the diazomethane derivative include bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfinyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane.

Examples of the glyoxime derivative include bis(p-toluenesulfonyl)-α-dimethyl glyoxime, bis(p-toluenesulfonyl)-α-diphenyl glyoxime, bis(p-toluenesulfonyl)-α-dicyclohexyl glyoxime, bis(p-toluenesulfonyl)-2,3-pentanedione glyoxime, bis(p-toluenesulfonyl)-2-methyl-3,4-pentanedione glyoxime, bis(n-butanesulfonyl)-α-dimethyl glyoxime, bis(n-butanesulfonyl)-α-diphenyl glyoxime, bis(n-butanesulfonyl)-α-dicyclohexyl glyoxime, bis(n-butanesulfonyl)-2,3-pentanedione glyoxime, bis(n-butanesulfonyl)-2-methyl-3,4-pentanedione glyoxime, bis(methanesulfonyl)-α-dimethyl glyoxime, bis(trifluoromethanesulfonyl)-α-dimethyl glyoxime, bis(1,1,1-trifluoroethanesulfonyl)-α-dimethyl glyoxime, bis(tert-butanesulfonyl)-α-dimethyl glyoxime, bis(perfluorooctanesulfonyl)-α-dimethyl glyoxime, bis(cyclohexanesulfonyl)-α-dimethyl glyoxime, bis(benzenesulfonyl)-α-dimethyl glyoxime, bis(p-fluorobenzenesulfonyl)-α-dimethyl glyoxime, bis(p-tert-butylbenzenesulfonyl)-α-dimethyl glyoxime, bis(xylenesulfonyl)-α-dimethyl glyoxime, and bis(camphorsulfonyl)-α-dimethyl glyoxime.

Examples of the bissulfone derivative include bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane.

Examples of the β-ketosulfonic acid derivative include 2-cyclohexylcarbonyl-2-(p-toluenesulfonyl)propane, and 2-isopropylcarbonyl-2-(p-toluenesulfonyl)propane.

Examples of the disulfone derivative include diphenyldisulfone derivative and dicyclohexyldisulfone derivative.

Examples of the nitrobenzyl sulfonate derivative include 2,6-dinitrobenzyl p-toluenesulfonate and 2,4-dinitrobenzyl p-toluenesulfonate.

Examples of the sulfonic ester derivative include 1,2,3-tris(methanesulfonyloxy)benzene, 1,2,3-tris(trifluoromethanesulfonyloxy)benzene, and 1,2,3-tris(p-toluenesulfonyloxy)benzene.

Examples of the sulfonic ester of N-hydroxyimide compound include N-hydroxysuccinimide methanesulfonic ester, N-hydroxysuccinimide trifluoromethanesulfonic ester, N-hydroxysuccinimide ethanesulfonic ester, N-hydroxysuccinimide 1-propanesulfonic ester, N-hydroxysuccinimide 2-propanesulfonic ester, N-hydroxysuccinimide 1-penntanesulfonic ester, N-hydroxysuccinimide 1-octanesulfonic ester, N-hydroxysuccinimide p-toluenesulfonic ester, N-hydroxysuccinimide p-methoxybenzenesulfonic ester, N-hydroxysuccinimide 2-chloroethanesulfonic ester, N-hydroxysuccinimide benzenesulfonic ester, N-hydroxysuccinimide 2,4,6-trimethylbenzenesulfonic ester, N-hydroxysuccinimide 1-naphthalenesulfonic ester, N-hydroxysuccinimide 2-naphthalenesulfonic ester, N-hydroxy-2-phenylsuccinimide methanesulfonic ester, N-hydroxymaleimide methanesulfonic ester, N-hydroxymaleimide ethanesulfonic ester, N-hydroxy-2-phenylmaleimide methanesulfonic ester, N-hydroxyglutarimide methanesulfonic ester, N-hydroxyglutarimide benzenesulfonic ester, N-hydroxyphthalimide methanesulfonic ester, N-hydroxyphthalimide benzenesulfonic ester, N-hydroxyphthalimide trifluoromethanesulfonic ester, N-hydroxyphthalimide p-toluenesulfonic ester, N-hydroxynaphthalimide methanesulfonic ester, N-hydroxynaphthalimide benzenesulfonic ester, N-hydroxy-5-norbornene-2,3-dicarboximide methanesulfonic ester, N-hydroxy-5-norbornene-2,3-dicarboximide trifluoromethanesulfonic ester, and N-hydroxy-5-norbornene-2,3-dicarboximide p-toluenesulfonic ester. Particularly preferred are the onium salt such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate; the diazomethane derivative such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; the glyoxime derivative such as bis(p-toluenesulfonyl)-α-dimethyl glyoxime and bis(n-butanesulfonyl)-α-dimethyl glyoxime; the bissulfone derivative such as bisnaphthylsulfonylmethane; and the sulfonic ester derivative of N-hydroxyimide compound such as N-hydroxysuccinimide methanesulfonic ester, N-hydroxysuccinimide trifluoromethanesulfonic ester, N-hydroxysuccinimide 1-propanesulfonic ester, N-hydroxysuccinimide 2-propanesulfonic ester, N-hydroxysuccinimide 1-penntanesulfonic ester, N-hydroxysuccinmide p-toluenesulfonic ester, N-hydroxynaphthalimide methanesulfonic ester, and N-hydroxynaphthalimide benzenesulfonic ester.

The acid generator (C) may be used singly or in combination of two or more. The blending amount of the acid generator (C) is preferably 0.1 to 50 parts and more preferably 0.5 to 40 parts based on 100 parts of the polyphenol compound. If being less than 0.1 part, the amount of generated acid is small and the crosslinking reaction may proceed insufficiently. If exceeding 50 parts, the generated acid moves into an upper resist to likely cause the mixing phenomenon.

The composition for under coat film of the invention may further contain a basic compound to enhance the storage stability.

The basic compound acts as a quencher to acid which prevents the acid generated by the acid generator (C) in a small amount from promoting the crosslinking reaction. Examples of the basic compound include a primary, secondary or tertiary aliphatic amine, a mixed amine, an aromatic amine, a heterocyclic amine, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and imide derivative.

The primary aliphatic amine may include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine; the secondary aliphatic amine may include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine; and the tertiary aliphatic amine include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, trietylamine, N,N,N',N'-tetramethylethylenediamine, N,N,N',N'-tetramethylethylenediamine, and N,N,N',N'-tetramethyltetraethylene pentamine.

Examples of the mixed amine include dimethylethylamine, methylethylpropylamine, benzylamine, phenethylamine, and benzyldimethylamine. Examples of the aromatic amine and the heterocyclic amine include aniline derivative (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphtharene, pyrrole derivative (for example, pyrrole, 2H-pyrrole, 1-methylpyrrole, 2,4-dimethylpyrrole, 2,5-dimethylpyrrole, and N-methylpyrrole), oxazole derivative (for example, oxazole and isoxazole), thiazole derivative (for example, thiazole and isothiazole), imidazole derivative (for example, imidazole, 4-methylimidazole, and 4-methyl-2-phenylimidazole), pyrazole derivative, furazan derivative, pyrroline derivative (for example, pyrroline and 2-methyl-1-pyrroline), pyrrolizine derivative (for example, pyrrolizine, N-methylpyrrolizine, pyrrolizinone, and N-methylpyrrolidone), imidazoline derivative, imidazolidine derivative, pyridine derivative (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolizinopyridine, 1-methyl-4-phenylpyridine, 2-(1-ethylpropyl)pyridine, aminopyridine, and dimethylaminopyridine), pyridazine derivative, pyrimidine derivative, pyrazine derivative, pyrazoline derivative, pyrazolidine derivative, piperidine derivative, piperazine derivative, morpholine derivative, indole derivative, isoindole derivative, 1H-indazole derivative, indoline derivative, quinoline derivative (for example, quinoline, and 3-quinolinecarbonitrile), isoquinoline derivative, cinnoline derivative, quinazoline derivative, quinoxaline derivative, phthalazine derivative, purine derivative, pteridine derivative, carbazole derivative, phenanthridine derivative, acridine derivative, phenazine derivative, 1,10-phenanthroline derivative, adenine derivative, adenosine derivative, guanine derivative, guanosine derivative, uracil derivative, and uridine derivative.

The nitrogen-containing compound having a carboxyl group may include aminobenzoic acid, indolecarboxylic acid, and an amino acid derivative (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). The nitrogen-containing compound having a sulfonyl group may include 3-pyridinesulfonic acid and pyridinium p-toluenesulfonate. Examples of the nitrogen-containing compound having a hydroxyl group, nitrogen-containing compound having a hydroxyphenyl group, and alcoholic nitrogen-containing compound include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-aminol-propanol, 4-aminol-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolizine, 1-(2-hydroxyethyl)-2-pyrrolizinone, 3-piperidino-1,2-propanediol, 3-pyrrolizino-1,2-propanediol, 8-hydroxyjulolidine, 3-quinuclidinol, 3-tropanol, 1-methyl-2-pyrrolizineethanol, 1-aziridine ethanol, N-(2-hydroxyethyl)phthalimide, and N-(2-hydroxyethyl)isonicotinamide. The amide derivative may include formamide, N-methylformamide, N,N-dimethylformamide, acetamide, N-methylacetamide, N,N-dimethylacetamide, propioaminde and benzaminde, and the imide derivative may include phthalimide, succinimide, and maleimide.

The blending amount of the basic compound is preferably 0.001 to 2 parts and particularly preferably 0.01 to 1 part based on 100 parts of the cyclic compound. If less than 0.001 part, the effect of blending is not obtained. If exceeding 2 parts, the basic compound traps the acid generated by heating completely to inhibit the crosslinking reaction.

The composition for under coat film of the invention may further contain another type of polymer to control the absorbance. A polymer highly transparent to 193 nm light is usable, which is selected from a resin having a naphthalene ring, a phenanthrenequinone, a biphenyl ring such as fluorene or a hetero ring such as thiophene and indene, or a resin containing no aromatic ring. Examples thereof include a naphthol resin, a naphthol-modified xylene resin, a phenol-modified naphtharene resin, a dicyclopentadiene resin, a (meth)acrylate resin, a vinylnaphtharene resin, and polyacenaphthylene.

By introducing a condensed aromatic group or an alicyclic group into the polymer, the glass transition point can be made lower than that of a typical novolak resin. Although depending upon the kind of the group to be introduced, the glass transition point can be reduced by 10 to 50° C.

Alternatively, the glass transition point can be reduced by replacing the hydroxy hydrogen atom of hydroxystyrene with a linear, branched or cyclic alkyl group having 1 to 20 carbon atoms, t-butyl group, t-amyl group, a group unstable to acid such as acetal, acetyl group, or pivaloyl group. The hydroxy group is replaced by 10 to 80 mol %, preferably 15 to 70 mol %.

The organic solvent for the composition for under coat film is not specifically limited as long as the cyclic compound, acid generator (C), crosslinking agent (G), and other additives (F) are soluble in the organic solvent.

Examples thereof include a ketone solvent such as acetone, methyl ethyl ketone, methyl isobutyl ketone, and cyclohexanone; a cellosolve solvent such as propylene glycol monomethyl ether and propylene glycol monomethyl ether acetate; an ester solvent such as ethyl lactate, methyl acetate, ethyl acetate, butyl acetate, isoamyl acetate, ethyl lactate, methyl methoxypropionate, and methyl hydroxyisobutyrate; an alcohol solvent such as methanol, ethanol, isopropanol, and 1-ethoxy-2-propanol; and an aromatic hydrocarbon such as toluene and xylene, with cyclohexanone, propylene glycol monomethyl ether, ethyl lactate, and methyl hydroxyisobutyrate being particularly preferred.

The blending amount of the solvent is preferably 200 to 10,000 parts and particularly preferably 300 to 5,000 parts, each based on 100 parts of the cyclic compound.

The under coat film is formed by spin-coating the composition, evaporating off the solvent, and preferably baking the resultant film to promote the crosslinking reaction, thereby preventing the mixing with an upper resist. The baking is conducted preferably at 80 to 300° C. for 10 to 300 s. The thickness of the under coat film is suitably selected, and preferably 30 to 20,000 nm, particularly preferably 50 to 15,000 nm. In the two-layer process, a silicon-containing resist layer or a single resist layer of hydrocarbon generally used is formed on the under coat film. In the three-layer process, a silicon-containing intermediate layer and then a silicon-free single resist layer are successively formed on the under coat film. The resist layer may be formed by a known photoresist composition.

In the two-layer process, a positive-type photoresist composition containing, as the base polymer, a silicon-containing polymer such as a polysilsesquioxane derivative and a vinylsilane derivative, an organic solvent, an acid generator, and an optional basic compound is used because a high resistance to the oxygen gas etching is obtained. The silicon-containing polymer may be selected from known polymers used in this type of resist composition. The silicon-containing intermediate layer of the three-layer process is preferably based on the polysilsesquioxane. The reflection is prevented by making the intermediate layer anti-reflective.

If the under coat film is made of a material containing a large number of aromatic groups and having a high substrate etching resistance, the k-value becomes larger to increase the reflection of 193 nm light on a substrate. By making the intermediate layer anti-reflective, the 110 reflectance on the substrate is reduced to 0.5% or less. To make the intermediate layer anti-reflective against the 193 nm exposure, an acid- or heat-crosslinkable polysilsesquioxane into which a light absorbing group such as phenyl group and silicon-silicon bond is introduced is preferably used. The intermediate layer formed by chemical vapor deposition (CVD) is also effective. A SiON film formed by CVD is known as a highly anti-reflective intermediate layer. The spin coating method is preferable to the CVD method in view of easiness to form the intermediate layer and production cost. The upper resist layer in the three-layer process is either positive type or negative type, and may be formed from a resist composition generally used for forming a single layer resist.

The under coat film of the invention is also usable as an anti-reflective film for known single layer resist, and additionally, expected as a hard mast for use in a primary processing because of its high resistance against the etching for primary processing.

The present invention further relates to a method of forming a multi-layer resist pattern which comprises a step of forming an under coat film on a substrate, a step of forming at least one photoresist layer on the under coat film, a step of irradiating the photoresist layer with radiation in a pattern, a step of alkali-developing the irradiated photoresist layer to form a resist pattern, and a step of etching the under coat film with a plasma containing oxygen gas using the resist pattern as a mask, thereby transferring the resist pattern to the under coat film.

Like the formation of the under coat film, the photoresist composition is made into a resist layer preferably by a spin coating. After spin-coating, the coated resist composition is baked preferably at 80 to 180° C. for 10 to 300 s. Thereafter, the resist pattern is obtained by following the exposure, the post exposure bake (PEB), and an alkali development, each being conducted in a known manner. The thickness of the resist film is preferably 30 to 500 nm and particularly preferably 50 to 400 nm, although not limited thereto.

The light for exposure may include high energy rays with a wavelength of 300 nm or less such as excimer lasers of 248 nm, 193 nm or 157 nm, soft X-rays with a wavelength of 3 to 20 nm, electron beams and X-rays.

Then, the under coat film is etched by using the obtained resist pattern as a mask. In the two-layer process, the under coat film is etched using oxygen gas. In addition to oxygen gas, the etching gas may contain an inert gas such as He and Ar and other gas such as CO, $CO_2$, $NH_3$, $SO_2$, $N_2$, $NO_2$ and $H_2$. The etching may be carried out only using the gas such as CO, $CO_2$, $NH_3$, $SO_2$, $N_2$, $NO_2$ and $H_2$ without using oxygen gas. The gas such as CO, $CO_2$, $NH_3$, $SO_2$, $N_2$, $NO_2$ and $H_2$ is used particularly to protect the side wall of the pattern from undercutting. In the three-layer process, the intermediate layer is etched with a flon gas using the resist pattern as a mask. Then, the under coat film is etched with oxygen gas using the patterned intermediate layer as a mask.

The substrate thus processed is then etched in a known manner, for example, etched mainly with a flon gas when the substrate is made of $SiO_2$ or SiN, or etched mainly with a chlorine-containing gas or a bromine-containing gas when the substrate is made of p—Si, Al or W. When the substrate is etched with a flon gas, the silicon-containing resist layer in the two-layer process and the silicon-containing intermediate layer in the three-layer process are simultaneously removed. When the substrate is etched with a chlorine-containing gas or a bromine-containing gas, the silicon-containing resist layer and the silicon-containing intermediate layer are removed by an additional dry etching with a flon gas after etching the substrate.

The under coat film of the present invention is highly resistant against the conditions of etching the substrate.

The substrate to be processed is formed on a support. The support is made of a material different from that of the substrate to be processed, and selected from, but not limited to, Si, α—Si, p—Si, $SiO_2$, SiN, SiON, W, TiN, and Al. A low-k film or a stopper film having a thickness generally of 50 to 10,000 nm, particularly of 100 to 5,000 nm made of Si, $SiO_2$, SiON, SiN, p—Si, α—Si, W, W—Si, Al, Cu, or Al—Si is used as the substrate to be processed.

Production Method (1) of Cyclic Compound (B0)

The present invention further relates to a method of producing a cyclic compound (B0), comprising a first stage reaction in which an aldehyde compound (A1b) having 2 to 59 carbon atoms, a reactive functional group and 1 to 4 formyl groups is allowed to react with a reagent for introducing an acid-dissociating functional group, thereby synthesizing an aldehyde compound (A1c) having the acid-dissociating functional group introduced, and a second stage reaction in which the aldehyde compound (A1c) and a phenol compound (A2) are subjected to a condensation reaction.

The cyclic compound (B0) synthesized by the condensation reaction of the aldehyde compound (A1c) with the phenol compound (A2) has a molecular weight of 800 to 5000.

The cyclic compound (B0) is produced through the first stage reaction in which an acid-dissociating functional group is introduced into the aldehyde compound (A1b) having 2 to 59 carbon atoms and 1 to 4 formyl groups to synthesize the aldehyde compound (A1c), and the second stage reaction in which the aldehyde compound (A1c) and the phenol compound (A2) are subjected to the condensation reaction.

Generally, a cyclic low-molecular compound having an acid-dissociating functional group is produced by synthesizing a cyclic low-molecular polyphenol compound and then allowing the cyclic low-molecular polyphenol compound to react with a compound for introducing an acid-dissociating functional group which is described below.

However, in such a known method, the cyclic low-molecular compound is sparingly soluble in the organic reaction solvent such as tetrahydrofuran (THF) to make the reaction with the compound for introducing an acid-dissociating functional group difficult, in some cases. Even if the cyclic low-molecular compound is soluble in the organic solvent, the reaction between the cyclic low-molecular compound and the compound for introducing an acid-dissociating functional group is less selective to produce a mixture of a non-substituted compound and various kinds of substituted compounds. It is generally difficult to isolate only the aimed cyclic low-molecular compound having an acid-dissociating functional group selectively from the mixture. Therefore, the known method is poor in the yield and less practical.

In contrast, in the method of the invention, the aldehyde compound (A1c) is synthesized by introducing the acid-dissociating functional group into the aldehyde compound (A1b) having 2 to 59 carbon atoms and 1 to 4 formyl groups in the first stage reaction. Since the compound (A1b) having 2 to 59 carbon atoms and 1 to 4 formyl groups and the compound for introducing an acid-dissociating functional group are both soluble in the organic reaction solvent such as THF, the reaction for synthesizing the aldehyde compound (A1c) proceeds without any trouble.

Thereafter, in the second stage reaction, the aldehyde compound (A1c) having the acid-dissociating functional group introduced and the phenol compound (A2) are allowed to react to obtain the cyclic compound (B0) into which the acid-dissociating functional group is introduced. Since the solubility of each reactant in the organic reaction solvent is good, the reaction in not adversely affected. In the obtained cyclic compound (B0), the acid-dissociating functional group is present in the moiety derived from the aldehyde compound (A1c) and not present in the moiety derived from the phenol compound (A2). Thus, the method of the invention provides the cyclic compound (B0) into which the acid-dissociating functional group is selectively introduced in high yields and high productivity.

The aldehyde compound (A1c) having the acid-dissociating functional group is a compound having 3 to 60 carbon atoms and 1 to 4 formyl groups.

The acid-dissociating functional group referred to in the present invention is a characteristic group which generates an alkali-soluble group by dissociation in the presence of an acid. Examples of the alkali-soluble group include phenolic hydroxyl group, carboxyl group, sulfonic acid group, and hexafluoroisopropyl group, with phenolic hydroxyl group and carboxyl group being preferred and phenolic hydroxyl group being particularly preferred. To form a pattern with a high sensitivity and resolution, it is preferred that the acid-dissociating functional group is dissociated succeedingly by a chain reaction in the presence of acid.

The acid-dissociating functional group is suitably selected from those proposed as the groups for hydroxystyrene resins and (meth)acrylic acid resins which are used in the chemical-amplified resist composition for KrF and ArF. Examples thereof include a substituted methyl group, a 1-substituted ethyl group, a 1-substituted n-propyl group, a 1-branched alkyl group, silyl group, an acyl group, a 1-substituted alkoxymethyl group, a cyclic ether group, and an alkoxycarbonyl group. An acid-dissociating functional group having no crosslinkable functional group is preferred.

The aldehyde compound (A1c) is produced by introducing the acid-dissociating functional group into the compound (A1b) having 2 to 59 carbon atoms and 1 to 4 formyl groups.

The aldehyde compound having 2 to 59 carbon atoms and 1 to 4 formyl groups is an aliphatic aldehyde compound, an alicyclic aldehyde compound or an aromatic aldehyde compound, although not limited thereto.

Examples of the aliphatic aldehyde compound include acetaldehyde, Ra—CHO (Ra is an alkyl group optionally having a substituent having 2 to 20 carbon atoms), OHC—Rb—CHO (Rb is an alkylene group optionally having a substituent having 1 to 20 carbon atoms), Rc-(CHO)$_3$ (Rc is a trivalent organic group optionally having a substituent having 2 to 20 carbon atoms), and Rd-(CHO)$_4$ (Rd is a quatervalent organic group optionally having a substituent having 2 to 20 carbon atoms). In the above, the substituent is an alkyl group, a cycloalkyl group, an aryl group, an alkoxyl group, cyano group, nitro group, hydroxyl group, a heterocyclic group, a halogen atom, carboxyl group, an alkylsilyl group, or a functional group selected from derivatives of the preceding groups.

Examples of the alicyclic aldehyde compound include cyclohexane carbaldehyde, cyclooctane carbaldehyde, norbornane carbaldehyde, adamantane carbaldehyde, furfural, diformylcyclohexane, diformylcyclooctane, diformylnorbornane, diformyladamantane, triformylcyclohexane, triformylcyclooctane, triformylnorbornane, triformyladamantane, triformylcyclohexane, tetraformylcyclooctane, tetraformylnorbornane, and tetraformyladamantane, each optionally having a substituent having 2 to 20 carbon atoms. In the above, the substituent is an alkyl group, a cycloalkyl group, an aryl group, an alkoxyl group, cyano group, nitro group, hydroxyl group, a heterocyclic group, a halogen atom, carboxyl group, an alkylsilyl group, or a functional group selected from derivatives of the preceding groups.

Examples of the aromatic aldehyde compound include benzaldehyde, tolylaldehyde, and benzaldehyde, anisaldehyde, naphthaldehyde, anthraldehyde, biphenylaldehyde, formylfluorene, formylbiphenyl, formylanthracene, formylphenanthrene, formylphenothiazine, formylpyrene, formylbenzopyrene, formylindacene, formylphenacene, formylacenaphthylene, formylnaphthacene, formylpentacene, formyltriphenylene, formylpyridine, formylovalene, diformylbenzene, diformyltoluene, diformylxylene, diformylnaphtharene, diformylbiphenyl, diformylterphenyl, diformylanthracene, diformylphenanthrene, diformylpyrene, diformylindacene, diformylphenalene, diformylacenaphthylene, diformylphenalene, diformylnaphthacene, diformylpentacene, diformyltriphenylene, diformylpyridine, diformylimidazole, diformylfuran, diformylthiazole, diformylflavone, diformylisoflavone, triformylbenzene, triformyltoluene, triformylxylene, triformylnaphtharene, triformylbiphenyl, triformylterphenyl, triformylanthracene, triformylphenanthrene, triformylpyrene, triformylindacene, triformylphenalene, triformylacenaphthylene, triformylphenalene, triformylnaphthacene, triformylpentacene, triformyltriphenylene, triformylterpyridine, triformylimidazole, triformylfuran, triformylthiazole, triformylflavone, triformylisoflavone, tetraformylbenzene, tetraformylnaphtharene, tetraformylbiphenyl, tetraformylterphenyl, tetraformylanthracene, tetraformylphenanthrene, tetraformylpyrene, tetraformylindacene, tetraformylphenalene, tetraformylacenaphthylene, tetraformylphenalene, tetraformylnaphthacene, tetraformylpentacene, tetraformyltetraphenylene, tetraformylquaterpyridine, tetraformylimidazole, tetraformylfuran, tetraformylthiazole, tetraformylflavone, and tetraformylisoflavone, each optionally having a substituent having 2 to 20 carbon atoms. In the above, the substituent is alkyl group, cycloalkyl group, aryl group, alkoxyl group, cyano group, nitro group, hydroxyl group, boronic acid group, heterocyclic group, halogen atom, carboxyl group, alkylsilyl group, or a functional group selected from derivatives of the preceding groups.

Examples of heterocyclic aldehyde compound include furfural, nicotinealdehyde, 2-tetrahydrofuran carbaldehyde, and 2-thiophene carbaldehyde.

These compounds are preferably substituted by hydroxyl group, boronic acid group, a halogen atom or carboxyl group, because the acid-dissociating functional group is easily introduced.

Of the above, preferred is an aromatic aldehyde having 1 to 4 formyl groups in view of the etching resistance, more preferred is an aromatic aldehyde having 1 to 2 formyl groups in view of forming fine patterns, still more preferred is an aromatic aldehyde having one formyl group because such aromatic aldehyde and the cyclic compound (B0) can be produced in high yields and high purity.

The compound for introducing the acid-dissociating functional group is synthesized by a known method or commercially easily available and is selected from, but not limited to, active carboxylic acid derivatives such as an acid chloride, an acid anhydride and a dicarbonate, an alkyl halide, a vinyl alkyl ether, dihydropyran, and an alkyl halocarboxylate. The purity of the compound having 2 to 59 carbon atoms and 1 to 4 formyl groups and the compound for introducing an acid-dissociating functional group is, but not particularly limited to, generally 95% by weight or more and preferably 99% by weight or more. The compound having 2 to 59 carbon atoms and 1 to 4 formyl groups and the compound for introducing an acid-dissociating functional group may be used alone or in combination of two or more, respectively, and preferably used alone in view of the uniformity of the solid component in resist films.

For example, the aldehyde compound (A1c) is produced as follows. A benzaldehyde compound having a phenolic hydroxyl group such as 4-hydroxybenzaldehyde is dissolved or suspended in an organic solvent such as acetone and tetrahydrofuran. After adding an alkyl halide such as cyclohexylchloromethyl ether or an alkyl halocarboxylate such as methyladamantyl bromoacetate, the reaction is allowed to proceed in the presence of an alkali catalyst such as potassium carbonate under atmospheric pressure at 20 to 110° C. for 0.1 to 72 h. After neutralization, the reaction product liquid is poured into distilled water to precipitate a white solid matter. The separated white solid matter is washed with distilled water and dried, to obtain the aldehyde compound (A1c).

Alternatively, a benzaldehyde compound having a phenolic hydroxyl group such as 4-hydroxybenzaldehyde is dissolved or suspended in an aprotic solvent such as acetone, tetrahydrofuran and propylene glycol monomethyl ether acetate. After adding a vinyl alkyl ether such as cyclohexyl vinyl ether, the reaction is allowed to proceed in the presence of an acid catalyst such as pyridinium p-toluenesulfonate under atmospheric pressure at 20 to 60° C. for 0.1 to 72 h. After neutralizing with an alkali compound, the reaction product liquid is poured into distilled water to precipitate a white solid matter. The separated white solid matter is washed with distilled water and dried, to obtain the aldehyde compound (A1c).

The aldehyde compound (A1) is produced by the reaction of a carboxybenzaldehyde such as 3-carboxybenzaldehyde and an alcohol having an acid-dissociating functional group such as methyladamantylmethanol in an organic solvent such as tetrahydrofuran in the presence of an acid or base esterification catalyst.

The aldehyde compound (A1c) is also produced by a Grignard reaction between a halobenzaldehyde such as 4-chlorobenzaldehyde and 4-bromobenzaldehyde or 4-chloromethylbenzaldehyde and a Grignard reagent in the presence of a copper catalyst.

The aldehyde compound (A1c) is also produced by a Grignard reaction between a halobenzaldehyde such as 4-chlorobenzaldehyde and 4-bromobenzaldehyde or 4-chloromethylbenzaldehyde and a Grignard reagent in an organic solvent such as tetrahydrofuran in the presence of a copper catalyst.

Further, the aldehyde compound (A1c) is produced by a Suzuki coupling reaction of a formylphenyl borate such as 4-formylphenyl borate with an alkyl halide such as cyclohexyl chloromethyl ether or a alkyl halocarboxylate such as methyladamantyl bromoacetate in an organic solvent such as tetrahydrofuran in the presence of a palladium and base catalyst.

Examples of the aldehyde compound (A1c) include, but not limited to, a compound obtained by introducing the acid-dissociating functional group into the compound having 2 to 59 carbon atoms and 1 to 4 formyl groups mentioned above. Preferred is an aromatic aldehyde compound in view of the etching resistance, more preferred is an aromatic aldehyde compound having 1 to 2 formyl groups in view of forming fine patterns, and still more preferred is an aromatic aldehyde compound having one formyl group.

The aldehyde compound (A1c) is preferably represented by the following formula (47):

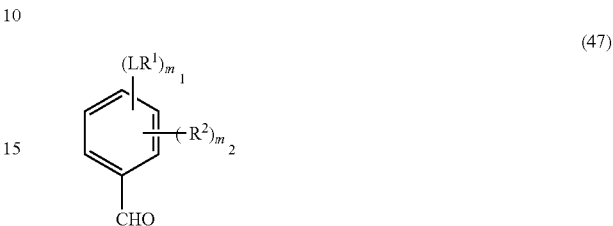

(47)

wherein L is a divalent organic group selected from the group consisting of a single bond, an alkylene group having 1 to 20 carbon atoms, a cycloalkylene group having 3 to 20 carbon atoms, an arylene group having 6 to 20 carbon atoms, —O—, —OC(=O)—, —OC(=O)O—, —N($R_5$)—C(=O)—, —N($R_5$)—C(=O)O—, —S—, —SO—, —$SO_2$—, and any combination of the preceding groups; $R^1$ is hydrogen atom or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms, and an alkoxycarbonylalkyl group; $R^2$ is hydrogen atom, an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, a heterocyclic group, a halogen atom, carboxyl group, an alkylsilyl group having 1 to 20 carbon atoms, or a functional group selected from derivatives of the preceding groups; $R^5$ is hydrogen atom or an alkyl group having 1 to 10 carbon atoms; $m_1$ is an integer of 1 to 5 and $m_2$ is an integer of 0 to 4 satisfying $m_1+m_2=5$ The compound of the formula (47) is produced by the methods described above.

The aldehyde compound (A1c) is more preferably represented by the following formula (48):

(48)

wherein L, $R^1$, and $m_1$ are the same as defined above.

The compound of the formula (48) is produced by the methods described above.

The aldehyde compound (A1c) is still more preferably represented by the following formula (49):

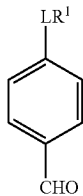
(49)

wherein L and $R^1$ are the same as defined above.

The compound of the formula (49) is produced by the methods described above.

The aldehyde compound (A1c) is particularly preferably represented by the following formula (50):

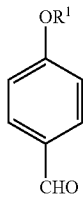
(50)

wherein $R^1$ is the same as defined above.

The compound of the formula (50) is produced by the methods described above.

In the formulae (47) to (50), $R^1$ is an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group having 2 to 20 carbon atoms. Examples thereof are selected from those as described above with respect to the cyclic compound. Plural $R^1$ are the same or different, preferably the same in view of the uniformity of the solid component in resist films.

$R^1$ is more preferably an acid-dissociating functional group having a structure selected from a cycloalkane having 3 to 20 carbon atoms, a lactone, and an aromatic ring having 6 to 12 carbon atoms. The cycloalkane having 3 to 12 carbon atoms may be monocyclic or polycyclic, and preferably polycyclic. Examples thereof include a monocycloalkane, a bicycloalkane, a tricycloalkane, and a tetracycloalkane, and more specifically include a monocycloalkane such as cyclopropane, cyclobutane, cyclopentane, and cyclohexane and a polycycloalkane such as adamantane, norbornane, isobornane, tricyclodecane, and tetracyclodecane, with adamantane, tricyclodecane, and tetracyclodecane being preferred, and adamantane and tricyclodecane being particularly preferred. The cycloalkane having 3 to 12 carbon atoms may be substituted. Examples of the lactone include butyrolactone and a cycloalkane having 3 to 12 carbon atoms and a lactone ring. Examples of the aromatic ring having 6 to 12 carbon atoms include benzene ring, naphthalene ring, anthracene ring, phenanthrene ring, and pyrene ring, with benzene ring and naphthalene ring being preferred and naphthalene ring being particularly preferred.

The acid-dissociating functional group is particularly preferably represented by the following formula (50-1), because the resultant resist pattern has a high resolution and a small LER.

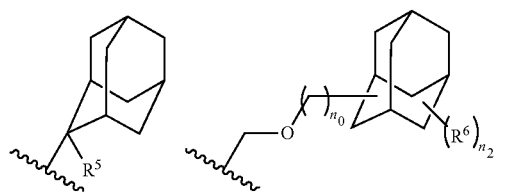
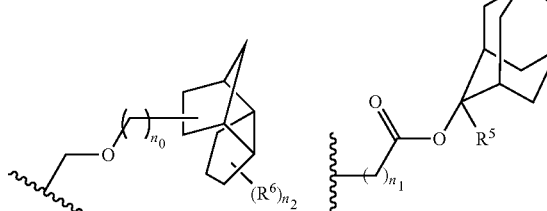
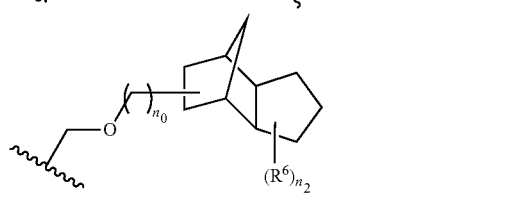
(50-1)

In the formula (50-1), $R^5$, $R^6$, $n_0$, $n_1$, and $n_2$ are the same as defined above.

Examples of the phenol compound (A2) include phenol, catechol, resorcinol, hydroquinone, and pyrogallol, with resorcinol and pyrogallol being preferred, and resorcinol being more preferred. The phenol compound (A2) may be substituted by a group selected from the group consisting of a halogen atom, an alkyl group, a cycloalkyl group, an aryl group, an aralkyl group, an alkoxyl group, an alkenyl group, carboxyl group, an acyl group, an alkoxycarbonyl group, an alkyloyloxy group, an aryloyloxy group, cyano group, nitro group, a heterocyclic group, an alkylsilyl group, a substituted methyl group, a 1-substituted ethyl group, a 1-substituted n-propyl group, a 1-branched alkyl group, silyl group, a 1-substituted alkoxyalkyl group, a cyclic ether group and an alkoxycarbonylalkyl group, as long as the effect of the present invention is not adversely affected. The purity of the phenol compound (A2) is, but not limited to, generally 95% by weight or more and preferably 99% by weight or more. The phenol compound (A2) may be used alone or in combination of two or more, and preferably used alone in view of the uniformity of the solid component of the resist film.

The molecular weight of the cyclic compound (B0) is 800 to 5000, preferably 1000 to 2500, and more preferably 1500 to 2000. Within the above ranges, the resolution is improved while maintaining the film-forming properties necessary for the resists.

In an embodiment of the present invention, the cyclic compound (B0) is preferably represented by the following formula (51):

(51)

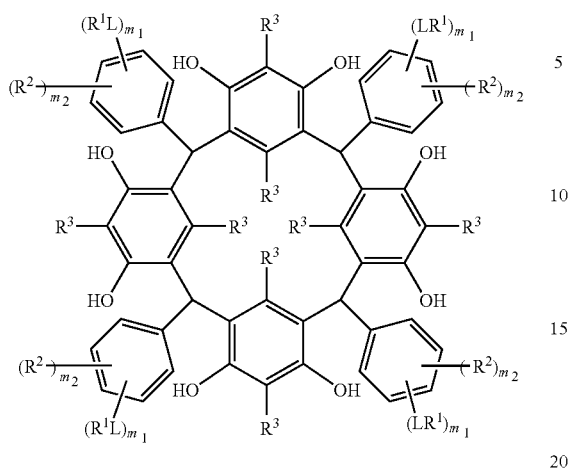

wherein $R^3$ is independently hydrogen atom; a functional group selected from the group consisting of an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, heterocyclic group, halogen atom, carboxyl group, an alkylsilyl group having 1 to 20 carbon atoms, and groups derived from the preceding groups; or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; and L, $R^1$, $R^2$, $m_1$ and $m_2$ are the same as defined in the formula (47).

Plural $R^3$ are the same or different, preferably the same in view of increasing the uniformity of the radiation-sensitive composition and reducing the roughness of the resist pattern to be obtained.

The cyclic compound (B0) of the formula (51) is produced as follows. For example, 1 mol of the aldehyde compound (A1c) and 0.1 to 10 mol of the phenol compound (A2) are allowed to react in an organic solvent such as methanol and ethanol in the presence of an acid catalyst (hydrochloric acid, sulfuric acid, p-toluenesulfonic acid, etc.) at 0 to 100° C. for about 0.5 to 72 h. After filtration, the collected precipitates are washed with an alcohol such as methanol, washed with water, and dried to obtain the cyclic compound (B0). Alternatively, the cyclic compound (B0) may be obtained by the same reaction except for using a basic catalyst (sodium hydroxide, barium hydroxide, 1,8-diazabicyclo[5.4.0]undecane 7, etc.) in place of the acid catalyst. In addition, the cyclic compound (B0) may be produced by converting the aldehyde compound (A1c) to a dihalide using a hydrogen halide or halogen gas and allowing the isolated dihalide to react with the phenol compound (A2).

The cyclic compound (B0) is preferably represented by the following formula (52):

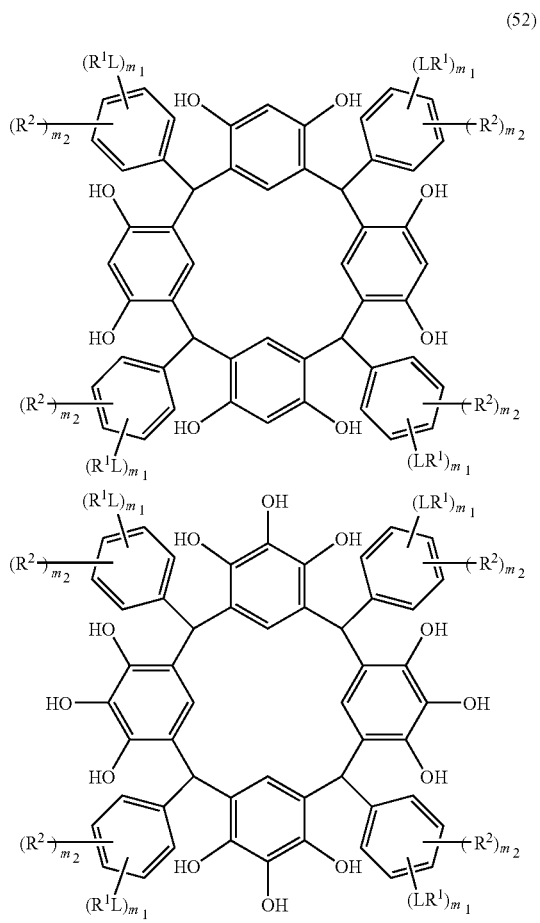

wherein L, $R^1$, $R^2$, $m_1$ and $m_2$ are the same as defined in the formula (51).

The cyclic compound (B0) of the formula (52) is produced by the methods described above.

The cyclic compound (B0) is more preferably represented by the following formula (53):

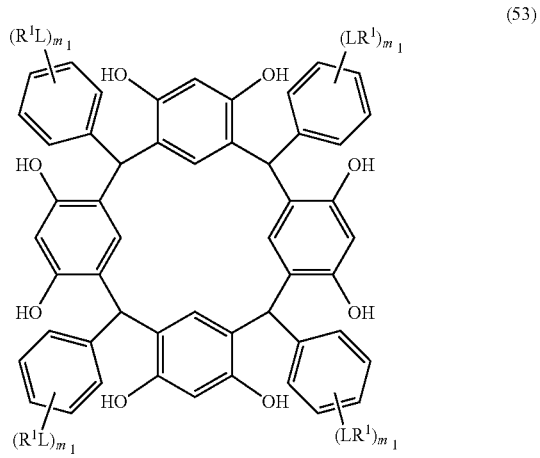

-continued

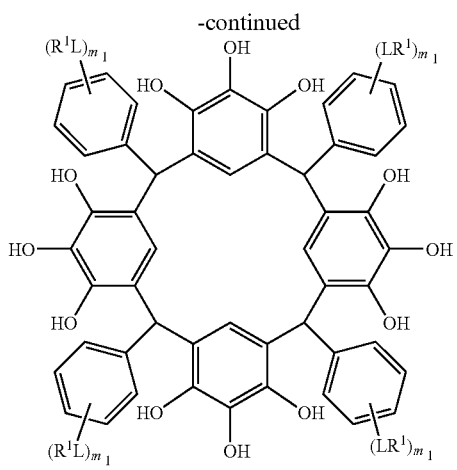

wherein L, $R^1$ and $m_1$ are the same as defined in the formula (51).

The cyclic compound (B0) of the formula (53) is produced by the methods described above.

The cyclic compound (B0) is particularly preferably represented by the following formula (54):

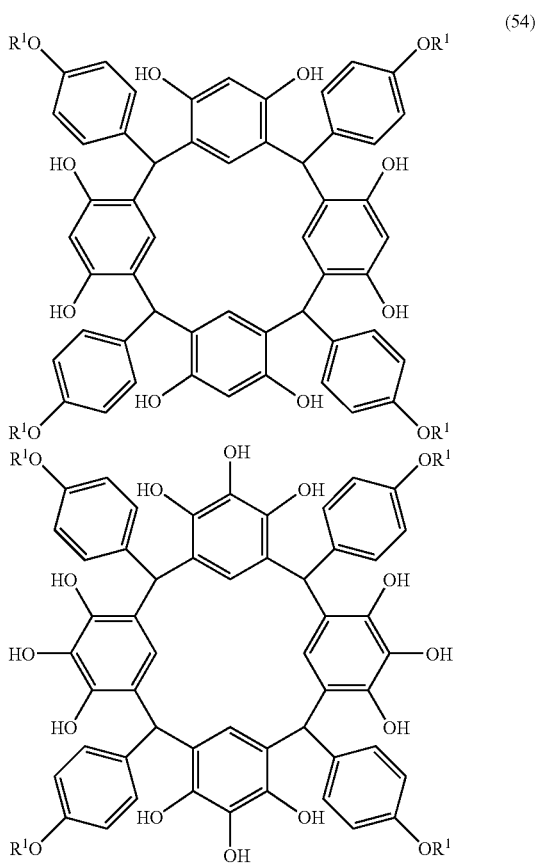

(54)

wherein $R^1$ is the same as defined in the formula (51).

The cyclic compound (B0) of the formula (54) is produced by the methods described above.

In the formula (51), $R^3$ is hydrogen atom, an alkyl group, a cycloalkyl group, an aryl group, an alkoxyl group, cyano group, nitro group, hydroxyl group, a heterocyclic group, a halogen atom, carboxyl group, an alkylsilyl group, a functional group selected from derivatives of the preceding groups, or an acid-dissociating functional group selected from the group consisting of a $C_{2-20}$ substituted methyl group, a $C_{3-20}$ 1-substituted ethyl group, a $C_{4-20}$ 1-substituted n-propyl group, a $C_{3-20}$ 1-branched alkyl group, a $C_{1-20}$ silyl group, a $C_{2-20}$ acyl group, a $C_{2-20}$ 1-substituted alkoxyalkyl group, a $C_{2-20}$ cyclic ether group, and a $C_{2-20}$ alkoxycarbonyl group.

Examples of the $C_{2-20}$ substituted methyl group, $C_{3-20}$ 1-substituted ethyl group, $C_{20}$ 1-substituted n-propyl group, $C_{3-20}$ 1-branched alkyl group, $C_{1-20}$ silyl group, $C_{2-20}$ acyl group, $C_{2-20}$ 1-substituted alkoxyalkyl group, $C_{2-20}$ cyclic ether group, and $C_{2-20}$ alkoxycarbonyl group are selected from the acid-dissociating functional groups as described above with respect to $R^1$.

An acid-dissociating functional group may be introduced into at least one phenolic hydroxyl group of the cyclic compound (B0), as long as the effect of the present invention is not adversely affected. The method thereof is known. For example, the introduction is effected by the same method as in the introduction of the acid-dissociating functional group into the compound having 2 to 59 carbon atoms and 1 to 4 formyl groups.

For example, the cyclic compound (B0) is dissolved or suspended in an aprotic solvent such as acetone, tetrahydrofuran (THF) and propylene glycol monomethyl ether acetate. After adding vinyl alkyl ether such as ethyl vinyl ether or dihydropyran, the reaction is allowed to proceed in the presence of an acid catalyst such as pyridinium p-toluenesulfonate under atmospheric pressure at 20 to 60° C. for 6 to 72 h. The reaction product liquid is neutralized by an alkali compound and then poured into distilled water to precipitate a white solid matter. The white solid matter is separated, washed with distilled water and dried to obtain the aimed compound.

An acid-non-dissociating functional group may be introduced into at least one phenolic hydroxyl group of the cyclic compound (B0), as long as the effect of the present invention is not adversely affected. The acid-non-dissociating functional group is a characteristic group which is not dissociated in the presence of acid, thereby failing to generate an alkali-soluble group. Examples thereof include a group which is not dissociated by the action of acid such as a $C_{1-20}$ alkyl group, a $C_{3-20}$ cycloalkyl group, a $C_{6-20}$ aryl group, a $C_{1-20}$ alkoxyl group, cyano group, nitro group, hydroxyl group, a heterocyclic group, a halogen atom, carboxyl group, a $C_{1-20}$ alkylsilyl group, and a functional group derived from derivatives of the preceding groups.

A naphthoquinonediazido ester group may be introduced into at least one phenolic hydroxyl group of the cyclic compound (B0). The cyclic compound (B0) having at least one phenolic hydroxyl group into which the naphthoquinonediazido ester group is introduced may be used as the main component of a positive-type radiation-sensitive composition, or may be added to a radiation-sensitive composition as an acid generator or additive.

An acid-generating functional group which generates an acid upon the irradiation with radiation may be introduced into at least one phenolic hydroxyl group of the cyclic compound (B0). The cyclic polyphenol compound obtained by introducing the acid-generating functional group into at least one phenolic hydroxyl group of the cyclic compound (B0) may be used as the main component of a positive-type radiation-sensitive composition, or may be added to a radiation-sensitive composition as an acid generator or additive.

Irrespective of its low molecular weight, the cyclic compound (B0) is excellent in the film-forming properties, heat resistance, and dry-etching resistance and is of low outgas. In addition, the cyclic compound (B0) is structurally pure to enhance the uniformity of the resist film. Therefore, the cyclic compound (B0) is preferably used as a resist component of a radiation-sensitive composition. With a radiation-sensitive composition containing the cyclic compound (B0), a high resolution, a high sensitivity, and a small line edge roughness are obtained.

Production Method (2) of Cyclic Compound (B0)

The present invention further relates to a method of producing a cyclic compound (B0), comprising a first stage reaction in which an aldehyde compound (A1d) having 2 to 59 carbon atoms, 1 to 2 carboxyl groups or ester groups and 1 to 4 formyl groups and a phenol compound (A2) are subjected to a condensation reaction, thereby synthesizing a cyclic compound (A0) having 1 to 8 carboxyl groups and a molecular weight of 800 to 5000, and a second stage reaction in which the cyclic compound (A0) is allowed to react with a compound (A3) having a halomethyl ether group.

The cyclic compound (B0) is also produced by using an alkyl halocarboxylate (A4) in place of the halomethyl ether compound (A3).

Examples of the alkyl halocarboxylate (A4) include, but not limited to, an aliphatic compound having 1 to 2 haloalkylcarbonyl groups, an alicyclic compound having 1 to 2 haloalkylcarbonyl groups, and an aromatic compound having 1 to 2 haloalkylcarbonyl groups. Preferred is a compound represented by the following formula (55):

(55)

wherein $R^7$ is a linear alkyl group having 1 to 20 carbon atoms, a branched alkyl group having 3 to 20 carbon atoms, a cycloalkyl group having 3 to 20 carbon atoms or an aryl group having 6 to 20 carbon atoms, X is a halogen atom, and $L_1$ is a single bond or a divalent organic group selected from linear and branched alkylene groups having 1 to 4 carbon atoms.

Examples of the linear alkyl group having 1 to 20 carbon atoms, preferably 1 to 12 carbon atoms include methyl group, ethyl group, n-propyl group, n-butyl group, n-pentyl group, n-octyl group, and n-dodecyl group.

Examples of the branched alkyl group having 3 to 20 carbon atoms, preferably 3 to 10 carbon atoms include isopropyl group, t-butyl group, isopentyl group, and neopentyl group.

The cycloalkyl group has 3 to 20 carbon atoms, preferably 6 to 14 carbon atoms. The aliphatic ring in the cycloalkyl group may be a monocyclic or polycyclic ring, preferably a polycyclic ring, for example, a monocycloalkane, a bicycloalkane, a tricycloalkane, and a tetracycloalkane, particularly, a monocycloalkane such as cyclopropane, cyclobutane, cyclopentane, and cyclohexane or a polycycloalkane such as adamantane, norbornane, isobornane, tricyclodecane, and tetracyclodecane. Preferred are adamantane, tricyclodecane, and tetracyclodecane, and particularly preferred are adamantane and tricyclodecane.

Examples of the aryl group having 6 to 20 carbon atoms include phenyl group, tolyl group, xylyl group, and naphthyl group.

Examples of the halogen atom include fluorine, chlorine, bromine, and iodine, with chlorine, bromine, and iodine being preferred, bromine and iodine being more preferred, and bromine being still more preferred.

The alkyl halocarboxylate (A4) may be produced as follows. For example, an alcohol compound such as 2-methyl-2-adamantanol is dissolved in an organic solvent such as tetrahydrofuran. After adding a base such as pyridine in an amount of 0.8 to 2.4 equivalent to the alcohol compound and a halocarboxylic acid halide such as bromoacetyl bromide in an amount of 0.8 to 2.4 equivalent to the alcohol compound, the reaction is allowed to proceed at 0 to 100° C. After the reaction, the aimed alkyl halocarboxylate (A4) is isolated from the product mixture by column chromatography.

The cyclic compound (B0) may be produced by the reaction between the cyclic compound (A0) having a carboxyl group and the alkyl halocarboxylate (A4). For example, the cyclic compound (A0) having a carboxyl group is dissolved or suspended in an aprotic solvent such as acetone, THF and propylene glycol monomethyl ether acetate. After adding the alkyl halocarboxylate (A4), the reaction is allowed to proceed under atmospheric pressure at 0 to 110° C. for 1 to 168 h in the presence of an alkali catalyst such as pyridine, triethylamine, diazabicycloundecene and potassium carbonate in an amount of 0.5 to 4 equivalent, preferably 0.9 to 1.1 equivalent, more preferably 1.0 equivalent based on the carboxyl group of the cyclic compound (A0). After washing with an alcohol such as methanol, washing with water and filtering, the separated matter is dried to obtain the cyclic compound (B0), which may be purified by a column chromatography, etc., if necessary.

The other details are the same as described with respect to the radiation-sensitive composition B.

Method of Forming Resist Pattern

The present invention further relates to a method of forming a resist pattern comprising a step of forming a resist film on a substrate using any of the radiation-sensitive compositions A to C, a step of exposing the resist film to radiation, and a step of developing the resist film to form the resist pattern.

In the formation of a resist pattern, the radiation-sensitive composition of the present invention is first applied on a substrate such as a silicon wafer and an aluminum-coated wafer by a coating method such as spin coating, cast coating and roll coating to form a resist film. The substrate may be treated in advance with a surface treating agent such as hexamethylenedisilazane, if necessary.

Then, the coated substrate is heated, if necessary. The heating temperature varies according to the blending ratio of each component in the radiation-sensitive composition, and preferably from 20 to 250° C. and more preferably from 20 to 150° C. The adhesion of the resist to the substrate is preferably improved in some cases by the heating. Then, the resist film is exposed in a desired pattern to a radiation selected from the group consisting of visible lights, ultraviolet rays, excimer lasers, electron beams, extreme ultraviolet rays (EUV), X-rays, and ion beams. The exposing conditions can be suitably selected according to the blending ratio of each component in the radiation-sensitive composition. In the present invention, it is preferred to conduct a heat treatment after the irradiation of radiation to stably form highly accurate fine patterns by the exposure. The heating temperature is preferably from 20 to 250° C. and more preferably from 20 to 150° C., although depending upon the blending ratio of each component in the radiation-sensitive composition.

Then, the exposed resist film is developed with an alkali developing solution to form desired resist patterns. As the alkali developing solution, there may be used an aqueous alkaline solution dissolving, for example, at least one alkaline compound selected from mono-, di- or trialkylamines, mono-, di- or trialkanolamines, heterocyclic amines, tetramethylammonium hydroxide (TMAH) and choline in a concentration of preferably from 1 to 10% by mass and more preferably from 1 to 5% by mass. The dissolution of the exposed portion in the developing solution is preferably prevented if the concentration is 10% by mass or less.

The alkali developing solution may contain an appropriate amount of an alcohol such as methanol, ethanol and isopropyl alcohol, or a surfactant mentioned above, with the addition of isopropyl alcohol in 10 to 30% by mass being particularly preferred, because the wetting between the resist and the developing solution is enhanced. After developing with such an aqueous alkaline solution, the developed patterns are generally washed with water.

After forming resist patterns, the substrate is etched to obtain a patterned wiring board. The etching may be performed by known methods such as a dry-etching using a plasma gas and a wet-etching using an alkali solution, a copper (II) chloride solution, an iron (III) chloride solution, etc.

After forming resist patterns, the substrate may be plated, for example, by copper plating, solder plating, nickel plating or gold plating.

The remaining resist patterns after etching may be stripped off by an organic solvent or an alkaline aqueous solution stronger than the aqueous alkali solution used for the development. Examples of the organic solvent include PGMEA (propylene glycol monomethyl ether acetate), PGME (propylene glycol monomethyl ether) and EL (ethyl lactate). Examples of the strong alkaline aqueous solution include a 1 to 20% by mass aqueous sodium hydroxide solution and 1 to 20% by mass aqueous potassium hydroxide solution. The stripping of the resist patterns may be performed by dipping method, spray method, etc. The wiring board having the resist patterns thereon may be a multi-layered wiring board and may be formed with small through-holes.

The wiring board may be produced by a lift-off method in which a metal is vacuum-deposited after the formation of resist patterns and then the remaining resist patterns are removed by dissolution into a solution.

EXAMPLES

The present invention will be described in more detail with reference to the following examples. However, it should be noted that the following examples are only illustrative and do not limit the scope of the present invention thereto. In the following synthesis examples and examples, the structure of each compound was identified by $^1$H-NMR measurement.

Synthesis Example 1

Synthesis of Cyclic Compound (A)

Synthesis of CR-1

A four-neck flack (1000 L) equipped with a dropping funnel, Dimroth condenser, a thermometer and a stirring device was sufficiently dried and purged with nitrogen. Into the flask, resorcinol (22 g, 0.2 mol, manufactured by Kanto Chemical Co., Inc.), 4-isopropylbenzaldehyde (29.6 g, 0.2 mol) and absolute ethanol (200 ml) were charged under nitrogen stream to prepare an ethanol solution. The solution was heated to 85° C. on a mantle heater under stirring. After adding 75 ml of a concentrated hydrochloric acid (35%) from the dropping funnel over 30 min, the solution was continuously stirred at 85° C. for 3 h. After the reaction, the solution was allowed to stand to reach room temperature and then cooled in an ice bath. After leaving at rest for 1 h, pale yellow crystals were generated. The separated crude crystals were washed twice with 500 ml of methanol, filtered and vacuum-dried to obtain the aimed compound (CR-1) (45.6 g, 95% yield). The result of LC-MS analysis showed that the compound had a molecular weight of 960 of the aimed compound.

$^1$H-NMR Chemical Shifts (δ ppm, TMS reference) in heavy dimethyl sulfoxide:

1.1-1.2 (m, 24H), 2.6-2.7 (m, 4H), 5.5 (s, 4H), 6.0-6.8 (m, 24H), 8.4, 8.5 (d, 8H)

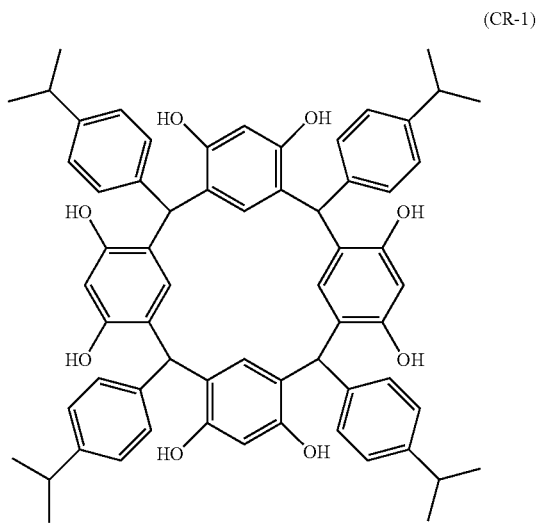

(CR-1)

Synthesis of CR-2

In the same manner as in Synthesis Example of CR-1 except for using 4-n-propylbenzaldehyde in place of 4-isopropylbenzaldehyde, CR-2 was synthesized (45.6 g, 95% yield). The result of LC-MS analysis showed that the compound had a molecular weight of 960 of the aimed compound.

$^1$H-NMR Chemical Shifts (δ ppm, TMS reference) in heavy dimethyl sulfoxide:

0.9-1.0 (m, 12H), 1.4-1.6 (m, 8H), 2.3-2.5 (m, 8H), 5.5 (s, 4H), 6.0-6.8 (m, 24H), 8.4, 8.5 (d, 8H)

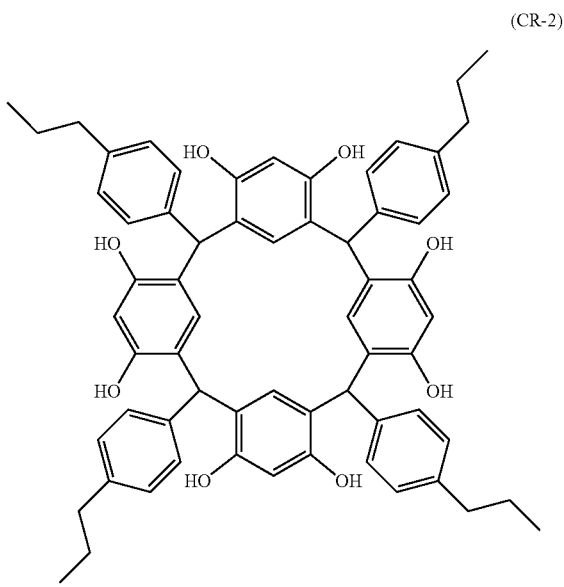

(CR-2)

Synthesis of CR-3

In the same manner as in Synthesis Example of CR-1 except for replacing a half the molar amount of 4-isopropylbenzaldehyde with 4-n-propylbenzaldehyde, 45.6 g of CR-3 was obtained. The result of LC-MS analysis showed that the compound had a molecular weight of 960 of the aimed compound.

$^1$H-NMR Chemical Shifts (δ ppm, TMS reference) in heavy dimethyl sulfoxide:

0.9-1.2 (m, 36H), 1.4-1.6 (m, 8H), 2.3-2.7 (m, 12H), 5.5 (d, 8H), 6.0-6.8 (m, 48H), 8.4, 8.5 (m, 16H)

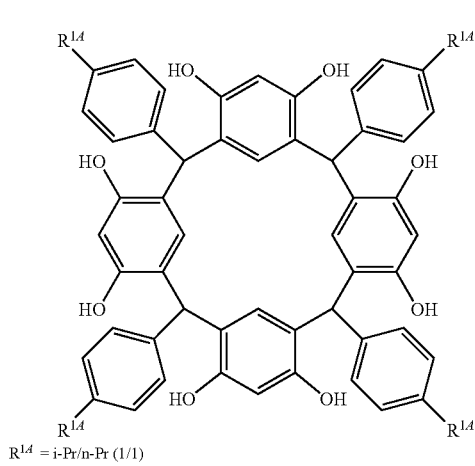

(CR-3)

$R^{1A}$ = i-Pr/n-Pr (1/1)

Synthesis of CR-4

In the same manner as in Synthesis Example of CR-1 except for replacing ¼ the molar amount of 4-isopropylbenzaldehyde with bromobenzaldehyde, 45.5 g of CR-4 was obtained.

$^1$H-NMR Chemical Shifts (δ ppm, TMS reference) in heavy dimethyl sulfoxide:

1.1-1.2 (m, 18H), 2.6-2.7 (m, 3H), 5.5 (m, 4H), 6.0-6.8 (m, 24H), 8.4-8.5 (m, 8H)

From the chemical shifts of $^1$H-NMR, the ratio of the number of bromine atoms to the total number of constituent atoms of CR-4 was 0.8%.

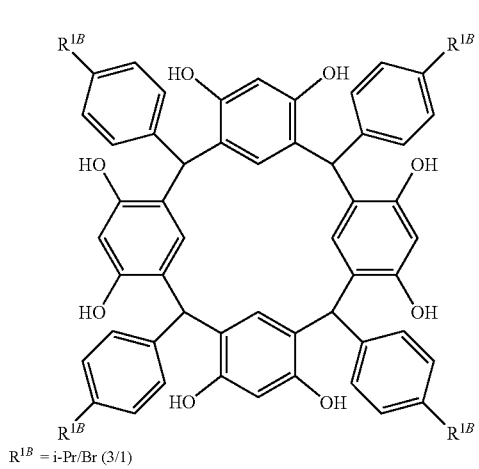

(CR-4)

$R^{1B}$ = i-Pr/Br (3/1)

Synthesis of CR-5

In the same manner as in Synthesis Example of CR-1 except for replacing ¼ the molar amount of 4-isopropylbenzaldehyde with bromobenzaldehyde and ⅛ with dimethylaminobenzaldehyde, 45.5 g of CR-5 was obtained.

$^1$H-NMR Chemical Shifts (δ ppm, TMS reference) in heavy dimethyl sulfoxide:

1.1-1.2 (m, 300H), 2.6-2.7 (m, 5H), 2.9 (m, 6H), 5.5 (m, 8H), 6.0-6.8 (m, 48H), 8.4, 8.5 (m, 16H)

From the chemical shifts of H-NMR, the ratio of the number of bromine atoms to the total number of constituent atoms of CR-5 was 0.8% and the ratio of the number of nitrogen atoms to the total number of constituent atoms of CR-5 was 0.4%.

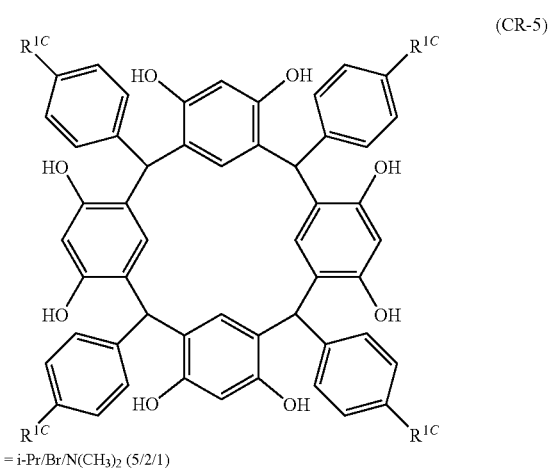

(CR-5)

$R^{1C}$ = i-Pr/Br/N(CH$_3$)$_2$ (5/2/1)

Synthesis of CR-6

In the same manner as in Synthesis Example of CR-1 except for using 2,4-dimethylbenzaldehyde in place of 4-isopropylbenzaldehyde, CR-6 was obtained (44.3 g, 98% yield). The result of LC-MS analysis showed that the compound had a molecular weight of 904 of the aimed compound.

$^1$H-NMR Chemical Shifts (δ ppm, TMS reference) in heavy dimethyl sulfoxide:

0.9-1.0 (d, 12H), 1.4-1.6 (d, 12H), 5.6 (t, 4H), 6.1-6.5 (m, 20H), 8.3-8.5 (m, 8H)

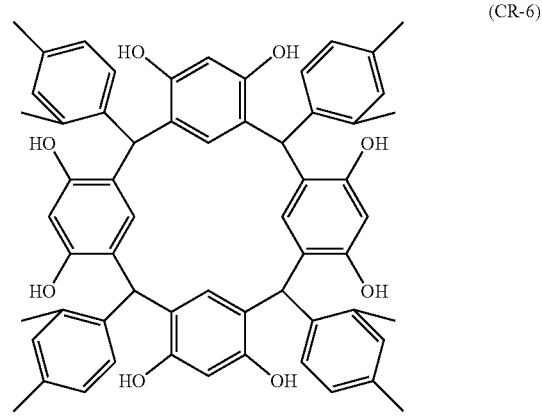

(CR-6)

Synthesis of CR-7

In the same manner as in Synthesis Example of CR-1 except for using isobutylbenzaldehyde in place of 4-isopropylbenzaldehyde, CR-7 was obtained (49.0 g, 96% yield). The result of LC-MS analysis showed that the compound had a molecular weight of 1017 of the aimed compound.

¹H-NMR Chemical Shifts (δ ppm, TMS reference) in heavy dimethyl sulfoxide:
1.7 (m, 4H), 2.3-2.4 (m, 8H), 5.5 (d, 4H), 5.8-6.8 (m, 24H), 8.4-8.6 (t, 8H)

(CR-7)

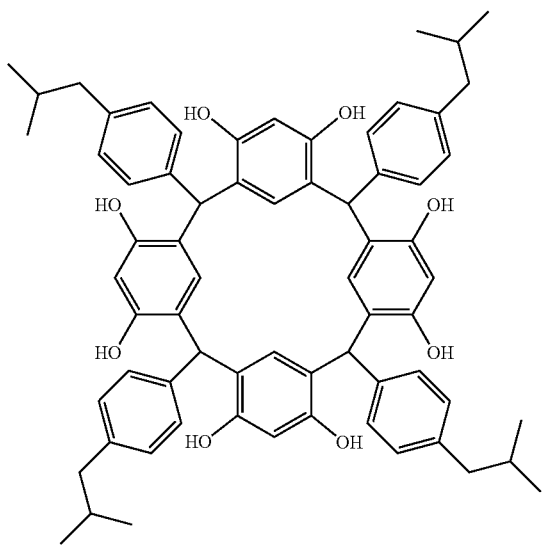

Synthesis of CR-8
In the same manner as in Synthesis Example of CR-1 except for using biphenylaldehyde in place of 4-isopropylbenzaldehyde, CR-8 was obtained (53.5 g, 98% yield). The result of LC-MS analysis showed that the compound had a molecular weight of 1096 of the aimed compound.

¹H-NMR Chemical Shifts (δ ppm, TMS reference) in heavy dimethyl sulfoxide:
6.0-7.4 (d, 4H), 6.1-6.5 (m, 24H), 8.6-8.7 (t, 8H)

(CR-8)

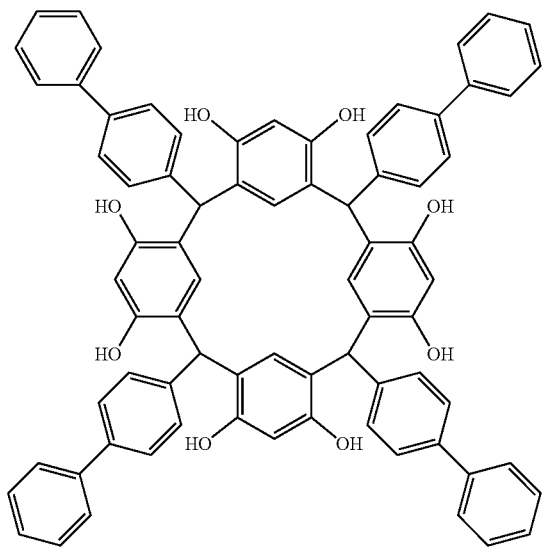

Synthesis of CR-9
In the same manner as in Synthesis Example of CR-1 except for using 3-bromo-4-methylbenzaldehyde in place of 4-isopropylbenzaldehyde, CR-9 was obtained (56.3 g, 97% yield). The result of LC-MS analysis showed that the compound had a molecular weight of 1160 of the aimed compound.

¹H-NMR Chemical Shifts (δ ppm, TMS reference) in heavy dimethyl sulfoxide:
1.0-1.2 (d, 12H), 6.0-7.4 (d, 4H), 6.1-6.5 (m, 20H), 8.6-8.7 (t, 8H)

(CR-9)

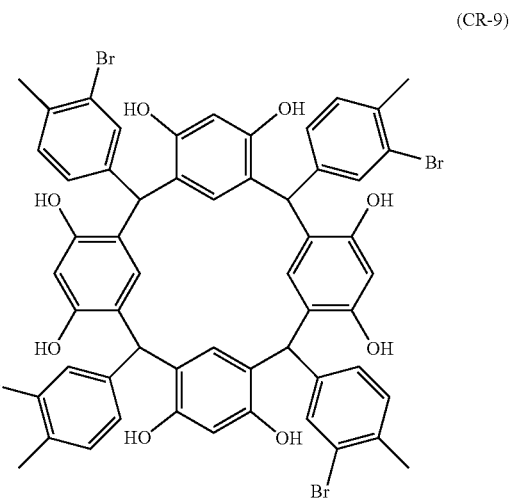

Synthesis of CR-10
In the same manner as in Synthesis Example of CR-1 except for using 5-bromo-2,4-dimethylbenzaldehyde in place of 4-isopropylbenzaldehyde, CR-10 was obtained (57.8 g, 95% yield). The result of LC-MS analysis showed that the compound had a molecular weight of 1216 of the aimed compound.

¹H-NMR Chemical Shifts (δ ppm, TMS reference) in heavy dimethyl sulfoxide:
0.9-1.0 (d, 12H), 1.4-1.6 (d, 12H), 6.0-7.4 (d, 4H), 6.1-6.5 (m, 16H), 8.6-8.7 (t, 8H)

(CR-10)

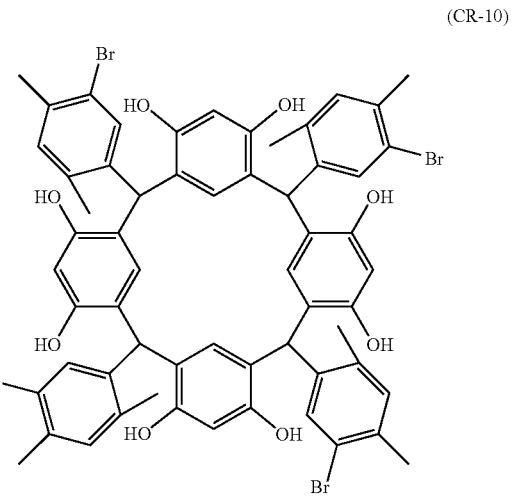

Synthesis of CP-1

In the same manner as in Synthesis Example of CR-1 except for using pyrogallol in place of resorcinol, CP-1 was obtained (49.9 g, 97% yield). The result of LC-MS analysis showed that the compound had a molecular weight of 1024 of the aimed compound.

$^1$H-NMR Chemical Shifts (δ ppm, TMS reference) in heavy dimethyl sulfoxide:
0.9-1.0 (m, 12H), 1.4-1.6 (m, 8H), 2.3-2.5 (m, 8H), 5.5 (s, 4H), 6.0-6.8 (m, 20H), 8.4-8.5 (m, 12H)

(CP-1)

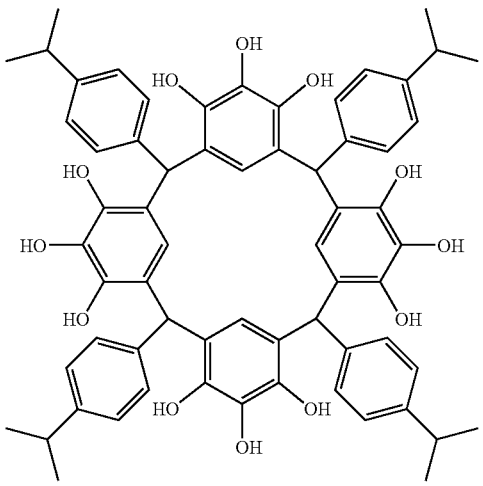

Synthesis of CP-2

In the same manner as in Synthesis Example of CR-1 except for using 4-biphenylaldehyde in place of 4-isopropylbenzaldehyde and using pyrogallol in place of resorcinol, CP-2 was obtained (55.8 g, 96% yield). The result of LC-MS analysis showed that the compound had a molecular weight of 1160 of the aimed compound.

$^1$H-NMR Chemical Shifts (δ ppm, TMS reference) in heavy dimethyl sulfoxide:
6.0-7.4 (d, 4H), 6.1-6.5 (m, 20H), 8.6-8.7 (m, 12H)

(CP-2)

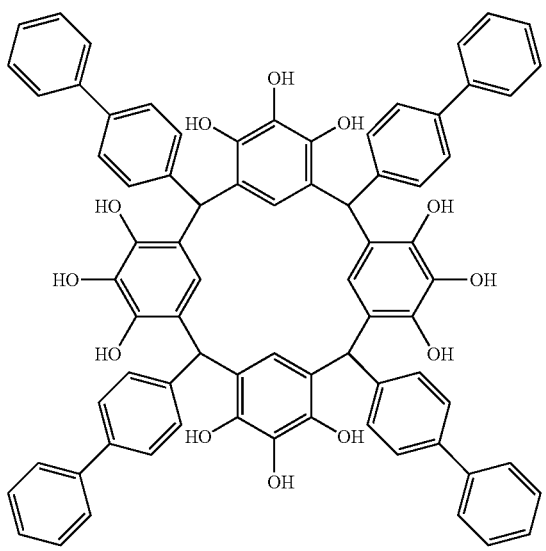

Synthesis Example 2

Synthesis of Cyclic Compound (B)

Synthesis of BOC50CR-1

A four-neck flask (1000 L) equipped with a dropping funnel, Dimroth condenser, a thermometer and a stirring device was sufficiently dried and purged with nitrogen. Into a solution of 9.6 g (10 mmol) of CR-1 synthesized in Synthesis Example 1, 0.1 g (1 mmol) of 4,4'-dimethylaminopyridine and 500 ml of acetone in the flask, 8.7 g (40 mmol) of di-t-butyl dicarbonate was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 13.0 g of BOC50CR-1 in which 50 mol % of the phenolic hydroxyl groups were substituted by t-butoxycarbonyl groups.

$^1$H-NMR Chemical Shifts (δ ppm, TMS reference) in heavy dimethyl sulfoxide:
1.1-1.3 (m, 60H), 2.6-2.7 (m, 4H), 5.5 (s, 4H), 6.0-6.8 (m, 24H), 8.4, 8.5 (d, 4H)

Synthesis of tBu50CR-1

A four-neck flask (1000 L) equipped with a dropping funnel, Dimroth condenser, a thermometer and a stirring device was sufficiently dried and purged with nitrogen. Into a solution of 9.6 g (10 mmol) of CR-1 synthesized in Synthesis Example 1, 13.8 g of potassium carbonate and 400 ml of THF in the flask, a solution of 7.7 g (40 mmol) of t-butyl bromoacetate in 100 ml of THF was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 12.9 g of tBu50CR-1 in which 50 mol % of the phenolic hydroxyl groups were substituted by t-butoxycarbonylmethyl groups.

$^1$H-NMR Chemical Shifts (δ ppm, TMS reference) in heavy dimethyl sulfoxide:
1.1-1.2 (m, 24H), 1.5 (d, 36H), 2.6-2.7 (m, 4H), 4.4-4.5 (d, 4H), 5.5 (s, 4H), 6.0-6.8 (m, 24H), 8.4, 8.5 (d, 4H)

Synthesis of MAD50CR-1

A four-neck flack (1000 L) equipped with a dropping funnel, Dimroth condenser, a thermometer and a stirring device was sufficiently dried and purged with nitrogen. Into a solution of 9.6 g (10 mmol) of CR-1 synthesized in Synthesis Example 1, 13.8 g of potassium carbonate and 400 ml of THF in the flask, a solution of 11.4 g (40 mmol) of methyladamantyl bromoacetate in 100 ml of THF was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 14.0 g of MAD50CR-1 in which 50 mol % of the phenolic hydroxyl groups were substituted by methyladamantyloxycarbonylmethyl groups.

$^1$H-NMR Chemical Shifts (δ ppm, TMS reference) in heavy dimethyl sulfoxide:
1.1-1.2 (m, 24H), 1.4-2.2 (m, 68H), 2.6-2.7 (m, 4H), 4.4-4.5 (d, 4H), 5.5 (s, 4H), 6.0-6.8 (m, 24H), 8.4, 8.5 (d, 4H)

Synthesis of EE50CR-1

A four-neck flack (1000 L) equipped with a dropping funnel, Dimroth condenser, a thermometer and a stirring device was sufficiently dried and purged with nitrogen. Into a solution of 9.6 g (10 mmol) of CR-1 synthesized in Synthesis Example 1, 2.5 g of pyridinium p-toluenesulfonate and 400 ml of acetone in the flask, 2.9 g (40 mmol) of ethyl vinyl ether was added dropwise under nitrogen stream. The reaction liquid was stirred at room temperature for 24 h. After the reaction, the solvent was removed. The obtained solid was purified by column chromatography using a mixed solvent of hexane/ethyl acetate=1/3, to obtain 11.2 g of EE50CR-1 in which 50 mol % of the phenolic hydroxyl groups were substituted by ethoxyethyl groups.

$^1$H-NMR Chemical Shifts (δ ppm, TMS reference) in heavy dimethyl sulfoxide:

0.9-1.0 (m, 12H), 1.1-1.2 (m, 24H), 1.3-1.4 (m, 12H), 2.6-2.7 (m, 4H), 3.3-3.4 (m, 8H), 5.1 (m, 4H), 5.5 (s, 4H), 6.0-6.8 (m, 24H), 8.4, 8.5 (d, 4H)

Synthesis of CE50CR-1

A four-neck flack (1000 L) equipped with a dropping funnel, Dimroth condenser, a thermometer and a stirring device was sufficiently dried and purged with nitrogen. Into a solution of 9.6 g (10 mmol) of CR-1 synthesized in Synthesis Example 1, 2.5 g of pyridinium p-toluenesulfonate and 400 ml of 1,3-dioxolane in the flask, 5.0 g (40 mmol) of cyclohexyl vinyl ether was added dropwise under nitrogen stream. The reaction liquid was stirred at room temperature for 24 h. After the reaction, the solvent was removed. The obtained solid was purified by column chromatography using a mixed solvent of hexane/ethyl acetate=1/3, to obtain 12.2 g of CE50CR-1 in which 50 mol % of the phenolic hydroxyl groups were substituted by cyclohexyloxyethyl groups.

$^1$H-NMR Chemical Shifts (δ ppm, TMS reference) in heavy dimethyl sulfoxide:

1.1-1.2 (m, 24H), 1.3-1.4 (m, 12H), 2.6-2.7 (m, 4H), 5.1 (m, 4H), 5.5 (s, 4H), 6.0-6.8 (m, 24H), 8.4, 8.5 (d, 4H)

Synthesis of BOC50CR-2

In the same manner as in the synthesis of BOC50CR-1 except for using CR-2 in place of CR-1, 30.0 g of OC50CR-2 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:

0.9-1.0 (m, 12H), 1.4-1.6 (m, 8H), 2.3-2.5 (m, 8H), 5.5 (s, 4H), 6.0-6.8 (m, 24H), 8.4, 8.5 (d, 4H)

Synthesis of tBu50CR-2

In the same manner as in the synthesis of tBu50CR-1 except for using CR-2 in place of CR-1, 30.0 g of BOC50CR-2 in which 50 mol % of the phenolic hydroxyl groups were substituted by t-butoxycarbonylmethyl groups was obtained.

$^1$H-NMR Chemical Shifts (δ ppm, TMS reference) in heavy dimethyl sulfoxide:

0.9-1.0 (m, 12H), 1.4-1.6 (m, 44H), 2.3-2.5 (m, 8H), 4.4-4.5 (d, 4H), 5.5 (s, 4H), 6.0-6.8 (m, 24H), 8.4, 8.5 (d, 4H)

Synthesis of MAD50CR-2

In the same manner as in the synthesis of MAD50CR-1 except for using CR-2 in place of CR-1, 30.0 g of MAD50CR-2 in which 50 mol % of the phenolic hydroxyl groups were substituted by methyladamantyloxycarbonylmethyl groups was obtained.

$^1$H-NMR Chemical Shifts (δ ppm, TMS reference) in heavy dimethyl sulfoxide:

0.9-1.0 (m, 12H), 1.4-2.2 (m, 76H), 2.3-2.5 (m, 8H), 4.4-4.5 (d, 4H), 5.5 (s, 4H), 6.0-6.8 (m, 24H), 8.4, 8.5 (d, 4H)

Synthesis of EE50CR-2

In the same manner as in the synthesis of EE50CR-1 except for using CR-2 in place of CR-1, 30.0 g of EE50CR-2 in which 50 mol % of the phenolic hydroxyl groups were substituted by ethoxyethyl groups was obtained.

$^1$H-NMR Chemical Shifts (δ ppm, TMS reference) in heavy dimethyl sulfoxide:

0.9-1.0 (m, 12H), 1.3-1.4 (m, 12H), 3.3-3.4 (m, 8H), 5.1 (m, 4H), 5.5 (s, 4H), 6.0-6.8 (m, 24H), 8.4, 8.5 (d, 4H)

Synthesis of CE50CR-2

In the same manner as in the synthesis of CE50CR-1 except for using CR-2 in place of CR-1, 30.0 g of CE50CR-2 in which 50 mol % of the phenolic hydroxyl groups were substituted by cyclohexyloxyethyl groups was obtained.

$^1$H-NMR Chemical Shifts (δ ppm, TMS reference) in heavy dimethyl sulfoxide:

0.9-1.0 (m, 12H), 1.3-1.4 (m, 12H), 1.4-1.6 (m, 8H), 2.3-2.5 (m, 8H), 5.1 (m, 4H), 5.5 (s, 4H), 6.0-6.8 (m, 24H), 8.4, 8.5 (d, 4H)

Synthesis of BOC50CR-3

In the same manner as in the synthesis of BOC50CR-1 except for using CR-3 in place of CR-1, 30.0 g BOC50CR-3 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:

0.9-1.2 (m, 36H), 1.2-1.3 (m, 72H), 1.4-1.6 (m, 8H), 2.3-2.7 (m, 12H), 5.5 (d, 8H), 6.0-6.8 (m, 48H), 8.4, 8.5 (m, 8H)

Synthesis of BOC50CR-4

In the same manner as in the synthesis of BOC50CR-1 except for using CR-4 in place of CR-1, 30.0 g of BOC50CR-4 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide: 1.1-1.2 (m, 18H), 1.2-1.3 (m, 36H), 2.6-2.7 (m, 3H), 5.5 (m, 4H), 6.0-6.8 (m, 24H), 8.4-8.5 (m, 4H)

Synthesis of BOC50CR-5

In the same manner as in the synthesis of BOC50CR-1 except for using CR-5 in place of CR-1, 30.0 g of BOC50CR-5 in which 50 mol % of the phenolic hydroxyl groups were substituted by t-butoxycarbonyl groups was obtained.

$^1$H-NMR Chemical Shifts (δ ppm, TMS reference):

1.1-1.2 (m, 30H), 1.2-1.3 (m, 72H), 2.6-2.7 (m, 5H), 2.9 (m, 6H), 5.5 (m, 8H), 6.0-6.8 (m, 48H), 8.4, 8.5 (m, 8H)

Synthesis of BOC50CR-6

In the same manner as in the synthesis of BOC50CR-1 except for using CR-6 in place of CR-1, 31.0 g of BOC50CR-6 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:

0.9-1.0 (d, 12H), 1.4-1.6 (d, 12H), 5.6 (t, 4H), 6.1-6.5 (m, 20H), 8.3-8.5 (m, 4H)

Synthesis of BOC50CR-7

In the same manner as in the synthesis of BOC50CR-1 except for using CR-7 in place of CR-1, 30.8 g of BOC50CR-7 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:

0.8-0.9 (d, 24H), 1.1-1.3 (s, 36H), 1.7 (m, 4H), 2.3-2.4 (m, 8H), 5.5 (d, 4H), 5.8-6.8 (m, 24H), 8.4-8.6 (t, 4H)

Synthesis of BOC50CR-8

In the same manner as in the synthesis of BOC50CR-1 except for using CR-8 in place of CR-1, 30.5 g of BOC50CR-8 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:

1.1-1.3 (s, 36H), 6.0-7.4 (d, 4H), 6.1-6.5 (m, 24H), 8.6-8.7 (t, 4H)

Synthesis of BOC50CR-9

In the same manner as in the synthesis of BOC50CR-1 except for using CR-9 in place of CR-1, 29.5 g of BOC50CR-9 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:
1.0-1.2 (d, 12H), 1.1-1.3 (s, 36H), 6.0-7.4 (d, 4H), 6.1-6.5 (m, 20H), 8.6-8.7 (t, 4H)

Synthesis of BOC50CR-10

In the same manner as in the synthesis of BOC50CR-1 except for using CR-10 in place of CR-1, 29.4 g of BOC50CR-10 in which 50 mol % of the phenolic hydroxyl groups were substituted by t-butoxycarbonyl groups was obtained.

$^1$H-NMR Chemical Shifts (δ ppm, TMS reference) in heavy dimethyl sulfoxide:
0.9-1.0 (d, 12H), 1.1-1.3 (s, 36H), 1.4-1.6 (d, 12H), 6.0-7.4 (d, 4H), 6.1-6.5 (m, 16H), 8.6-8.7 (t, 4H)

Synthesis of BOC67CP-1

In the same manner as in the synthesis of BOC50CR-1 except for using CP-1 in place of CR-1, 37.2 g of BOC67CP-1 in which 67 mol % of the phenolic hydroxyl groups were substituted by t-butoxycarbonyl groups was obtained.

$^1$H-NMR Chemical Shifts (δ ppm, TMS reference) in heavy dimethyl sulfoxide:
0.9-1.0 (m, 12H), 1.1-1.3 (s, 72H), 1.4-1.6 (m, 8H), 2.3-2.5 (m, 8H), 5.5 (s, 4H), 6.0-6.8 (m, 20H), 8.4-8.5 (m, 4H)

Synthesis of BOC67CP-2

In the same manner as in the synthesis of BOC50CR-1 except for using CP-2 in place of CR-1, 38.6 g of BOC67CP-2 in which 67 mol % of the phenolic hydroxyl groups were substituted by t-butoxycarbonyl groups was obtained.

$^1$H-NMR Chemical Shifts (δ ppm, TMS reference) in heavy dimethyl sulfoxide:
1.1-1.3 (s, 72H), 6.0-7.4 (d, 4H), 6.1-6.5 (m, 20H), 8.6-8.7 (m, 4H)

Examples 1-57 and Comparative Examples 1-3

The components shown in Table 1 were blended to obtain a uniform solution, which was then filtered through a Teflon membrane filter with a 0.2 μm pore size to prepare each resist composition. Each composition was evaluated for the following properties. The results are shown in Table 2.

(1) Evaluation of Resist Film-Forming Properties

A resist composition was spin-coated on a silicon wafer by using a spin coater. The surface appearance of the 10×10 mm resist film was visually observed. The surface appearance was good for all the resist compositions.

(2) Patterning Test (2-1) Evaluation of Resolution

After spin-coating a resist composition onto a clean silicon wafer, the applied resist composition was subjected to pre-exposure baking (PB) in an oven to form a resist film having a thickness of 0.1 μm. The resist film was irradiated with electron beams in a 1:1 line-and-space pattern with intervals of 50 nm using an electron beam lithography system (ELS-7500 manufactured by Elionix Co., Ltd.). After the irradiation, each resist film was heated at a predetermined temperature for 90 s and developed by immersing in a 2.38% by weight aqueous solution of TMAH for 60 s. Thereafter, by rinsing with distilled water for 30 s and drying, a positive-type resist pattern was formed. The obtained line-and-space pattern was observed under a scanning electron microscope (S-4800 manufactured by Hitachi High-Technologies Corporation). The dose (μC/cm$^2$) of the electron beam irradiation was taken as the sensitivity.

(2-2) Evaluation of Pattern Shape

The obtained 1:1 line-and-space pattern with intervals of 50 nm was cross-sectionally observed under the scanning electron microscope (S-4800 manufactured by Hitachi High-Technologies Corporation).
A: rectangular pattern (good)
B: nearly rectangular pattern (nearly good)
C: not rectangular pattern (poor)

(2-3) Evaluation of Line Edge Roughness (LER)

The distance between the edge and the base line was measured at 300 points which were randomly selected along the lengthwise direction (0.75 μm) of the 50-nm interval 1:1 line-and-space pattern, using Hitachi Semiconductor SEM, terminal PC and V5 off-line measuring software (available from Hitachi Science Systems, Ltd.). From the measured results, the standard deviation (3σ) was calculated.
A: LER (3σ)≦3.0 nm (good)
B: 3.0 nm<LER (3σ)≦3.5 nm (nearly good)
C: 3.5 nm<LER (3σ) (poor)

(2-4) Measurement of Outgas

A portion (1.2×1.2 mm) of the resist film was irradiated with electron beams in a dose (μC/cm$^2$) twice as much as that used in (2-1). Thereafter, the difference in film thickness between the portion irradiated with electron beams and the portion not irradiated was measured using a scanning probe microscope. The difference in film thickness was used as an indication of the outgas. The results were compared with the film loss measured in the same manner except for using a modified polyhydroxystyrene (PHS) in which 50 mol % of the hydroxyl groups had been substituted by t-butoxycarbonyl groups.
A: film loss is equal to or smaller than film loss of modified PHS
B: film loss is larger than film loss of modified PHS (3) Solubility in Safety Solvents The solubility of each compound obtained in Synthesis Example 2 in safety solvents was measured at 23° C. The solubility was evaluated by the largest dissolved amount in the following solvents: propylene glycol monomethyl ether acetate, propylene glycol monomethyl ether, 2-heptanone, anisole, butyl acetate, ethyl propionate, ethyl lactate, and cyclohexanone.
A: 10.0 wt %≦dissolved amount
B: 1.0 wt %≦dissolved amount <10.0 wt %
C: dissolved amount <1.0 wt %

TABLE 1

|  | Compound (A) (g) | Acid generator (C) (g) | Low molecular weight solubilizer (D) (g) | Acid-diffusion controller (E) (g) | Solvent (g) | Surfactant (F) (g) |
|---|---|---|---|---|---|---|
| Examples |  |  |  |  |  |  |
| 1 | BOC50CR-1 | P-1 | — | Q-1 | S-1 | — |
|  | 1.0 | 0.3 | — | 0.03 | 30.0 | — |
| 2 | BOC50CR-1 | P-1 | CR-1 | Q-1 | S-1 | — |
|  | 0.8 | 0.3 | 0.2 | 0.03 | 30.0 | — |
| 3 | tBu50CR-1 | P-1 | — | Q-1 | S-1 | — |
|  | 1.0 | 0.3 | — | 0.03 | 30.0 | — |

TABLE 1-continued

| | Compound (A) (g) | Acid generator (C) (g) | Low molecular weight solubilizer (D) (g) | Acid-diffusion controller (E) (g) | Solvent (g) | Surfactant (F) (g) |
|---|---|---|---|---|---|---|
| 4 | tBu50CR-1 0.8 | P-1 0.3 | CR-1 0.2 | Q-1 0.03 | S-1 30.0 | — |
| 5 | MAD50CR-1 1.0 | P-1 0.3 | — | Q-1 0.03 | S-1 30.0 | — |
| 6 | MAD50CR-1 0.8 | P-1 0.3 | CR-1 0.2 | Q-1 0.03 | S-1 30.0 | — |
| 7 | EE50CR-1 1.0 | P-1 0.3 | — | Q-1 0.03 | S-1 30.0 | — |
| 8 | EE50CR-1 0.8 | P-1 0.3 | CR-1 0.2 | Q-1 0.03 | S-1 30.0 | — |
| 9 | CE50CR-1 1.0 | P-1 0.3 | — | Q-1 0.03 | S-1 30.0 | — |
| 10 | CE50CR-1 0.8 | P-1 0.3 | CR-1 0.2 | Q-1 0.03 | S-1 30.0 | — |
| 11 | BOC50CR-1 1.0 | P-1 0.1 | — | Q-1 0.01 | S-1 30.0 | — |
| 12 | BOC50CR-1 0.8 | P-1 0.1 | CR-1 0.2 | Q-1 0.01 | S-1 30.0 | — |
| 13 | BOC50CR-1 1.0 | P-1 0.2 | — | Q-1 0.02 | S-1 30.0 | — |
| 14 | BOC50CR-1 0.8 | P-1 0.2 | CR-1 0.2 | Q-1 0.02 | S-1 30.0 | — |
| 15 | BOC50CR-1 1.0 | P-1/P-2 0.15/0.15 | — | Q-1 0.03 | S-1 30.0 | — |
| 16 | BOC50CR-1 1.0 | P-1 0.2 | — | Q-1 0.02 | S-1 30.0 | D-1 0.02 |
| 17 | BOC50CR-1 1.0 | P-1 0.2 | — | Q-1 0.02 | S-1 30.0 | D-2 0.02 |
| 18 | BOC50CR-1 0.8 | P-1 0.2 | CR-1 0.2 | Q-1 0.02 | S-1 30.0 | D-1 0.02 |
| 19 | BOC50CR-1 0.8 | P-2 0.2 | CR-1 0.2 | Q-1 0.02 | S-1 30.0 | — |
| 20 | CE50CR-1 0.8 | P-3 0.2 | CR-1 0.2 | Q-2 0.02 | S-1 30.0 | — |
| 21 | BOC50CR-2 1.0 | P-1 0.3 | — | Q-1 0.03 | S-1 30.0 | — |
| 22 | BOC50CR-2 0.8 | P-1 0.3 | CR-1 0.2 | Q-1 0.03 | S-1 30.0 | — |
| 23 | tBu50CR-2 1.0 | P-1 0.3 | — | Q-1 0.03 | S-1 30.0 | — |
| 24 | tBu50CR-2 0.8 | P-1 0.3 | CR-1 0.2 | Q-1 0.03 | S-1 30.0 | — |
| 25 | MAD50CR-2 1.0 | P-1 0.3 | — | Q-1 0.03 | S-1 30.0 | — |
| 26 | MAD50CR-2 0.8 | P-1 0.3 | CR-1 0.2 | Q-1 0.03 | S-1 30.0 | — |
| 27 | EE50CR-2 1.0 | P-1 0.3 | — | Q-1 0.03 | S-1 30.0 | — |
| 28 | EE50CR-2 0.8 | P-1 0.3 | CR-1 0.2 | Q-1 0.03 | S-1 30.0 | — |
| 29 | CE50CR-2 1.0 | P-1 0.3 | — | Q-1 0.03 | S-1 30.0 | — |
| 30 | CE50CR-2 0.8 | P-1 0.3 | CR-1 0.2 | Q-1 0.03 | S-1 30.0 | — |
| 31 | BOC50CR-2 1.0 | P-1 0.1 | — | Q-1 0.01 | S-1 30.0 | — |
| 32 | BOC50CR-2 0.8 | P-1 0.1 | CR-1 0.2 | Q-1 0.01 | S-1 30.0 | — |
| 33 | BOC50CR-2 1.0 | P-1 0.2 | — | Q-1 0.02 | S-1 30.0 | — |
| 34 | BOC50CR-2 0.8 | P-1 0.2 | CR-1 0.2 | Q-1 0.02 | S-1 30.0 | — |
| 35 | BOC50CR-2 1.0 | P-1/P-2 0.15/0.15 | — | Q-1 0.03 | S-1 30.0 | — |
| 36 | BOC50CR-2 1.0 | P-1 0.2 | — | Q-1 0.02 | S-1 30.0 | D-1 0.02 |

TABLE 1-continued

| | Compound (A) (g) | Acid generator (C) (g) | Low molecular weight solubilizer (D) (g) | Acid-diffusion controller (E) (g) | Solvent (g) | Surfactant (F) (g) |
|---|---|---|---|---|---|---|
| 37 | BOC50CR-2 1.0 | P-1 0.2 | — | Q-1 0.02 | S-1 30.0 | D-2 0.02 |
| 38 | BOC50CR-2 0.8 | P-1 0.2 | CR-1 0.2 | Q-1 0.02 | S-1 30.0 | D-1 0.02 |
| 39 | BOC50CR-2 0.8 | P-2 0.2 | CR-1 0.2 | Q-1 0.02 | S-1 30.0 | — |
| 40 | CE50CR-2 0.8 | P-3 0.2 | CR-1 0.2 | Q-2 0.02 | S-1 30.0 | — |
| 41 | BOC50CR-3 1.0 | P-1 0.1 | — | Q-1 0.01 | S-1 30.0 | — |
| 42 | BOC50CR-4 1.0 | P-1 0.1 | — | Q-1 0.01 | S-1 30.0 | — |
| 43 | BOC50CR-5 1.0 | P-1 0.1 | — | Q-1 0.01 | S-1 30.0 | — |
| Comparative Examples | | | | | | |
| 1 | BOC75CR-11 1.0 | P-1 0.1 | — | Q-1 0.01 | S-1 30.0 | — |
| 2 | BOC50CR-12 1.0 | P-1 0.1 | — | Q-1 0.01 | S-1 30.0 | — |
| 3 | BOC50CR-13 1.0 | P-1 0.1 | — | Q-1 0.01 | S-1 30.0 | — |
| Examples | | | | | | |
| 44 | BOC50CR-6 1.0 | P-1 0.3 | — | Q-1 0.03 | S-1 30.0 | — |
| 45 | BOC50CR-6 0.8 | P-1 0.3 | CR-6 0.2 | Q-1 0.03 | S-1 30.0 | — |
| 46 | BOC50CR-7 1.0 | P-1 0.3 | — | Q-1 0.03 | S-1 30.0 | — |
| 47 | BOC50CR-7 0.8 | P-1 0.3 | CR-7 0.2 | Q-1 0.03 | S-1 30.0 | — |
| 48 | BOC50CR-8 1.0 | P-1 0.3 | — | Q-1 0.03 | S-1 30.0 | — |
| 49 | BOC50CR-8 0.8 | P-1 0.3 | CR-8 0.2 | Q-1 0.03 | S-1 30.0 | — |
| 50 | BOC50CR-9 1.0 | P-1 0.3 | — | Q-1 0.03 | S-1 30.0 | — |
| 51 | BOC50CR-9 0.8 | P-1 0.3 | CR-7 0.2 | Q-1 0.03 | S-1 30.0 | — |
| 52 | BOC50CR-10 1.0 | P-1 0.3 | — | Q-1 0.03 | S-1 30.0 | — |
| 53 | BOC50CR-10 0.8 | P-1 0.3 | CR-8 0.2 | Q-1 0.03 | S-1 30.0 | — |
| 54 | BOC75CP-1 1.0 | P-1 0.3 | — | Q-1 0.03 | S-1 30.0 | — |
| 55 | BOC75CP-1 0.8 | P-1 0.3 | CP-1 0.2 | Q-1 0.03 | S-1 30.0 | — |
| 56 | BOC75CP-2 1.0 | P-1 0.3 | — | Q-1 0.03 | S-1 30.0 | — |
| 57 | BOC75CP-2 0.8 | P-1 0.3 | CP-2 0.2 | Q-1 0.03 | S-1 30.0 | — |

Comparative Compounds

BOC75CR-11

In the same manner as in Synthesis Example 1 except for using 4-hydroxybenzaldehyde in place of 4-isopropylbenzaldehyde, CR-11 of the following formula was obtained. Then, in the same manner as in Synthesis Example 2 except for using CR-11 in place of CR-1, the aimed compound BOC75CR-11 in which 75 mol % of the phenolic hydroxyl groups were substituted by t-butoxycarbonyl groups was obtained.

BOC50CR-12

In the same manner as in Synthesis Example 1 except for using acetaldehyde in place of 4-isopropylbenzaldehyde, CR-12 of the following formula was obtained. Then, in the same manner as in Synthesis Example 2 except for using CR-12 in place of CR-1, the aimed compound BOC50CR-12 in which 50 mol % of the phenolic hydroxyl groups were substituted by t-butoxycarbonyl groups was obtained.

BOC50CR-13

In the same manner as in Synthesis Example 1 except for using 4-t-butylbenzaldehyde in place of 4-isopropylbenzaldehyde, CR-13 of the following formula was obtained. Then, in the same manner as in Synthesis Example 2 except for using CR-13 in place of CR-1, the aimed compound BOC50CR-13 in which 50 mol % of the phenolic hydroxyl groups were substituted by t-butoxycarbonyl groups was obtained.

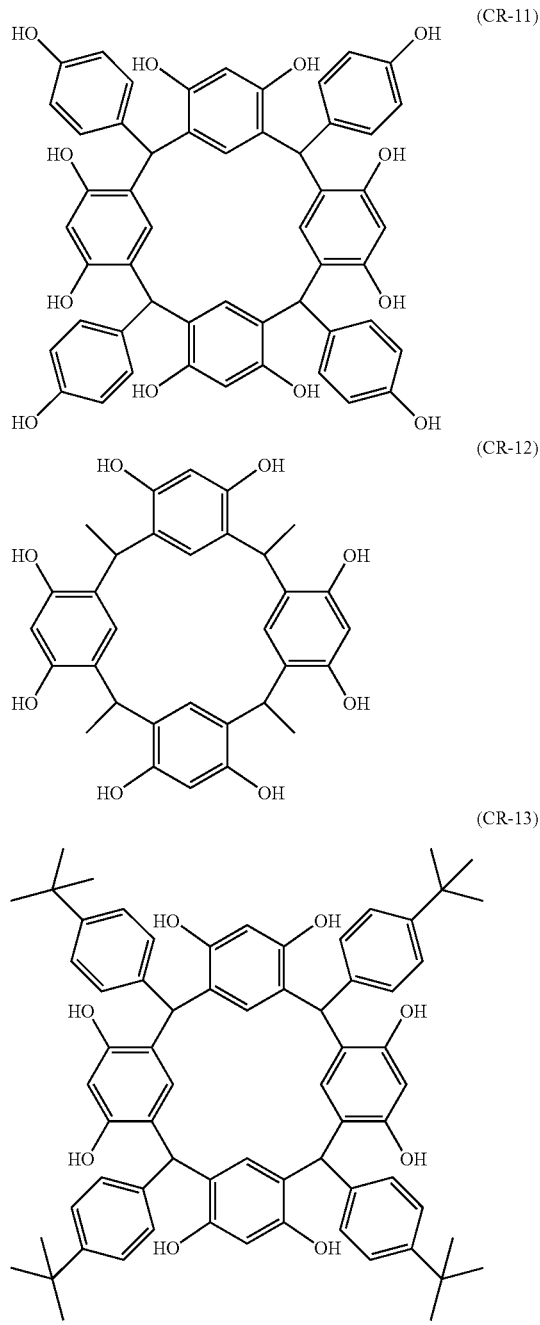

(CR-11)

(CR-12)

(CR-13)

Acid Generator (C)

P-1: triphenylbenzenesulfonium nonafluorobutanesulfonate (manufactured by Midori Kagaku Co., Ltd.)

P-2: triphenylbenzenesulfonium trifluoromethanesulfonate (manufactured by Midori Kagaku Co., Ltd.)

P-3: diphenyltrimethylphenylsulfonium p-toluenesulfonate (manufactured by Wako Pure Chemical Industries, Ltd.)

Acid-Diffusion Controller (E)

Q-1: trioctylamine (manufactured by Tokyo Kasei Kogyo Co., Ltd.)

Q-2: Lophine (manufactured by Tokyo Kasei Kogyo Co., Ltd.)

Other Component (F) (Surfactant)

D-1: Megafac R-08 (manufactured by Dainippon Ink & Chemicals, Inc.)

D-2: BYK-302 (manufactured by BYK Chemie Japan Co., Ltd.) Solvent

S-1: propylene glycol monomethyl ether (manufactured by Tokyo Kasei Kogyo Co., Ltd.)

TABLE 2

| | PEB (° C.) | Sensitivity ($\mu C/cm^2$) | Shape of pattern | LER | Outgas | Solubility |
|---|---|---|---|---|---|---|
| Examples | | | | | | |
| 1 | 130 | 15.0 | A | A | B | B |
| 2 | 130 | 10.0 | B | A | B | B |
| 3 | 115 | 15.0 | A | A | B | B |
| 4 | 115 | 10.0 | B | A | B | B |
| 5 | 115 | 15.0 | A | A | B | B |
| 6 | 115 | 10.0 | B | A | B | B |
| 7 | 110 | 15.0 | A | A | B | B |
| 8 | 110 | 10.0 | B | A | B | B |
| 9 | 110 | 15.0 | A | A | B | B |
| 10 | 110 | 10.0 | B | A | B | B |
| 11 | 130 | 18.0 | A | A | B | B |
| 12 | 130 | 12.0 | B | A | B | B |
| 13 | 130 | 20.0 | A | A | B | B |
| 14 | 130 | 15.0 | B | A | B | B |
| 15 | 110 | 15.0 | A | A | B | B |
| 16 | 130 | 18.0 | A | A | B | B |
| 17 | 130 | 18.0 | A | A | B | B |
| 18 | 130 | 12.0 | A | A | B | B |
| 19 | 115 | 15.0 | A | A | B | B |
| 20 | 110 | 15.0 | A | A | B | B |
| 21 | 130 | 15.0 | A | A | B | B |
| 22 | 130 | 10.0 | B | A | B | B |
| 23 | 115 | 15.0 | A | A | B | B |
| 24 | 115 | 10.0 | B | A | B | B |
| 25 | 115 | 15.0 | A | A | B | B |
| 26 | 115 | 10.0 | B | A | B | B |
| 27 | 110 | 15.0 | A | A | B | B |
| 28 | 110 | 10.0 | B | A | B | B |
| 29 | 110 | 15.0 | A | A | B | B |
| 30 | 110 | 10.0 | B | A | B | B |
| 31 | 130 | 18.0 | A | A | B | B |
| 32 | 130 | 12.0 | B | A | B | B |
| 33 | 130 | 20.0 | A | A | B | B |
| 34 | 130 | 15.0 | B | A | B | B |
| 35 | 110 | 15.0 | A | A | B | B |
| 36 | 130 | 18.0 | A | A | B | B |
| 37 | 130 | 18.0 | A | A | B | B |
| 38 | 130 | 12.0 | A | A | B | B |
| 39 | 115 | 15.0 | A | A | B | B |
| 40 | 110 | 15.0 | A | A | B | B |
| 41 | 130 | 12.5 | A | A | B | A |
| 42 | 130 | 10.0 | A | A | B | A |
| 43 | 130 | 12.5 | A | A | B | A |
| Comparative Examples | | | | | | |
| 1 | 130 | 20.0 | C | C | A | B |
| 2 | 130 | 18.0 | C | C | C | B |
| 3 | 130 | 18.0 | C | C | C | B |
| Examples | | | | | | |
| 44 | 130 | 15.0 | A | A | B | B |
| 45 | 130 | 10.0 | B | A | B | B |
| 46 | 130 | 15.0 | A | A | B | B |
| 47 | 130 | 10.0 | B | A | B | B |
| 48 | 130 | 15.0 | A | A | B | B |
| 49 | 130 | 10.0 | B | A | B | B |
| 50 | 130 | 8.0 | A | A | B | B |
| 51 | 130 | 6.0 | B | A | B | B |
| 52 | 130 | 8.0 | A | A | B | B |
| 53 | 130 | 6.0 | B | A | B | B |

TABLE 2-continued

|    | PEB (° C.) | Sensitivity (μC/cm²) | Shape of pattern | LER | Outgas | Solubility |
|----|------------|----------------------|------------------|-----|--------|------------|
| 54 | 130 | 15.0 | A | A | B | B |
| 55 | 130 | 10.0 | B | A | B | B |
| 56 | 130 | 15.0 | A | A | B | B |
| 57 | 130 | 10.0 | B | A | B | B |

PEB: temperature of the post electron beam-exposure heating.

Synthesis Example 1A

Synthesis of Benzaldehyde Compound Having 10 to 24 Carbon Atoms and a Group Including Aliphatic or Aromatic Ring Into a 500-ml thermo-controllable autoclave made of SUS316L equipped with an electromagnetic stirring device, 74.3 g (3.71 mol) of dry HF and 50.5 g (0.744 mol) of $BF_3$ were charged. While stirring the contents and maintaining the liquid temperature at −30° C., the pressure was raised to 2 MPa by introducing carbon monoxide. Then, a mixed raw material of 57.0 g (0.248 mol) of 4-cyclohexylbenzene and 50.0 g of n-heptane was introduced into the autoclave while maintaining the pressure at 2 MPa and the liquid temperature at −30° C. After further maintaining for 1 h, the contents were poured into ice, diluted with benzene and neutralized. The oil layer was analyzed by gas chromatography. The conversion of 4-cyclohexylbenzene was 100% and the selectivity of 4-cyclohexylbenzaldehyde was 97.3%. The result of GC-MS analysis showed that the component isolated by a single distillation had a molecular weight of 188 of the aimed 4-cyclohexylbenzaldehyde (CHBAL).

$^1$H-NMR Chemical Shifts (δ ppm, TMS reference) in heavy chloroform:
1.0-1.6 (m, 10H), 2.55 (m, 1H), 7.36 (d, 2H), 7.8 (d, 2H), 10.0 (s, 1H)

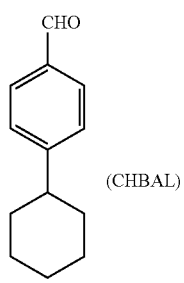

(CHBAL)

Synthesis Example 2A

Synthesis of Cyclic Polyphenol Compound A

A four-neck flack (1000 L) equipped with a dropping funnel, Dimroth condenser, a thermometer and a stirring device was sufficiently dried and purged with nitrogen. Into the flask, resorcinol (22 g, 0.2 mol, manufactured by Kanto Chemical Co., Inc.), 4-cyclohexylbenzaldehyde (46.0 g, 0.2 mol) synthesized in Synthesis Example A1 and absolute ethanol (200 ml) were charged under nitrogen stream to prepare an ethanol solution. The solution was heated to 85° C. in a mantle heater under stirring. After adding 75 ml of a concentrated hydrochloric acid (35%) from the dropping funnel over 30 min, the solution was continuously stirred at 85° C. for 3 h. After the reaction, the solution was allowed to stand to reach room temperature and then cooled in an ice bath. After leaving at rest for 1 h, pale yellow crystals were generated. The separated crude crystals were washed twice with 500 ml of methanol, filtered and vacuum-dried to obtain the aimed compound (CR-1A) (50 g, 91% yield). The result of LC-MS analysis showed that the compound had a molecular weight of 1121 of the aimed compound.

$^1$H-NMR Chemical Shifts (δ ppm, TMS reference) in heavy chloroform:
0.8-1.9 (m, 56H), 5.5, 5.6 (d, 4H), 6-6.8 (m, 24H), 8.4, 8.5 (m, 8H)

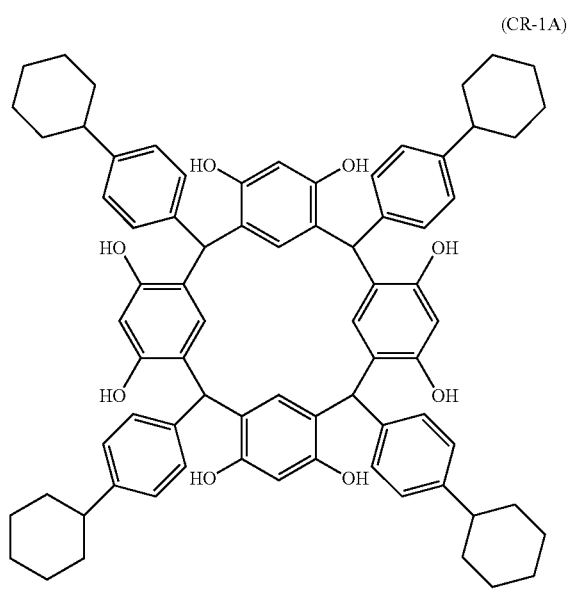

(CR-1A)

Synthesis Example 3A

Synthesis of Cyclic Compound (B)

Synthesis of BOC50CR-1A

A four-neck flack (1000 L) equipped with a dropping funnel, Dimroth condenser, a thermometer and a stirring device was sufficiently dried and purged with nitrogen. Into a solution of 11.2 g (10 mmol) of CR-1A synthesized in Synthesis Example 2A, 0.1 g (1 mmol) of 4,4'-dimethylaminopyridine and 500 ml of acetone in the flask, 8.7 g (40 mmol) of di-t-butyl dicarbonate was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 13.0 g of BOC50CR-1A in which 50 mol % of the phenolic hydroxyl groups were substituted by t-butoxycarbonyl groups.

$^1$H-NMR Chemical Shifts (δ ppm, TMS reference) in heavy chloroform:
0.8-1.9 (m, 92H), 5.5, 5.6 (d, 4H), 6-6.8 (m, 24H), 8.4, 8.5 (m, 4H)

Synthesis of tBu50CR-1A

A four-neck flack (1000 L) equipped with a dropping funnel, Dimroth condenser, a thermometer and a stirring device was sufficiently dried and purged with nitrogen. Into a solution of 11.2 g (10 mmol) of CR-1A synthesized in Synthesis Example 2A, 13.8 g of potassium carbonate and 400 ml of THF in the flask, a solution of 7.7 g (40 mmol) of t-butyl bromoacetate in 100 ml of THF was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 12.9 g of tBu50CR-1A in which 50 mol % of the phenolic hydroxyl groups were substituted by t-butoxycarbonylmethyl groups.

$^1$H-NMR Chemical Shifts (δ ppm, TMS reference) in heavy chloroform:
0.8-1.9 (m, 92H), 4.7 (s, 8H), 5.5, 5.6 (d, 4H), 6-6.8 (m, 24H), 8.4, 8.5 (m, 4H)

Synthesis of MAD50CR-1A

A four-neck flack (1000 L) equipped with a dropping funnel, Dimroth condenser, a thermometer and a stirring device was sufficiently dried and purged with nitrogen. Into a solution of 11.2 g (10 mmol) of CR-1A synthesized in Synthesis Example 2A, 13.8 g of potassium carbonate and 400 ml of THF in the flask, a solution of 11.4 g (40 mmol) of methyladamantyl bromoacetate in 100 ml of THF was added dropwise under nitrogen stream. The reaction liquid was stirred at room temperature for 1 h. After the reaction, the solvent was removed. The obtained solid was purified by column chromatography using a mixed solvent of hexane/ethyl acetate=1/3, to obtain 14.0 g of MAD50CR-1A in which 50 mol % of the phenolic hydroxyl groups were substituted by methyladamantyloxycarbonylmethyl groups.

$^1$H-NMR Chemical Shifts (δ ppm, TMS reference) in heavy chloroform:
0.8-2.1 (m, 124H), 4.7 (s, 8H), 5.5, 5.6 (d, 4H), 6-6.8 (m, 24H), 8.4, 8.5 (m, 4H)

Synthesis of EE50CR-1A

A four-neck flack (1000 L) equipped with a dropping funnel, Dimroth condenser, a thermometer and a stirring device was sufficiently dried and purged with nitrogen. Into a solution of 11.2 g (10 mmol) of CR-1A synthesized in Synthesis Example 2A, 2.5 g of pyridinium p-toluenesulfonate and 400 ml of acetone in the flask, 2.9 g (40 mmol) of ethyl vinyl ether was added dropwise under nitrogen stream. The reaction liquid was stirred at room temperature for 24 h. After the reaction, the solvent was removed. The obtained solid was purified by column chromatography using a mixed solvent of hexane/ethyl acetate=1/3, to obtain 11.2 g of EE50CR-1A in which 50 mol % of the phenolic hydroxyl groups were substituted by ethoxyethyl groups.

$^1$H-NMR Chemical Shifts (δ ppm, TMS reference) in heavy chloroform:
0.8-1.9 (m, 80H), 3.5 (m, 8H), 5.5, 5.6 (d, 8H), 6-6.8 (m, 24H), 8.4, 8.5 (m, 4H)

Synthesis of CE50CR-1A

A four-neck flack (1000 L) equipped with a dropping funnel, Dimroth condenser, a thermometer and a stirring device was sufficiently dried and purged with nitrogen. Into a solution of 11.2 g (10 mmol) of CR-1A synthesized in Synthesis Example 2A, 2.5 g of pyridinium p-toluenesulfonate and 400 ml of 1,3-dioxolane in the flask, 5.0 g (40 mmol) of cyclohexyl vinyl ether was added dropwise under nitrogen stream. The reaction liquid was stirred at room temperature for 24 h. After the reaction, the solvent was removed. The obtained solid was purified by column chromatography using a mixed solvent of hexane/ethyl acetate=1/3, to obtain 12.2 g of CE50CR-1A in which 50 mol % of the phenolic hydroxyl groups were substituted by cyclohexyloxyethyl groups.

$^1$H-NMR Chemical Shifts (δ ppm, TMS reference) in heavy chloroform:
0.8-1.9 (m, 108H), 3.5 (m, 4H), 5.5, 5.6 (d, 8H), 6-6.8 (m, 24H), 8.4, 8.5 (m, 4H)

Examples 1A-20A

The components shown in Table 1A were blended to obtain a uniform solution, which was then filtered through a Teflon membrane filter with a 0.2 μm pore size to prepare each resist composition. The same acid generator (C), acid-diffusion controller (E), other additive (F), and solvent as in Examples 1-43 were used. The evaluations were made in the same manner except for evaluating the patterning test by the following ratings.

(2-3) Evaluation of Line Edge Roughness (LER)
A: LER (3σ)≦3.5 nm (good)
B: 3.5 nm<LER (3σ)≦4.5 nm (nearly good)
C: 4.5 nm<LER (3σ) (poor)

In the test of solubility in safety solvents (3), all the tested compounds dissolved in an amount of 2.5 wt % or more.

TABLE 1A

| Examples | Compound (g) | Acid generator (C) (g) | Low molecular weight solubilizer (D) (g) | Acid-diffusion controller (E) (g) | Solvent (g) | Surfactant (F) (g) |
|---|---|---|---|---|---|---|
| 1A | BOC50CR-1A | P-1 | — | Q-1 | S-1 | — |
|    | 1.0 | 0.3 | — | 0.03 | 30.0 | — |
| 2A | BOC50CR-1A | P-1 | CR-1 | Q-1 | S-1 | — |
|    | 0.8 | 0.3 | 0.2 | 0.03 | 30.0 | — |
| 3A | tBu50CR-1A | P-1 | — | Q-1 | S-1 | — |
|    | 1.0 | 0.3 | — | 0.03 | 30.0 | — |
| 4A | tBu50CR-1A | P-1 | CR-1 | Q-1 | S-1 | — |
|    | 0.8 | 0.3 | 0.2 | 0.03 | 30.0 | — |
| 5A | MAD50CR-1A | P-1 | — | Q-1 | S-1 | — |
|    | 1.0 | 0.3 | — | 0.03 | 30.0 | — |
| 6A | MAD50CR-1A | P-1 | CR-1 | Q-1 | S-1 | — |
|    | 0.8 | 0.3 | 0.2 | 0.03 | 30.0 | — |
| 7A | EE50CR-1A | P-1 | — | Q-1 | S-1 | — |
|    | 1.0 | 0.3 | — | 0.03 | 30.0 | — |
| 8A | EE50CR-1A | P-1 | CR-1 | Q-1 | S-1 | — |
|    | 0.8 | 0.3 | 0.2 | 0.03 | 30.0 | — |
| 9A | CE50CR-1A | P-1 | — | Q-1 | S-1 | — |
|    | 1.0 | 0.3 | — | 0.03 | 30.0 | — |

TABLE 1A-continued

| Examples | Compound (g) | Acid generator (C) (g) | Low molecular weight solubilizer (D) (g) | Acid-diffusion controller (E) (g) | Solvent (g) | Surfactant (F) (g) |
|---|---|---|---|---|---|---|
| 10A | CE50CR-1A 0.8 | P-1 0.3 | CR-1 0.2 | Q-1 0.03 | S-1 30.0 | — |
| 11A | BOC50CR-1A 1.0 | P-1 0.1 | — | Q-1 0.01 | S-1 30.0 | — |
| 12A | BOC50CR-1A 0.8 | P-1 0.1 | CR-1 0.2 | Q-1 0.01 | S-1 30.0 | — |
| 13A | BOC50CR-1A 1.0 | P-1 0.2 | — | Q-1 0.02 | S-1 30.0 | — |
| 14A | BOC50CR-1A 0.8 | P-1 0.2 | CR-1 0.2 | Q-1 0.02 | S-1 30.0 | — |
| 15A | BOC50CR-1A 1.0 | P-1/P-2 0.15/0.15 | — | Q-1 0.03 | S-1 30.0 | — |
| 16A | BOC50CR-1A 1.0 | P-1 0.2 | — | Q-1 0.02 | S-1 30.0 | D-1 0.02 |
| 17A | BOC50CR-1A 1.0 | P-1 0.2 | — | Q-1 0.02 | S-1 30.0 | D-2 0.02 |
| 18A | BOC50CR-1A 0.8 | P-1 0.2 | CR-1 0.2 | Q-1 0.02 | S-1 30.0 | D-1 0.02 |
| 19A | BOC50CR-1A 0.8 | P-2 0.2 | CR-1 0.2 | Q-1 0.02 | S-1 30.0 | — |
| 20A | CE50CR-1A 0.8 | P-3 0.2 | CR-1 0.2 | Q-2 0.02 | S-1 30.0 | — |

TABLE 2A

| Examples | PEB (° C.) | Sensitivity ($\mu C/cm^2$) | Shape of pattern | LER (3σ) | Outgas |
|---|---|---|---|---|---|
| 1A | 130 | 15.0 | A | A | A |
| 2A | 130 | 10.0 | B | A | A |
| 3A | 115 | 15.0 | A | A | A |
| 4A | 115 | 10.0 | B | A | A |
| 5A | 115 | 15.0 | A | A | A |
| 6A | 115 | 10.0 | B | A | A |
| 7A | 110 | 15.0 | A | A | A |
| 8A | 110 | 10.0 | B | A | A |
| 9A | 110 | 15.0 | A | A | A |
| 10A | 110 | 10.0 | B | A | A |
| 11A | 130 | 18.0 | A | A | A |
| 12A | 130 | 12.0 | B | A | A |
| 13A | 130 | 20.0 | A | A | A |
| 14A | 130 | 15.0 | B | A | A |
| 15A | 110 | 15.0 | A | A | A |
| 16A | 130 | 18.0 | A | A | A |
| 17A | 130 | 18.0 | A | A | A |
| 18A | 130 | 12.0 | A | A | A |
| 19A | 115 | 15.0 | A | A | A |
| 20A | 110 | 15.0 | A | A | A |

PEB: temperature of the post electron beam-exposure heating.

Synthesis Example 1B

Synthesis of Compound for Introducing Acid-Dissociating Functional Group

Synthesis of Methyladamantyl Bromoacetate

A four-neck flask (1000 L) equipped with a dropping funnel, Dimroth condenser, a thermometer and a stirring device was sufficiently dried and purged with nitrogen. Into a solution of 2-methyl-2-adamantanol (manufactured by Golden Elephant Chemical Co., Ltd.) (8.31 g, 50 mmol), pyridine (5.0 g, 62.7 mmol), and 100 ml of THF in the flask, a solution of bromoacetyl bromide (12.65 g, 62.7 mmol) in 20 ml THF was added dropwise at 0° C. under nitrogen stream. The reaction liquid was stirred at room temperature for 72 h.

After the reaction, the undissolved matter was filtered off. The sold obtained by removing the solvent from the filtrate was purified by column chromatography using a mixed solvent of hexane/ethyl acetate=50/1, to obtain 9.0 g (62% yield) of methyladamantyl bromoacetate shown below.

$^1$H-NMR Chemical Shifts (δ ppm, TMS reference) in heavy chloroform:

1.0-2.5 (m, 17H), 4.5 (m, 2H)

Synthesis of Ethyladamantyl Bromoacetate

In the same manner as in the synthesis of methyladamantyl bromoacetate except for using 2-ethyl-2-adamantanol (manufactured by Mitsubishi Gas Chemical Company, Inc.) in place of 2-methyl-2-adamantanol, ethyladamantyl bromoacetate shown below was synthesized.

$^1$H-NMR Chemical Shifts (δ ppm, TMS reference) in heavy chloroform:

1.0-2.5 (m, 17H), 4.5 (m, 2H)

Synthesis of Ethyladamantyl Bromopropionate

In the same manner as in the synthesis of methyladamantyl bromoacetate except for using 2-ethyl-2-adamantanol (manufactured by Golden Elephant Chemical Co., Ltd.) in place of 2-methyl-2-adamantanol and using bromopropionyl bromide in place of bromoacetyl bromide, ethyladamantyl bromopropionate shown below was synthesized.

$^1$H-NMR Chemical Shifts (δ ppm, TMS reference) in heavy chloroform:

1.0-2.5 (m, 19H), 4.5 (m, 2H)

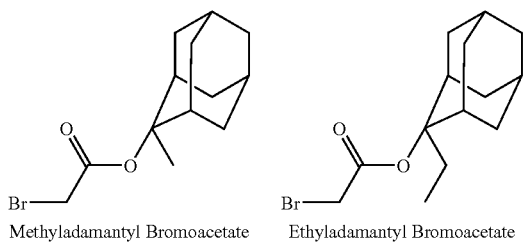

Methyladamantyl Bromoacetate    Ethyladamantyl Bromoacetate

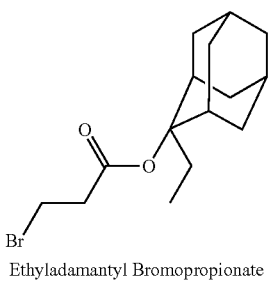

Ethyladamantyl Bromopropionate

As described below, an aldehyde compound (A1) was first synthesized and then a cyclic compound was synthesized.

Synthesis Example 2B

Synthesis of Aldehyde Compound (A1)

Synthesis of AD1-HBA

A four-neck flask (1000 L) equipped with a dropping funnel, Dimroth condenser, a thermometer and a stirring device was sufficiently dried and purged with nitrogen. Into a solution of p-hydroxybenzaldehyde (12.2 g, 100 mmol), potassium carbonate (13.8 g, 100 mmol) and 200 ml of THF in the flask, a solution of 28.6 g (100 mmol) of methyladamantyl bromoacetate in 100 ml of THF was added dropwise under nitrogen stream. The reaction liquid was stirred for 24 h under reflux.

After the reaction, the solvent was removed to obtain a solid, which was purified by column chromatography using a mixed solvent of hexane/ethyl acetate=1/3, to obtain 29.0 g of AD1-HBA shown below in which the phenolic hydroxyl group is substituted by methyladamantyloxycarbonylmethyl group.

$^1$H-NMR Chemical Shifts (δ ppm, TMS reference) in heavy chloroform:

1.5-2.2 (m, 17H), 4.9 (s, 2H), 7.8-8.4 (m, 4H), 10.0 (m, 1H)

Synthesis of AD2-HBA

In the same manner as in the synthesis of AD1-HBA except for using ethyladamantyl bromoacetate in place of methyladamantyl bromoacetate, 30.1 g of AD2-HBA shown below in which the phenolic hydroxyl group is substituted by ethyladamantyloxycarbonylmethyl group was obtained.

$^1$H-NMR Chemical Shifts (δ ppm, TMS reference) in heavy chloroform:

1.5-2.2 (m, 19H), 4.9 (s, 2H), 7.8-8.4 (m, 4H), 10.0 (m, 1H)

Synthesis of AD3-HBA

In the same manner as in the synthesis of AD1-HBA except for using ethyladamantyl bromopropionate in place of methyladamantyl bromoacetate, 31.1 g of AD3-HBA shown below in which the phenolic hydroxyl group is substituted by ethyladamantyloxycarbonylethyl group was obtained.

$^1$H-NMR Chemical Shifts (δ ppm, TMS reference) in heavy chloroform:

1.5-2.2 (m, 19H), 2.7 (m, 2H), 4.9 (s, 2H), 7.8-8.4 (m, 4H), 10.0 (m, 1H)

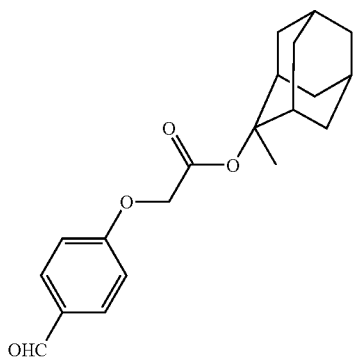

(AD1-HBA)

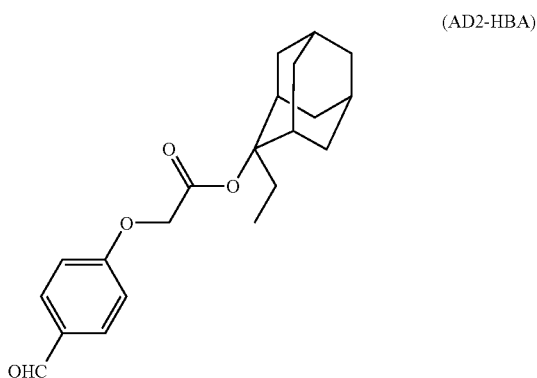

(AD2-HBA)

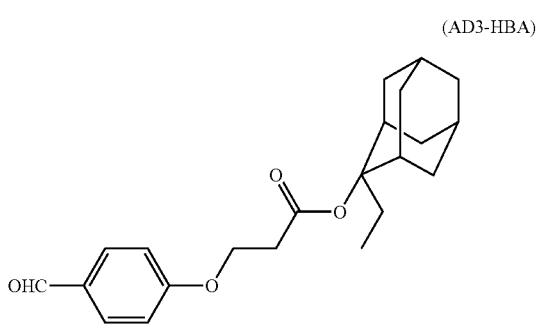

(AD3-HBA)

Synthesis Example 3B

Synthesis of Cyclic Compound

Synthesis of AD1-CR-1

A four-neck flack (1000 L) equipped with a dropping funnel, Dimroth condenser, a thermometer and a stirring device was sufficiently dried and purged with nitrogen. Into the flask, resorcinol (5.5 g, 50 mmol, manufactured by Kanto Chemical Co., Inc.), AD1-HBA (16.4 g, 50 mol) synthesized in Synthesis Example 2B, and ethanol (330 ml) were charged under nitrogen stream to prepare an ethanol solution. After adding 75 ml of a concentrated hydrochloric acid (35%) from the dropping funnel over 60 min, the solution was continuously stirred at room temperature for 6 h. After the reaction, the reaction product solution was cooled in an ice bath, to precipitate pale yellow crystals. The separated crude crystals were washed with 300 ml of distilled water and then 300 ml of methanol twice, filtered and vacuum-dried, to obtain 20.2 g of the aimed product (AD1-CR-1). The result of LC-MS analysis showed that the compound had a molecular weight of 1681 of the aimed compound.

$^1$H-NMR Chemical Shifts (δ ppm, TMS reference) in heavy chloroform:
1.5-2.2 (m, 68H), 4.9 (s, 8H), 5.4-5.7 (m, 4H), 6.1-6.5 (m, 24H), 7.8-8.4 (m, 8H)

Synthesis of AD2-CR-1

In the same manner as in the synthesis of AD1-CR-1 except for using AD2-HBA in place of AD1-HBA, 30.0 g of AD2-CR-1 was obtained. The result of LC-MS analysis showed that the compound had a molecular weight of 1733 of the aimed compound.

$^1$H-NMR Chemical Shifts (δ ppm, TMS reference) in heavy chloroform:
1.5-2.2 (m, 25H), 4.9 (s, 2H), 7.8-8.4 (m, 4H), 10.0 (m, 1H)

Synthesis of AD3-CR-1

In the same manner as in the synthesis of AD1-CR-1 except for using AD3-HBA in place of AD1-HBA, 32.0 g of AD3-CR-1 was obtained. The result of LC-MS analysis showed that the compound had a molecular weight of 1793 of the aimed compound.

$^1$H-NMR Chemical Shifts (δ ppm, TMS reference) in heavy chloroform:
1.5-2.2 (m, 25H), 2.7 (m, 8H), 4.9 (s, 2H), 7.8-8.4 (m, 4H), 10.0 (m, 1H)

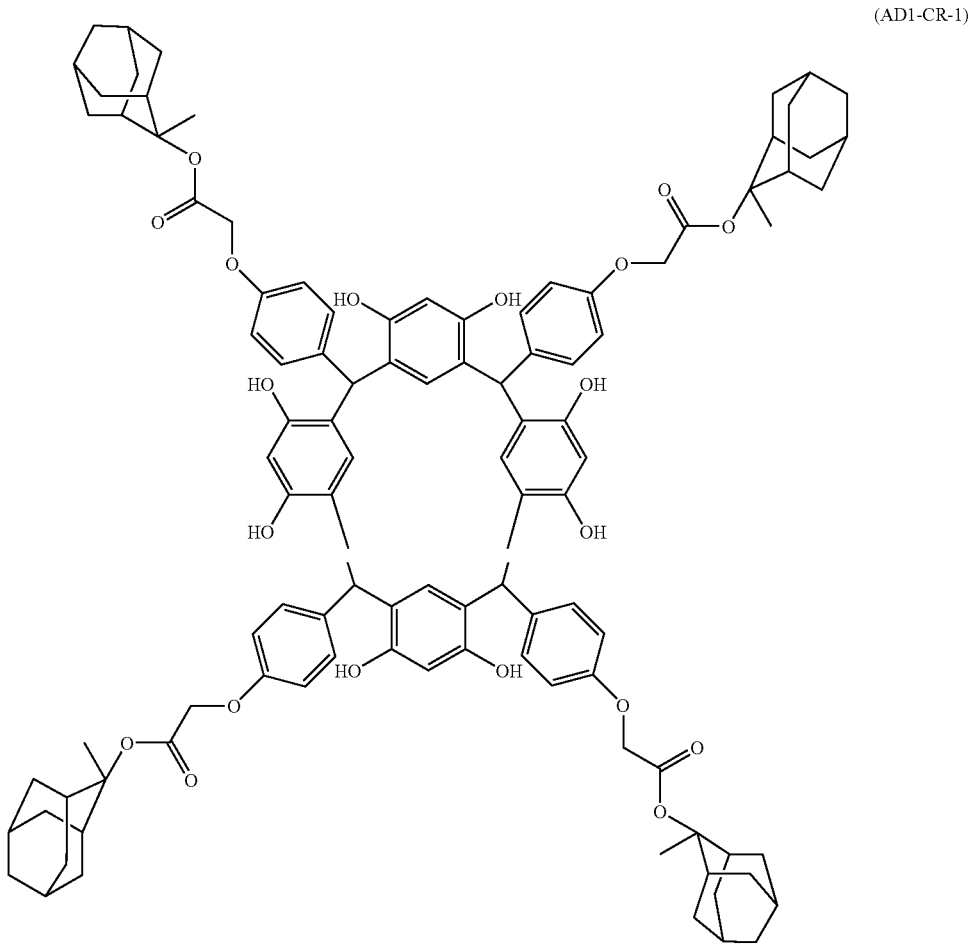

(AD1-CR-1)

(AD2-CR-1)
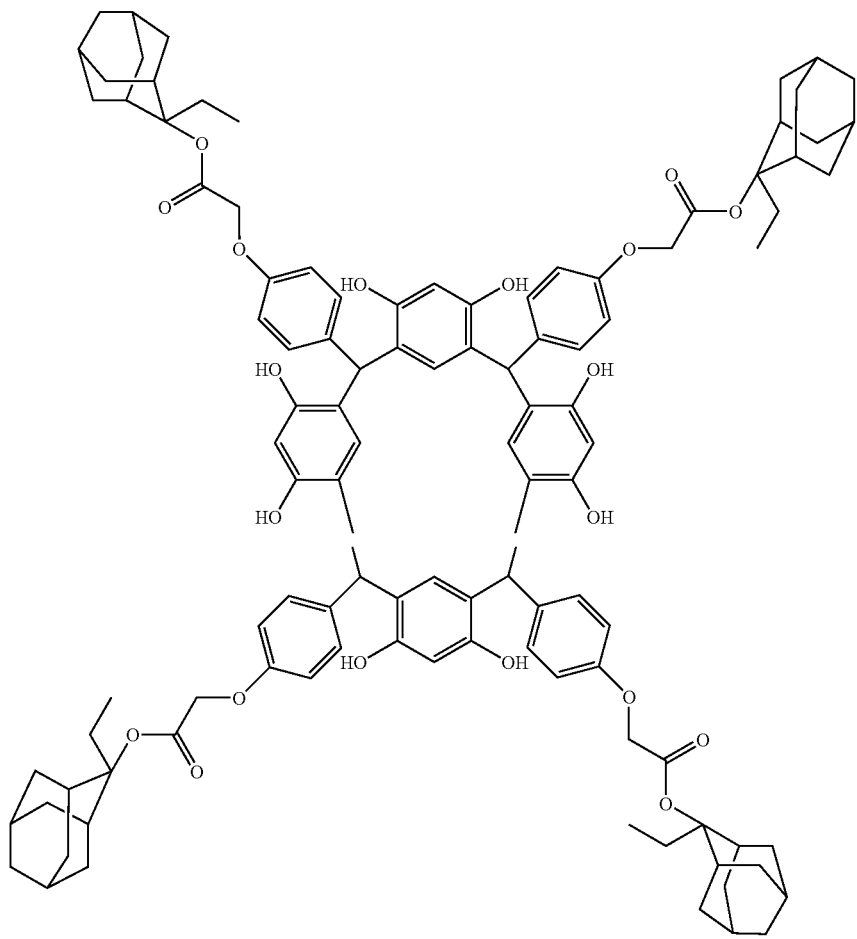
(AD3-CR-1)
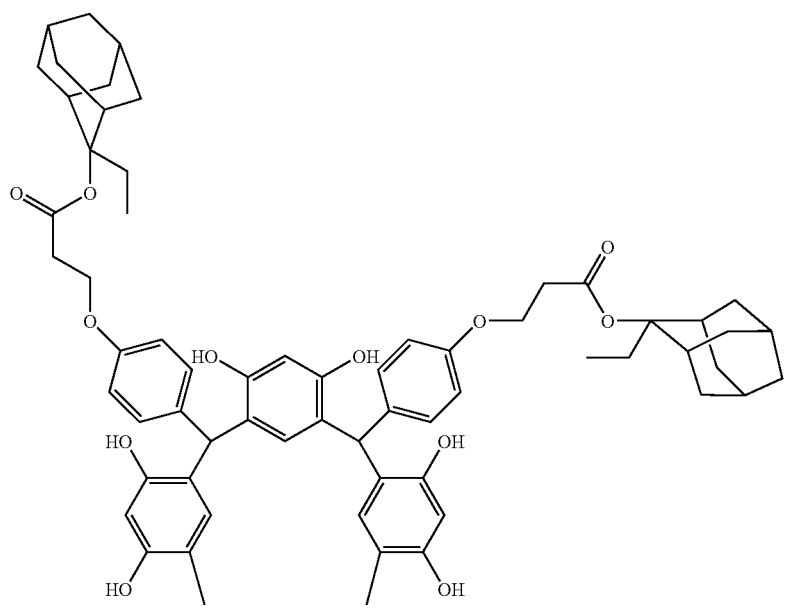

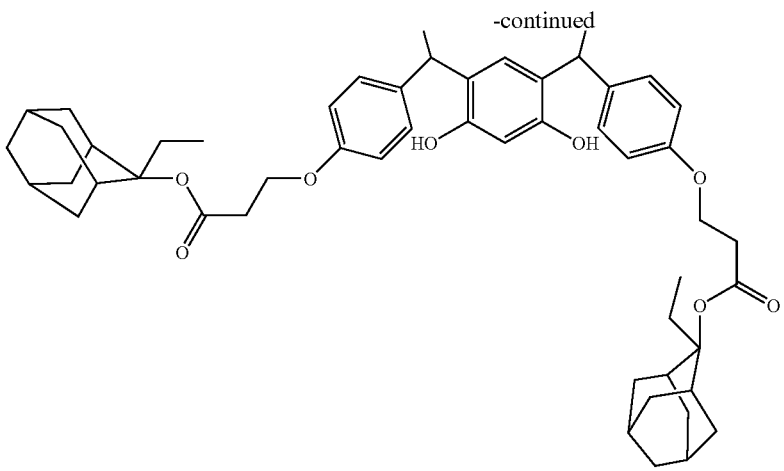
-continued

Synthesis of Comparative Compound AD4-CR-2

After the synthesis of CR-11 in Comparative Example 1, the four-neck flack (1000 L) equipped with a dropping funnel, Dimroth condenser, a thermometer and a stirring device was sufficiently dried and purged with nitrogen. Into a solution of 11.2 g (10 mmol) of CR-2 and 13.8 g of potassium carbonate in 400 ml of THF in the flask, a slm of 11.4 g (40 mmol) of methyladamantyl bromoacetate in 100 ml of THF was added dropwise under nitrogen stream. The reaction liquid was stirred at room temperature for 1 h. After the reaction, the solvent was removed and the obtained solid was purified by column chromatography using a mixed solvent hexane/ethyl acetate=1/3, to obtain 14.0 g of AD4-CR-2 in which 50% of the phenolic hydroxyl groups are substituted by methyladamantyloxycarbonylmethyl groups.

$^1$H-NMR Chemical Shifts (δ ppm, TMS reference) in heavy chloroform: 1.5-2.2 (m, 102H), 4.9 (s, 12H), 5.4-5.7 (m, 4H), 6.1-6.5 (m, 24H), 7.8-8.4 (m, 6H)

Synthesis Example 4B

Synthesis of Aldehyde Compound (A1d)

Synthesis of MADM-4HBA

A four-neck flack (1000 L) equipped with a dropping funnel, Dimroth condenser, a thermometer and a stirring device was sufficiently dried and purged with nitrogen. Into a solution of p-hydroxybenzaldehyde (12.2 g, 100 mmol), potassium carbonate (13.8 g, 100 mmol) and 200 ml of THF in the flask, a solution of 28.6 g (100 mmol) of methyladamantyl bromoacetate in 100 ml of THF was added dropwise under nitrogen stream. The reaction liquid was stirred for 24 h under reflux.

After the reaction, the solvent was removed. The obtained solid was purified by column chromatography using a mixed solvent of hexane/ethyl acetate=1/3, to obtain 29.0 g of MADM-HBA in which the phenolic hydroxyl group was substituted by methyladamantyloxycarbonylmethyl group.

$^1$H-NMR Chemical Shifts (δ ppm, TMS reference) in heavy DMSO:
1.5-2.2 (m, 17H), 4.9 (s, 2H), 7.8-8.4 (m, 4H), 10.0 (s, 1H)
Synthesis of tBuM-4HBA In the same manner as in the synthesis of MADM-4HBA except for using tert-butyl bromoacetate in place of methyladamantyl bromoacetate, 20.0 g of tBuM-4HBA in which the phenolic hydroxyl group was substituted by tert-butyloxycarbonylmethyl group was obtained.

$^1$H-NMR Chemical Shifts (δ ppm, TMS reference) in heavy DMSO:
1.4 (s, 9H), 5.0 (s, 2H), 7.1-7.9 (m, 4H), 9.9 (s, 1H)
Synthesis of tBuM-3HBA In the same manner as in the synthesis of MADM-4HBA except for using tert-butyl bromoacetate in place of methyladamantyl bromoacetate and using m-hydroxybenzaldehyde in place of p-hydroxybenzaldehyde, 20.0 g of tBuM-3HBA in which the phenolic hydroxyl group was substituted by tert-butyl oxycarbonylmethyl group was obtained.

$^1$H-NMR Chemical Shifts (δ ppm, TMS reference) in heavy DMSO:
1.4 (s, 9H), 4.9 (s, 2H), 7.3-7.6 (m, 4H), 10.0 (s, 1H)
Synthesis of tBuM-2HBA In the same manner as in the synthesis of MADM-4HBA except for using tert-butyl bromoacetate in place of methyladamantyl bromoacetate and using o-hydroxybenzaldehyde in place of p-hydroxybenzaldehyde, 20.0 g of tBuM-2HBA in which the phenolic hydroxyl group was substituted by tert-butyloxycarbonylmethyl group was obtained.

$^1$H-NMR Chemical Shifts (δ ppm, TMS reference) in heavy DMSO:
1.4 (s, 9H), 4.9 (s, 2H), 7.1-7.8 (m, 4H), 10.5 (s, 1H)
Synthesis of tBuM-3Br4HBA In the same manner as in the synthesis of MADM-4HBA except for using tert-butyl bromoacetate in place of methyladamantyl bromoacetate and using 3-bromo-4-hydroxybenzaldehyde in place of p-hydroxybenzaldehyde, 19.5 g of tBuM-3Br4HBA in which the phenolic hydroxyl group was substituted by tert-butyloxycarbonylmethyl group was obtained.

$^1$H-NMR Chemical Shifts (δ ppm, TMS reference) in heavy DMSO:
1.4 (s, 9H), 5.0 (s, 2H), 7.2-8.2 (m, 3H), 9.9 (s, 1H)
Synthesis of MeM-4HBA In the same manner as in the synthesis of MADM-4HBA except for using methyl bromoacetate in place of methyladamantyl bromoacetate, 15.2 g of MeM-4HBA in which the phenolic hydroxyl group was substituted by methoxycarbonylmethyl group was obtained.

$^1$H-NMR Chemical Shifts (δ ppm, TMS reference) in heavy DMSO:
3.7 (s, 3H), 5.0 (s, 2H), 7.1-7.9 (m, 4H), 9.9 (s, 1H)
Synthesis of EtM-4HBA In the same manner as in the synthesis of MADM-4HBA except for using ethyl bromoacetate in place of methyladamantyl bromoacetate, 15.8 g of EtM-4HBA in which the phenolic hydroxyl group was substituted by ethoxycarbonylmethyl group was obtained.

¹H-NMR Chemical Shifts (δ ppm, TMS reference) in heavy DMSO:
1.3 (t, 9H), 4.3 (m, 2H), 4.8 (s, 2H), 7.1-7.9 (m, 4H), 9.9 (s, 1H)

Synthesis Example 5B

Synthesis of Compound (A3) Having Halomethyl Ether Group

Synthesis of ADCME

A four-neck flask (1000 L) equipped with a dropping funnel, Dimroth condenser, a thermometer and a stirring device was sufficiently dried and purged with nitrogen. Into a solution of 1-adamantylmethanol (3.32 g, 10 mmol) in 63 ml chloroform in the flask, 92% paraformaldehyde (1.20 g, 20 mmol) was added under nitrogen stream. Then, the mixture was stirred for 2.5 h under cooling on ice while blowing hydrogen chloride gas.

After the reaction, the blowing of hydrogen chloride gas was stopped and the temperature was returned to room temperature. After removing the insoluble layer using a separatory funnel, the n-hexane layer was added with anhydrous sodium sulfate, stirred at room temperature, and filtered. The solvent was removed from the filtrate to obtain 4.1 g of the aimed ADCME.

¹H-NMR Chemical Shifts (δ ppm, TMS reference) in heavy chloroform:
1.0-1.6 (m, 15H), 3.3-3.6 (m, 2H), 5.5 (s, 2H)

Synthesis of CHCME

In the same manner as in the synthesis of ADCME except for using cyclohexanol in place of 1-adamantylmethanol, 6.0 g of the aimed CHCME was obtained.

¹H-NMR Chemical Shifts (δ ppm, TMS reference) in heavy chloroform:
1.4-1.6 (m, 10H), 2.8 (m, 1H), 5.5 (s, 2H)

Synthesis Example 6B

Synthesis of Cyclic Compound (B0)

As described below, a cyclic compound (A0) was first synthesized and then a cyclic compound (B0) was successively synthesized.

Synthesis of CM-CR-1

A four-neck flack (1000 L) equipped with a dropping funnel, Dimroth condenser, a thermometer and a stirring device was sufficiently dried and purged with nitrogen. Into the flask, resorcinol (5.5 g, 50 mmol, manufactured by Kanto Chemical Co., Inc.), MADM-4HBA (16.4 g, 50 mmol) synthesized in Synthesis Example 1B and 330 ml of ethanol were charged under nitrogen stream to prepare an ethanol solution. After adding 75 ml of a concentrated hydrochloric acid (35%) from the dropping funnel over 60 min, the solution was continuously stirred at 80° C. for 48 h. After the reaction, the temperature was returned to room temperature and the reaction mixture was added with an aqueous solution of sodium hydroxide and stirred for 24 h. The reaction mixture was shaken with diethyl ether in a separatory funnel. After removing the water layer, the organic layer was neutralized with hydrochloric acid. The precipitated solid was separated and vacuum-dried to obtain 10.2 g of the aimed CM-CR-1. The result of LC-MS analysis showed that the compound had a molecular weight of 1088 of the aimed compound.

¹H-NMR Chemical Shifts (δ ppm, TMS reference) in heavy DMSO:
4.5-4.6 (t, 8H), 5.3-5.5 (t, 4H), 6.1-6.5 (m, 24H), 8.4-8.5 (t, 8H), 12.7 (brs, 4H)

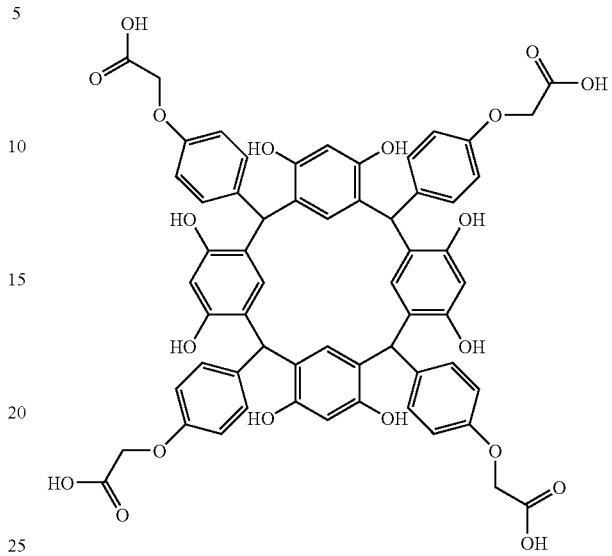

Synthesis of CM-CR-1

In the same manner as in the synthesis of CM-CR-1 except for using tBuM-4HBA in place of MADM-4HBA, 10.2 g of the aimed CM-CR-1 was obtained. The result of LC-MS analysis showed that the compound had a molecular weight of 1088 of the aimed compound.

¹H-NMR Chemical Shifts (δ ppm, TMS reference) in heavy DMSO:
4.5-4.6 (t, 8H), 5.3-5.5 (t, 4H), 6.1-6.5 (m, 24H), 8.4-8.5 (t, 8H), 12.7 (brs, 4H)

Synthesis of CM-CR-2

In the same manner as in the synthesis of CM-CR-1 except for using tBuM-3HBA in place of MADM-4HBA, 10.0 g of the aimed CM-CR-2 was obtained. The result of LC-MS analysis showed that the compound had a molecular weight of 1088 of the aimed compound.

¹H-NMR Chemical Shifts (δ ppm, TMS reference) in heavy DMSO:
4.3-4.4 (d, 8H), 5.5-5.6 (s, 4H), 6.1-6.9 (m, 24H), 8.5 (brs, 8H), 12.9 (brs, 4H)

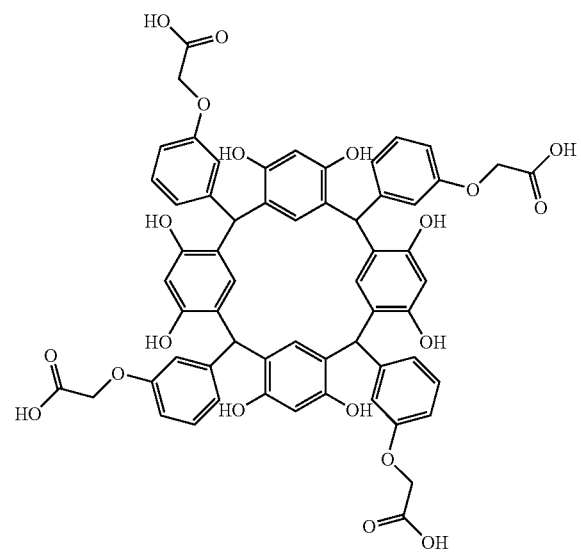

Synthesis of CM-CR-3

In the same manner as in the synthesis of CM-CR-1 except for using tBuM-2HBA in place of MADM-4HBA, 10.0 g of the aimed CM-CR-3 was obtained. The result of LC-MS analysis showed that the compound had a molecular weight of 1088 of the aimed compound.

$^1$H-NMR Chemical Shifts (δ ppm, TMS reference) in heavy DMSO:

4.1 (t, 8H), 5.8-5.9 (t, 4H), 6.0-7.0 (m, 24H), 8.0 (brs, 8H), 12.5 (brs, 4H)

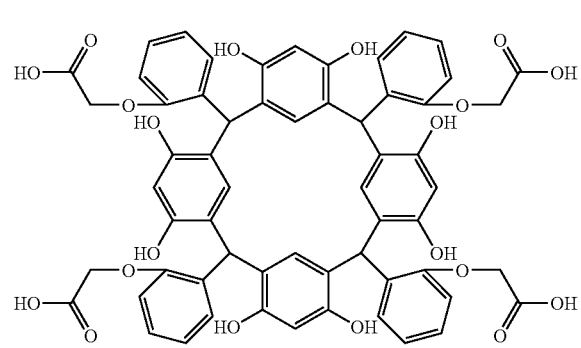

Synthesis of CM-CR-4

In the same manner as in the synthesis of CM-CR-1 except for using tBuM-3Br4HBA in place of MADM-4HBA, 11.0 g of the aimed CM-CR-4 was obtained. The result of LC-MS analysis showed that the compound had a molecular weight of 1400 of the aimed compound.

$^1$H-NMR Chemical Shifts (δ ppm, TMS reference) in heavy DMSO:

4.7 (s, 8H), 5.2-5.5 (t, 4H), 6.0-6.8 (m, 20H), 8.6 (brs, 8H), 12.9 (brs, 4H)

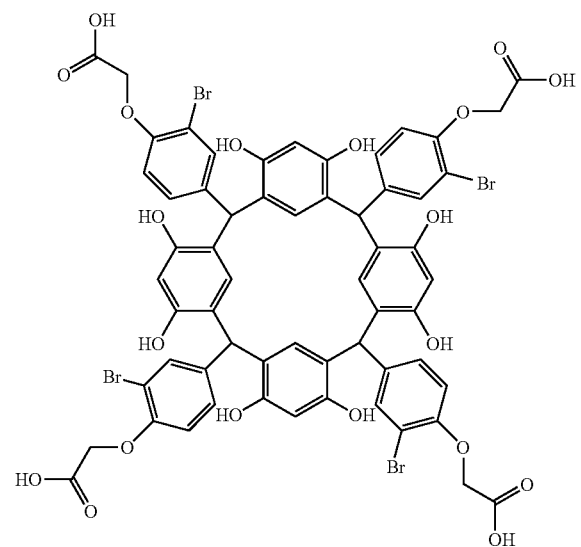

Synthesis of CM-CR-5

In the same manner as in the synthesis of CM-CR-1 except for using 4-formylbenzoic acid (manufactured by Aldrich Chemical Co., Inc.) in place of MADM-4HBA, 5.0 g of the aimed CM-CR-5 was obtained. The result of LC-MS analysis showed that the compound had a molecular weight of 968 of the aimed compound.

$^1$H-NMR Chemical Shifts (δ ppm, TMS reference) in heavy DMSO:

5.5-5.7 (t, 4H), 6.1-7.7 (m, 24H), 8.6-8.8 (t, 8H), 12.3 (brs, 4H)

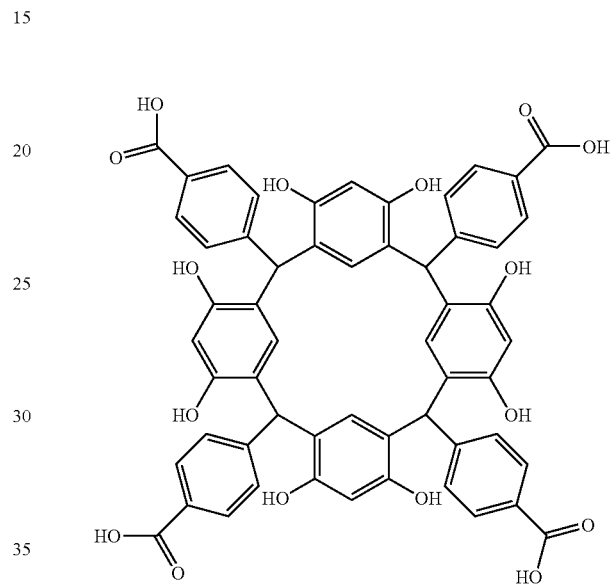

Synthesis of ADM-CR-1

A four-neck flack (1000 L) equipped with a dropping funnel, Dimroth condenser, a thermometer and a stirring device was sufficiently dried and purged with nitrogen. Into a solution of CM-CR-1 (10.9 g, 10 mmol) synthesized in Synthesis Example 1 and 13.8 g of potassium carbonate in 330 ml of THF in the flask, a solution of ADCME (8.6 g, 40 mmol) synthesized in Synthesis Example 5B in 100 ml or THF was added under nitrogen stream to prepare a tetrahydrofuran solution. The solution was stirred at room temperature for 6 h. After the reaction, the reaction product liquid was condensed and purified by column chromatography. After removing the developing solvent, the resultant solid was separated and vacuum-dried to obtain 15.2 g of the aimed ADM-CR-1. The result of LC-MS analysis showed that the compound had a molecular weight of 1801 of the aimed compound.

$^1$H-NMR Chemical Shifts (δ ppm, TMS reference) in heavy DMSO:

1.0-1.6 (m, 60H), 3.3-3.6 (m, 8H), 4.5-4.6 (t, 8H), 5.3-5.5 (m, 12H), 6.1-6.5 (m, 24H), 8.4-8.5 (t, 8H)

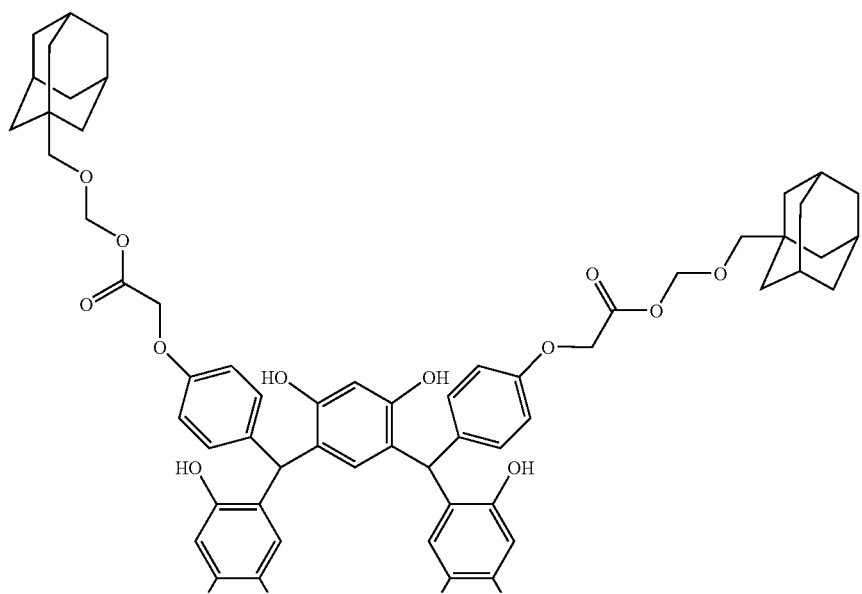
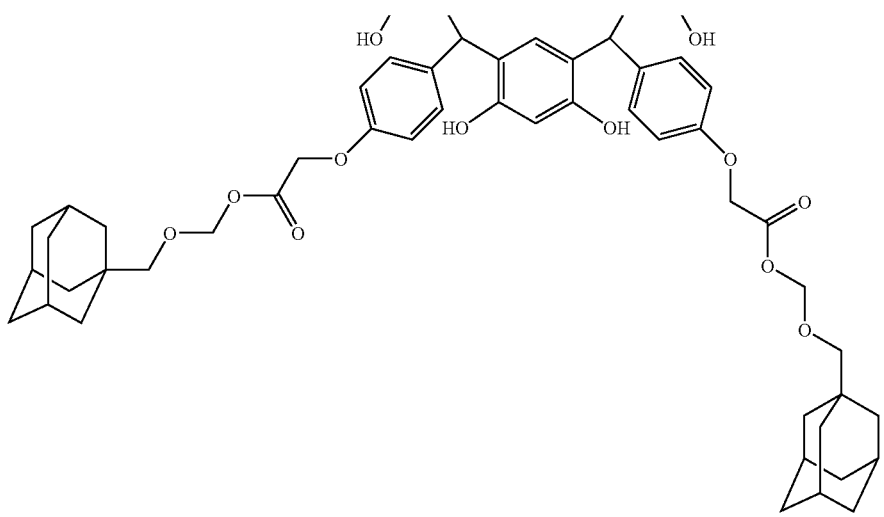
Synthesis of ADM-CR-2
In the same manner as in the synthesis of ADM-CR-1 except for using CM-CR-2 in place of CM-CR-1, 9.2 g of the aimed ADM-CR-2 was obtained. The result of LC-MS analysis showed that the compound had a molecular weight of 1801 of the aimed compound.
$^1$H-NMR Chemical Shifts (δ ppm, TMS reference) in heavy DMSO:
1.0-1.6 (m, 60H), 3.3-3.6 (m, 8H), 4.3-4.4 (t, 8H), 5.3-5.6 (m, 12H), 6.1-6.9 (m, 24H), 8.4-8.5 (t, 8H)

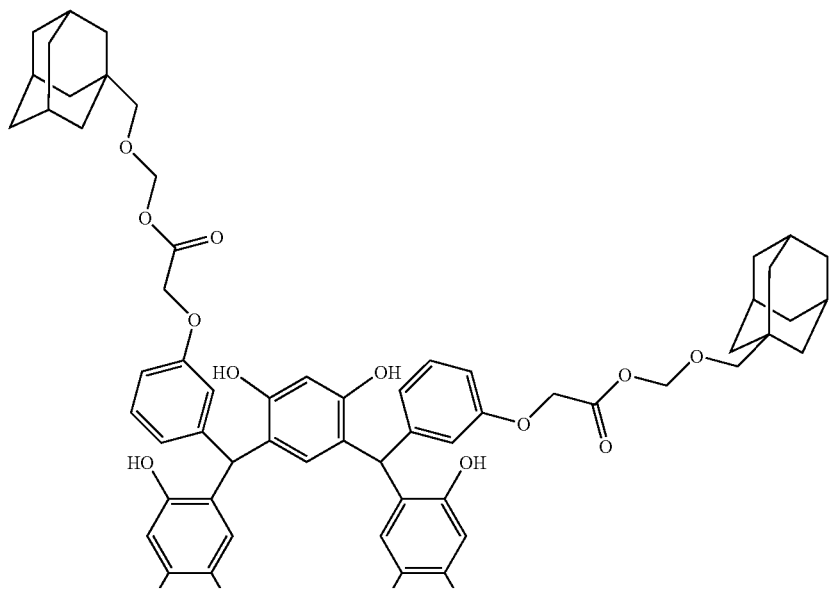
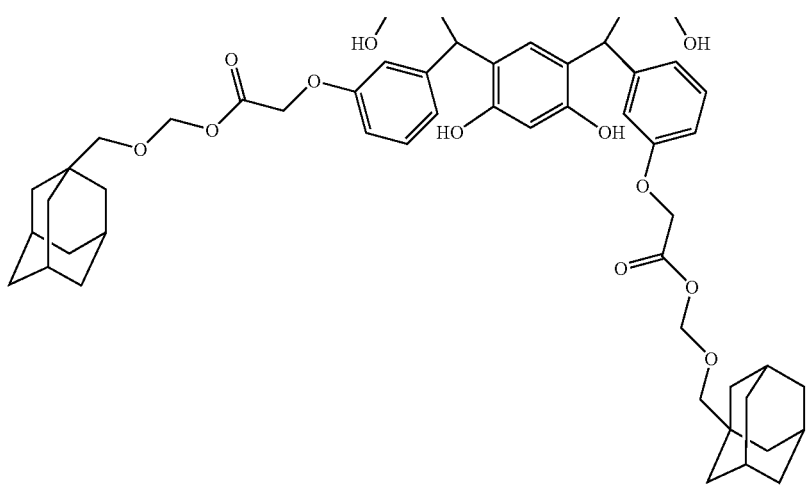
Synthesis of ADM-CR-3
In the same manner as in the synthesis of ADM-CR-1 except for using CM-CR-3 in place of CM-CR-1, 9.8 g of the aimed ADM-CR-3 was obtained. The result of LC-MS analysis showed that the compound had a molecular weight of 1801 of the aimed compound.
$^1$H-NMR Chemical Shifts (δ ppm, TMS reference) in heavy DMSO:
1.0-1.6 (m, 60H), 3.3-3.6 (m, 8H), 4.1-4.2 (t, 8H), 5.8-5.9 (m, 12H), 6.0-7.0 (m, 24H), 8.1 (t, 8H)

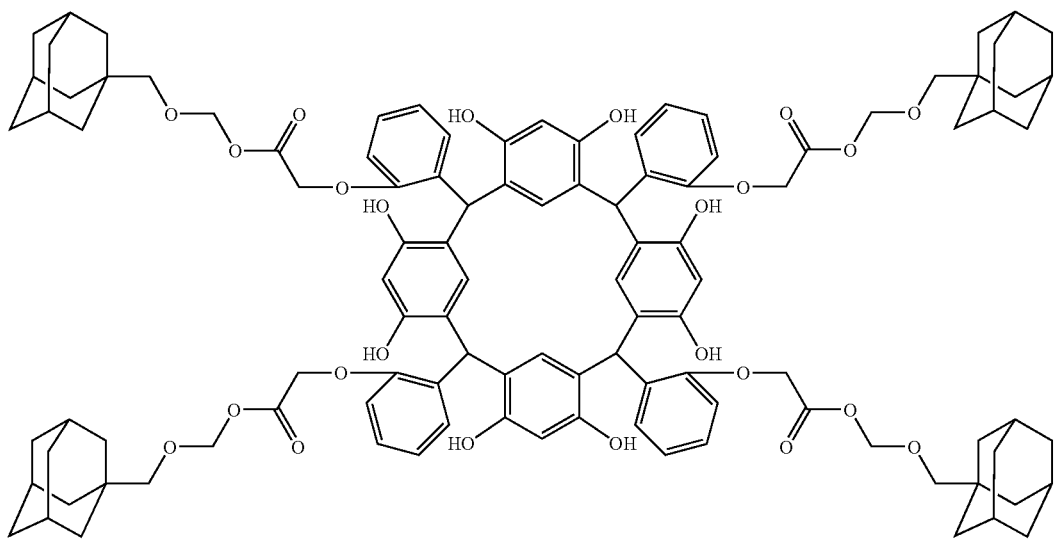
Synthesis of ADM-CR-4
In the same manner as in the synthesis of ADM-CR-1 except for using CM-CR-4 in place of CM-CR-1, 11.2 g of the aimed ADM-CR-4 was obtained. The result of LC-MS analysis showed that the compound had a molecular weight of 2112 of the aimed compound.
$^1$H-NMR Chemical Shifts (δ ppm, TMS reference) in heavy DMSO:
1.0-1.6 (m, 60H), 3.3-3.6 (m, 8H), 4.7 (t, 8H), 5.2-5.5 (m, 12H), 6.0-6.8 (m, 20H), 8.6 (brs, 8H)
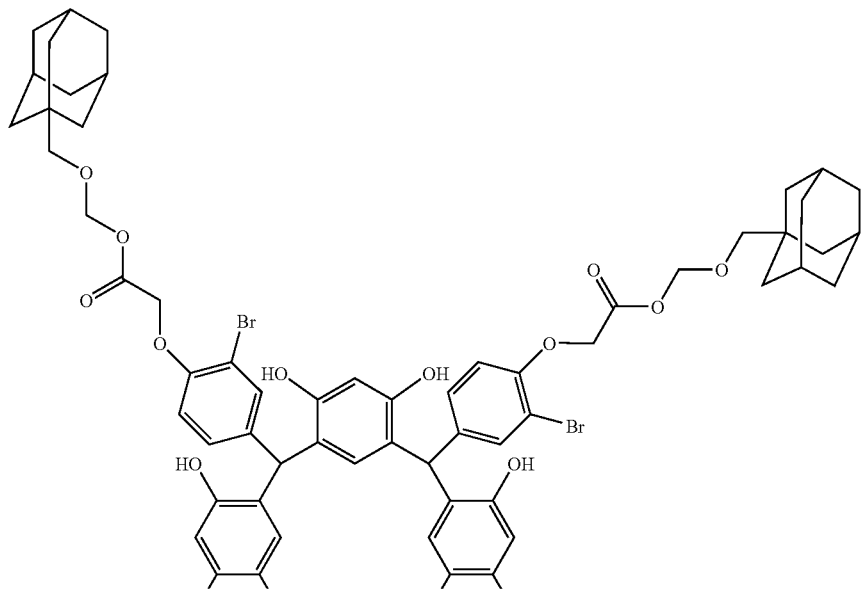

-continued
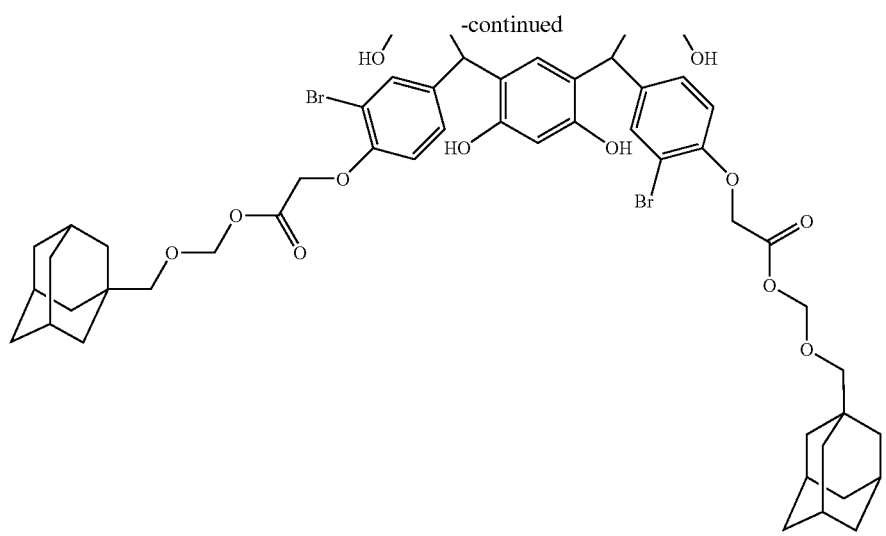
Synthesis of ADM-CR-5
In the same manner as in the synthesis of ADM-CR-1 except for using CM-CR-5 in place of CM-CR-1, 6.2 g of the aimed ADM-CR-5 was obtained. The result of LC-MS analysis showed that the compound had a molecular weight of 1680 of the aimed compound.
$^1$H-NMR Chemical Shifts (δ ppm, TMS reference) in heavy DMSO:
1.0-1.6 (m, 60H), 3.3-3.6 (m, 8H), 5.3-5.5 (m, 12H), 6.1-7.7 (m, 24H), 8.6-8.8 (t, 8H)
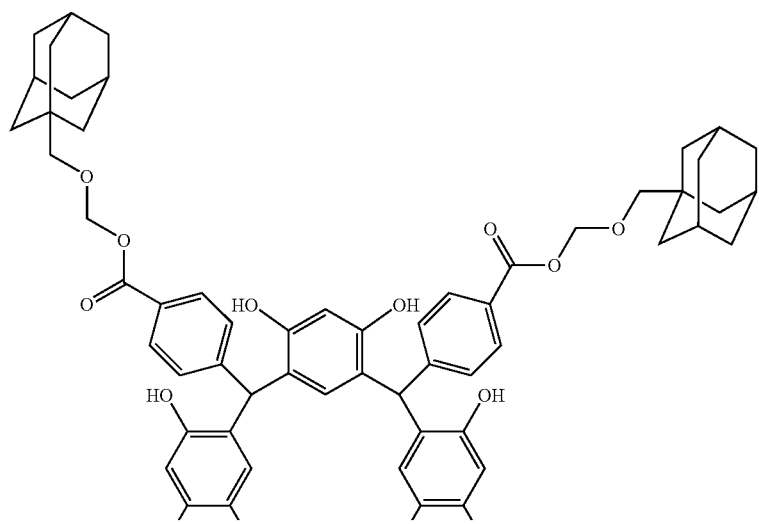

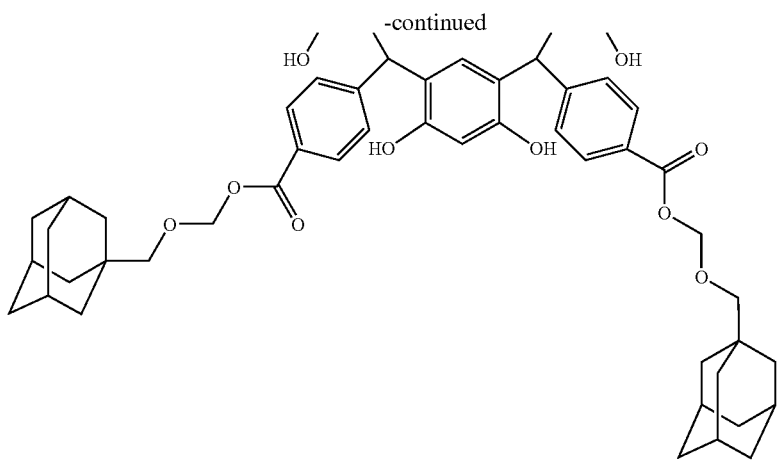
Synthesis of CHM-CR-1
In the same manner as in the synthesis of ADM-CR-1 except for using CHCME in place of ADCME, 10.1 g of the aimed CHM-CR-1 was obtained. The result of LC-MS analysis showed that the compound had a molecular weight of 1537 of the aimed compound.
$^1$H-NMR Chemical Shifts (δ ppm, TMS reference) in heavy DMSO:
1.4-1.6 (m, 40H), 2.8 (m, 4H), 4.5-4.6 (t, 8H), 5.3-5.5 (m, 12H), 6.1-6.5 (m, 24H), 8.4-8.5 (t, 8H)
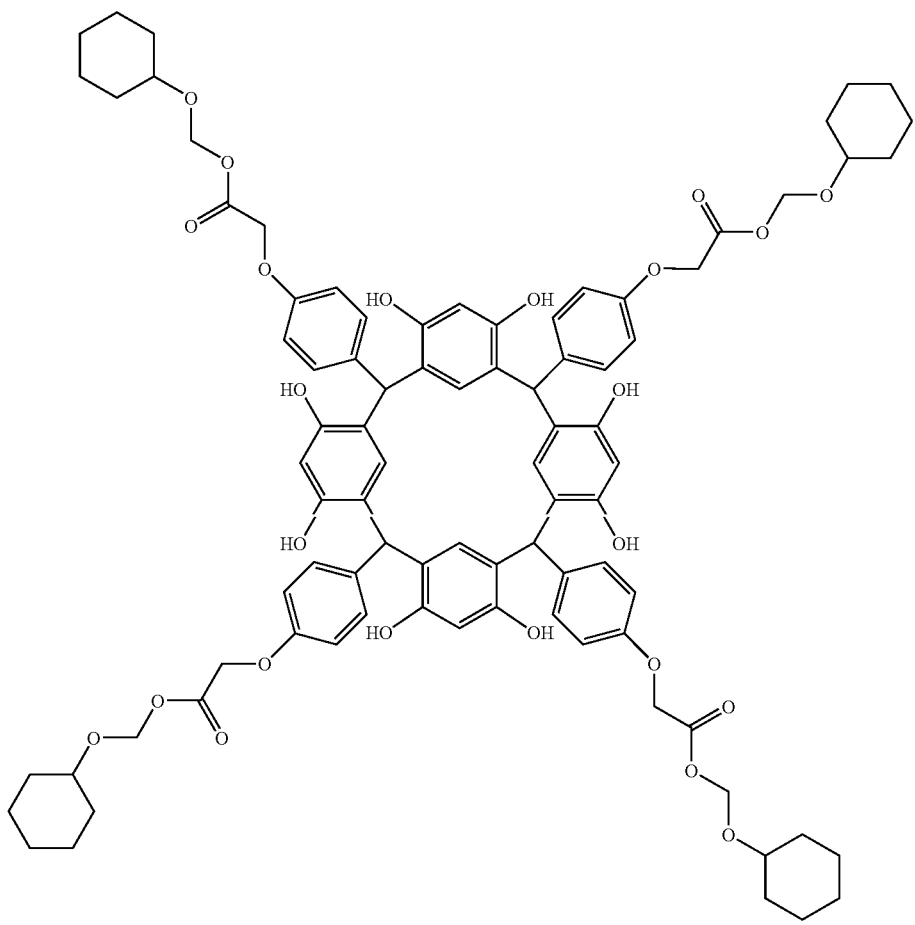

Synthesis of CHM-CR-4

In the same manner as in the synthesis of ADM-CR-4 except for using CHCME in place of ADCME, 10.2 g of the aimed CHM-CR-4 was obtained. The result of LC-MS analysis showed that the compound had a molecular weight of 1848 of the aimed compound.

$^1$H-NMR Chemical Shifts (δ ppm, TMS reference) in heavy DMSO:

1.4-1.6 (m, 40H), 2.8 (m, 4H), 4.7 (t, 8H), 5.2-5.5 (m, 12H), 6.0-6.8 (m, 20H), 8.6 (brs, 8H)

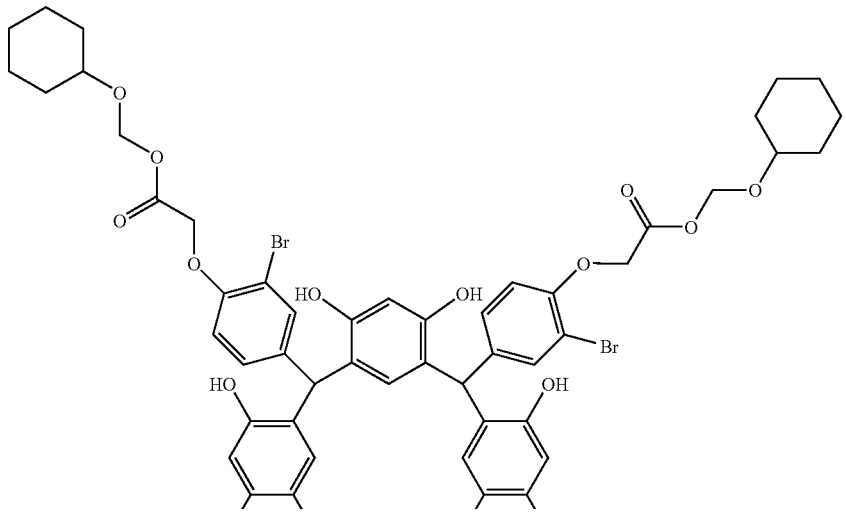

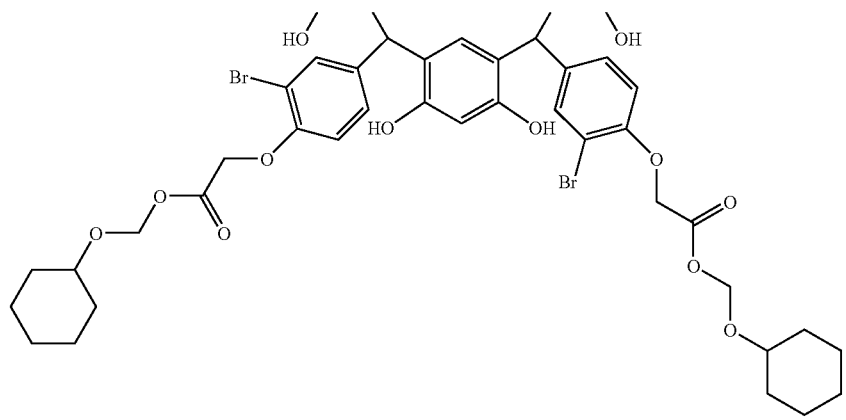

Synthesis of NOM-CR-1

In the same manner as in the synthesis of ADM-CR-1 except for using n-octyl chloromethyl ether in place of ADCME, 8.2 g of the aimed NOM-CR-1 was obtained. The result of LC-MS analysis showed that the compound had a molecular weight of 1657 of the aimed compound.

$^1$H-NMR Chemical Shifts (δ ppm, TMS reference) in heavy DMSO:

1.0-1.5 (60m, 8H), 3.4 (m, 8H), 4.5-4.6 (t, 8H), 5.3-5.5 (m, 12H), 6.1-6.5 (m, 24H), 8.4-8.5 (t, 8H)

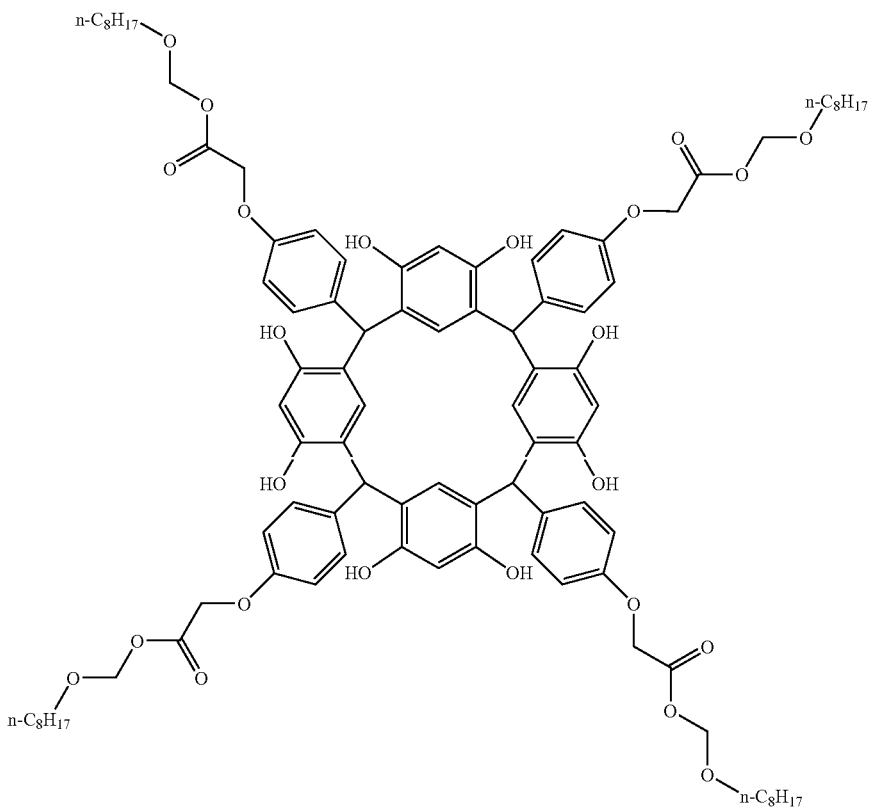
Synthesis of MADM-CR-1
In the same manner as in the synthesis of ADM-CR-1 except for using 2-methyl-2-adamantyl bromoacetate in place of ADCME, 9.8 g of the aimed MADM-CR-1 was obtained. The result of LC-MS analysis showed that the compound had a molecular weight of 1913 of the aimed compound.
$^1$H-NMR Chemical Shifts (δ ppm, TMS reference) in heavy DMSO:
1.5-2.2 (m, 68H), 4.5-4.6 (t, 8H), 4.9 (s, 8H), 5.3-5.5 (t, 4H), 6.1-6.5 (m, 24H), 8.4-8.5 (t, 8H)
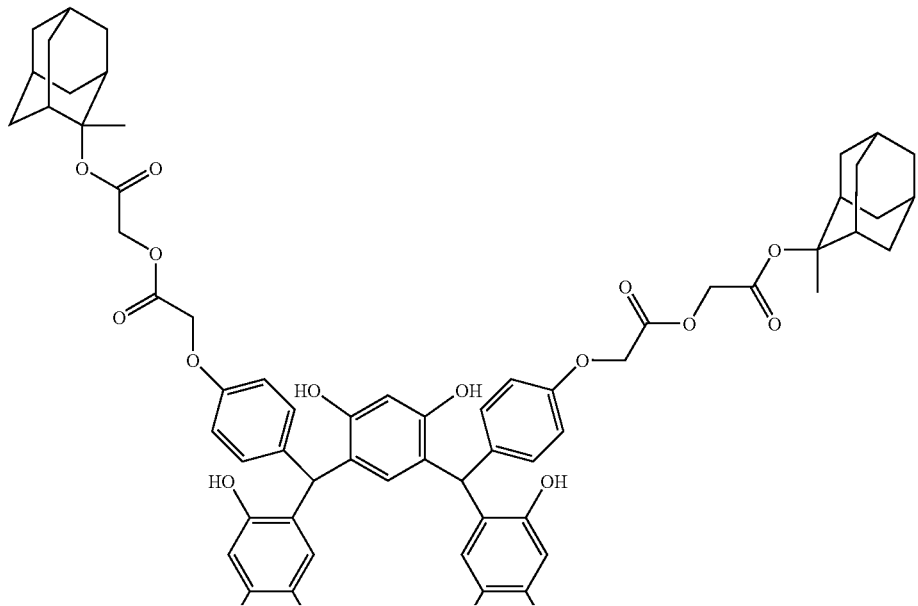

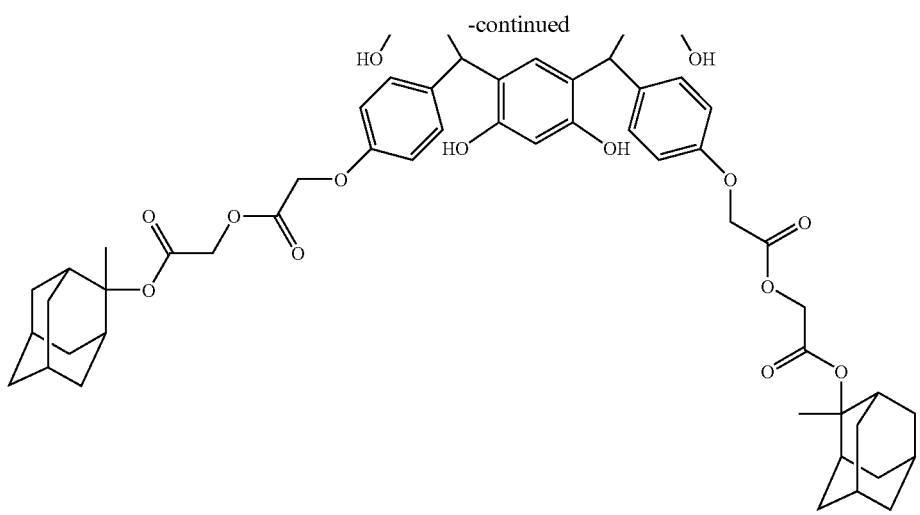
Synthesis of MADM-CR-5
In the same manner as in the synthesis of ADM-CR-5 except for using 2-methyl-2-adamantyl bromoacetate in place of ADCME, 10.2 g of the aimed MADM-CR-1 was obtained. The result of LC-MS analysis showed that the compound had a molecular weight of 2224 of the aimed compound.
$^1$H-NMR Chemical Shifts (δ ppm, TMS reference) in heavy DMSO:
1.5-2.2 (m, 68H), 4.5-4.6 (t, 8H), 4.9 (s, 8H), 5.3-5.5 (t, 4H), 6.1-7.7 (m, 20H), 8.4-8.5 (t, 8H)
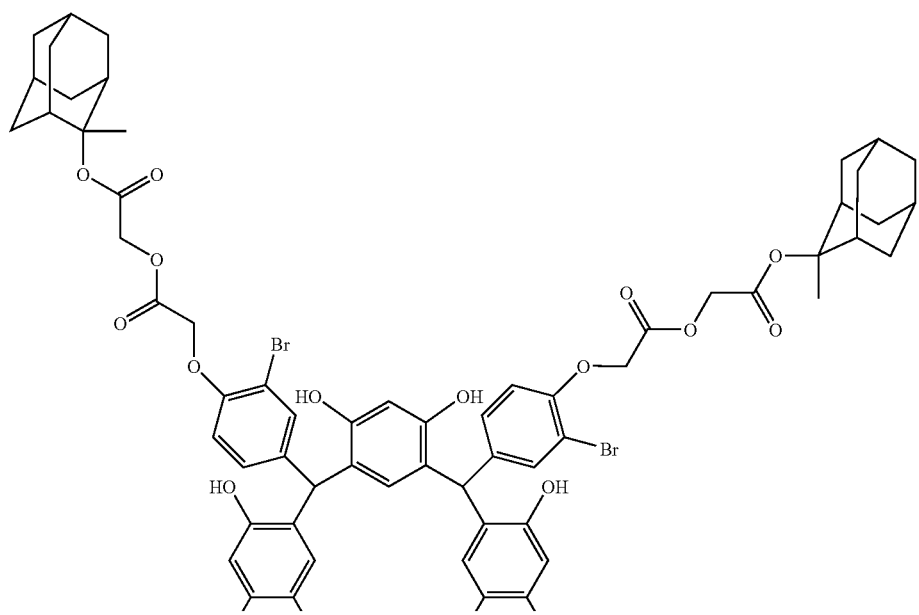

-continued

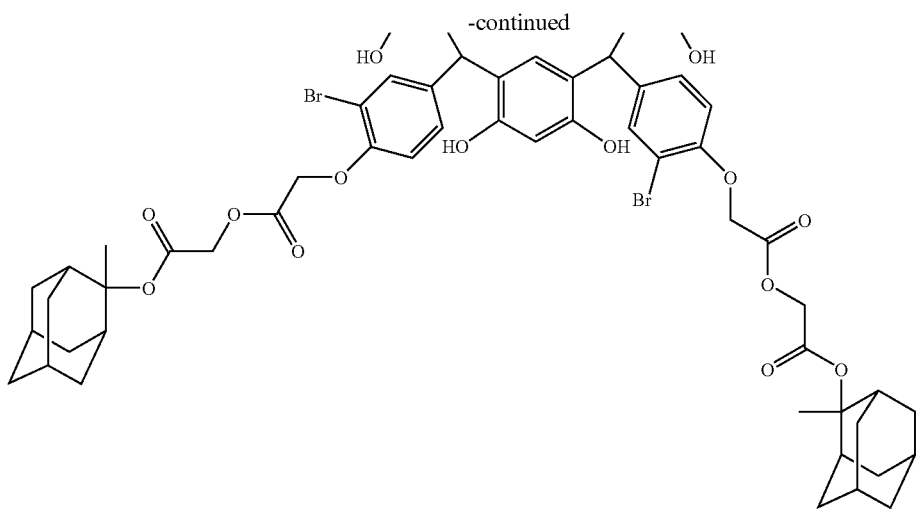

Examples 1B-44B and Comparative Example 1B

The components shown in Table 1B were blended to obtain a uniform solution, which was then filtered through a Teflon membrane filter with a 0.2 μm pore size to prepare each radiation-sensitive composition. The same acid generator (C), acid-diffusion controller (E), other additive (F), and solvent as used in Examples 1A-20A were used, and the evaluations were made in the same manner. The results are shown in Table 2B.

TABLE 1B

| | Compound (A) (g) | Acid generator (C) (g) | Acid-diffusion controller (E) (g) | Solvent (g) | Surfactant (F) (g) |
|---|---|---|---|---|---|
| Examples | | | | | |
| 1B | AD1-CR-1 | P-1 | Q-1 | S-1 | — |
| | 1.0 | 0.3 | 0.03 | 30.0 | — |
| 2B | AD1-CR-1 | P-2 | Q-1 | S-1 | — |
| | 1.0 | 0.3 | 0.03 | 30.0 | — |
| 3B | AD1-CR-1 | P-2 | Q-1 | S-1 | D-1 |
| | 1.0 | 0.3 | 0.03 | 30.0 | 0.02 |
| 4B | AD2-CR-1 | P-1 | Q-1 | S-1 | — |
| | 1.0 | 0.3 | 0.03 | 30.0 | — |
| 5B | AD2-CR-1 | P-2 | Q-1 | S-1 | — |
| | 1.0 | 0.3 | 0.03 | 30.0 | — |
| 6B | AD2-CR-1 | P-2 | Q-1 | S-1 | D-1 |
| | 1.0 | 0.3 | 0.03 | 30.0 | 0.02 |
| 7B | AD3-CR-1 | P-1 | Q-1 | S-1 | — |
| | 1.0 | 0.3 | 0.03 | 30.0 | — |
| 8B | AD3-CR-1 | P-2 | Q-1 | S-1 | — |
| | 1.0 | 0.3 | 0.03 | 30.0 | — |
| 9B | AD3-CR-1 | P-2 | Q-1 | S-1 | D-1 |
| | 1.0 | 0.3 | 0.03 | 30.0 | 0.02 |
| 10B | AD1-CR-1 | P-2 | Q-1 | S-1 | — |
| | 1.0 | 0.2 | 0.02 | 30.0 | — |
| 11B | AD1-CR-1 | P-2 | Q-1 | S-1 | D-1 |
| | 1.0 | 0.2 | 0.02 | 30.0 | 0.02 |
| 12B | AD1-CR-1 | P-2 | Q-1 | S-1 | D-2 |
| | 1.0 | 0.2 | 0.02 | 30.0 | 0.02 |
| 13B | AD2-CR-1 | P-2 | Q-1 | S-1 | — |
| | 1.0 | 0.2 | 0.02 | 30.0 | — |
| 14B | AD2-CR-1 | P-2 | Q-1 | S-1 | D-1 |
| | 1.0 | 0.2 | 0.02 | 30.0 | 0.02 |
| 15B | AD2-CR-1 | P-2 | Q-1 | S-1 | D-2 |
| | 1.0 | 0.2 | 0.02 | 30.0 | 0.02 |
| 16B | AD3-CR-1 | P-2 | Q-1 | S-1 | — |
| | 1.0 | 0.2 | 0.02 | 30.0 | — |
| 17B | AD3-CR-1 | P-2 | Q-1 | S-1 | D-1 |
| | 1.0 | 0.2 | 0.02 | 30.0 | 0.02 |
| 18B | AD3-CR-1 | P-2 | Q-1 | S-1 | D-2 |
| | 1.0 | 0.2 | 0.02 | 30.0 | 0.02 |
| Comparative Example | | | | | |
| 1B | AD4-CR-2 | P-2 | Q-1 | S-1 | — |
| | 1.0 | 0.3 | 0.03 | 30.0 | — |

TABLE 1B-continued

| | Compound (A) (g) | Acid generator (C) (g) | Acid-diffusion controller (E) (g) | Solvent (g) | Surfactant (F) (g) |
|---|---|---|---|---|---|
| Examples | | | | | |
| 19B | ADM-CR-1 1.0 | P-1 0.3 | Q-1 0.03 | S-1 30.0 | — |
| 20B | ADM-CR-1 1.0 | P-2 0.3 | Q-1 0.03 | S-1 30.0 | — |
| 21B | ADM-CR-1 1.0 | P-2 0.3 | Q-1 0.03 | S-1 30.0 | D-1 0.02 |
| 22B | ADM-CR-1 1.0 | P-2 0.2 | Q-1 0.02 | S-1 30.0 | — |
| 23B | ADM-CR-1 1.0 | P-2 0.2 | Q-1 0.02 | S-1 30.0 | D-1 0.02 |
| 24B | ADM-CR-1 1.0 | P-2 0.2 | Q-1 0.02 | S-1 30.0 | D-2 0.02 |
| 25B | ADM-CR-2 1.0 | P-1 0.3 | Q-1 0.03 | S-1 30.0 | — |
| 26B | ADM-CR-2 1.0 | P-2 0.3 | Q-1 0.03 | S-1 30.0 | — |
| 27B | ADM-CR-3 1.0 | P-1 0.3 | Q-1 0.03 | S-1 30.0 | — |
| 28B | ADM-CR-3 1.0 | P-2 0.3 | Q-1 0.03 | S-1 30.0 | — |
| 29B | ADM-CR-4 1.0 | P-1 0.3 | Q-1 0.03 | S-1 30.0 | — |
| 30B | ADM-CR-4 1.0 | P-2 0.3 | Q-1 0.03 | S-1 30.0 | — |
| 31B | ADM-CR-4 1.0 | P-2 0.3 | Q-1 0.03 | S-1 30.0 | D-1 0.02 |
| 32B | ADM-CR-4 1.0 | P-2 0.2 | Q-1 0.02 | S-1 30.0 | — |
| 33B | ADM-CR-4 1.0 | P-2 0.2 | Q-1 0.02 | S-1 30.0 | D-1 0.02 |
| 34B | ADM-CR-4 1.0 | P-2 0.2 | Q-1 0.02 | S-1 30.0 | D-2 0.02 |
| 35B | ADM-CR-5 1.0 | P-1 0.3 | Q-1 0.03 | S-1 30.0 | — |
| 36B | ADM-CR-5 1.0 | P-2 0.3 | Q-1 0.03 | S-1 30.0 | — |
| 37B | CHM-CR-1 1.0 | P-1 0.3 | Q-1 0.03 | S-1 30.0 | — |
| 38B | CHM-CR-1 1.0 | P-2 0.3 | Q-1 0.03 | S-1 30.0 | — |
| 39B | CHM-CR-4 1.0 | P-1 0.3 | Q-1 0.03 | S-1 30.0 | — |
| 40B | CHM-CR-4 1.0 | P-2 0.3 | Q-1 0.03 | S-1 30.0 | — |
| 41B | NOM-CR-1 1.0 | P-1 0.3 | Q-1 0.03 | S-1 30.0 | — |
| 42B | NOM-CR-1 1.0 | P-2 0.3 | Q-1 0.03 | S-1 30.0 | — |
| 43B | MDAM-CR-1 1.0 | P-1 0.3 | Q-1 0.03 | S-1 30.0 | — |
| 44B | MDAM-CR-1 1.0 | P-2 0.3 | Q-1 0.03 | S-1 30.0 | — |

TABLE 2B

| | PEB (° C.) | Sensitivity (μC/cm$^2$) | Shape of pattern | LER |
|---|---|---|---|---|
| Examples | | | | |
| 1B | 110 | 7.5 | A | A |
| 2B | 110 | 10.0 | A | A |
| 3B | 110 | 7.5 | A | A |
| 4B | 100 | 7.0 | A | A |
| 5B | 100 | 9.0 | A | A |
| 6B | 100 | 7.0 | A | A |
| 7B | 90 | 7.0 | A | A |
| 8B | 90 | 10.0 | A | A |
| 9B | 90 | 7.0 | A | A |
| 10B | 110 | 7.5 | A | A |
| 11B | 110 | 7.0 | A | A |
| 12B | 110 | 7.0 | A | A |
| 13B | 100 | 6.5 | A | A |
| 14B | 100 | 6.0 | A | A |
| 15B | 100 | 6.0 | A | A |
| 16B | 90 | 7.5 | A | A |
| 17B | 90 | 7.0 | A | A |
| 18B | 90 | 7.0 | A | A |
| Comparative Example | | | | |
| 1B | 110 | 15.0 | C | C |

TABLE 2B-continued

|  | PEB (° C.) | Sensitivity (μC/cm$^2$) | Shape of pattern | LER |
|---|---|---|---|---|
| Examples | | | | |
| 19B | 100 | 7.5 | A | A |
| 20B | 100 | 10 | A | A |
| 21B | 100 | 7.5 | A | A |
| 22B | 100 | 7.5 | A | A |
| 23B | 100 | 7 | A | A |
| 24B | 100 | 7 | A | A |
| 25B | 100 | 7.5 | A | A |
| 26B | 100 | 10 | A | A |
| 27B | 100 | 7.5 | A | A |
| 28B | 100 | 10 | A | A |
| 29B | 100 | 6.5 | A | A |
| 30B | 100 | 9 | A | A |
| 31B | 100 | 6.5 | A | A |
| 32B | 100 | 6.5 | A | A |
| 33B | 100 | 6 | A | A |
| 34B | 100 | 6 | A | A |
| 35B | 100 | 7.5 | A | A |
| 36B | 100 | 10 | A | A |
| 37B | 100 | 7.5 | A | A |
| 38B | 100 | 10 | A | A |
| 39B | 100 | 6.5 | A | A |
| 40B | 100 | 9 | A | A |
| 41B | 100 | 7.5 | B | A |
| 42B | 100 | 10 | B | A |
| 43B | 110 | 7.5 | A | A |
| 44B | 110 | 10 | A | A |

PEB: temperature of the post electron beam-exposure heating.

Synthesis Example 1D

Synthesis of Cyclic Compound (A)

In the same manner as in Examples 1-57, each cyclic compound (A), i.e., CR-1 to CR-10, CR-11, and CR-12 were synthesized.

Examples 1D-43D and Comparative Examples 1D and 2D

The components shown in Table 1D were blended to obtain a uniform solution, which was then filtered through a Teflon membrane filter with a 0.2 μm pore size to prepare each resist composition. The same comparative compound, acid generator (C), acid-diffusion controller (E), and solvent as used in Examples 1-57 were used, and the evaluations were made in the same manner. The results are shown in Table 2D.

TABLE 1D

| | Compound (A) (g) | Acid generator (C) (g) | Cross-linking agent (G) (g) | Acid-diffusion controller (E) (g) | Solvent (g) | Surfactant (F) (g) |
|---|---|---|---|---|---|---|
| Examples | | | | | | |
| 1D | CR-1 1.0 | P-1 0.3 | C-1 0.3 | Q-1 0.03 | S-1 30.0 | — |
| 2D | CR-1 1.0 | P-2 0.3 | C-1 0.3 | Q-1 0.03 | S-1 30.0 | — |
| 3D | CR-1 1.0 | P-3 0.3 | C-1 0.3 | Q-2 0.03 | S-1 30.0 | — |
| 4D | CR-1 1.0 | P-1 0.1 | C-1 0.1 | Q-1 0.01 | S-1 30.0 | — |
| 5D | CR-1 1.0 | P-1 0.3 | C-1 0.3 | Q-1 0.03 | S-1 30.0 | D-1 0.02 |
| 7D | CR-1 1.0 | P-1/P-2 0.15/0.15 | C-1 0.3 | Q-1 0.03 | S-1 30.0 | D-2 0.02 |
| 8D | CR-1 1.0 | P-1 0.3 | C-2 0.3 | Q-1 0.03 | S-1 30.0 | — |
| 9D | CR-1 1.0 | P-1 0.3 | C-3 0.3 | Q-1 0.03 | S-1 30.0 | — |
| 10D | CR-1 1.0 | P-1 0.3 | C-4 0.3 | Q-1 0.03 | S-1 30.0 | — |
| 11D | CR-2 1.0 | P-1 0.3 | C-1 0.3 | Q-1 0.03 | S-1 30.0 | — |
| 12D | CR-2 1.0 | P-3 0.3 | C-1 0.3 | Q-2 0.03 | S-1 30.0 | — |
| 13D | CR-2 1.0 | P-1/P-2 0.15/0.15 | C-1 0.3 | Q-1 0.03 | S-1 30.0 | D-1 0.02 |
| 14D | CR-3 1.0 | P-1 0.3 | C-1 0.3 | Q-1 0.03 | S-1 30.0 | — |
| 15D | CR-3 1.0 | P-3 0.3 | C-1 0.3 | Q-2 0.03 | S-1 30.0 | — |
| 16D | CR-3 1.0 | P-1/P-2 0.15/0.15 | C-1 0.3 | Q-1 0.03 | S-1 30.0 | D-1 0.02 |
| 17D | CR-4 1.0 | P-1 0.3 | C-1 0.3 | Q-1 0.03 | S-1 30.0 | — |
| 18D | CR-4 1.0 | P-3 0.3 | C-1 0.3 | Q-2 0.03 | S-1 30.0 | — |
| 19D | CR-4 1.0 | P-1/P-2 0.15/0.15 | C-1 0.3 | Q-1 0.03 | S-1 30.0 | D-1 0.02 |
| 20D | CR-5 1.0 | P-1 0.3 | C-1 0.3 | Q-1 0.03 | S-1 30.0 | — |

TABLE 1D-continued

| | Compound (A) (g) | Acid generator (C) (g) | Cross-linking agent (G) (g) | Acid-diffusion controller (E) (g) | Solvent (g) | Surfactant (F) (g) |
|---|---|---|---|---|---|---|
| 21D | CR-5 1.0 | P-3 0.3 | C-1 0.3 | Q-2 0.03 | S-1 30.0 | — — |
| 22D | CR-5 1.0 | P-1/P-2 0.15/0.15 | C-1 0.3 | Q-1 0.03 | S-1 30.0 | D-1 0.02 |
| Comparative Examples | | | | | | |
| 1D | CR-11 1.0 | P-1 0.2 | C-1 0.2 | Q-1 0.02 | S-1 30.0 | — — |
| 2D | CR-12 1.0 | P-1 0.3 | C-1 0.3 | Q-1 0.03 | S-1 30.0 | — — |
| Examples | | | | | | |
| 23D | CR-6 1.0 | P-1 0.3 | C-1 0.3 | Q-1 0.03 | S-1 30.0 | — — |
| 24D | CR-6 1.0 | P-3 0.3 | C-1 0.3 | Q-2 0.03 | S-1 30.0 | — — |
| 25D | CR-6 1.0 | P-1/P-2 0.15/0.15 | C-1 0.3 | Q-1 0.03 | S-1 30.0 | D-1 0.02 |
| 26D | CR-7 1.0 | P-1 0.3 | C-1 0.3 | Q-1 0.03 | S-1 30.0 | — — |
| 27D | CR-7 1.0 | P-3 0.3 | C-1 0.3 | Q-2 0.03 | S-1 30.0 | — — |
| 28D | CR-7 1.0 | P-1/P-2 0.15/0.15 | C-1 0.3 | Q-1 0.03 | S-1 30.0 | D-1 0.02 |
| 29D | CR-8 1.0 | P-1 0.3 | C-1 0.3 | Q-1 0.03 | S-1 30.0 | — — |
| 30D | CR-8 1.0 | P-3 0.3 | C-1 0.3 | Q-2 0.03 | S-1 30.0 | — — |
| 31D | CR-8 1.0 | P-1/P-2 0.15/0.15 | C-1 0.3 | Q-1 0.03 | S-1 30.0 | D-1 0.02 |
| 32D | CR-9 1.0 | P-1 0.3 | C-1 0.3 | Q-1 0.03 | S-1 30.0 | — — |
| 33D | CR-9 1.0 | P-3 0.3 | C-1 0.3 | Q-2 0.03 | S-1 30.0 | — — |
| 34D | CR-9 1.0 | P-1/P-2 0.15/0.15 | C-1 0.3 | Q-1 0.03 | S-1 30.0 | D-1 0.02 |
| 35D | CR-10 1.0 | P-1 0.3 | C-1 0.3 | Q-1 0.03 | S-1 30.0 | — — |
| 36D | CR-10 1.0 | P-3 0.3 | C-1 0.3 | Q-2 0.03 | S-1 30.0 | — — |
| 37D | CR-10 1.0 | P-1/P-2 0.15/0.15 | C-1 0.3 | Q-1 0.03 | S-1 30.0 | D-1 0.02 |
| 38D | CP-1 1.0 | P-1 0.3 | C-1 0.3 | Q-1 0.03 | S-1 30.0 | — — |
| 39D | CP-1 1.0 | P-3 0.3 | C-1 0.3 | Q-2 0.03 | S-1 30.0 | — — |
| 40D | CP-1 1.0 | P-1/P-2 0.15/0.15 | C-1 0.3 | Q-1 0.03 | S-1 30.0 | D-1 0.02 |
| 41D | CP-2 1.0 | P-1 0.3 | C-1 0.3 | Q-1 0.03 | S-1 30.0 | — — |
| 42D | CP-2 1.0 | P-3 0.3 | C-1 0.3 | Q-2 0.03 | S-1 30.0 | — — |
| 43D | CP-2 1.0 | P-1/P-2 0.15/0.15 | C-1 0.3 | Q-1 0.03 | S-1 30.0 | D-1 0.02 |

(C) Acid crosslinking agent
C-1: Nikalac MW-100LM (manufactured by Sanwa Chemical Co., Ltd.)
C-2: Nikalac MX-270 (manufactured by Sanwa Chemical Co., Ltd.)
C-3: Nikalac MX-290 (manufactured by Sanwa Chemical Co., Ltd.)
C-4: 2,6-bis(hydroxymethyl)-p-cresol (manufactured by Tokyo Kasei Kogyo Co., Ltd.)

TABLE 2D

| | PEB (° C.) | Sensitivity (μC/cm$^2$) | Shape of pattern | LER | Solubility |
|---|---|---|---|---|---|
| Examples | | | | | |
| 1D | 110 | 30.0 | A | B | B |
| 2D | 110 | 30.0 | B | B | B |
| 3D | 110 | 15.0 | A | B | B |
| 4D | 110 | 30.0 | A | B | B |
| 5D | 110 | 25.0 | A | B | B |
| 6D | 110 | 25.0 | A | B | B |
| 7D | 110 | 25.0 | A | B | B |
| 8D | 110 | 30.0 | A | B | B |
| 9D | 110 | 30.0 | A | B | B |
| 10D | 110 | 30.0 | A | B | B |
| 11D | 110 | 25.0 | A | B | B |
| 12D | 110 | 25.0 | B | B | B |
| 13D | 110 | 20.0 | A | B | B |
| 14D | 110 | 27.5 | A | B | A |

TABLE 2D-continued

| | PEB (° C.) | Sensitivity (μC/cm²) | Shape of pattern | LER | Solubility |
|---|---|---|---|---|---|
| 15D | 110 | 27.5 | B | B | A |
| 16D | 110 | 22.5 | A | B | A |
| 17D | 110 | 20.0 | A | B | A |
| 18D | 110 | 20.0 | A | B | A |
| 19D | 110 | 15.0 | A | B | A |
| 20D | 110 | 25.0 | A | A | A |
| 21D | 110 | 25.0 | A | A | A |
| 22D | 110 | 20.0 | A | A | A |
| Comparative Examples | | | | | |
| 1D | 110 | 60.0 | C | C | B |
| 2D | 110 | 60.0 | C | C | B |
| Examples | | | | | |
| 23D | 110 | 25.0 | A | B | B |
| 24D | 110 | 25.0 | B | B | B |
| 25D | 110 | 20.0 | A | B | B |
| 26D | 110 | 25.0 | A | B | B |
| 27D | 110 | 25.0 | B | B | B |
| 28D | 110 | 20.0 | A | B | B |
| 29D | 110 | 25.0 | A | B | B |
| 30D | 110 | 25.0 | B | B | B |
| 31D | 110 | 20.0 | A | B | B |
| 32D | 110 | 15.0 | A | B | B |
| 33D | 110 | 15.0 | B | B | B |
| 34D | 110 | 12.5 | A | B | B |

TABLE 2D-continued

| | PEB (° C.) | Sensitivity (μC/cm²) | Shape of pattern | LER | Solubility |
|---|---|---|---|---|---|
| 35D | 110 | 15.0 | A | B | B |
| 36D | 110 | 15.0 | B | B | B |
| 37D | 110 | 12.5 | A | B | B |
| 38D | 110 | 35.0 | A | B | B |
| 39D | 110 | 35.0 | B | B | B |
| 40D | 110 | 30.0 | A | B | B |
| 41D | 110 | 35.0 | A | B | B |
| 42D | 110 | 35.0 | B | B | B |
| 43D | 110 | 30.0 | A | B | B |

PEB: temperature of the post electron beam-exposure heating.

Examples 1E-10E and Comparative Examples 1E-2E

In the same manner as in Examples 1A-20A, a benzaldehyde compound having 10 to 24 carbon atoms and a group including an aliphatic or aromatic ring and a cyclic compound (A) were synthesized.

The components shown in Table 1E were blended to obtain a uniform solution, which was then filtered through a Teflon membrane filter with a 0.2 μm pore size to prepare each resist composition. The same comparative compound, acid generator (C), acid-diffusion controller (E), and solvent as used in Examples 1D-43D were used, and the evaluations were made in the same manner except for evaluating the patterning test by the following ratings.

(2-3) Evaluation of Line Edge Roughness (LER)
A: LER (3σ)≦3.5 nm (good)
C: 3.5 nm<LER (3σ) (poor)

TABLE 1E

| | Compound (g) | Acid generator (C) (g) | Cross-linking agent (G) (g) | Acid-diffusion controller (E) (g) | Solvent (g) | Surfactant (F) (g) |
|---|---|---|---|---|---|---|
| Examples | | | | | | |
| 1E | CR-1 1.0 | P-1 0.3 | C-1 0.3 | Q-1 0.03 | S-1 30.0 | — |
| 2E | CR-1 1.0 | P-2 0.3 | C-1 0.3 | Q-1 0.03 | S-1 30.0 | — |
| 3E | CR-1 1.0 | P-3 0.3 | C-1 0.3 | Q-2 0.03 | S-1 30.0 | — |
| 4E | CR-1 1.0 | P-1 0.1 | C-1 0.1 | Q-1 0.01 | S-1 30.0 | — |
| 5E | CR-1 1.0 | P-1 0.3 | C-1 0.3 | Q-1 0.03 | S-1 30.0 | D-1 0.02 |
| 6E | CR-1 1.0 | P-1/P-2 0.15/0.15 | C-1 0.3 | Q-1 0.03 | S-1 30.0 | D-1 0.02 |
| 7E | CR-1 1.0 | P-1/P-2 0.15/0.15 | C-1 0.3 | Q-1 0.03 | S-1 30.0 | D-2 0.02 |
| 8E | CR-1 1.0 | P-1 0.3 | C-2 0.3 | Q-1 0.03 | S-1 30.0 | — |
| 9E | CR-1 1.0 | P-1 0.3 | C-3 0.3 | Q-1 0.03 | S-1 30.0 | — |
| 10E | CR-1 1.0 | P-1 0.3 | C-4 0.3 | Q-1 0.03 | S-1 30.0 | — |
| Comparative Examples | | | | | | |
| 1E | CR-2 1.0 | P-1 0.2 | C-1 0.2 | Q-1 0.02 | S-1 30.0 | — |
| 2E | CR-3 1.0 | P-1 0.3 | C-1 0.3 | Q-1 0.03 | S-1 30.0 | — |

TABLE 2E

| | PEB (° C.) | Sensitivity (μC/cm²) | Shape of pattern | LER (3σ) |
|---|---|---|---|---|
| Examples | | | | |
| 1E | 110 | 30.0 | A | A |
| 2E | 110 | 30.0 | B | A |

TABLE 2E-continued

|  | PEB (° C.) | Sensitivity (μC/cm²) | Shape of pattern | LER (3σ) |
|---|---|---|---|---|
| 3E | 110 | 15.0 | A | A |
| 4E | 110 | 30.0 | A | A |
| 5E | 110 | 25.0 | A | A |
| 6E | 110 | 25.0 | A | A |
| 7E | 110 | 25.0 | A | A |
| 8E | 110 | 30.0 | A | A |
| 9E | 110 | 30.0 | A | A |
| 10E | 110 | 30.0 | A | A |
| Comparative Examples | | | | |
| 1E | 110 | 60.0 | C | C |
| 2E | 110 | 60.0 | C | C |

PEB: temperature of the post electron beam-exposure heating.

Synthesis Example 1F

Synthesis of Aldehyde Compounds (1) Synthesis of 4-(4-n-propylcyclohexyl)benzaldehyde Into a 500-ml thermo-controllable autoclave made of SUS316L equipped with an electromagnetic stirring device, 74.3 g (3.71 mol) of dry HF and 50.5 g (0.744 mol) of $BF_3$ were charged. While stirring the contents and maintaining the liquid temperature at −30° C., the pressure was raised to 2 MPa by introducing carbon monoxide. Then, a mixed raw material of 50.0 g (0.248 mol) of (trans-4-n-propylcyclohexyl)benzene (purity: 98% or more, manufactured by Kanto Chemical Co., Inc.) and 50.0 g of n-heptane was introduced into the autoclave while maintaining the pressure at 2 MPa and the liquid temperature at −30° C. After further maintaining for 1 h, the contents were poured into ice, diluted with benzene and neutralized. The oil layer was analyzed by gas chromatography. The conversion of (trans-4-n-propylcyclohexyl)benzene was 100% and the selectivity of 4-(trans-4-n-propylcyclohexyl)benzaldehyde was 95.2%. The result of GC-MS analysis showed that the component isolated by a single distillation had a molecular weight of 230 of the aimed 4-(trans-4-n-propylcyclohexyl)benzaldehyde.

$^1$H-NMR Chemical Shifts (δ ppm, TMS reference) in heavy chloroform:
0.9 (t, 3H), 1.0-1.6 (m, 9H), 1.9 (m, 4H), 2.55 (m, 1H), 7.36 (d, 2H), 7.8 (d, 2H), 10 (s, 1H)

The purity of 4-(4-n-propylcyclohexyl)benzaldehyde was 98.3% and the trans-isomer purity was 99.0%.

(2) Synthesis of 4-(trans-4-n-pentylcyclohexyl)benzaldehyde

In the same manner as in the synthesis (1) except for using a mixed raw material of 57.0 g (0.248 mol) of (trans-4-n-pentylcyclohexyl)benzene and 57.0 g of n-heptane, the formylation reaction was conducted and the obtained reaction product liquid was treated in the same manner. The obtained oil layer was analyzed by gas chromatography. The conversion of (trans-4-n-pentylcyclohexyl)benzene was 100% and the selectivity of 4-(trans-4-n-pentylcyclohexyl)benzaldehyde was 96.2%.

(3) Synthesis of 4-cyclohexylbenzaldehyde

In the same manner as in the synthesis (1) except for using a mixed raw material of 57.0 g (0.248 mol) of 4-cyclohexylbenzene and 57.0 g of n-heptane, the formylation reaction was conducted and the obtained reaction product liquid was treated in the same manner. The obtained oil layer was analyzed by gas chromatography. The conversion of 4-cyclohexylbenzene was 100% and the selectivity of 4-cyclohexylbenzaldehyde was 97.3%.

Preparation of Composition for Under Coat Film

Synthesis Example 2F

Synthesis of Cyclic Compound (CR)

(1) Synthesis of CR-1F

A four-neck flack (1000 L) equipped with a dropping funnel, Dimroth condenser, a thermometer and a stirring device was sufficiently dried and purged with nitrogen. Into the flask, resorcinol (22 g, 0.2 mol, manufactured by Kanto Chemical Co., Inc.), 4-(4-n-propylcyclohexyl)benzaldehyde (46.0 g, 0.2 mol) synthesized in Synthesis Example 1F and absolute ethanol (200 ml) were charged under nitrogen stream to prepare an ethanol solution. The solution was heated to 85° C. in a mantle heater under stirring. After adding 75 ml of a concentrated hydrochloric acid (35%) from the dropping funnel over 30 min, the solution was continuously stirred at 85° C. for 3 h. After the reaction, the solution was allowed to stand to reach room temperature and then cooled in an ice bath. After leaving at rest for 1 h, pale yellow crystals were generated. The separated crude crystals were washed twice with 500 ml of methanol, filtered and vacuum-dried to obtain CR-1F having a structure of the formula (4) wherein $R^4$ are all n-propyl groups (58 g, 91% yield). The result of LC-MS analysis showed that the compound had a molecular weight of 1289 of the aimed compound.

$^1$H-NMR Chemical Shifts (δ ppm, TMS reference) in heavy chloroform:
0.9-1.9 (m, 68H), 5.5, 5.6 (d, 4H), 6-6.8 (m, 24H), 8.4, 8.5 (m, 8H)

The thermogravimetric loss of CR-1F was 1% or less when heated to 200° C., showing that CR-1F was less sublimable.

(2) Synthesis of CR-2F

In the same manner as in the synthesis of CR-1F except for using 4-(trans-4-n-pentylcyclohexyl)benzaldehyde synthesized in Synthesis Example 2F in place of 4-(4-n-propylcyclohexyl)benzaldehyde, CR-2F represented by the formula (4) wherein $R^4$ are all n-pentyl groups was obtained (63.0 g, 90% yield). The result of LC-MS analysis showed that the compound had a molecular weight of 1401 of the aimed compound.

$^1$H-NMR Chemical Shifts (δ ppm, TMS reference) in heavy chloroform:
0.8-1.9 (m, 84H), 5.5, 5.6 (d, 4H), 6-6.8 (m, 24H), 8.4, 8.5 (m, 8H)

The thermogravimetric loss of CR-2F was 1% or less when heated to 200° C., showing that CR-2F was less sublimable.

(3) Synthesis of CR-3F

In the same manner as in the synthesis of CR-1F except for using 4-cyclohexylbenzaldehyde synthesized in Synthesis Example 2F in place of 4-(4-n-propylcyclohexyl)benzaldehyde, CR-3F represented by the formula (3) wherein $R^3$ are all hydrogen atoms was obtained (87% yield). The structure of the compound was identified by NMR measurement, IR measurement, elemental analysis, etc. The result of LC-MS analysis showed that the compound had a molecular weight of 1117 of the aimed compound.

$^1$H-NMR Chemical Shifts (δ ppm, TMS reference) in heavy chloroform:

0.8-1.9 (m, 56H), 5.5, 5.6 (d, 4H), 6-6.8 (m, 24H), 8.4, 8.5 (m, 8H)

The thermogravimetric loss of CR-3F was 1% or less when heated to 200° C., showing that CR-3F was less sublimable.

(4) Synthesis of CR-4F

In the same manner as in the synthesis of CR-1F except for using cuminaldehyde (manufactured by Mitsubishi Gas Chemical Company, Inc.) in place of 4-(4-n-propylcyclohexyl)benzaldehyde, CR-4F represented by the formula (2) wherein $R^2$ are all isopropyl groups was obtained (47% yield). The structure of the compound was identified by NMR measurement, IR measurement, elemental analysis, etc.

The thermogravimetric loss of CR-4F was 1% or less when heated to 200° C., showing that CR-4F was less sublimable.

(5) Synthesis of CR-5F

In the same manner as in the synthesis of CR-1F except for using n-propylbenzaldehyde (manufactured by Mitsubishi Gas Chemical Company, Inc.) in place of 4-(4-n-propylcyclohexyl)benzaldehyde, CR-5F represented by the formula (2) wherein $R^2$ are all n-propyl groups was obtained (63.0 g, 90% yield). The structure of the compound was identified by NMR measurement, IR measurement, elemental analysis, etc.

The thermogravimetric loss of CR-5F was 1% or less when heated to 200° C., showing that CR-5F was less sublimable.

(6) Synthesis of CR-6F

In the same manner as in the synthesis of CR-1F except for using t-butylbenzaldehyde (manufactured by Aldrich Chemical Co., Inc.) in place of 4-(4-n-propylcyclohexyl)benzaldehyde, CR-6F represented by the formula (2) wherein $R^2$ are all t-butyl groups was obtained (30% yield). The structure of the compound was identified by NMR measurement, IR measurement, elemental analysis, etc.

The thermogravimetric loss of CR-6F was 1% or less when heated to 200° C., showing that CR-6F was less sublimable.

(7) Synthesis of CR-7F

In the same manner as in the synthesis of CR-1F except for using 1-decanal (manufactured by Kanto Chemical Co., Inc.) in place of 4-(4-n-propylcyclohexyl)benzaldehyde, CR-7F represented by the formula (1) wherein $R^1$ are all n-nonyl groups was obtained (67% yield). The structure of the compound was identified by NMR measurement, IR measurement, elemental analysis, etc.

The thermogravimetric loss of CR-7F was 1% or less when heated to 200° C., showing that CR-7F was less sublimable.

(8) Synthesis of CR-8F

Using CR-1F, a novolak resin CR-8F having CR-1F-methylene repeating units was produced by a known method. The results of GPC measurement showed that Mw was 9100 and Mw/Mn was 5.8.

The thermogravimetric loss of CR-8F was 1% or less when heated to 200° C., showing that CR-8F was less sublimable.

(9) Synthesis of Comparative Compound 1

In the same manner as in the synthesis of CR-1F except for using 1,3,5-benzenetrialdehyde in place of 4-(4-n-propylcyclohexyl)benzaldehyde, using 2,3,6-trimethylphenol in place of resorcinol, and using 1 ml of concentrated sulfuric acid in place of concentrated hydrochloric acid in toluene, the following compound was obtained (85% yield). The structure of the compound was identified by NMR measurement, IR measurement, elemental analysis, etc.

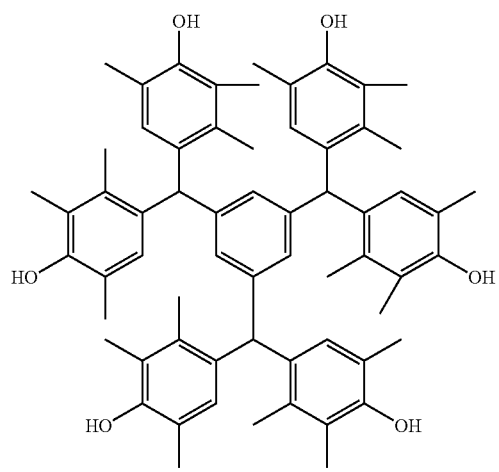

(10) Synthesis of Comparative Compound 2

In the same manner as in the synthesis of the comparative compound 1 except for using 2-adamantanone in place of 1,3,5-benzenetrialdehyde, the following compound was obtained (81% yield). The structure of the compound was identified by NMR measurement, IR measurement, elemental analysis, etc.

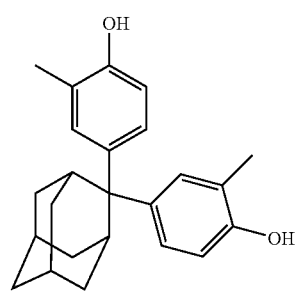

Production Example 1F

Production of Under Coat Film

Each of CR-1F to CR-8F, the comparative compounds 1 and 2, polyhydroxystyrene (referred to as "PHS," Mw: 8000, manufactured by Aldrich Chemical Co., Inc.) and m-cresol novolak resin (referred to as "novolak," Mw:8800) was dissolved in PGME (propylene glycol monomethyl ether) to prepare a 5% by mass solution, which was then filtered through a 0.1-μm filter made of a fluorine resin to prepare each solution for forming under coat film.

The solution for forming under coat film was spin-coated onto a silicon substrate and baked at 110° C. for 90 s to form an under coat film with a thickness of 200 nm (under coat films 1-9 and comparative under coat films 1-4). Each under coat film was subjected to ellipsometry at a wavelength of 193 nm using a variable angle spectroscopic ellipsometer "VASE" manufactured by J. A. Woollam Co., Inc. The measured absorption was fitted by a Gaussian oscillator approximation utilizing a General Oscillator Model to determine the refractive index n and extinction coefficient k of the under coat films 1-9 and the comparative under coat films 1-4. The results are shown in Table 1F.

TABLE 1F

| | Polyphenol compound (parts by mass) | Crosslinking agent (parts by mass) | Acid generator (parts by mass) | Solvent (parts by mass) | n | k |
|---|---|---|---|---|---|---|
| Under Coat Films | | | | | | |
| 1 | CR-1F (5) | — | — | PGME (95) | 1.51 | 0.25 |
| 2 | CR-2F (5) | — | — | PGME (95) | 1.73 | 0.68 |
| 3 | CR-3F (5) | — | — | PGME (95) | 1.45 | 0.31 |
| 4 | CR-4F (5) | — | — | PGME (95) | 1.34 | 0.48 |
| 5 | CR-5F (5) | — | — | PGME (95) | 1.32 | 0.63 |
| 6 | CR-6F (5) | — | — | PGME (95) | 1.30 | 0.32 |
| 7 | CR-7F (5) | — | — | PGME (95) | 1.34 | 0.27 |
| 8 | CR-8F (5) | — | — | PGME (95) | 1.50 | 0.23 |
| 9 | CR-3F (5) | Nikalac (0.5) | TPS109 (0.1) | PGME (95) | 1.53 | 0.26 |
| Comparative Under Coat Films | | | | | | |
| 1 | 101 (5) | — | — | PGME (95) | 1.15 | 0.56 |
| 2 | 102 (5) | — | — | PGME (95) | 1.25 | 0.51 |
| 3 | PHS (5) | — | — | PGME (95) | 1.59 | 1.03 |
| 4 | novolak (5) | — | — | PGME (95) | 1.19 | 0.80 |

Acid generator: triphenylsulfonium nonafluoromethanesulfonate (TPS109)
Crosslinking agent: Nikalac MX270 manufactured by Sanwa Chemical Co., Ltd.

Next, the solution for forming under coat film was coated onto a $SiO_2$ substrate with a thickness of 300 nm and baked at 250° C. for 60 s to form an under coat film with a thickness of 200 nm. Then, a resist solution for ArF was coated on the under coat film and baked at 130° C. for 60 s to form a photoresist film. The resist solution for ArF was prepared by blending 5 parts of the compound of the following formula (110), 1 part of TPS109, 2 parts of tributylamine, and 92 parts of PGMEA.

The photoresist film was irradiated with electron beams at 50 keV using an electron beam lithography system (ELS-7500 manufactured by Elionix Co., Ltd.), baked at 115° C. for 90 s (PEB), and developed by a 2.38% by weight aqueous solution of tetramethylammonium hydroxide (TMAH) for 60 s, to obtain a positive-type pattern. The obtained 60 nm L/S (1:1) pattern was observed for its shape. The results are shown in Table 2F.

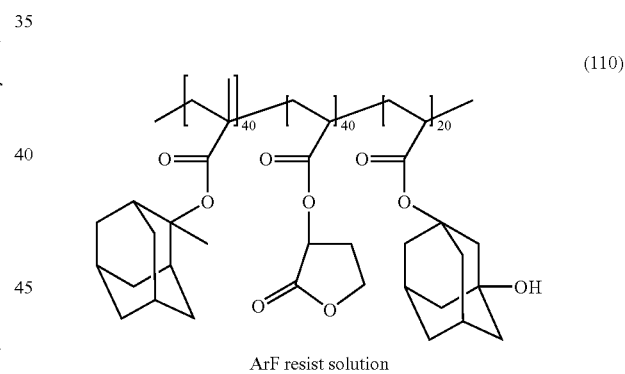

ArF resist solution

TABLE 2F

| | Under coat film | Resolution | Sensitivity |
|---|---|---|---|
| Invention | 1 | 60 nm L & S | 12 µC/cm² |
| Invention | 2 | 60 nm L & S | 12 µC/cm² |
| Invention | 3 | 60 nm L & S | 12 µC/cm² |
| Invention | 8 | 60 nm L & S | 12 µC/cm² |
| Invention | 9 | 60 nm L & S | 12 µC/cm² |
| Comparison | omitted | 80 nm L & S | 26 µC/cm² |

Next, the resist pattern obtained by the above exposure to electron beams and development was transferred to the under coat film by etching under the following conditions.
Etching apparatus: manufactured by Elionix Co., Ltd.
Voltage: 400 V
Current density: 0.9 mA/cm²
Time: 2 min
Ar gas flow:$CF_4$ gas flow:$O_2$ gas flow=10:1:1 (by volume)

The cross section of the pattern was observed by an electron microscope "S-4800" manufactured by Hitachi, Ltd. for its shape.

The multi-layer resist was good in the shape of resist after development and the shape of under coat film was also good after oxygen etching and after processing the substrate by etching. Also, the shape of the resist was good in the shape after development and after processing the substrate by etching even when the resist was singly used as a hard mask.

INDUSTRIAL APPLICABILITY

The resist compound having a specific chemical structure and the radiation-sensitive composition containing such a resist compound of the present invention are useful as the acid-amplified, non-polymeric resist material. The radiation-sensitive composition is suitably used to form an under coat film and a resist pattern.

What is claimed is:

1. A method of producing a cyclic compound chosen from

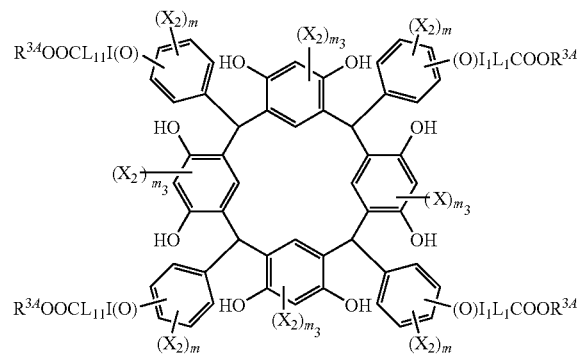

(33-0)

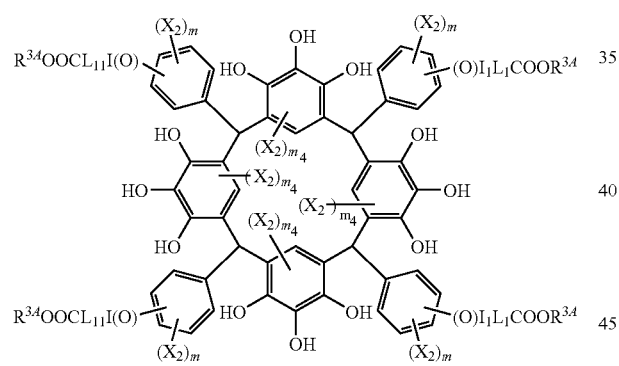

(33)

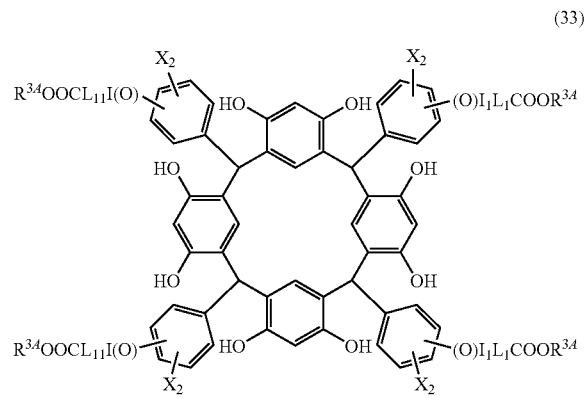

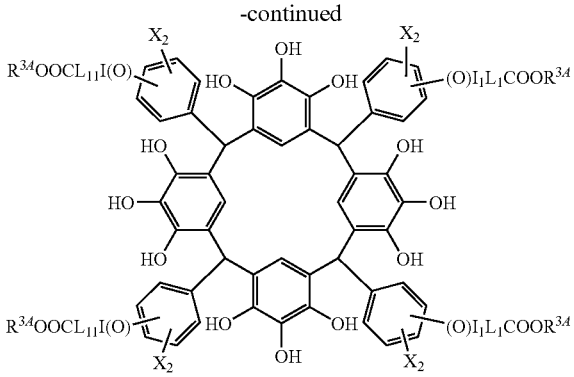

wherein $R^{34}$ is a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms, and an alkoxycarbonylalkyl group having 2 to 20 carbon atoms; and $X_2$ is hydrogen atom or a halogen atom; $L_1$ is a single bond or a divalent organic group selected from a linear or branched alkylene group having 1 to 4 carbon atoms; $l_1$ is 0 or 1; m is an integer of 1 to 4, $m_3$ is an integer of 1 to 2; and $m_4$ is 1, comprising a first stage reaction in which an aldehyde compound (A1b) having 2 to 59 carbon atoms, a reactive functional group and 1 to 4 formyl groups is allowed to react with a reagent for introducing an acid-dissociating functional group, thereby synthesizing an aldehyde compound (A1c) having the acid-dissociating functional group introduced, and a second stage reaction in which the aldehyde compound (A1c) and a phenol compound (A2) are subjected to a condensation reaction.

2. A method of producing a cyclic compound chosen from

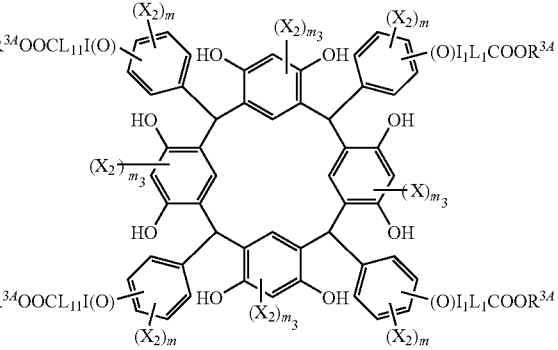

(33-0)

-continued

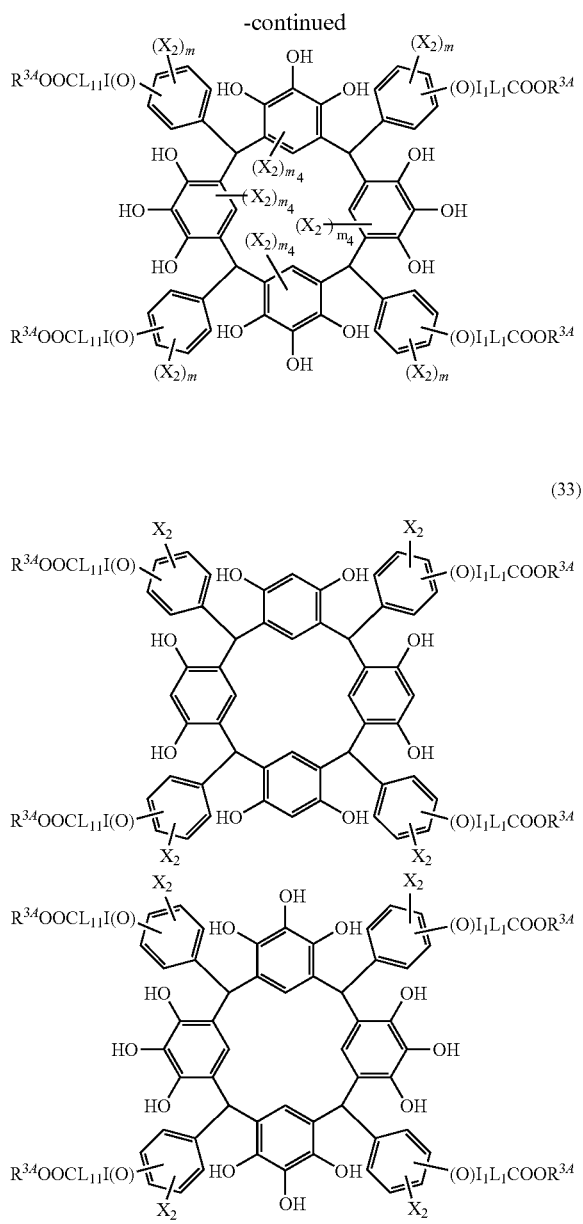

(33)

wherein $R^{34}$ is a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms, and an alkoxycarbonylalkyl group having 2 to 20 carbon atoms; and $X_2$ is hydrogen atom or a halogen atom; $L_1$ is a single bond or a divalent organic group selected from a linear or branched alkylene group having 1 to 4 carbon atoms; $l_1$ is 0 or 1; m is an integer of 1 to 4, $m_3$ is an integer of 1 to 2; and $m_4$ is 1, comprising a first stage reaction in which an aldehyde compound (A1d) having 2 to 59 carbon atoms, 1 to 4 formyl groups, and 1 to 2 carboxyl groups or ester groups and a phenol compound (A2) are subjected to a condensation reaction, thereby synthesizing a cyclic compound (A0) having 1 to 8 carboxyl groups and a molecular weight of 800 to 5000, and a second stage reaction in which the cyclic compound (A0) is allowed to react with a compound (A3) having a halomethyl ether group.

3. A composition comprising a resin having repeating units derived from a water-eliminating condensation of a cyclic compound represented by the following formula (1):

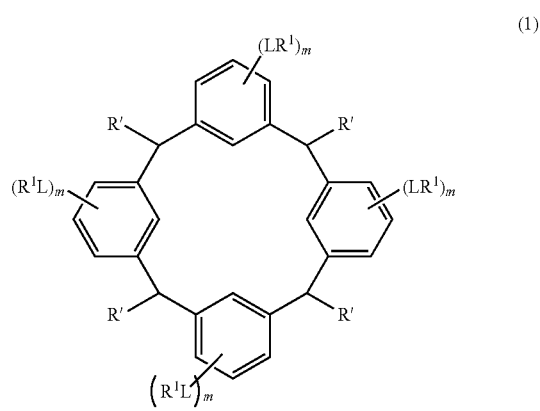

(1)

wherein L is independently a divalent organic group selected from a single bond, a linear or branched alkylene group having 1 to 20 carbon atoms, a cycloalkylene group having 3 to 20 carbon atoms, an arylene group having 6 to 24 carbon atoms, —O—, —OC(=O)—, —OC(=O)O—, —N(R⁵)—C(=O)—, —N(R⁵)—C(=O)O—, —S—, —SO—, —SO₂—, and any combination of the preceding groups; $R^1$ is independently hydrogen atom, a functional group selected from an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, heterocyclic group, halogen atom, carboxyl group, an alkylsilyl group having 1 to 20 carbon atoms, and a group derived from the preceding groups, or an acid-dissociating functional group selected from a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; R' is independently an alkyl group having 2 to 20 carbon atoms, an aryl group having 6 to 24 carbon atoms represented by the following formula:

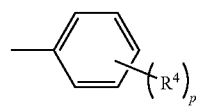

or a group derived from the preceding groups; $R^4$ is a functional group selected from an alkyl group having 1 to 20 carbon atoms exclusive of t-butyl group, a cycloalkyl group having 3 to 20 carbon atoms, an aryl group having 6 to 20 carbon atoms, an alkoxyl group having 1 to 20 carbon atoms, cyano group, nitro group, heterocyclic group, halogen atom, carboxyl group, an alkylsilyl group having 1 to 20 carbon atoms, and a group derived from the preceding groups, or an acid-dissociating functional group selected from the group consisting of a substituted methyl group having 2 to 20 carbon atoms, a 1-substituted ethyl group having 3 to 20 carbon atoms, a 1-substituted n-propyl group having 4 to 20 carbon atoms, a 1-branched alkyl group having 3 to 20 carbon atoms, a silyl group having 1 to 20 carbon atoms, an acyl group having 2 to 20 carbon atoms, a 1-substituted alkoxyalkyl group having 2 to 20 carbon atoms, a cyclic ether group having 2 to 20 carbon atoms, an alkoxycarbonyl group having 2 to 20 carbon atoms and an alkoxycarbonylalkyl group; $R^5$ is hydrogen atom or an alkyl group having 1 to 10 carbon atoms; m is an integer of 1 to 4; and p is an integer of 1 to 3 with an aldehyde compound (A1a) in the presence of an acid catalyst, wherein the cyclic compound according to formula (1) has a molecular weight of 700 to 5000 and is synthesized by a condensation reaction of an aldehyde compound (A1) having 2 to 59 carbon atoms and 1 to 4 formyl groups with a phenol compound (A2) having 6 to 15 carbon atoms and 1 to 3 phenolic hydroxyl groups.

4. An under coat film comprising the composition according to claim 3.

* * * * *